US012734215B2

(12) United States Patent
Emmerich et al.

(10) Patent No.: US 12,734,215 B2
(45) **Date of Patent: *Sep. 15, 2026**

(54) BIASED IL2 MUTEINS METHODS AND COMPOSITIONS

(71) Applicant: Synthekine, Inc., Menlo Park, CA (US)

(72) Inventors: Jan Emmerich, Redwood City, CA (US); Steve Kauder, San Carlos, CA (US); Scott Alan McCauley, San Francisco, CA (US); Martin Oft, Palo Alto, CA (US)

(73) Assignee: SYNTHEKINE, INC., Menlo Park, CA (US)

( * ) Notice: Subject to any disclaimer, the term of this patent is extended or adjusted under 35 U.S.C. 154(b) by 1008 days.

This patent is subject to a terminal disclaimer.

(21) Appl. No.: 17/833,235

(22) Filed: Jun. 6, 2022

(65) Prior Publication Data

US 2023/0031597 A1 Feb. 2, 2023

Related U.S. Application Data

(63) Continuation of application No. 17/149,405, filed on Jan. 14, 2021, now Pat. No. 11,491,205.

(60) Provisional application No. 63/136,599, filed on Jan. 12, 2021, provisional application No. 62/961,141, filed on Jan. 14, 2020.

(51) Int. Cl.

| | |
|---|---|
| ***A61K 38/20*** | (2006.01) |
| ***A61K 35/17*** | (2025.01) |
| ***A61K 35/76*** | (2015.01) |
| ***A61K 38/00*** | (2006.01) |
| ***A61K 39/395*** | (2006.01) |
| ***A61K 45/06*** | (2006.01) |
| ***A61K 47/60*** | (2017.01) |

(52) U.S. Cl.

CPC .......... *A61K 38/2013* (2013.01); *A61K 35/17* (2013.01); *A61K 35/76* (2013.01); *A61K 39/3955* (2013.01); *A61K 45/06* (2013.01); *A61K 47/60* (2017.08); *A61K 38/00* (2013.01)

(58) Field of Classification Search

CPC ............................ A61K 38/2013; A61P 35/00

See application file for complete search history.

(56) References Cited

U.S. PATENT DOCUMENTS

| | | | |
|---|---|---|---|
| 4,401,756 | A | 8/1983 | Gillis |
| 4,470,461 | A | 9/1984 | Stapp |
| 4,518,584 | A | 5/1985 | Mark et al. |
| 4,522,811 | A | 6/1985 | Eppstein |
| 4,530,787 | A | 7/1985 | Shaked |
| 4,569,790 | A | 2/1986 | Koths |
| 4,572,798 | A | 2/1986 | Koths |
| 4,588,585 | A | 5/1986 | Mark et al. |
| 4,604,377 | A | 8/1986 | Fernandes |
| 4,656,132 | A | 4/1987 | Ben-Bassat |
| 4,738,927 | A | 4/1988 | Taniguchi et al. |
| 4,748,234 | A | 5/1988 | Dorin |
| 4,752,585 | A | 6/1988 | Koths et al. |
| 4,766,106 | A | 8/1988 | Katre |
| 4,849,329 | A | 7/1989 | Leung |
| 4,863,727 | A | 9/1989 | Zimmerman et al. |
| 4,879,111 | A | 11/1989 | Chong |
| 4,931,543 | A | 6/1990 | Halenbeck |
| 4,931,544 | A | 6/1990 | Katre et al. |
| 4,938,956 | A | 7/1990 | Howard et al. |
| 4,992,271 | A | 2/1991 | Hanisch |
| RE33,653 | E | 7/1991 | Mark et al. |
| 5,037,644 | A | 8/1991 | Shaked |
| 5,078,997 | A | 1/1992 | Hora |
| 5,089,261 | A | 2/1992 | Nitecki et al. |
| 5,102,872 | A | 4/1992 | Singh |
| 5,116,943 | A | 5/1992 | Koths et al. |
| 5,122,464 | A | 6/1992 | Wilson |
| 5,126,132 | A | 6/1992 | Rosenberg |
| 5,206,344 | A | 4/1993 | Katre et al. |
| 5,359,046 | A | 10/1994 | Capon et al. |
| 5,419,899 | A | 5/1995 | Koths et al. |
| 5,442,043 | A | 8/1995 | Fukuta |
| 5,445,090 | A | 8/1995 | Conley, Jr. |
| 5,635,599 | A | 6/1997 | Pastan et al. |
| 5,643,565 | A | 7/1997 | Doyle et al. |
| 5,696,079 | A | 12/1997 | Lane et al. |
| 5,696,234 | A | 12/1997 | Zurawski et al. |
| 5,814,314 | A | 9/1998 | Lando et al. |
| 5,830,452 | A | 11/1998 | Bauer et al. |

(Continued)

FOREIGN PATENT DOCUMENTS

| | | | |
|---|---|---|---|
| EP | 338841 | A1 | 10/1989 |
| EP | 2279753 | B1 | 9/2015 |

(Continued)

OTHER PUBLICATIONS

Yaghoubi et al (Biomedicine & Pharmacotherapy, 2019, vol. 110, pp. 312-318) (Year: 2019).*

Schneider et al (Journal of Thoracic Oncology, 2011, vol. 6, pp. 432-438) (Year: 2011).*

Abstract of Eikawa et al (Cancer Research, 2010, vol. 70, No. 8., suppl., abstract No. 1915) (Year: 2010).*

Rozkova et al (Clinical Immunology, 2009, vol. 131, pp. 1-10) (Year: 2009).*

Koopmans et al (Oncoimmunology, 2018, vol. 7, e1466016, 11 pages). (Year: 2018).*

Au et al (The Oncologist, ePub Nov. 14, 2019, vol. 25, e709-e715) (Year: 2019).*

(Continued)

*Primary Examiner* — Karen A. Canella

(74) *Attorney, Agent, or Firm* — Kilpatrick Townsend & Stockton LLP

(57) ABSTRACT

The present disclosures related to human interleukin-2 (hIL2) muteins, pharmaceutical formulations thereof, methods for preparing interleukin-2 muteins, recombinant vectors and cells comprising nucleic acids encoding IL2 muteins and methods for the treatment of human disease.

38 Claims, 24 Drawing Sheets

Specification includes a Sequence Listing.

(56) References Cited

U.S. PATENT DOCUMENTS

| | | | |
|---|---|---|---|
| 5,874,076 | A | 2/1999 | Lando et al. |
| 5,900,461 | A | 5/1999 | Harris |
| 5,931,462 | A | 8/1999 | Harris |
| 6,168,785 | B1 | 1/2001 | Theze et al. |
| 6,348,192 | B1 | 2/2002 | Chan et al. |
| 6,410,008 | B1 | 6/2002 | Strom |
| 6,436,386 | B1 | 8/2002 | Roberts |
| 6,437,025 | B1 | 8/2002 | Harris |
| 6,448,369 | B1 | 9/2002 | Bentley |
| 6,451,308 | B1 | 9/2002 | Strom |
| 6,468,798 | B1 | 10/2002 | Debs |
| 6,495,659 | B2 | 12/2002 | Bentley |
| 6,514,491 | B1 | 2/2003 | Bentley |
| 6,515,100 | B2 | 2/2003 | Harris |
| 6,548,055 | B1 | 4/2003 | Lane et al. |
| 6,596,853 | B1 | 7/2003 | Theze et al. |
| 6,617,135 | B1 | 9/2003 | Gillies |
| 6,689,353 | B1 | 2/2004 | Wang et al. |
| 6,825,334 | B1 | 11/2004 | Theze et al. |
| 6,929,791 | B2 | 8/2005 | Theze et al. |
| 6,955,807 | B1 | 10/2005 | Shanafelt et al. |
| 7,091,321 | B2 | 8/2006 | Gillies |
| 7,101,965 | B2 | 9/2006 | Theze et al. |
| 7,105,653 | B2 | 9/2006 | Shanafelt et al. |
| 7,186,804 | B2 | 3/2007 | Gillies et al. |
| 7,371,371 | B2 | 5/2008 | Epstein et al. |
| 7,462,350 | B2 | 12/2008 | Gillies |
| 7,514,073 | B2 | 4/2009 | Epstein et al. |
| 7,569,215 | B2 | 8/2009 | Wittrup et al. |
| 7,662,368 | B2 | 2/2010 | Theze |
| 7,704,490 | B2 | 4/2010 | Theze |
| 7,888,071 | B2 | 2/2011 | Gillies |
| 7,951,360 | B2 | 5/2011 | Wittrup et al. |
| 8,124,066 | B2 | 2/2012 | Epstein et al. |
| 8,349,311 | B2 | 1/2013 | Wittrup et al. |
| 8,759,486 | B2 | 6/2014 | León Monzón et al. |
| 8,906,356 | B2 | 12/2014 | Wittrup et al. |
| 9,206,243 | B2 | 12/2015 | León Monzón et al. |
| 9,266,938 | B2 | 2/2016 | Ast et al. |
| 9,428,567 | B2 | 8/2016 | Garcia et al. |
| 9,580,486 | B2 | 2/2017 | Gavin |
| 9,616,105 | B2 | 4/2017 | Paulsen et al. |
| 9,669,071 | B2 | 6/2017 | Klatzmann et al. |
| 9,732,134 | B2 | 8/2017 | Gavin et al. |
| 9,844,582 | B2 | 12/2017 | Wittrup et al. |
| 9,861,705 | B2 | 1/2018 | Bossard et al. |
| 10,010,587 | B2 | 7/2018 | Addepalli et al. |
| 10,035,836 | B1 | 7/2018 | Greve et al. |
| 10,086,046 | B2 | 10/2018 | Paulsen et al. |
| 10,093,711 | B2 | 10/2018 | Kannan |
| 10,150,802 | B2 | 12/2018 | Garcia et al. |
| 10,166,257 | B2 | 1/2019 | Wardell et al. |
| 10,174,091 | B1 | 1/2019 | Higginson-Scott et al. |
| 10,183,980 | B2 | 1/2019 | Garcia et al. |
| 10,293,028 | B2 | 5/2019 | Klatzmann et al. |
| 10,654,905 | B2 | 5/2020 | Garcia |
| 11,491,205 | B2 | 11/2022 | Emmerich et al. |
| 2002/0041865 | A1 | 4/2002 | Austin |
| 2003/0166163 | A1 | 9/2003 | Gillies |
| 2004/0175357 | A1 | 9/2004 | Shanafelt |
| 2006/0008872 | A1 | 1/2006 | Chung et al. |
| 2006/0199250 | A1 | 9/2006 | Zhao et al. |
| 2006/0269515 | A1 | 11/2006 | Denis-Mize et al. |
| 2006/0292116 | A1 | 12/2006 | Epstein et al. |
| 2007/0274948 | A1 | 11/2007 | Hurst et al. |
| 2009/0098609 | A1 | 4/2009 | Gillies et al. |
| 2010/0028350 | A1 | 2/2010 | Jevnikar et al. |
| 2010/0273723 | A1 | 10/2010 | Theze |
| 2010/0285014 | A1 | 11/2010 | Cox |
| 2011/0091413 | A1 | 4/2011 | Epstein et al. |
| 2011/0150826 | A1 | 6/2011 | Paulsen |
| 2012/0315245 | A1 | 12/2012 | León Monzón et al. |
| 2014/0046026 | A1 | 2/2014 | Garcia |
| 2014/0328791 | A1 | 11/2014 | Bossard |
| 2014/0343252 | A1 | 11/2014 | Gavin |
| 2015/0017120 | A1 | 1/2015 | Wittrup et al. |
| 2015/0218260 | A1 | 8/2015 | Klein et al. |
| 2016/0208017 | A1 | 7/2016 | Ast et al. |
| 2017/0015722 | A1 | 1/2017 | Garcia |
| 2017/0044229 | A1 | 2/2017 | Garcia et al. |
| 2017/0137485 | A1 | 5/2017 | Gavin et al. |
| 2017/0304402 | A1 | 10/2017 | Klatzmann et al. |
| 2017/0313753 | A1 | 11/2017 | Gavin et al. |
| 2018/0016316 | A1 | 1/2018 | Garcia et al. |
| 2018/0125941 | A1 | 5/2018 | Greve et al. |
| 2018/0142037 | A1 | 5/2018 | Ast et al. |
| 2018/0228842 | A1 | 8/2018 | Garcia et al. |
| 2018/0237489 | A1 | 8/2018 | Kannan |
| 2018/0303754 | A1 | 10/2018 | Mariau |
| 2018/0319859 | A1 | 11/2018 | Gavin et al. |
| 2018/0326010 | A1 | 11/2018 | Deak et al. |
| 2018/0340014 | A1 | 11/2018 | Viney et al. |
| 2019/0022239 | A1 | 1/2019 | Hamzah et al. |
| 2019/0023760 | A1 | 1/2019 | Bode |
| 2019/0060407 | A1 | 2/2019 | Klatzmann et al. |
| 2019/0062395 | A1 | 2/2019 | Merchant et al. |
| 2019/0106488 | A1 | 4/2019 | Rondon |
| 2019/0119346 | A1 | 4/2019 | Garcia et al. |
| 2019/0202917 | A1 | 7/2019 | Campbell |
| 2019/0263877 | A1 | 8/2019 | Yeung |
| 2020/0299349 | A1 | 9/2020 | Garcia |

FOREIGN PATENT DOCUMENTS

| | | | |
|---|---|---|---|
| EP | 2918285 | B1 | 9/2015 |
| EP | 3102595 | B1 | 11/2018 |
| JP | 2005507870 | A | 3/2005 |
| JP | 2017518361 | A | 7/2017 |
| WO | 99/47178 | A1 | 9/1999 |
| WO | 1999/060128 | A1 | 11/1999 |
| WO | 2005/086751 | A2 | 9/2005 |
| WO | 2008156712 | A1 | 12/2008 |
| WO | 2012/088446 | A1 | 6/2012 |
| WO | 2012119093 | A1 | 9/2012 |
| WO | 2013/177187 | A2 | 11/2013 |
| WO | 2014/153111 | A2 | 9/2014 |
| WO | 2014/201378 | A1 | 12/2014 |
| WO | 2015164815 | A1 | 10/2015 |
| WO | 2016/014428 | A1 | 1/2016 |
| WO | 2016/014428 | A2 | 1/2016 |
| WO | 2016/025385 | A1 | 2/2016 |
| WO | 2017/068031 | A1 | 4/2017 |
| WO | 2017/093410 | A1 | 6/2017 |
| WO | 2017/220989 | A1 | 12/2017 |
| WO | 2018119114 | A1 | 6/2018 |
| WO | 2018234862 | A1 | 12/2018 |
| WO | 2019028419 | A1 | 2/2019 |
| WO | 2019/104092 | A1 | 5/2019 |
| WO | 2019/177986 | A1 | 9/2019 |
| WO | 2019222295 | A1 | 11/2019 |
| WO | 2019246404 | A1 | 12/2019 |
| WO | 2020/069398 | A1 | 4/2020 |
| WO | 2021/146485 | A2 | 7/2020 |
| WO | 2021/146481 | A1 | 7/2021 |
| WO | 2021/146485 | A1 | 7/2021 |

OTHER PUBLICATIONS

Baluna et al., "Evidence for a Structural Motif in Toxins and Interleukin-2 That May Be Responsible for Binding to Endothelial Cells and Initiating Vascular Leak Syndrome", Proceedings of the National Academy of Sciences, vol. 96, No. 7, Mar. 30, 1999, pp. 3957-3962.

Conlon et al., "Cytokines in the Treatment of Cancer", Journal of Interferon & Cytokine Research, vol. 39, No. 1, Jan. 2019, pp. 1-16.

Meghnem et al., "Cutting Edge: Differential Fine-Tuning of IL-2- and IL-15-Dependent Functions by Targeting Their Common IL-2/15Rβ/γc Receptor", The Journal of Immunology, vol. 198, No. 12, Jun. 2017, pp. 4563-4568.

Mizui , "Natural and Modified IL-2 for the Treatment of Cancer and Autoimmune Diseases", Clinical Immunology, vol. 206, Sep. 2019, pp. 63-70.

(56) References Cited

OTHER PUBLICATIONS

Perez Horta et al., "Human and Murine IL2 Receptors Differentially Respond to the Human-IL2 Component of Immunocytokines", OncoImmunology, vol. 8, No. 6, e1238538, 2019, 15 pages.
Pol et al., "Effects of Interleukin-2 in Immunostimulation and Immunosuppression", Journal of Experimental Medicine, vol. 217, No. 1, 2020, pp. 1-15.
Bazan, et al (1992) Unraveling the Structure of IL-2 Science 257:410-413.
Berndt, et al (1994) Biochemistry 33:6571-76.
Imler et al. Identification of three adjacent amino acids of interleukin-2 receptor beta chain which control the affinity and the specificity of the interaction with interleukin-2. The EMBO journal. Jun. 1992;11(6):2047-53.
Jones, E. (2019) Designer protein delivers signal of choice; Nature 565:165-166.
Kagoya et al. A novel chimeric antigen receptor containing a JAK-STAT signaling domain mediates superior antitumor effects. Nature medicine. Mar. 2018;24(3):352.
Kallal et al. Changing partners at the dance: variations in STAT concentrations for shaping cytokine function and immune responses to viral infections. Jak-Stat. Jan. 1, 2013;2(1):e23504.
Klingmüller et al. Multiple tyrosine residues in the cytosolic domain of the erythropoietin receptor promote activation of STAT5. Proceedings of the National Academy of Sciences. Aug. 6, 1996;93(16):8324-8.
Leon, et al (2013) Mathematical models of the impact of IL2 modulation therapies on T cell dynamics Frontiers in *Immunology* published: Dec. 11, 2013 doi: 10.3389/fimmu.2013.00439.
Leon, et al Combining computational and experimental biology to develop therapeutically valuable IL2 muteins (2018) *Seminars in Oncology* 45 (2018) 95-104.
Levin, et al (2012) Exploiting a natural conformational switch to engineer an Interleukin-2 superkine; *Nature*. ; 484(7395): 529-533.
Mackall. Engineering a designer immunotherapy. Science. Mar. 2, 2018;359(6379):990-1.
Malek et al., (2010) Interleukin-2 Receptor Signaling: At the Interface between Tolerance and Immunity Immunity 33:153-165.
Mitra et al. Interleukin-2 activity can be fine tuned with engineered receptor signaling clamps. Immunity. May 19, 2015;42(5):826-38.
Naeger et al. Identification of a STAT4 binding site in the interleukin-12 receptor required for signaling. Journal of Biological Chemistry. Jan. 22, 1999;274(4):1875-8.
Peterson, et al (2018) A long-lived IL-2 mutein that selectively activates and expands regulatory T cells as a therapy for autoimmune disease; Journal of Autoimmunity 95:1-14.
Rao, et al (2005) Biochemistry 44:10696-10701.
Rao, et al (2004) Molecular Pharmacology 66:864-869.
Rao, et al (2003) Protein Engineering 16(12):1081-1087.
Ring, et al (2012) Mechanistic and structural insight into the functional dichotomy between interleukin-2 and interleukin-15; *Nature Immunol*.13(12): 1187-1195.
Rojas, et al. (2018) Directed evolution of super-secreted variants from phage-displayed human Interleukin-2; Scientific Reports 9:800; | DOI:10.1038/s41598-018-37280-5.
Rozwarski, et al (1994) Structural Comparisons Among the Short Chain Helical Cytokines; Strucutre 2(3); 159-173.
Schmitz et al. The cytoplasmic tyrosine motifs in full-length glycoprotein 130 have different roles in IL-6 signal transduction. The Journal of Immunology. Jan. 15, 2000;164(2):848-54.
Sim, et al (2016) IL2 Variant Circumvents ICOSb Regulatory T-cell Expansion and Promotes NK Cell Activation; Cancer Immunol Res; 4(11):983-994.
Smith (1993) Lowest Dose Interleukin-2 Immunotherapy *Blood*, vol. 81, pp. 1414-1423.
Sockolosky et al. Selective targeting of engineered T cells using orthogonal IL-2 cytokine-receptor complexes. Science. Mar. 2, 2018;359(6379):1037-42.
Waldmann the multi-subunit interleukin-2 receptor. Annual review of biochemistry. Jul. 1989;58(1):875-905.
Wang, et al (1997) 126Gln is the residue of human IL-2 binding to IL-2R γ subunit*; Science in China Series C: Life Sciences 40(2):159-168.
Wang, et al (2005) Science 310:1159-1163.
Ward et al. IL-2/CD25: a long-acting fusion protein that promotes immune tolerance by selectively targeting the IL-2 receptor on regulatory T cells. The Journal of Immunology. Nov. 1, 2018;201(9):2579-92.
Yang et al., (2000) Molecular modeling on some human interleukins sharing γc of interleukin-2 receptor, and structure-function relationships Journal of Molecular Structure: Theochem; 532:1-10.
Zurawski, et al. (1988) EMBO J. 7(4):1061-1069.
Zurawski, et al. (1990) EMBO J. 9(12):3899-3905.
Zurawski, et al. (1993) EMBO J. 12(13):5113-5119.
Rosalia, et al 2014) Use of enhanced interleukin-2 formulations for improved immunotherapy against cancer DOI: https://doi.org/10.1016/j.cbpa.2014.09.006.
Ju, et al (1987) Structure-Function Analysisof Human Interleukin-2 Journal of Biological Chemistry 262(12)5723-5731.
Tsytsikov, et al (1996) Identification and Characterization of Two Alternative Splice Variants of Human Interleukin-2; Journal of Biological Chemistry 271(38):23055-23060.
Fiers, et al (1983) Molecular cloning of human interieukin 2 cDNA and its expression in *E. coli*; Nucleic Acids Research 11(13):4307-4323.
Silva, et al (2019De novo design of potent and selective mimics of IL-2 and IL-15 Nature 565:186-191.
Liu, et al (2009) Engineered Interleukin-2 Antagonists for the Inhibition of Regulatory T cells *J Immunother*. Author manuscript; available in PMC Jul. 2, 2014. *J Immunother*. 2009 ; 32(9): 887-894.
Bukowski, R. (1997) Natural History and Therapy of Metastatic Renal Cell Carcinoma—The Role of Interleukin-2; Cancer 80(7):1198-1220.
Vlasveld et al., (1994) Recombinant interleukin-2 in cancer: basic and clinical aspects ; Cancer Treatment Review 20(3):275-311.
Smith, K. (2006) The structure of IL2 bound to the three chains of the IL2 receptor and how signaling occurs; *Medical Immunology* 2006, 5:3.
Carmenate, et al (2013) Human IL-2 Mutein with Higher Antitumor Efficacy Than Wild Type IL-2 *J Immunol* 2013; 190:6230-6238; Prepublished online May 15, 2013.
Collins, et al (1988) Identification of specific residues of human interleukin 2 that affect binding to the 70-kDa subunit (p70) of the interleukin 2 receptor Proc. Nati. Acad. Sci. USA 85:7709-7713.
Kim, et al (2001) The Basis for IL-2-Induced IL-2 Receptor □ Chain Gene Regulation: Importance of Two Widely Separated IL-2 Response Elements Immunity 15:159-17.
Stauber, et al (2006) Crystal structure of the IL-2 signaling complex: Paradigm for a heterotrimeric cytokine receptor PNAS 103(8): 2788-2793.
Kreig, et al (2010) Improved IL-2 immunotherapy by selective stimulation of IL-2 receptors on lymphocytes and endothelial cells; PNAS 107(26):11906-11911.
Meyers, et al (1991) A phase I study including pharmacokinetics of polyethylene glycol conjugated interleukin-2; Clinical Pharmacology & Therapeutics 49(3):307-13.
Katre, et al (1990) Immunogenicity of recombinant IL-2 modified by covalent attachment of polyethylene glycol; The Journal of Immunology 144(1):209-13.
Jevsevar, et al (2010) PEGylation of therapeutic proteins; Biotechnol. J. 5: 113-128.
Goodson, et al., (1990). Site-Directed Pegylation of Recombinant Interleukin-2 at its Glycosylation Site; Biotechnology 8:343-346.
Wang, et al (1995) Two Partial Antagonists of Human Interleukin2; Chinese Science Abstracts Series B > 1995 > 14 > 6 Part B > 4748.
Gillies, et al. (2011) A Low-Toxicity IL-2-Based Immunocytokine Retains Antitumor Activity Despite Its High Degree of IL-2 Receptor Selectivity; Clinical Cancer Research 17(11): 3673-3685.
Office Action in U.S. Appl. No. 17/320,174, mailed Sep. 30, 2021, 32 pages.
International Preliminary Report on Patentability issued in Internationa Application No. PCT/US2014/042341, dated Dec. 15, 2015, 10 pages.

(56) References Cited

OTHER PUBLICATIONS

Argos P. A possible homology between immunodeficiency virus p24 core protein and picornaviral VP2 coat protein: prediction of HIV p24 antigenic sites. The EMBO journal. Mar. 1989;8(3):779-85.
Altschul, et al. Basic local alignment search tool. Journal of molecular biology. Oct. 5, 1990;215(3):403-10.
Baldari et al. A novel leader peptide which allows efficient secretion of a fragment of human interleukin 1 beta in *Saccharomyces cerevisiae*. The EMBO Journal. Jan. 1987;6(1):229-34.
Baldassari et al. Daclizumab: development, clinical trials, and practical aspects of use in multiple sclerosis. Neurotherapeutics. Oct. 2017;14(4):842-58.
Bergmann CA. The amphipathicity of interleukin-2 (Doctoral dissertation, Case Western Reserve University (Health Sciences)).
Bielekova et al. Humanized anti-CD25 (daclizumab) inhibits disease activity in multiple sclerosis patients failing to respond to interferon β. Proceedings of the National Academy of Sciences. Jun. 8, 2004;101(23):8705-8.
Blanar et al. Interaction cloning: identification of a helix-loop-helix zipper protein that interacts with c-Fos. Science. May 15, 1992;256(5059):1014-8.
Boder et al. Yeast surface display for screening combinatorial polypeptide libraries. Nature biotechnology. Jun. 1997;15(6):553-7.
Boozarpour et al. Bacterial overexpression of the human interleukin-2 in insoluble form via the pET Trx fusion system. Iranian Journal of Biotechnology. Oct. 1, 2010;8(4):270-4.
Busse et al, Daclizumab Asthma Study Group. Daclizumab improves asthma control in patients with moderate to severe persistent asthma: a randomized, controlled trial. American journal of respiratory and critical care medicine. Nov. 15, 2008;178(10):1002-8.
Buter J. Clinical studies with biological response modifiers in the treatment of solid tumors. [University Library Groningen][Host]; 1994.
Carneiro et al. When three is not a crowd: a crossregulation model of the dynamics and repertoire selection of regulatory CD4+ T cells. Immunological reviews. Apr. 2007:216(1):48-68.
Cassell et al. Therapeutic enhancement of IL-2 through molecular design. Current pharmaceutical design. Nov. 1, 2002;8(24):2171-83.
Cate et al. Isolation of the bovine and human genes for Müllerian inhibiting substance and expression of the human gene in animal cells. Cell. Jun. 6, 1986;45(5):685-98.
Chang et al. Structural analogs of interleukin-2: a point mutation that facilitates biological response. Molecular pharmacology. Jan. 1, 1995;47(1):206-11.
Chang-Cheng, "Searching for Peptide Ligands of Interleukin-2 Receptor a Chain in Phage-Displayed Peptide Library," Chemical Research in Chinese Universities, 14(4):430-432.
Charych et al. NKTR-214, an engineered cytokine with biased IL2 receptor binding, increased tumor exposure, and marked efficacy in mouse tumor models. Clinical Cancer Research. Feb. 1, 2016;22(3):680-90.
Chen et al. A novel human IL-2 mutein with minimal systemic toxicity exerts greater antitumor efficacy than wild-type IL-2. Cell death & disease. Sep. 24, 2018;9(10):1-2.
Database Genbank (Jul. 28, 2020) "Cytokine Receptor Subunit Gamma Isoform a Precursor [Mus Musculus]" Genbank Accession No. NP_038591.1, 3 pages.
Database Genbank (Jul. 25, 2020) "Cytokine Receptor Common Subunit Gamma Precursor [*Homo sapiens*]" Genbank Accession No. NP_000197.1, 3 pages.
Database Genbank (Jul. 24, 2020) "*Homo sapiens* Interleukin 2 Receptor Subunit Alpha (IL2RA) Transcript Variant 1, Mma" Genbank Accession No. NM_000417.3, 5 pages.
Database Genbank (Jul. 23, 2020) "*Homo sapiens* Interleukin 2 Receptor Subunit Beta (IL2RB) Transcript Variant 1, Mma" Genbank Accession No. NM_000878.5, 5 pages.
Database Genbank (Jul. 25, 2020) "*Homo sapiens* Interleukin 2 Receptor Subunit Gamma (IL2RG) Mma" Genbank Accession No. NM_000206.3, 5 pages.
Database Genbank (Jul. 11, 2020) "Interleukin-2 Precursor [*Homo sapiens*]" Genbank Accession No. NP_000577.2, 3 pages.
Database Genbank (Jul. 24, 2020) "Interleukin-2 Receptor Subunit Alpha Isoform 1 Precursor [*Homo sapiens*] " Genbank Accession No. NP_000408.1, 3 pages.
Database Genbank (Jul. 23, 2020) "Interleukin-2 Receptor Subunit Beta Precursor Precursor [*Homo sapiens*] " Genbank Accession No. NP_000869.1, 4 pages.
Database Genbank (Jul. 28, 2020) "Mus Musculus Interleukin 2 Receptor, Gamma Chain (Il2rg), Transcript Variant A, Mrna" Genbank Accession No. NP_013563.4, 4 pages.
Devereux et al. A comprehensive set of sequence analysis programs for the VAX. Nucleic acids research. Jan. 11, 1984;12(1Part1):387-95.
Dhupkar, Pooja. "Targeting PD-1/PDL-1 Signaling in the Treatment of Osteosarcoma Lung Metastasis." (Dec. 2016), UT GSBS Dissertations and Theses,208 pages.
Diab et al. Bempegaldesleukin (NKTR-214) plus nivolumab in patients with advanced solid tumors: phase I dose-escalation study of safety, efficacy, and immune activation (PIVOT-02). Cancer discovery. Aug. 1, 2020;10(8):1158-73.
Drescher et al. Surface plasmon resonance (SPR) analysis of binding interactions of proteins in inner-ear sensory epithelia. InAuditory and Vestibular Research 2009 (pp. 323-343). Humana Press.
Epstein et al. Identification of a protein fragment of interleukin 2 responsible for vasopermeability. Journal of the National Cancer Institute. May 21, 2003;95(10):741-9.
Frick et al. Interleukin-2 functionalized nanocapsules for T cell-based immunotherapy. Acs Nano. Oct. 25, 2016;10(10):9216-26.
Fujita et al. Structure of the human interleukin 2 gene. Proceedings of the National Academy of Sciences. Dec. 1, 1983;80(24):7437-41.
Fukushima et al., "Carbohydrate recognition mechanism of interleukin 2 and its physiological significance," The Journal of Biological Chemistry, 276(33):31202-31208.
Fukushima et al. Carbohydrate recognition site of interleukin-2 in relation to cell proliferation. Journal of Biological Chemistry. Aug. 1, 2001;276(33):31202-8.
Gai S. Engineering persistent interleukin-2 for cancer immunotherapy (Doctoral dissertation, Massachusetts Institute of Technology), 2012, 113 pages.
Garber K. Cytokine resurrection: engineered IL-2 ramps up immuno-oncology responses. Nature biotechnology. May 1, 2018;36(5):378-80.
Hollander, "On the stochastic regulation of interleukin-2 transcription," Seminars in Immunology, 11(5), 2 pages.
Gold et al. Daclizumab high-yield process in relapsing-remitting multiple sclerosis (Select): a randomised, double-blind, placebo-controlled trial. The Lancet. Jun. 22, 2013;381(9884):2167-75.
Hershberger et al. Daclizumab to prevent rejection after cardiac transplantation. New England Journal of Medicine. Jun. 30, 2005;352(26):2705-13.
Jacques et al. "The renewal of interleukin 2," Medical Sciences Paris, 32(6-7):612-618, 9 pages.
Jiang et al. Interleukin-2: structural and biological relatedness to opioid peptides. Neuroimmunomodulation. 2000;8(1):20-4.
Kaartinen et al. Low interleukin-2 concentration favors generation of early memory T cells over effector phenotypes during chimeric antigen receptor T-cell expansion. Cytotherapy. Jun. 1, 2017;19(6):689-702.
Kalsoom, "Computer-Guided Design and Synthesis of IL-2 Inhibitors as Immunomodulating Agents," Departmentr of Chemistry, 181 pages.
Kaufman et al. Construction of a modular dihydrofolate reductase cDNA gene: analysis of signals utilized for efficient expression. Molecular and cellular biology. Nov. 1982;2(11):1304-19.
Kaufman et al. Translational efficiency of polycistronic mRNAs and their utilization to express heterologous genes in mammalian cells. The EMBO journal. Jan. 1987;6(1):187-93.
Krinks et al. KY1043, a novel PD-L1 IL-2 immunocytokine directed towards CD25, delivers potent anti-tumour activity in vitro and in vivo, Kymab P625, 1 page.

(56) References Cited

OTHER PUBLICATIONS

Kurjan et al. Structure of a yeast pheromone gene (MFα): a putative α-factor precursor contains four tandem copies of mature α-factor. Cell. Oct. 1, 1982;30(3):933-43.
Langowski et al. Abstract, Cancer Immunology Research, 2016, vol. 4, No. 11, Abstract No. B057, 2016.
Langowski et al. NKTR-358: a selective, first-in-class IL-2 pathway agonist which increases number and suppressive function of regulatory T cells for the treatment of immune inflammatory disorders. Arthritis Rheumatol. Oct. 1, 2017;69(suppl 10).
Leclair et al. The p50 subunit of NF-kappa B associates with the NF-IL6 transcription factor. Proceedings of the National Academy of Sciences. Sep. 1, 1992;89(17):8145-9.
Lee et al. Proliferin secreted by cultured cells binds to mannose 6-phosphate receptors. Journal of Biological Chemistry. Mar. 5, 1988;263(7):3521-7.
Liang et al., Characterization of human interleukin 2 derived from *Escherichia coli*. Biochemical Journal. Jul. 15, 1985;229(2):429-39.
Lipiäinen et al. Formulation and stability of cytokine therapeutics. Journal of pharmaceutical sciences. Feb. 1, 2015;104(2):307-26.
Liu et al. Dual targeting of innate and adaptive checkpoints on tumor cells limits immune evasion. Cell reports. Aug. 21, 2018;24(8):2101-11.
Liu et al., "Engineered Interleukin-2 Antagonists for the Inhibition of Regulatory T Cells," Journal of Immunotherapy, 32(9):887-894.
Luckow et al. High level expression of nonfused foreign genes with Autographa californica nuclear polyhedrosis virus expression vectors. Virology. May 1, 1989;170(1):31-9.
Mao et al. Study of the molecular mechanism of interleukin-2 mutein D10 binding to IL-2 receptors by molecular simulations. Molecular Simulation. Aug. 13, 2018;44(12):973-80.
Marston F. The purification of eukaryotic polypeptides synthesized in *Escherichia coli*. Biochemical Journal. Nov. 15, 1986;240(1):1-2.
Mccaffrey et al. RNA interference in adult mice. Nature. Jul. 2002;418(6893):38-9.
Morris et al. Preclinical and phase I clinical trial of blockade of IL-15 using Mikβ1 monoclonal antibody in T cell large granular lymphocyte leukemia. Proceedings of the National Academy of Sciences. Jan. 10, 2006;103(2):401-6.
Naing et al, editors. Immunotherapy. Springer International Publishing; Mar. 20, 2017, 183 pages.
Parisi et al. Persistence of adoptively transferred T cells with a kinetically engineered IL-2 receptor agonist. Nature communications. Jan. 31, 2020;11(1):1-2.
Pérol et al. New molecular and cellular mechanisms of tolerance: tolerogenic actions of IL-2. Suppression and Regulation of Immune Responses. 2016:11-28.
Plieth et al., "Cytokines emerge as 2018's immuno-oncology stars," Evaluate, 1-7, Mar. 2018.
Putnam. Antisense strategies and therapeutic applications. American Journal of Health System Pharmacy. Jan. 15, 1996;53(2):151-60.
Rao BM. Interleukin-2 Engineering for improved therapeutic effectiveness (Doctoral dissertation, Massachusetts Institute of Technology).
Rao, et al. "Interleukin-2 mutants with enhanced α-receptor subunit binding affinity." Protein engineering 16, No. 12 (2003): 1081-1087.
Ren et al. Structural and functional characterisation of ferret interleukin-2. Developmental & Comparative Immunology. Feb. 1, 2016;55:32-8.
Rodríguez-Silva et al. Scale-up purification of a mutant of recombinant human Interleukin 2 by reverse-phase high performance liquid chromatography. Biotecnología Aplicada. 2001;18(3):159-62.
Rosenberg et al. Vectors for selective expression of cloned DNAs by T7 RNA polymerase. Gene. Jan. 1, 1987;56(1):125-35.
Sambrook et al. Molecular cloning: a laboratory manual. Cold spring harbor laboratory press; $4^{th}$ edition, 1989, 34 pages.
Scheller et al. Immunoreceptor engineering and synthetic cytokine signaling for therapeutics. Trends in immunology. Mar. 1, 2019;40(3):258-72.
Schultz et al. Expression and secretion in yeast of a 400-kDa envelope glycoprotein derived from Epstein-Barr virus. Gene. Jan. 1, 1987;54(1):113-23.
Seed B. An LFA-3 cDNA encodes a phospholipid-linked membrane protein homologous to its receptor CD2. Nature. Oct. 1987;329(6142):840-2.
Smith et al. Production of human beta interferon in insect cells infected with a baculovirus expression vector. Molecular and cellular biology. Dec. 1983;3(12):2156-65.
Spangler, et al., 2015. Antibodies to interleukin-2 elicit selective T cell subset potentiation through distinct conformational mechanisms. Immunity, 42(5), pp. 815-825.
Spangler, et al., 2018. Engineering a single-agent cytokine/antibody fusion that selectively expands regulatory T cells for autoimmune disease therapy. The Journal of Immunology, 201(7), pp. 2094-2106.
Tchao, et al. "Amg 592 is an investigational IL-2 mutein that induces highly selective expansion of regulatory T cells." (2017): 696-696.
Thanos, et al. "Potent small-molecule binding to a dynamic hot spot on IL-2." Journal of the American Chemical Society 125, No. 50 (2003): 15280-15281.
Tilley, et al. "Identification of a small molecule inhibitor of the IL-2/IL-2Rα receptor interaction which binds to IL-2." Journal of the American Chemical Society 119, No. 32 (1997): 7589-7590.
Tkaczuk, et al. "Effect of Anti-IL-2Rα Antibody on IL-2-induced Jak/STAT Signaling." American Journal of Transplantation 2, No. 1 (2002): 31-40.
Trotta et al. "A human anti-IL-2 antibody that potentiates regulatory T cells by a structure-based mechanism." Nature medicine 24, No. 7 (2018): 1005-1014.
Vincenti, et al. "Interleukin-2-receptor blockade with daclizumab to prevent acute rejection in renal transplantation." New England Journal of Medicine 338, No. 3 (1998): 161-165.
Wada, et al. "Codon usage tabulated from the GenBank genetic sequence data." Nucleic acids research 20, No. Suppl (1992): 2111.
Waldmann, et al. "Phase 1 trial of IL-15 trans presentation blockade using humanized Mik-Beta-1 mAb in patients with T-cell large granular lymphocytic leukemia." Blood, The Journal of the American Society of Hematology 121, No. 3 (2013): 476-484.
Wang, Wei, Y. John Wang, and D. Q. Wang. "Dual effects of Tween 80 on protein stability." International journal of pharmaceutics 347, No. 1-2 (2008): 31-38.
Wang, Alice, Shi-Da Lu, and David F. Mark. "Site-specific mutagenesis of the human interleukin-2 gene: structure-function analysis of the cysteine residues." Science 224, No. 4656 (1984): 1431-1433.
Wang, Xinquan, Mathias Rickert, and K. Christopher Garcia. "Structure of the Quaternary Complex of Interleukin-2 with Its α, β, and γc Receptors." Science 310, No. 5751 (2005): 1159-1163.
Wittrup, K. Dane. "Antitumor antibodies can drive therapeutic T cell responses." Trends in cancer 3, No. 9 (2017): 615-620.
Wrangle, John M., Alicia Patterson, C. Bryce Johnson, Daniel J. Neitzke, Shikhar Mehrotra, Chadrick E. Denlinger, Chrystal M. Paulos, Zihai Li, David J. Cole, and Mark P. Rubinstein. "IL-2 and beyond in cancer immunotherapy." Journal of Interferon & Cytokine Research 38, No. 2 (2018): 45-68.
Xia, Haibin, Qinwen Mao, Henry L. Paulson, and Beverly L. Davidson. "siRNA-mediated gene silencing in vitro and in vivo." Nature biotechnology 20, No. 10 (2002): 1006-1010.
Zalipsky, Samuel. "Functionalized poly (ethylene glycols) for preparation of biologically relevant conjugates." Bioconjugate chemistry 6, No. 2 (1995): 150-165.
Zorn, E., Nelson, E.A., Mohseni, M., Porcheray, F., Kim, H., Litsa, D., Bellucci, R., Raderschall, E., Canning, C., Soiffer, R.J. and Frank, D.A., 2006. IL-2 regulates FOXP3 expression in human CD4+ CD25+ regulatory T cells through a STAT-dependent mechanism and induces the expansion of these cells in vivo. Blood, 108(5), pp. 1571-1579.

(56) References Cited

OTHER PUBLICATIONS

Zurawski SM, Zurawski G. Identification of three critical regions within mouse interleukin 2 by fine structural deletion analysis. The EMBO journal. Apr. 1988;7(4):1061-9.
Zurawski SM, Zurawski G. Receptor antagonist and selective agonist derivatives of mouse interleukin-2. The EMBO journal. Nov. 1992;11(11):3905-10.
International Search Report and Written Opinion in PCT/US2021/013456, mailed Jul. 22, 2021, 15 pages.
Kaplan et al., "Demonstration of an interferon γ-dependent tumor surveillance system in immunocompetent mice," Proc. Natl. Acad. Sci. USA, vol. 95, Jun. 1998, pp. 7556-7561.
Bluestone, et al. (2015) IL2: Change Structure . . . Change Function Immunity 42:779-781.
Bradhuber, et al. (1987) J. Biol Chem 25(2):12306-12308.
Carnemolla, et al (2002) Enhancement of the antitumor properties of interleukin-2 by its targeted delivery to the tumor blood vessel extracellular matrix ; Blood 99(5) :1659-1665.
Gaffen et al. Distinct tyrosine residues within the interleukin-2 receptor β chain drive signal transduction specificity, redundancy, and diversity. Journal of Biological Chemistry. Aug. 30, 1996;271(35):21381-90.
Gerhartz et al. Differential activation of acute phase response factor/STAT3 and STAT1 via the cytoplasmic domain of the interleukin 6 signal transducer gp130: I. Definition of a novel phosphotyrosine motif mediating STAT1 activation. Journal of Biological Chemistry. May 31, 1996:271(22):12991-8.
Ghasemi, et al (2016) Selective targeting of IL-2 to NKG2D bearing cells for improved immunotherapy; Nature Communications 7:12878 | DOI: 10.1038/ncomms12878 |.
Hargadon, et al. "Immune checkpoint blockade therapy for cancer: an overview of FDA-approved immune checkpoint inhibitors." International immunopharmacology 62 (2018): 29-39.
He, et al (2016) Low-dose interleukin-2 treatment selectively modulates CD4+ T cell subsets in patients with systemic lupus erythematosus Nature Medicine 22(9):991-993.

* cited by examiner

| 128 | 64 | 32 | 16 | 8 | 4 | 2 | Dilution Factor |
|---|---|---|---|---|---|---|---|
| 1.2 | 1.0 | 6.0 | 6.0 | 6.0 | 0.7 | 0.7 | Human IL2 wt |
| 3.9 | 2.4 | 1.6 | 1.3 | 1.0 | 0.9 | 0.8 | Human IL2 REH |
| 3.4 | 2.0 | 1.5 | 1.2 | 1.0 | 0.9 | 0.8 | YEH |
| 11.8 | 8.3 | 5.6 | 3.1 | 1.8 | 1.2 | 1.0 | HEH |
| 11.9 | 7.9 | 5.1 | 2.6 | 1.8 | 1.1 | 0.9 | NEH |
| 9.9 | 10.6 | 8.2 | 7.5 | 4.2 | 2.0 | 0.9 | DEH |
| 5.2 | 3.3 | 1.9 | 1.3 | 6.0 | 0.6 | 0.5 | TEH |
| 6.9 | 5.5 | 3.4 | 2.1 | 1.1 | 0.8 | 0.6 | RGH |
| 3.7 | 2.3 | 1.4 | 1.2 | 0.8 | 0.7 | 0.6 | RAH |
| 6.7 | 4.9 | 3.3 | 2.5 | 1.5 | 1.1 | 0.8 | RLH |
| 5.1 | 3.9 | 2.3 | 1.4 | 1.1 | 0.8 | 0.6 | RMH |
| 10.6 | 7.4 | 4.3 | 2.5 | 1.3 | 0.8 | 0.7 | RFH |
| 9.1 | 5.0 | 3.0 | 2.0 | 1.2 | 0.8 | 0.8 | RWH |
| 11.0 | 8.1 | 5.5 | 3.0 | 1.8 | 11 | 1.0 | RKH |
| 6.8 | 5.0 | 2.8 | 1.8 | 1.1 | 0.9 | 1.0 | RSH |
| 8.0 | 5.3 | 3.3 | 1.9 | 1.4 | 0.9 | 0.9 | RVH |
| 11.5 | 8.4 | 6.0 | 3.8 | 2.4 | 1.5 | 1.1 | RIH |
| 10.5 | 11.8 | 8.7 | 5.5 | 3.4 | 2.2 | 0.9 | RYH |
| 16.0 | 10.6 | 6.3 | 3.9 | 2.7 | 2.0 | 2.0 | RHH |
| 19.0 | 14.6 | 10.3 | 6.5 | 3.8 | 2.8 | 2.3 | RRH |
| 13.0 | 7.7 | 5.2 | 3.6 | 2.6 | 2.0 | 2.1 | RNH |
| 7.0 | 4.4 | 2.9 | 2.2 | 2.1 | 1.8 | 1.7 | RDH |
| 14.3 | 9.1 | 5.4 | 3.6 | 2.6 | 1.9 | 2.3 | RTH |

| 128 | 64 | 32 | 16 | 8 | 4 | 2 | Dilution Factor |
|---|---|---|---|---|---|---|---|
| 1.1 | 1.1 | 0.9 | 0.9 | 1.0 | 0.9 | 0.8 | Human IL2 wt |
| 4.7 | 2.9 | 1.8 | 1.3 | 1.1 | 1.0 | 0.9 | Human IL2 REH |
| 2.7 | 1.4 | 1.1 | 1.0 | 1.0 | 0.9 | 0.8 | huIL2 L18R (R--) |
| 2.0 | 1.3 | 1.0 | 1.0 | 0.9 | 0.9 | 0.8 | huIL2 Q22E (-E-) |
| 2.0 | 1.2 | 1.1 | 1.0 | 0.9 | 0.9 | 0.8 | huIL2 Q126H (--H) |
| 2.8 | 1.4 | 1.1 | 1.0 | 0.9 | 1.0 | 0.8 | huIL2 (RE-) |
| 5.5 | 2.7 | 1.8 | 1.4 | 1.2 | 1.1 | 0.9 | huIL2 (R-H) |
| 3.4 | 2.3 | 1.6 | 1.3 | 1.3 | 1.1 | 0.8 | huIL2 (-EH) |
| 10.7 | 6.7 | 4.2 | 2.3 | 1.5 | 1.2 | 1.0 | huIL2 V91K |
| 16.8 | 15.3 | 13.5 | 10.1 | 5.9 | 2.9 | 1.4 | huIL2 REE |
| 13.1 | 11.8 | 7.7 | 4.8 | 2.6 | 1.6 | 1.1 | huIL2 REK |
| 18.8 | 17.5 | 16.2 | 13.2 | 7.2 | 3.5 | 1.5 | GEH |
| 17.9 | 16.6 | 14.1 | 9.7 | 5.7 | 2.6 | 1.3 | AEH |
| 4.5 | 2.7 | 1.8 | 1.4 | 1.2 | 1.2 | 0.9 | MEH |
| 4.7 | 2.9 | 1.7 | 1.4 | 1.3 | 1.2 | 0.9 | FEH |
| 10.0 | 6.4 | 3.9 | 2.2 | 1.5 | 1.4 | 1.1 | WEH |
| 4.0 | 2.3 | 1.6 | 1.4 | 1.1 | 1.0 | 1.1 | KEH |
| 11.7 | 8.3 | 5.8 | 3.1 | 1.8 | 1.3 | 1.1 | QEH |
| 17.0 | 16.9 | 14.7 | 8.4 | 4.8 | 2.3 | 1.4 | EEH |
| 15.1 | 11.4 | 7.8 | 4.0 | 2.5 | 1.5 | 1.2 | SEH |
| 14.8 | 10.9 | 6.3 | 3.6 | 2.4 | 1.6 | 1.2 | VEH |
| 10.9 | 7.2 | 4.6 | 2.6 | 1.6 | 1.4 | 1.2 | IEH |

FIG. 3

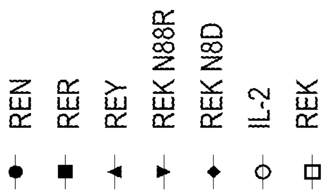
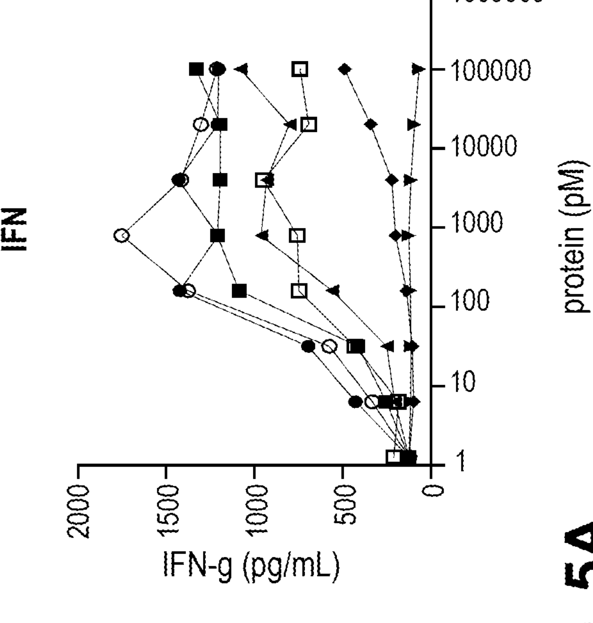
FIG. 5A
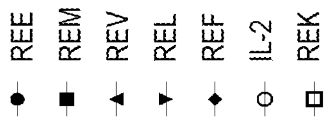
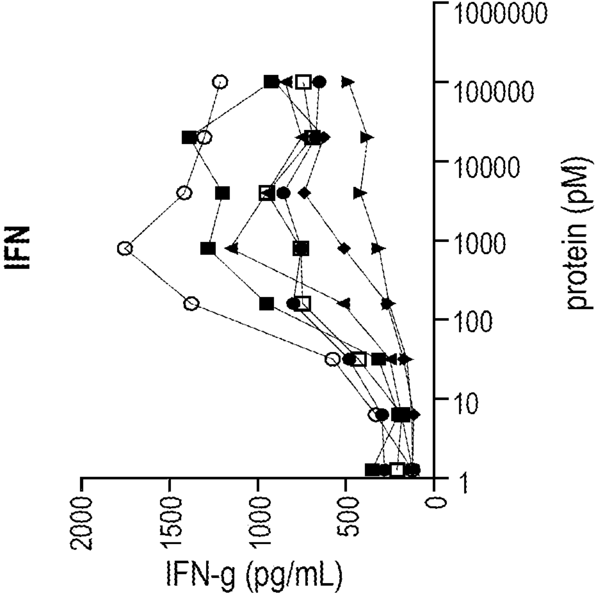

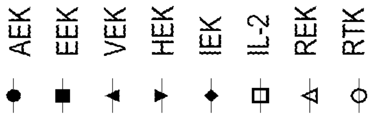
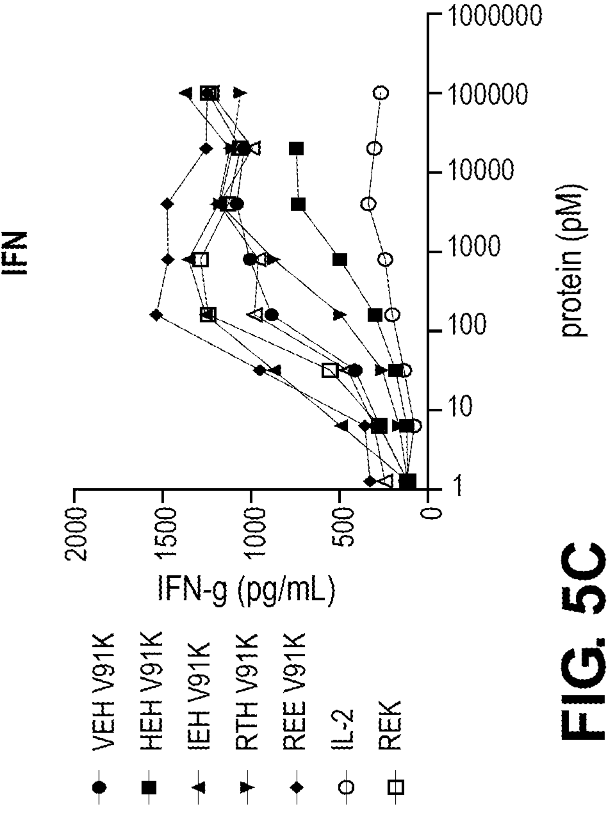
FIG. 5C
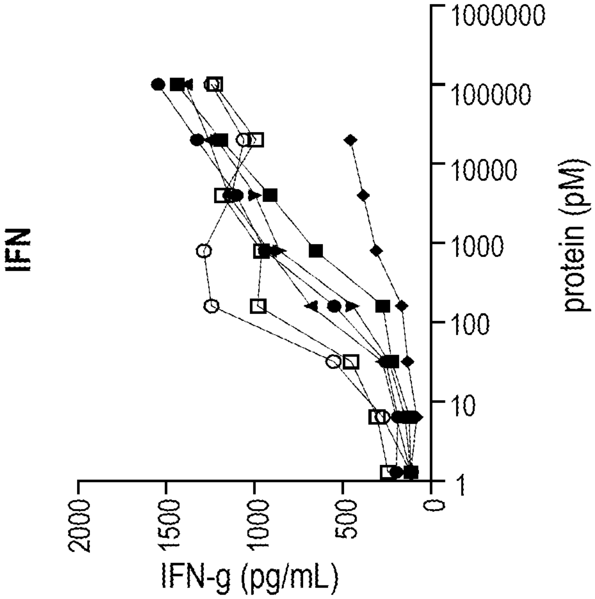

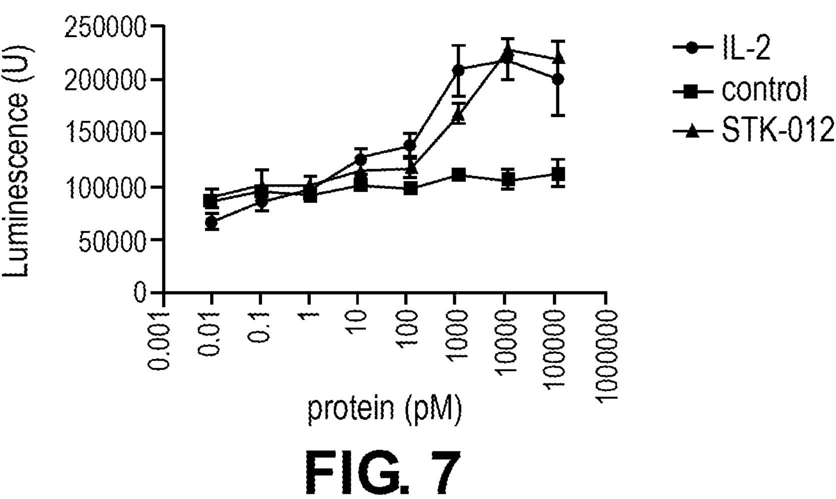
FIG. 7
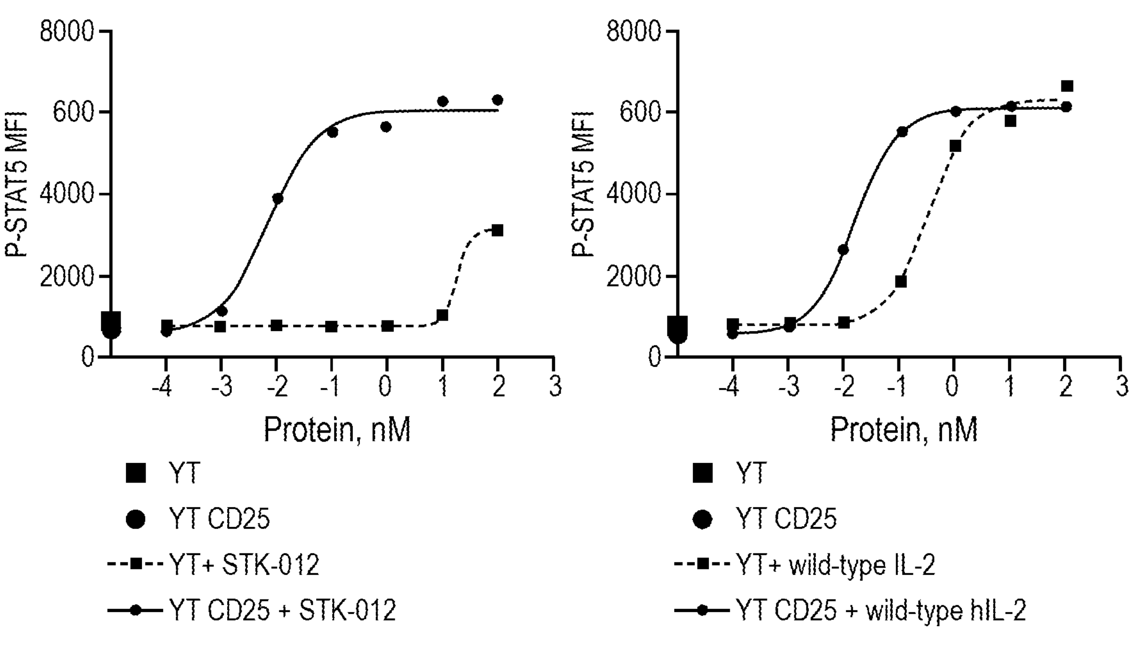
FIG. 8A
FIG. 8B

BIASED IL2 MUTEINS METHODS AND COMPOSITIONS

RELATED APPLICATIONS

The present application is a Continuation Application of U.S. Application Ser. No. 17/149,405, filing date Jan. 14, 2021 which claims the priority of U.S. Provisional Patent Application Ser. No. 62/961,141, filed Jan. 14, 2020, and U.S. Provisional Patent Application Ser. No. 63/136,599, filed Jan. 12, 2021, each of which are incorporated by reference for all purposes.

STATEMENT REGARDING GOVERNMENT FUNDING

No United States government funding was used in the conception or reduction to practice of the subject matter of the present disclosure.

REFERENCE TO SUBMISSION OF A SEQUENCE LISTING AS A TEXT FILE

The instant application contains a Sequence Listing which has been submitted electronically in ASCII format and is hereby incorporated by reference in its entirety. Said ASCII copy, created on Jun. 3, 2022, is named Sequence_Listing_1331211.txt and is 31,607 bytes in size.

BACKGROUND OF THE INVENTION

Tumor Immunotherapy: Tumor immunotherapy (or cancer immunotherapy) is a form of treatment for neoplastic disease that is based on the enhancement of the innate ability of the immune system to attack neoplastic, cells. Although the current understanding of the mechanism of the immune system has greatly aided the development of cancer immunotherapeutics, the concept of modulating the immune system to treat cancer may be traced by more than 100 years. Currently, there are a variety of approaches for immunotherapy of cancer, such as anticancer vaccines, engineered immune cells, allogenic TIL therapy, cytokines, and checkpoint modulating antibodies. A common principle underlying of all of these approaches is the fundamental belief that the innate and adaptive immune systems of a subject are effective to attack neoplastic cells and eliminate neoplasms. Anti-tumor immunity in human cancer patients is limited by a low prevalence of anti-tumor, immune checkpoint-positive CD8+ T cells and/or their exhaustion.

Interleukin 2: IL2 is a pluripotent cytokine which is produced by antigen activated T cells. IL2 exerts a wide spectrum of effects on the immune system and plays important roles in regulating both immune activation, suppression and homeostasis. IL2 promotes the proliferation and expansion of activated T lymphocytes, induces proliferation and activation of naïve T cells, potentiates B cell growth, and promotes the proliferation and expansion of NK cells. Human interleukin 2 (IL2) is a 4 alpha-helix bundle cytokine of 133 amino acids. IL2 is a member of the IL2 family of cytokines which includes IL2, IL-4, IL-7, IL 9, IL-15 and IL21. However, the function of IIL2 is non-redundant, evidenced by genetic knockouts in mice (Schorle, et al. (1991) Nature 352(6336): 621-624). The amino acid sequence of a hIL2 (SEQ ID NO: 1) is found in Genbank under accession locator NP_000577.2.

IL2 Receptor: IL2 exerts its effect on mammalian immune cells through interaction with three different cell surface proteins: (1) CD25 (also referred to as the IL2 receptor alpha, IL2Rα, p55), CD122 (also referred to as the interleukin-2 receptor beta, IL2Rβ, 1L15Rβ and p70-75), and CD132 (also referred to as the interleukin 2 receptor gamma, IL2Rγ; or common gamma chain as it is a component of other multimeric receptors in the IL2 receptor family).

CD25(IL2Rα): CD25 is a 55 kD polypeptide that is constitutively expressed in Treg cells and inducibly expressed on other T cells in response to activation. hIL2 binds to hCD25 with a $K_d$ of approximately $10^{-8}$ M. CD25 is also referred to in the literature as the "low affinity" IL2 receptor. The human CD25 ("hCD25") is expressed as a 272 amino acid pre-protein comprising a 21 amino acid signal sequence which is post-translationally removed to render a 251 amino acid mature protein. Amino acids 22-240 (amino acids 1-219 of the mature protein) correspond to the extracellular domain. Amino acids 241-259 (amino acids 220-238 of the mature protein) correspond to transmembrane domain. Amino acids 260-272 (amino acids 239-251 of the mature protein) correspond to intracellular domain. The intracellular domain of CD25 is comparatively small (13 amino acids) and has not been associated with any independent signaling activity. The IL2/CD25 complex has not been observed to produce a detectable intracellular signaling response. Human CD25 nucleic acid and protein sequences may be found as Genbank accession numbers NM_000417 and NP_0004Q8 respectively.

CD122 (IL2R): CD122 is a single pass type I transmembrane protein. The human CD122 (hCD122) is expressed as a 551 amino acid pre-protein, the first 26 amino acids comprising a signal sequence which is post-translationally cleaved in the mature 525 amino acid protein. Amino acids 27-240 (amino acids 1-214 of the mature protein) correspond to the extracellular domain, amino acids 241-265 (amino acids 225-239 of the mature protein) correspond to the transmembrane domain and amino acids 266-551 (amino acids 240-525 of the mature protein) correspond to the intracellular domain. As used herein, the term CD122 includes naturally occurring variants of the CD122 protein including the CD122 variants comprising the S57F and D365E substitutions (as numbered in accordance with the mature hCD122 protein). hCD122 is referenced at UniProtKB database as entry P14784. Human CD122 nucleic acid and protein sequences may be found as Genbank accession numbers NM_000878 and NP_000869 respectively.

CD132 (IL2Rγ): CD132 is a type 1 cytokine receptor and is shared by the receptor complexes for IL-4, IIL-7, IL-9, IL-15, and IL21, hence it being referred to in the literature as the "common" gamma chain. Human CD132 (hCD132) is expressed as a 369 amino acid pre-protein comprising a 22 amino acid N-terminal signal sequence. Amino acids 23-262 (amino acids 1-240 of the mature protein) correspond to the extracellular domain, amino acids 263-283 (amino acids 241-262 of the mature protein) correspond to the 21 amino acid transmembrane domain, and amino acids 284-369 (amino acids 262-347 of the mature protein) correspond to the intracellular domain. hCD132 is referenced at UniProtKB database as entry P31785. Human CD132 nucleic acid and protein sequences may be found as Genbank accession numbers: NM_000206 and NP_000197 respectively.

IL2 Intermediate and High Affinity Receptors: In addition to the "low affinity" CD25 IL2 receptor, two additional IL2 receptor complexes have been characterized: (a) an "intermediate affinity" dimeric IL2 receptor comprising CD122 and CD132 (also referred to as "IL2Rβγ"), and (b) a "high affinity" trimeric IL2 receptor complex comprising the CD25, CD122 and CD132 proteins (also referred to as "IL2Rαβγ"). hIL2 possesses a Kd of approximately $10^{-9}$M with respect to the intermediate affinity CD122/CD132 (IL2βγ) receptor complex. hIL2 possesses a Kd of approximately $10^{-11}$M with respect to the high IL2 affinity receptor complex.

IL2 Receptor Expression: The IL2 receptors are expressed on the surface of most lymphatic cells, in particular on T cells, NK cells, and B cells, but the expression level is variable and is dependent on a variety of factors include the activation stage of the cell. Inactive T cells and NK cells express almost exclusively the intermediate-affinity dimeric IL2 receptor, consisting of the two signaling receptors, CD122 and CD132 and demonstrate comparatively low responsiveness to I12 since they predominantly express the intermediate affinity CD122/CD132 complex which has comparatively low affinity for IL2 relative to the CD25/CD122/CD132 high affinity receptor. In contrast, activated T cells and regulatory T cells express the trimeric high-affinity IL2 receptor consisting of CD25, CD122 and CD132. TCR activated T cells (i.e., so called "antigen experienced" T cells) express the high-affinity trimeric I12 receptor. T cells, including tumor infiltrating T cells ("TILs") and tumor recognizing cells, upregulate the CD25 and CD122 upon receiving a T cell receptor (TCR) signal (Kalia, et al. (2010) Immunity 32(1): 91-103. The upregulation of CD25 and CD122 receptor in response to receiving a T cell receptor (TCR) signal renders the antigen activated T cell highly sensitive to the IL2 cytokine. Although, Tregs constitutively express CD25, and therefore express the high affinity trimeric IL2 receptor, TCR-activated T cells express higher levels of the trimeric receptor than regulatory T cells. As a consequence, the expansion of antigen activated T cells in antigen-challenged hosts significantly outpaces the expansion of Tregs. (Humblet-Baron, et al. (2016) J Allergy Clin Immunol 138(1): 200-209 e208).

IL2/IL2 Receptor Interaction: Monomeric IL2 forms a complex with both the trimeric "high affinity" form of the IL2 receptor and the dimeric intermediate affinity receptor (Wang, et al. (2005) Science 310:159-1163) through binding to the extracellular domains of the receptor components expressed on the cell surface. The binding of IL2 to CD25 induces a conformational change in IL2 facilitating increased binding to CD122. IL2 mutants, mimicking the CD25 binding-induced conformational change demonstrate increased binding to CD122 (Levin, et al. (2012) Nature 484(7395): 529-533). The association of CD132 provides formation of the dimeric intermediate-affinity or trimeric high-affinity receptor complexes which are associated with intracellular signaling. In addition to providing intracellular signaling via the JAK/STAT pathway (e.g. phosphorylation of STAT5) and other cellular systems, the interaction of hIL2 with the hIL2 high affinity trimeric receptor on a cell initiates a process by which CD122 is internalized, the membrane bound form of CD25 is released from the activated cell as a soluble protein (referred to as "soluble CD25" or "sCD25") as well as triggering the release of IL2 endogenously produced by the activated cell which is capable of acting in an autocrine and/or paracrine fashion.

Use of IL2 in the Treatment of Human Cancers: Recombinant hIL2 is indicated for the treatment of human adults with metastatic melanoma and metastatic renal cell carcinoma. Therapeutic application of High Dose hIL2 (HD-hIL2) induces tumor rejection in highly immune infiltrated melanomas and renal cell carcinomas (Atkins, et al. (1999) J Clin Oncol 17(7):2105-2116). However, HD-hIL2 therapy is associated with severe dose limiting toxicity, including impaired neutrophil function, fever, hypotension, diarrhea and requires expert management. Dutcher, et al. (2014) J Immunother Cancer 2(1): 26. HD-hIL2 treatment activates most lymphatic cells, including naïve T cells and NK cells, which predominantly express the intermediate affinity receptor (CD122/CD132) and CD25+ regulatory T cells (Tregs), which express the high affinity trimeric receptor (CD25/CD122/CD132). HD-hIL2 monotherapy may also induce generalized capillary leak syndrome which can lead to death. This limits the use of HD-IL2 therapy to mostly younger, very healthy patients with normal cardiac and pulmonary function. HD-IL2 therapy is typically applied in the hospital setting and frequently requires admission to an intensive care unit.

Clinical experience demonstrates that HD-IL2 treatment activates naïve T cells and NK cells, which predominantly express the intermediate affinity receptor as well as CD25+ regulatory T cells (Tregs) which mediate the activity of CD8+ T cells. Due to their constitutive expression of CD25, Tregs are particularly sensitive to IL2. To avoid preferential activation of Tregs, IL2 variants have been developed and introduced into clinical development, which are designed to avoid binding to CD25 and possess enhanced binding to the intermediate affinity CD122/CD132 receptor to activate NK cells and quiescent CD8+ T cells. Such IL2 muteins are often referred to in the literature as "non-α-IL2" or "β/γ-IL2" muteins. However, such "non-α-IL2" or "β/γ-IL2" muteins, by virtue of their reduced binding to CD25, also avoid binding to the antigen activated T cells which have been identified as the primary mediators of anti-tumor T cell response (Peace, D. J. and Cheever, M. A. (1989) J Exp Med 169(1):161-173).

Additionally, preclinical experiments have implicated NK cells as the dominant mechanism for IL2 mediated acute toxicity. Assier E, et al. (2004) J Immunol 172:7661-7668. As NK cells express the intermediate affinity (CD122/CD132; β/γ) IL2 receptor, the nature of such β/γ-IL2 muteins is to enhance the proliferation of such NK cells which may lead to enhanced toxicity. Additionally, although Tregs are associated with down-regulation of CD8+ T cells, Tregs have also been shown to limit the IL2 mediated off-tumor toxicity (Li, et al. (2017) Nature Communications 8(1):1762). Although nitric oxide synthase inhibitors have been suggested to ameliorate the symptoms of VLS, the common practice when VLS is observed is the withdrawal of IL2 therapy. To mitigate the VLS associated with HD IL2 treatment, low-dose IL2 regimens have been tested in patients. While low dose IL2 treatment regimens do partially mitigate the VLS toxicity, this lower toxicity was achieved at the expense of optimal therapeutic results in the treatment of neoplasms.

In light of the pluripotent effects of hIL2 and its demonstrated ability to modulate the activities of a wide variety of cell types associated with human disease, IL2 muteins that retain certain desirable features of the native molecule while minimizing undesirable features, depending on the therapeutic context, remain an active area of research.

SUMMARY OF THE DISCLOSURE

The present disclosure relates to human interleukin-2 (IL2) muteins exhibiting modified binding properties to one or more IL2 receptors and their use in the treatment of neoplastic disease. The hIL2 muteins of the present disclosure retain the desirable biological functions of L2 such as T cell proliferation and cytotoxic activity for antigen activated T cells without the systemic toxicity associated with HD IL2 treatment. Additionally, the compositions of the present disclosure demonstrate significantly lower levels of NK mediated toxicities including but not limited to capillary leak syndrome when compared to wild-type IL2 or β/γ-IL2 muteins. The hIL2 muteins of the disclosure retain binding to CD25 and CD122 but exhibit diminished binding to CD132 and preferentially activate CD25+ T cells relative to NK cells.

IL2 Muteins: The present disclosure provides compositions comprising and methods employing a human IL2 ("hIL2") mutein useful in the treatment and/or prevention of neoplastic disease, wherein the hIL2 mutein exhibits decreased binding affinity for CD132 relative to wild-type hIL2 ("wt hIL2"). In some embodiments, the hIL2 mutein exhibits decreased binding affinity for CD132 relative to wt hIL2 and retains significant binding affinity for CD122 and/or CD25. In some embodiments, the hIL2 mutein exhibits decreased binding affinity for CD132 relative to wt hIL2 and retains binding affinity for CD122 comparable to or greater than wt hIL2. In some embodiments, the hIL2 mutein exhibits decreased binding affinity for CD132 relative to wt hIL2 and retains binding affinity for CD25 comparable to or greater than wt hIL2. In some embodiments, the hIL2 mutein exhibits decreased binding affinity for CD132 relative to wt hIL2 and retains binding affinity for CD122 and CD25 comparable to or greater than wt hIL2. In some embodiments, the hIL2 mutein exhibits decreased binding affinity for CD132 relative to wt hIL2 and demonstrates increased binding affinity for CD122 in the presence of CD25, membrane bound CD25 or sCD25, comparable to or greater than wt hIL2. In some embodiments, the hIL2 mutein exhibits decreased binding affinity for CD132 relative to wt hIL2 and demonstrates increased binding affinity for CD122 in the presence of sCD25 comparable to or greater than wt hIL2. In some embodiments, the hIL2 mutein exhibits decreased binding affinity for hCD132 relative to wt hIL2 and demonstrates increased binding affinity to the hCD25/hCD122 receptor complex and/or the high affinity hCD25/hCD122/hCD132 receptor complex relative to wt hIL2. In one aspect, the present disclosure provides hIL2 muteins exhibiting significant or enhanced binding affinity for hCD25 and reduced binding affinity for the extracellular domain of hCD132 receptor as compared to wt hIL2. In some embodiments, the hIL2 muteins of the present disclosure comprise one or more amino acid substitutions that decrease CD132 receptor binding. In some embodiments, the one or more amino acid substitutions that decrease CD132 receptor binding affinity are selected from amino acid modifications at positions 18, 22, and 126 of the hIL2 mutein, numbered in accordance with mature wt hIL2.

Methods of Use in Neoplastic Disease: The present disclosure provides a method for the prevention and/or treatment of neoplastic disease in a mammalian subject in need of treatment or prevention, the method comprising the step of administering to the subject a therapeutically or prophylactically effective amount of an hIL2 mutein to a subject in need of treatment, wherein the hIL2 mutein is selected from an hIL2 that: (a) exhibits decreased binding affinity for CD132 relative to wt hIL2; (b) exhibits decreased binding affinity for CD132 relative to wt hIL2 and retains significant binding affinity for CD122 and/or CD25; (c) exhibits decreased binding affinity for CD132 relative to wt hIL2 and retains binding affinity for CD122 comparable to or greater than wt hIL2; (d) exhibits decreased binding affinity for CD132 relative to wt hIL2 and retains binding affinity for CD25 comparable to or greater than wt hIL2; (e), exhibits decreased binding affinity for CD132 relative to wt hIL2 and retains binding affinity for CD122 and CD25 comparable to or greater than wt hIL2; (f) exhibits decreased binding affinity for CD132 relative to wt hIL2 and demonstrates increased binding affinity for CD122 comparable to or greater than wt hIL2 in the presence of CD25; or (g) exhibits decreased binding affinity for CD132 relative to wt hIL2 and demonstrates increased binding affinity for CD122 relative to wt hIL2 in the presence of sCD25.

In some embodiments, the method further comprises the step of administering to the mammalian subject one or more supplementary agents, including but not limited to one or more of chemotherapeutics, immune checkpoint modulators, radiotherapy and/or physical interventional treatment methods such as surgery.

In some embodiments, the supplementary agent is a therapeutic antibody. In some embodiments, the therapeutic antibody binds to a tumor cell antigen.

In some embodiments, the supplementary agent is an immune cell. In some embodiments, the immune cell is an engineered immune cell, which includes but is not limited to a CAR T cell, an engineered NK cell, a TCR engineered cell, or an engineered Treg, or a cell population comprising one or more such engineered immune cell. In some embodiments the immune cell is a tumor infiltrating lymphocyte (TIL) or cell population comprising one or more TILs. In some embodiments, the present disclosure provides a method of treatment of the subject with an IL2 mutein of the present disclosure wherein the administering results in a serum concentration of the IL2 mutein in the subject at a level sufficient to promote proliferation of T cells expressing the high-affinity IL2 receptor (e.g. antigen activated T cells) but below the concentration sufficient to substantially induce activation of T-cells expressing primarily the intermediate affinity receptor (e.g., NK cells).

The present disclosure further provides nucleic acids encoding the hIL2 muteins of the present disclosure.

The present disclosure further provides recombinant vectors comprising a nucleic acid encoding the hIL2 muteins of the present disclosure operably linked to one or more expression control sequences operable in the host cell employed for recombinant production.

The present disclosure further provides a method for the prevention and/or treatment of neoplastic disease in a mammalian subject in need of treatment, the method comprising the step of administering to the subject a therapeutically or prophylactically effective amount of a nucleic acid encoding an hIL2 mutein of the present disclosure or recombinant vector encoding an hIL2 mutein of the present disclosure. In some embodiments, the recombinant vector may be a non-viral vector (e.g. a plasmid or other non-viral delivery system) or a viral vector including replication competent, replication deficient, and conditionally replicating viral vectors.

The present disclosure further provides engineered cells comprising a recombinant vector, the recombinant vector comprising a nucleic acid encoding a hIL2 mutein of the present disclosure operably linked to one or more expression control sequences.

The present disclosure further provides a method for the prevention and/or treatment of neoplastic disease in a mammalian subject in need of treatment, the method comprising the step of administering to the subject a therapeutically or prophylactically effective quantity of engineered eukaryotic cells, the engineered eukaryotic cells comprising a recombinant vector, the recombinant vector comprising a nucleic acid encoding a hIL2 mutein of the present disclosure operably linked to one or more expression control sequences operable in a eukaryotic cell. In some embodiments, the eukaryotic cell is a mammalian cell. In some embodiments the mammalian cell is an immune cell. In some embodiments, the mammalian immune cell may be an engineered immune cell.

The present disclosure further provides modified versions of the hIL2 muteins of the present disclosure wherein the hIL2 muteins are modified to increase their duration of action in a mammalian subject. Examples of such modifications include but are not limited to conjugation to one or more carrier proteins, PEGylation, acylation, or amino acid sequence modifications, substitutions or deletions of the hIL2 mutein.

The present disclosure further provides methods of making the hIL2 muteins of the present disclosure. Examples of such methods of making the hIL2 muteins include but are not limited to recombinant production in prokaryotic or eucaryotic cells or chemical synthesis.

The present disclosure further provides pharmaceutically acceptable formulations of the hIL2 muteins of the present disclosure or recombinant vectors comprising a nucleic acid sequence encoding the hIL2 mutein operably linked to one or more expression control sequences active in the target cell. In some embodiments, the pharmaceutically acceptable formulation may comprise one or more supplementary agents.

The present disclosure provides a method for the prevention and/or treatment of neoplastic disease in a mammalian subject the method comprising the step of administering to the subject a pharmaceutically acceptable dosage form comprising a therapeutically or prophylactically effective amount of an hIL2 mutein or vector encoding a hIL2 mutein of the present disclosure to a subject in need of treatment.

The present disclosure further provides a kit, the kit comprising a pharmaceutically acceptable dosage form of an hIL2 mutein of the present disclosure and instructions for use. The pharmaceutical dosage form may be provided in a pre-filled syringe. The kit may optionally further provide a quantity of a solution for admixture with the pharmaceutically acceptable dosage form of an hIL2 mutein, wherein the solution includes but is not limited to one or more of diluents, reconstitution buffers, activating agents, formulants, tonicity agents, or components of a controlled release formulation including but not limited to biodegradable or bioerodible biocompatible polymers. The kit may optionally provide a pharmaceutically acceptable formulation of comprising one or more supplementary agents. The kit may optionally include medical devices to facilitate administration (e.g. a syringe, or autoinjector device). The kit may also provide one or more components for maintaining the kit and its components at a refrigerated temperature for extended periods of time such as one or more gel ice packs and/or insulated packaging.

Garcia, et al. (International Application Number PCT/2018/062122, PCT International Publication No. WO 2019/104092 A1 published May 31, 2019, hereinafter "Garcia '092") describes certain IL2 muteins having modifications including positions 18, 22 and 126 that, among other things, exhibit diminished binding for CD132 while retaining partial IL2 activity that are useful in the practice of the presently described methods.

In some embodiments, the disclosure provides a method of treating a subject suffering from a neoplastic disease, disorder or condition by the administration to said subject of polypeptide that is at least 95% homologous to a polypeptide of the formula: 1 (SEQ ID NO: 10):

(AA1)a-(AA2)b-(AA3)c-(AA4)d-(AA5)e-(AA6)f-(AA7)g-(AA8)h-(AA9)i-T10-Q11-L12-Q13-L14-E15-H16-L17-(AA18)-L19-D20-L21-(AA22)-M23-I24-L25-N26-G27-I28-N29-N30-Y31-K32-N33-P34-(AA35)-L36-T37-(AA38)-(AA39)-L40-T41-F42-K43-F44-Y45-M46-P47-K48-K49-A50-T51-E52-L53-K54-(AA55)-L56-Q57-C58-L59-E60-E61-E62-L63-K64-P65-L66-E67-E68-(AA69)-L70-N71-L72-A73-(AA74)-S75-K76-N77-F78-H79-(AA80-(AA81)-P82-R83-D84-(AA85)-(AA86)-S87-N88-(AA89)-N90-(AA91)-(AA92)-V93-L94-E95-L96-(AA97)-G98-S99-E100-T101-T102-F103-(AA104)-C105-E106-Y107-A108-(AA109)-E110-T111-A112-(AA113)-I114-V115-E116-F117-L118-N119-R120-W121-I122-T123-F124-(AA125)-(AA126)-S127-I128-Il29-(AA130)-T131-L132-T133 wherein:

each of a, b, c, d, e, f, g, h, and i is individually selected from 0 or 1;

AA1 is A (wild type, a=1) or deleted (a=0);

AA2 is P (wild type, b=1) or deleted (b=0);

AA3 is T (wild type, c=1), C, A, G, Q, E, N, D, R, K, P, or deleted (c=0);

AA4 is S (wild type, d=1) or deleted (d=0);

AA5 is S (wild type, e=1) or deleted (e=0);

AA6 is S (wild type, f=1) or deleted (f=0);

AA7 is T (wild type, g=1) or deleted (g=0);

AA8 is K (wild type, h=1) or deleted (h=0);

AA9 is K (wild type, i=1) or deleted (i=0);

AA18 is L (wild type) or R, L, G, M, F, E, H, W, K, Q, S, V, I, Y, H, D or T;

AA22 is Q (wild type) or F, E, G, A, L, M, F, W, K, S, V, I, Y, H, R, N, D, T, or F;

AA35 is K (wildtype) or E;

AA38 is R (wild type), W or G;

AA39 is M (wildtype), L or V;

AA55 is H (wildtype) or Y;

AA69 is V (wildtype) or A;

AA74 is Q (wild type), P, N, H, S;

AA80 is L (wild type), F or V;

AA81 is R (wild type), I, D or T;

AA85 is L (wild type) or V;

AA86 is I (wild type) or V;

AA89 is I (wild type) or V;

AA91 is V (wild type), R, or K;

AA92 is I (wild type) or F;

AA97 is K (wild type) or Q;

AA104 is M (wild type) or A;

AA109 is D (wildtype), C or a non-natural amino acid with an activated side chain;

AA113 is T (wild type) or N;

AA125 is C (wild type), A or S;

AA126 is Q (wild type) or H, M, K, C, D, E, G, I, R, S, or T; and

AA130 is S (wild type), T, G or R.

In some embodiments, the polypeptide comprises the following mutations:

AA18 is selected from the group consisting of L (wild type) or R, L, G, M, F, E, H, W, K, Q, S, V, I, Y, H, D or T;

AA22 is selected from the group consisting of Q (wild type) or F, E, G, A, L, M, F, W, K, S, V, I, Y, H, R, N, D, T, or F; and AA126 is selected from the group consisting of Q (wild type) or H, M, K, C, D, E, G, I, R, S, or T.

In some embodiments, the polypeptide comprises the following mutations: a=0;

AA18 is selected from the group consisting of L (wild type) or R, L, G, M, F, E, H, W, K, Q, S, V, I, Y, H, D or T;

AA22 is selected from the group consisting of Q (wild type) or F, E, G, A, L, M, F, W, K, S, V, I, Y, H, R, N, D, T, or F; and AA126 is selected from the group consisting of Q (wild type) or H, M, K, C, D, E, G, I, R, S, or T.

In some embodiments, the polypeptide comprises a set of mutations selected from the following sets of mutations: L18R, Q22E, and Q126H; L18R, Q22E, and Q126K; L18R, Q22E and Q126M; L18R, Q22E Q126T; L18R; Q22E; V91K; V91R; Q126H; L18R, and Q126H; Q22E, and Q126H; L18G, Q22E and Q126H; L18A, Q22E and Q126H; L18M, Q22E and Q126H; L18F, Q22E and Q126H; L18W, Q22E and Q126H; L18K, Q22E and Q126H; L18Q, Q22E and Q126H; L18E, Q22E and Q126H; L18S, Q22E and Q126H; L18V, Q22E and Q126H; L18I, Q22E and Q126H; L18Y, Q22E and Q126H; L18H, Q22E and Q126H; L18N, Q22E and Q126H; L18D, Q22E and Q126H; L18T, Q22E and Q126H; L18R, Q22G and Q126H; L18R, Q22A and Q126H; L18R, Q22L and Q126H; L18R, Q22M and Q126H; L18R, Q22F and Q126H; L18R, Q22W and Q126H; L18R, Q22K and Q126H; L18R, Q22S and Q126H; L18R, Q22V and Q126H; L18R, Q22I and Q126H; L18R Q22Y and Q126H; L18R Q22H and Q126H; L18R Q22R and Q126H; L18R Q22N and Q126H; L18R Q22D and Q126H; and L18R Q22T and Q126H.

In some embodiments, the polypeptide is PEGylated. In some embodiments, the PEG component of such PEGylated polypeptide has a molecular weight of from about 1OkD to about 70 kD. In some embodiments, the PEG component of such PEGylated polypeptide has a molecular weight of from about 40 kD.

In some embodiments, the polypeptide is a fusion protein. In some embodiments, the fusion protein comprises an Fc domain.

Also provided is a nucleic acid encoding a polypeptide as described above or elsewhere herein. In some embodiments, the nucleic acid is DNA.

Also provides is a recombinant expression vector comprising the nucleic acid as described above.

In some embodiments, said vector is a viral vector. In some embodiments, said vector is a non-viral vector.

Also provided is a host cell transformed with a vector as described above.

Also provided is a pharmaceutical formulation comprising a polypeptide as described above, the nucleic acids as described above or a vector as described above.

Also provided is a method of treating a mammalian subject suffering from neoplastic disease disorder of condition comprising the administration of a therapeutically effective amount of pharmaceutical formulation as described above. In some embodiments, said method further comprises the administration of a supplementary agent to said subject. In some embodiments, said supplementary agent is selected from the group consisting of chemotherapeutic agents, antibodies, immune checkpoint modulators, TILs, CAR-T cells, and physical methods. In some embodiments, the supplementary agent is an immune checkpoint modulator. In some embodiments, the immune checkpoint modulator is an anti-PD-1 or anti-PD-L1 antibody. In some embodiments, the supplementary agent is an antibody selecte from the group consisting of [fam]-trastuzumab deruxtecan, enfortumab vedotin, polatuzumab vedotin, cemiplimab, moxetumomab pasudotox, mogamuizumab, tildrakizumab, ibalizumab, durvalumab, inotuzumab, ozogamicin, avelumab, atezolizumab, olaratumab, ixekizumab, aratumumab, elotuzumab, necitumumab, dinutuximab, nivolumab, blinatumomab, pembrolizumab, ramucirumab, siltuximab, obinutuzumab, ado-trastuzumab emtansine, pertuzumab, brentuximab vedotin, ipilimumab, ofatumumab, certolizumab pegol, catumaxomab, panitumumab, bevacizumab, cetuximab, tositumomab-I131, ibritumomab tiuxetan, gemtuzumab, ozogamicin, trastuzumab, infliximab, rituximab, and edrecolomab.

In some embodiments, the neoplastic disease disorder or condition is selected from the group consisting of: adenomas, fibromas, hemangiomas, hyperplasia, atypia, metaplasia, dysplasia, carcinomas, leukemias, breast cancers, sarcomas, leukemias, lymphomas, genitourinary cancers, ovarian cancers, urethral cancers, bladder cancers, prostate cancers, gastrointestinal cancers, colon cancers, esophageal cancers, stomach cancers, lung cancers; myelomas; pancreatic cancers; liver cancers; kidney cancers; endocrine cancers; skin cancers; gliomas, neuroblastomas, astrocytomas, myelodysplastic disorders; cervical carcinoma-in-situ; intestinal polyposes; oral leukoplakias; histiocytoses, hyperprofroliferative scars including keloid scars, respiratory system carcinomas, gastrointestinal system carcinomas, genitourinary system carcinomas, testicular carcinomas, breast carcinomas, prostatic carcinomas, endocrine system carcinomas, melanomas, adenocarcinomas, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage, promyeloid leukemia (APML), acute myelogenous leukemia (AML) and chronic myelogenous leukemia (CML), precursor lymphoid neoplasms, mature B-cell neoplasms, mature T-cell neoplasms, Hodgkin's Lymphoma, and immunodeficiency-associated lymphoproliferative disorders, lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). erythroblastic leukemia and acute megakaryoblastic leukemia, malignant lymphomas including, but are not limited to, non-Hodgkins lymphoma and variants thereof, peripheral T cell lymphomas, adult T-cell leukemia/lymphoma (ATL), cutaneous T cell lymphoma (CTCL), large granular lymphocytic leukemia (LGF), Hodgkin's disease and Reed-Stemberg disease.

In some embodiments, the method comprises administering to said subject a therapeutically effective amount of an hIL2 mutein of sufficient to maintain a serum concentration greater than about 50% of a period of time of at least 24 hours at or above the effective concentration of the IL2 mutein sufficient to promote proliferation of CD3-activated primary human T-cells at or below a serum concentration of such IL2 mutein sufficient to induce activation of T-cells with respect to such IL2 mutein.

BRIEF DESCRIPTION OF THE FIGURES

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 3 provides data in tabular form illustrating that hIL2 muteins demonstrated preferential pSTAT5 signaling activity relative to wild type hIL2 on CD25 positive YT CD25 cells relative to the CD25 negative YT cells at various dilutions.

FIG. 7 provides data illustrating that wt hIL-2 and STK-012 induced proliferation of NKL cells in a similar dose range demonstrating that STK-012 retains the ability to induce pSTAT5 in a human immune cell comparable to wt hIL2.

FIGS. 8A and 8B provides data relating to the percent P-STAT5-positive cells for the indicated cell lines after treatment with wild-type IL-2 (FIG. 8A) or STK-012 (FIG. 8B). Trend lines calculated by a 4-parameter fit are shown. The x-axis indicates protein concentration on a log 10 scale. Values for untreated cells are indicated on the y-axis.

DETAILED DESCRIPTION

Figure 1:
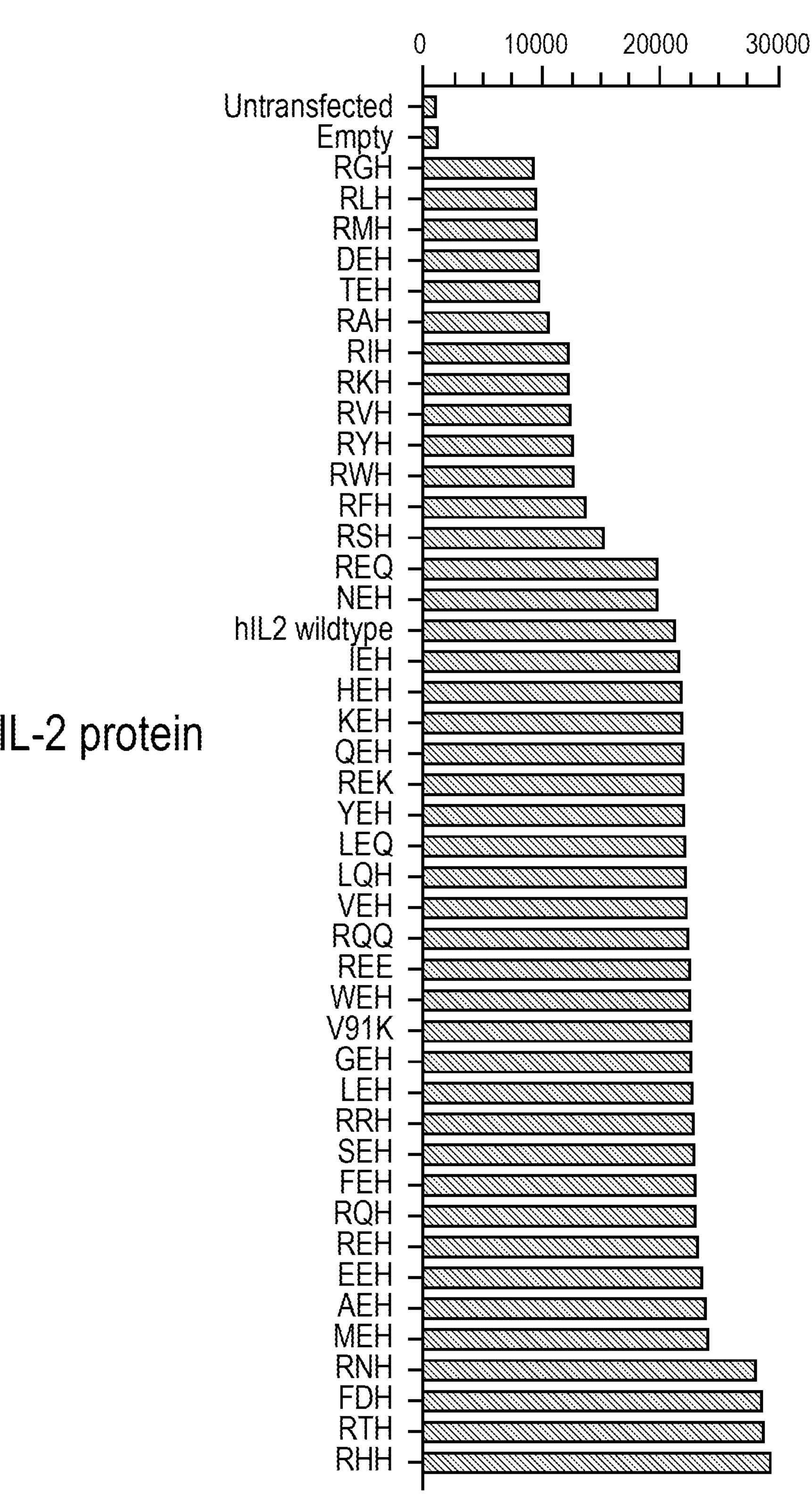
FIG. 1 of the attached drawings provides a graphical representation of pSTAT5 levels as measured in NKL cells treated with 293T transfection supernatant containing the indicated IL2 muteins (and controls) as described in the Examples. The vertical axis represents the level of IL2 activity as measured in accordance with the Examples and each bar indicates the level of activity of the particular IL2 peptide evaluated associated with the construct as identified by its 3 letter abbreviation as described in the Examples.

In order for the present disclosure to be more readily understood, certain terms and phrases are defined below as well as throughout the specification. The definitions provided herein are non-limiting and should be read in view of the knowledge of one of skill in the art would know.

Before the present methods and compositions are described, it is to be understood that this invention is not limited to particular method or composition described, as such may, of course, vary. It is also to be understood that the terminology used herein is for the purpose of describing particular embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms “a”, “an”, and “the” include plural referents unless the context clearly dictates otherwise. Thus, for example, reference to “a cell” includes a plurality of such cells and reference to “the peptide” includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless indicated otherwise, parts are parts by weight, molecular weight is weight average molecular weight, temperature is in degrees Celsius (° C.), and pressure is at or near atmospheric. Standard abbreviations are used, bp=base pair(s); kb=kilobase(s); s or sec=second(s); mi=minute(s); h or hr=hour(s); AA or aa=amino acid(s); kb=kilobase(s); nt=nucleotide(s); pg=picogram; ng=nanogram; μg=microgram; mg=milligram; g=gram; kg=kilogram; pl=picoliter(s); dl or dL=deciliter; da, μl or μL=microliter; ml or mL=milliliter; 1 or L=liter; μM or uM=micromolar; pM=picomolar; nM=nanomolar; fm=femtomolar; mM=millimolar; M=molar; kDa=kilodalton; SC or SQ=subcutaneous(ly); QD daily; QW=once weekly; QM=once monthly; BW=body weight; U=unit; ns=not statistically significant; PBS=phosphate-buffered saline; HSA=human serum albumin; MSA mouse serum albumin; as well as those abbreviations provided in Table 1 below:

TABLE 1

Additional Abbreviations

| Abbreviation | Description |
|---|---|
| ADA | Anti-Drug Antibodies |
| ADCC | antibody-dependent cell-mediated cytotoxicity |
| AEC | Anion Exchange Chromatography |
| ALT | Alanine transaminase |
| AST | Aspartate Transaminase |
| AUC | Area Under the Curve (pharmacological exposure) |
| BID | Twice daily |
| CD8+ T cell | Cytotoxic CD8+ T cell |
| clULN | Clinical Laboratory Upper Limit of Normal |
| Cmax | Maximum drug concentration |
| Cmin | Minimum drug concentration |
| CR | Complete Response (No Measurable Residual Tumor) |
| CRC | colorectal carcinoma |
| CTCAE | Common Terminology Criteria for Adverse Events |
| DLT | Dose Limiting Toxicity |
| ECG | Electrocardiogram |
| ECOG | Eastern Cooperative Oncology Group |
| EDTA | Ethylenediaminetetraacetic acid |
| ELISA | Enzyme-Linked Immunosorbent Assay |
| HIC | hydrophobic interaction chromatography |
| HNSTD | Highest Non-Severely Toxic Dose |
| HP-IEC | High Performance Ion Exchange Chromatography |
| HP-SEC | High Performance Size Exclusion Chromatography |
| HPLC | High Performance Liquid Chromatography |
| IEF | Isoelectric Focusing |
| IFNg, IFN□ | Interferon gamma |
| IHC | Immunohistochemistry |
| ID or i.d. | Intradermally |
| IM or i.m. | Intramuscularly |
| IV or i.v. | Intravenous |
| KD | Equilibrium Dissociation Constant |
| kDa | kilodalton |
| LAL | Limulus Amebocyte Lysate (Endotoxin Assay) |
| LC/MS | liquid chromatography-mass spectrometry |
| MCB | Master Cell Bank |
| MTD | Maximum Tolerated Dose |
| n/d; nd | not detectable; not detected; below limit of detection |
| NHL | Non-Hodgkin’s Lymphoma |
| NHP | Non-Human Primate |
| NK | Natural Killer cell |
| nM | Nanomolar (10−9 Molar) |
| NSG | NOD-scid-IL2Rγ-null immune compromised mouse strain |
| PCR | Polymerase Chain Reaction |
| PEG | Polyethylene glycol |
| PK | Pharmacokinetics |
| q.d.; qg | Latin: quaque die; “once per day” |
| q.o,d,; qod | Latin: quaque die; “once per day” |
| RP-HPLC | Reversed Phase HPLC |
| RT-PCR | Reverse Transcriptase Polymerase Chain Reaction |
| SAE | Serious Adverse Event |
| SC or s.c. | Subcutaneous |
| SDS-Page | Sodium Dodecyl Sulfate Polyacrylamide gel electrophoresis |
| SEC | Size Exclusion Chromatography |
| $T_{1/2}$ | Half life |
| TK | Toxicokinetics |
| TIL(s) | Tumor Infiltrating Lymphocytes |
| UF/DF | Ultrafiltration/Diafiltration |

It will be appreciated that throughout this disclosure reference is made to amino acids according to the single letter or three letter codes. For the reader’s convenience, the single and three letter amino acid codes are provided in Table 2 below:

TABLE 2

Amino Acid Abbreviations

| | | |
|---|---|---|
| G | Glycine | Gly |
| P | Proline | Pro |
| A | Alanine | Ala |
| V | Valine | Val |
| L | Leucine | Leu |
| I | Isoleucine | Ile |
| M | Methionine | Met |

TABLE 2-continued

| Amino Acid Abbreviations | | |
|---|---|---|
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Unless otherwise indicated, the following terms are intended to have the meaning set forth below. Other terms are defined elsewhere throughout the specification.

Definitions

Activate: As used herein the term "activate" is used in reference to a receptor or receptor complex to reflect the biological effect of the binding of an agonist ligand to the receptor. Activators are molecules that increase, activate, facilitate, enhance activation, sensitize, or up-regulate, e.g., a gene, protein, ligand, receptor, or cell. For example, the binding of an IL2 agonist to an IL2 receptor (e.g., the high affinity CD25/CD122/CD132 receptor complex) "activates" the signaling of the receptor to produce one or more intracellular biological effects (e.g. the phosphorylation of STAT5).

Activity: As used herein, the term "activity" is used with respect to a molecule to describe a property of the molecule with respect to a test system (e.g. an assay), a biological or chemical property of the molecule (e.g., the degree of binding of the molecule to another molecule) or of a physical property of a material or cell (e.g. modification of cell membrane potential. Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a biological activity per unit of administered agent such as [catalytic activity]/[mg protein], [immunological activity]/[mg protein], international units (IU) of activity, [STAT5 phosphorylation]/[mg protein], [T-cell proliferation]/[mg protein], plaque forming units (pfu), etc.

Administer/Administration: The terms "administration" and "administer" are used interchangeably herein to refer the act of contacting a subject, including contacting a cell, tissue, organ, or biological fluid in vitro, in vivo and/or ex vivo of a subject with an agent (e.g. an hIL2 mutein, a vector encoding a hIL2 mutein, an engineered cell expressing an hIL2 mutein, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, intracranial injection, intratumoral injection, transdermal, transmucosal, iontophoretic delivery, intralymphatic injection, intragastric infusion, intraprostatic injection, intravesical infusion (e.g., bladder), inhalation (e.g., respiratory inhalers including dry-powder inhalers), intraocular injection, intraabdominal injection, intralesional injection, intraovarian injection, intracerebral infusion or injection, intracerebroventricular injection (ICVI), and the like. The term "administration" includes contact of an agent to the cell, tissue or organ as well as the contact of an agent to a fluid, where the fluid is in contact with the cell. The term "administration" includes the ex vivo contact of a cell (or population of cells) that may be isolated from a subject and contacted with an agent and the cell (or population of cells) is administered to the same subject (e.g., autologous cell transfer) or a different subject (e.g., allogeneic cell transfer).

Adverse Event: As used herein, the term "adverse event" refers to any undesirable experience associated with the use of a therapeutic or prophylactic agent in a subject. Adverse events do not have to be caused by the administration of the therapeutic or prophylactic agent (e.g. the IL2 mutein) but may arise from unrelated circumstances. Adverse events are typically categorized as mild, moderate, or severe. As used herein, the classification of adverse events as used herein is in accordance with the Common Terminology Criteria for Adverse Events v5.0 (CTCAE) dated published Nov. 27, 2017 published by the United States Department of Health and Human Services, the National Institutes of Health and the National Cancer Institute.

Affinity: As used herein the term "affinity" refers to the degree of specific binding of a first molecule (e.g. a ligand) to a second molecule (e.g. a receptor) and is measured by the binding kinetics expressed as $K_d$, a ratio of the dissociation constant between the molecule and its target ($K_{off}$) and the association constant between the molecule and its target ($K_{on}$).

Agonist: As used herein, the term "agonist" refers to a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state resulting in a biological response that mimics the effect of the endogenous ligand of the receptor. The term "agonist" includes partial agonists, full agonists and superagonists. An agonist may be described as a "full agonist" when such agonist which leads to a substantially full biological response (i.e. the response associated with the naturally occurring ligand/receptor binding interaction) induced by receptor under study, or a partial agonist. A "superagonist" is a type of agonist that is capable of producing a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay. With respect to hIL2 muteins, the activity of the hIL2 mutein is expressed in accordance with WHO International Standard (NIBSC code: 86/500) wild type mature hIL2 when evaluated at similar concentrations in a comparable assay. It should be noted that the biological effects associated with the full agonist may differ in degree and/or in kind from those biological effects of partial or superagonists. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist.

In contrast to agonists, antagonists may specifically bind to a receptor but do not result the signal cascade typically initiated by the receptor and may to modify the actions of an agonist at that receptor. A "superagonist" is a type of agonist that is capable of producing a maximal response greater than the endogenous agonist for the target receptor, and thus has an efficacy of more than 100%. An IL2 superagonist of the present disclosure may have greater than 110%, alternatively greater than 120%, alternatively greater than 130%, alternatively greater than 140%, alternatively greater than 150%, alternatively greater than 160%, or alternatively greater than 170% of the activity of WHO International Standard (NIBSC code: 86/500) wild type mature hIL2 when evaluated at similar concentrations in a comparable assay. Inverse agonists are agents that produce a pharmacological response that is opposite in direction to that of an agonist.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway including an immune checkpoint pathway, or cell.

Antibody: As used herein, the term "antibody" refers collectively to: (a) glycosylated and non-glycosylated immunoglobulins (including but not limited to mammalian immunoglobulin classes IgG1, IgG2, IgG3 and IgG4) that specifically binds to target molecule and (b) immunoglobulin derivatives including but not limited to IgG(1-4)delta$C_H$2, F(ab')$_2$, Fab, ScFv, $V_H$, $V_L$, tetrabodies, triabodies, diabodies, dsFv, F(ab')$_3$, scFv-Fc and (scFv)$_2$ that competes with the immunoglobulin from which it was derived for binding to the target molecule. The term antibody is not restricted to immunoglobulins derived from any particular mammalian species and includes murine, human, equine, camelids, human antibodies. The term antibody includes so called "heavy chain antibodies" or "VHHs" or "Nanobodies®" as typically obtained from immunization of camelids (including camels, llamas and alpacas (see, e.g. Hamers-Casterman, et al. (1993) Nature 363:446-448). Antibodies having a given specificity may also be derived from non-mammalian sources such as VHHs obtained from immunization of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies. The term ""human antibody" includes antibodies obtained from human beings as well as antibodies obtained from transgenic mammals comprising human immunoglobulin genes such that, upon stimulation with an antigen the transgenic animal produces antibodies comprising amino acid sequences characteristic of antibodies produced by human beings. The term antibody includes both the parent antibody and its derivatives such as affinity matured, veneered, CDR grafted (including CDR grafted VHHs), humanized, camelized (in the case of non-camel derived VHHs), or binding molecules comprising binding domains of antibodies (e.g., CDRs) in non-immunoglobulin scaffolds. The term "antibody" is not limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries or chemically synthesized (e.g., solid phase protein synthesis). In one embodiment, an "antibody" is a mammalian immunoglobulin. In some embodiments, the antibody is a "full length antibody" comprising variable and constant domains providing binding and effector functions. In most instances, a full-length antibody comprises two light chains and two heavy chains, each light chain comprising a variable region and a constant region. In some embodiments the term "full length antibody" is used to refer to conventional IgG immunoglobulin structures comprising two light chains and two heavy chains, each light chain comprising a variable region and a constant region providing binding and effector functions. The term antibody includes antibody conjugates comprising modifications to prolong duration of action such as fusion proteins or conjugation to polymers (e.g., PEGylated) as described in more detail below.

Biological Sample: As used herein, the term "biological sample" or "sample" refers to a sample obtained or derived from a subject. By way of example, a biological sample comprises a material selected from the group consisting of body fluids, blood, whole blood, plasma, serum, mucus secretions, saliva, cerebrospinal fluid (CSF), bronchoalveolar lavage fluid (BALF), fluids of the eye (e.g., vitreous fluid, aqueous humor), lymph fluid, lymph node tissue, spleen tissue, bone marrow, and an immunoglobulin enriched fraction derived from one or more of these tissues. In some embodiments, the sample is obtained from a subject who has been exposed to a therapeutic treatment regimen including a pharmaceutical formulation of a an IL2 mutein, such as the repeated exposure to the same IL2 mutein. In other embodiments, the sample is obtained from a subject who has not recently been exposed to the IL2 mutein or obtained from the subject prior to the planned administration of the IL2 mutein.

"CAR" or "Chimeric Antigen Receptor": As used herein, the terms "chimeric antigen receptor" and "CAR" are used interchangeably to refer to a chimeric polypeptide comprising multiple functional domains arranged from amino to carboxy terminus in the sequence: (a) an extracellular domain (ECD) comprising an antigen binding domain (ABD) and "hinge" domain, (b) a transmembrane domain (TD); and (c) one or more cytoplasmic signaling domains (CSDs) wherein the foregoing domains may optionally be linked by one or more spacer domains. The CAR may also further comprise a signal peptide sequence which is conventionally removed during post-translational processing and presentation of the CAR on the cell surface of a cell transformed with an expression vector comprising a nucleic acid sequence encoding the CAR. CARs may be prepared in accordance with principles well known in the art. See e.g., Eshhar, et al. (U.S. Pat. No. 7,741,465 B1 issued Jun. 22, 2010); Sadelain, et al. (2013) Cancer Discovery 3(4):388-398; Campana and Imai (U.S. Pat. No. 8,399,645 issued Mar. 19, 2013) Jensen and Riddell (2015) Current Opinions in Immunology 33:9-15; Gross, et al. (1989) PNAS(USA) 86(24):10024-10028; Curran, et al. (2012) J Gene Med 14(6):405-15; Brogdon, et al. (U.S. Pat. No. 10,174,095 issued Jan. 8, 2019) Guedan, et al. (2019) Engineering and Design of Chimeric Antigen Receptors (2019) Molecular Therapy: Methods & Clinical Development Vol. 12: 145-156.

CAR-T Cell: As used herein, the terms "chimeric antigen receptor T-cell" and "CAR-T cell" are used interchangeably to refer to a T-cell that has been recombinantly modified to express a chimeric antigen receptor (CAR). Examples of commercially available CAR-T cell products include axicabtagene ciloleucel (marketed as Yescarta® commercially available from Gilead Pharmaceuticals) and tisagenlecleucel (marketed as Kymriah® commercially available from Novartis).

CD25: As used herein, the terms "CD25", "IL2 receptor alpha", "IL2Rα", "IL2Rα" and "p55" are used interchangeably to the 55 kD polypeptide that is constituitively expressed in Treg cells and inducibly expressed on other T cells in response to activation (e.g. by CD3CD25 is also referred to in the literature as the "low affinity" IL2 receptor. Human CD25 nucleic acid and protein sequences may be found as Genbank accession numbers NM_000417 and NP_0004Q8 respectively. The human CD25 is expressed as a 272 amino acid pre-protein comprising a 21 amino acid signal sequence which is post-translationally removed to render a 251 amino acid mature protein. Amino acids 22-240 (amino acids 1-219 of the mature protein) correspond to the extracellular domain. Amino acids 241-259 (amino acids 220-238 of the mature protein) correspond to transmembrane domain. Amino acids 260-272 (amino acids 239-251 of the mature protein) correspond to intracellular domain. The amino acid sequence of the mature form of hCD25 is:

```
                                           (Sequence ID No. 2)
ELCDDDPPEIPHATFKAMAYKEGTMLNCECKRGFRRIKSGSLYMLCT

GNSSHSSWDNQCQCTSSATRNTTKQVTPQPEEQKERKTTEMQSPMQP

VDQASLPGHCREPPPWENEATERIYHFVVGQMVYYQCVQGYRALHRG

PAESVCKMTHGKTRWTQPQLICTGEMETSQFPGEEKPQASPEGRPES
```

-continued

```
ETSCLVTTTDFQIQTEMAATMETSIFTTEYQVAVAGCVFLLISVLLL

SGLTWQRRQRKSRRTI
```

CD122: As used herein, the terms "CD122", "interleukin-2 receptor beta", "IL2Rb", "IL2Rβ", "IL15Rβ" and "p70-75" are used interchangeably to refer to the human CD122 transmembrane protein. The human CD122 (hCD122) is expressed as a 551 amino acid protein, the first 26 amino acids comprising a signal sequence which is post-translationally cleaved in the mature 525 amino acid protein. Amino acids 27-240 (amino acids 1-214 of the mature protein) correspond to the extracellular domain, amino acids 241-265 (amino acids 225-239 of the mature protein) correspond to the transmembrane domain and amino acids 266-551 (amino acids 240-525 of the mature protein) correspond to the intracellular domain. As used herein, the term CD122 includes naturally occurring variants of the CD122 protein including the S57F and D365E (as numbered in accordance with the mature hCD122 protein). hCD122 is referenced at UniProtKB database as entry P14784. Human CD122 nucleic acid and protein sequences may be found as Genbank accession numbers NM_000878 and NP_000869 respectively. An amino acid sequence of a mature hCD122 protein is:

```
                                                  (SEQ ID NO. 3)
AVNGTSQFTCFYNSRANISCVWSQDGALQDTSCQVHAWPDRRRWNQTCE

LLPVSQASWACNLILGAPDSQKLTTVDIVTLRVLCREGVRWRVMAIQDF

KPFENLRLMAPISLQVVHVETHRCNISWEISQASHYFERHLEFEARTLS

PGHTWEEAPLLTLKQKQEWICLETLTPDTQYEFQVRVKPLQGEFTTWSP

WSQPLAFRTKPAALGKDTIPWLGHLLVGLSGAFGFIILVYLLINCRNTG

PWLKKVLKCNTPDPSKFFSQLSSEHGGDVQKWLSSPFPSSSFSPGGLAP

EISPLEVLERDKVTQLLLQQDKVPEPASLSSNHSLTSCFTNQGYFFFHL

PDALEIEACQVYFTYDPYSEEDPDEGVAGAPTGSSPQPLQPLSGEDDAY

CTFPSRDDLLLFSPSLLGGPSPPSTAPGGSGAGEERMPPSLQERVPRDW

DPQPLGPPTPGVPDLVDFQPPPELVLREAGEEVPDAGPREGVSFPWSRP

PGQGEFRALNARLPLNTDAYLSLQELQGQDPTHLV
```

and the amino acid sequence of the extracellular domain of the hCD122 is:

```
                                                  (SEQ ID NO. 4)
AVNGTSQFTCFYNSRANISCVWSQDGALQDTSCQVHAWPDRRRWNQTCE

LLPVSQASWACNLILGAPDSQKLTTVDIVTLRVLCREGVRWRVMAIQDF

KPFENLRLMAPISLQVVHVETHRCNISWEISQASHYFERHLEFEARTLS

PGHTWEEAPLLTLKQKQEWICLETLTPDTQYEFQVRVKPLQGEFTTWSP

WSQPLAFRTKPAALGKDT
```

CD132: As used herein, the terms "CD132", "IL2 receptor gamma", "IL2Rg, "IL2Rγ" refers to a type 1 cytokine receptor and is shared by the receptor complexes for IL-4, IL-7, IL-9, IL-15, and IL21, hence the reference to the "common" gamma chain. Human CD132 (hCD132) is expressed as a 369 amino acid pre-protein comprising a 22 amino acid N-terminal signal sequence. Amino acids 23-262 (amino acids 1-240 of the mature protein) correspond to the extracellular domain, amino acids 263-283 (amino acids 241-262 of the mature protein) correspond to the 21 amino acid transmembrane domain, and amino acids 284-369 (amino acids 262-347 of the mature protein) correspond to the intracellular domain. hCD132 is referenced at UniProtKB database as entry P31785. Human CD132 nucleic acid and protein sequences may be found as Genbank accession numbers: NM_000206 and NP_000197 respectively. The amino acid sequence of the mature hCD132 protein is:

(SEQ ID NO. 5)

```
LNTTILTPNGNEDTTADFFLTTMPTDSLSVSTLPLPEVQCFVFNVEYMN
CTWNSSSEPQPTNLTLHYWYKNSDNDKVQKCSHYLFSEEITSGCQLQKK
EIHLYQTFVVQLQDPREPRRQATQMLKLQNLVIPWAPENLTLHKLSESQ
LELNWNNRFLNHCLEHLVQYRTDWDHSWTEQSVDYRHKFSLPSVDGQKR
YTFRVRSRFNPLCGSAQHWSEWSHPIHWGSNTSKENPFLFALEAVVISV
GSMGLIISLLCVYFWLERTMPRIPTLKNLEDLVTEYHGNFSAWSGVSKG
LAESLQPDYSERLCLVSEIPPKGGALGEGPGASPCNQHSPYWAPPCYTL
KPET
```

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., *J. Biol. Chem.* 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. In the context of the present disclosure, the numbering of the CDR positions is provided according to the Kabat numbering convention.

Comparable: As used herein, the term "comparable" is used to describe the degree of difference in two measurements of an evaluable quantitative or qualitative parameter. For example, where a first measurement of an evaluable quantitative parameter (e.g. the level of IL2 activity as determined by an CTLL-2 proliferation or phospho-STAT5 assay) and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Conservative Amino Acid Substitution: As used herein the term "conservative amino acid substitution" refers to the modification of the amino acid sequence of a polypeptide that one amino acid residue is changed to another amino acid residue such that the resulting protein retains comparable activity as the parent polypeptide in a similar test system. In some embodiments, the IL2 muteins of the present disclosure may further comprise one more conservative amino acid substitution within the wild type IL2 amino acid sequence. Examples of conservative substitutions include those described by Dayhoff in The Atlas of Protein Sequence and Structure 5 (1978), and by Argos in EMBO J., 8:779-785 (1989). Conservative substitutions are typically made in accordance with the following chart depicted as Table 3 below:

TABLE 3

Exemplary Conservative Amino Acid Substitutions

| Wild type Residue | Conservative Substitution(s) |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu, Met, Leu, Ile |
| Phe | Met, Leu, Tyr, Trp |
| Ser | Thr |
| Thr | Ser |
| Trp | Tyr, Phe |
| Tyr | Trp, Phe |
| Val | Ile, Leu |

Substantial changes in function or immunological identity may be made by selecting amino acid substitutions that are less conservative than those indicated in Table 3 ("non-conservative amino acid substitutions"). Examples of non-conservative amino acid substitutions as those substitutions that significantly affect the structure of the polypeptide backbone or disrupt secondary or tertiary elements including the substitution of an amino acid with a small uncharged side chain (e.g., glycine) with a large charge bulky side chain (e.g., asparagine).

Derived From: As used herein in the term "derived from", in the context of an amino acid sequence or polynucleotide sequence (e.g., an amino acid sequence "derived from" an IL2 polypeptide), is meant to indicate that the polypeptide or nucleic acid has a sequence that is based on that of a reference polypeptide or nucleic acid (e.g., a naturally occurring IL2 polypeptide or an IL2-encoding nucleic acid), and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent (e.g., an hIL2 mutein) in an amount sufficient to effect a response in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological observed at that concentration. For example, the concentration of a test agent sufficient to result in the induction of a measurable biological parameter in a test system that is 30% of the maximal level of such measurable biological parameter in response to such test agent, is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect. The EC of a particular effective concentration of a test agent may be abbreviated with respect to the with respect to particular parameter and test system. For example, concentration IL2 mutein with to induce 50% of the maximal level of STAT5 phosphorylation in a CD25+ T-cell may be abbreviated as "$EC_{50}^{pSTAT5\text{-}CD25+}$", or similar, depending on the context. As Emax is a factor of the parameter being measured (e.g., pSTAT5 induction, proliferation), the test agent (e.g. the particular IL2 mutein such as "REH" described below) and the test system (e.g., a CD25+ human T cell, a human CD25−cell, primary human T cells), the determination of the Emax and the concentrations of the test agent sufficient to product a certain percentage of the Emax (e.g. $EC_{20}$, $EC_{50}$, etc.) may be determined empirically in the particular test system. In some instances, there are standardized accepted measures of biological activity that have been established for a molecule. For example with respect to hIL2 potency, the standard methodology for the evaluation of hL2 potency in international units (IU) is measured in the murine cytotoxic T cell line CTLL-2 in accordance with standardized procedures as more fully described in Wadhwa, et al. (2013) "*The 2nd International standard for Interleukin-2 (IL2) Report of a collaborative study*" Journal of Immunological Methods 397:1-7. It should be noted in the context of the present disclosure that the murine IL2 receptor functions differently than the human IL2 receptor, particularly with respect to need for all components of the trimeric receptor complex to provide intracellular signal transduction signaling (e.g. STAT5 phosphorylation). See, e.g. Horta, et al., (2019) "*Human and murine IL2 receptors differentially respond to the human-IL2 component of immunocytokines*" Oncoimmunology 8(6): e1238538-1, el238538-15 and Nemoto, et al. (1995) "*Differences in the interleukin-2 (IL2) receptor system in human and mouse: alpha chain is require for formation of the functional mouse IL2 receptor*" European J Immunology 25(11)3001-5. Consequently, when evaluating the activity of a hIL2 muteins of the present disclosure, particularly with respect to selectivity with respect to CD25, the use of human cells or systems that recapitulate the biology of the human low, intermediate and high affinity IL2 receptors and receptor complexes is preferred and a molecule that exhibits selective binding or activation in a murine test system (e.g. an in vitro test system using murine cells or in vivo in mice) may not recapitulate such selective activity in a human system (e.g. an in vitro test system using human cells or in vivo in human subjects).

EC Proliferation: The term "effective concentration sufficient to induce proliferation of CD3 activated primary human T-cells" (abbreviated herein as "$EC^{PRO}$") refers to the effective concentration of an IL2 mutein sufficient to induce proliferation of CD3 activated primary human T-cells as determined in accordance with the teaching of a standard protocol in the art. Examples of such standard protocols to assess proliferation of CD3 activated primary human T-cells include bioluminescent assay that generates a luminescent signal that is proportional to the amount of ATP present which is directly proportional to the number of cells present in culture as described in Crouch, et al. (1993) "*The use of ATP bioluminescence as a measure of cell proliferation and cytotoxicity*" J. Immunol. Methods 160: 81-8 or a standardized commercially available assay system such as the CellTiter-Glo® 2.0 Cell Viability Assay or CellTiter-Glo® 3D Cell Viability kits commercially available from Promega Corporation, 2800 Woods Hollow Road, Madison WI 53711 as catalog numbers G9241 and G9681 respectively in substantial accordance with the instructions provided by the manufacturer. When the abbreviation $EC^{PRO}$ used with a subscript this is provided to indicate the concentration of the test agent sufficient to induce the indicated percentage of maximal primary human T cell proliferation in response to the test agent as measured by a given test protocol. By way of illustration, the abbreviation $EC_{30}^{PRO}$ may be used with respect to a hIL2 mutein to indicate the concentration associated with 30% of a maximal level of proliferation of CD3 activated primary human T-cells in response with respect to such IL2 mutein as measured by the CellTiter-Glo® 2.0 Cell Viability Assay.

EC Activation: The term "effective concentration sufficient to induce activation of T-cells" (abbreviated herein as "$EC^{A}cT$") refers to the effective concentration of an IL2 mutein sufficient induce activation and/or differentiation of human T-cells. The evaluable parameters to measure T-cell activation are well known in the art. In some embodiments, the level of activation of T-cells in response to the administration of a test agent may be determined by flow cytometric methods as described as determined by the level of STATS phosphorylation in accordance with methods well known in the art. STAT5 phosphorylation may be measured using flow cytometric techniques as described in Horta, et al. supra., Garcia, et al., supra, or commercially available kits such as the Phospho-STAT5 (Tyr694) kit (commercially available from Perkin-Elmer/cisbio Waltham MA as Part Number 64AT5PEG) in substantial accordance with the teaching of the manufacturer. When the abbreviation $EC^{ACT}$ is used with a subscript this is provided to indicate the concentration of the test agent sufficient to induce the indicated percentage of maximal STAT5 phosphorylation in a T cell in response to the application of the test agent as measured in accordance with the test protocol. By way of illustration, the abbreviation $EC_{30}^{PRO}$ may be used with respect to a hIL2 mutein to indicate the concentration associated with 30% of a maximal level of proliferation in a T cell in response with respect to such IL2 mutein.

Enriched: As used herein in the term "enriched" refers to a sample that is non-naturally manipulated so that a species (e.g. a molecule or cell) of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein (e.g., a cell surface receptor) which is external to of the plasma membrane of a cell. The cell surface protein may be transmembrane protein, a cell surface or membrane associated protein.

Identity: The term "identity," as used herein in reference to polypeptide or DNA sequences, refers to the subunit sequence identity between two molecules. When a subunit position in both of the molecules is occupied by the same monomeric subunit (i.e., the same amino acid residue or nucleotide), then the molecules are identical at that position. The similarity between two amino acid or two nucleotide sequences is a direct function of the number of identical positions. In general, the sequences are aligned so that the highest order match is obtained. If necessary, identity can be calculated using published techniques and widely available computer programs, such as the GCS program package (Devereux, et al., (1984) Nucleic Acids Res. 12:387), BLASTP, BLASTN, FASTA (Atschul, et al. (1990) J. Molecular Biol. 215:403-410). Algorithms that are suitable for determining percent sequence identity and sequence similarity are the BLAST and BLAST 2.0 algorithms, which are described in Altschul et al. (1990) *J Mol. Biol.* 215: 403-410 and Altschul, et al. (1977) *Nucleic Acids Res.* 25: 3389-3402. Software for performing BLAST analyses is publicly available through the National Center for Biotechnology Information (NCBI) web site. The algorithm involves first identifying high scoring sequence pairs (HSPs) by identifying short words of length W of the query sequence, which either match or satisfy some positive-valued threshold score "T" when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters "M" (the reward score for a pair of matching residues; always >0) and "N" (the penalty score for mismatching residues; always <0). For amino acid sequences, a scoring matrix is used to calculate the cumulative score. Extension of the word hits in each direction are halted when: (a) the cumulative alignment score falls off by the quantity X from its maximum achieved value; the cumulative score goes to zero or below, due to the accumulation of one or more negative-scoring residue alignments; or (b) the end of either sequence is reached. The BLAST algorithm parameters "W", "T", and "X" determine the sensitivity and speed of the alignment. The BLASTN program (for nucleotide sequences) functions similarly but uses as defaults a word size ("W") of 28, an expectation ("E") of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, (1989) PNAS(USA) 89:10915-10919).

IL2: As used herein, the term "interleukin-2" or "IL2" refers to a naturally occurring IL2 polypeptide that possesses IL2 activity. In some embodiments, IL2 refers to mature wild type human IL2. Mature wild type human IL2 (hIL2) occurs as a 133 amino acid mature polypeptide (less the signal peptide, consisting of an additional 20 N-terminal amino acids), as described in Fujita, et al., PNAS USA, 80, 7437-7441 (1983). As used herein, the numbering of residues of the hIL2 muteins is based on the hIL2 sequence UniProt ID P60568 excluding the signal peptide which is the same as that of SEQ ID NO:1. An amino acid sequence of naturally occurring variant of mature wild type human IL2 (hIL2) is:

```
                                        (SEQ ID NO: 1)
APTSSSTKKT QLQLEHLLLD LQMILNGINN YKNPKLTRML

TFKFYMPKKA TELKHLQCLE EELKPLEEVL NLAQSKNFHL

RPRDLISNIN VIVLELKGSE TTFMCEYADE TATIVEFLNR

WITFCQSIIS TLT
```

IL2 Activity: The term "IL2 activity" refers to one or more biological effects on a cell in response to contacting the cell with an effective amount of an IL2 polypeptide. IL2 activity may be measured, for example, in a cell proliferation assay using CTLL-2 mouse cytotoxic T cells, in substantial accordance with the teaching of Gearing, A. J. H. and C. B. Bird (1987) in Lymphokines and Interferons, A Practical Approach. Clemens, M. J. et al. (eds): IRL Press. 295. The specific activity of recombinant human IL2 (rhIL2) is approximately $2.1\times10^4$ IU/μg, which is calibrated against recombinant human IL2 WHO International Standard (NIBSC code: 86/500). In some embodiments, the level of IL2 activity may be expressed as the level of STAT5 phosphorylation which may be determined by flow cytometric methods known in the art.

IL2 mutein: As used herein, the term "IL2 mutein" refers to a mutein derived from a naturally occurring form of IL2 comprising modifications to amino acid sequence of the IL2 molecule. The IL2 muteins are characterized by amino acid insertions, deletions, substitutions and modifications at one or more sites in or at the other residues of the native parent IL2 polypeptide chain. In some embodiments, IL2 muteins of the present retain CD122 binding activity comparable to the activity of WHO International Standard (NIBSC code: 86/500) wild type mature human IL2 when evaluated at similar concentrations in a comparable assay. Exemplary muteins can include substitutions of 1, 2, 3, 4, 5, 6, 7, 8, 9, 10 or more amino acids.

In An Amount Sufficient to Effect a Response: As used herein the phrase "in an amount sufficient to cause a response" is used in reference to the amount of a test agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level of a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

In Need of Treatment: The term "in need of treatment" as used herein refers to a judgment made by a physician or other caregiver with respect to a subject that the subject requires or will potentially benefit from treatment. This judgment is made based on a variety of factors that are in the realm of the physician's or caregiver's expertise.

In Need of Prevention: As used herein the term "in need of prevention" refers to a judgment made by a physician or other caregiver with respect to a subject that the subject requires or will potentially benefit from preventative care. This judgment is made based upon a variety of factors that are in the realm of a physician's or caregiver's expertise.

Inhibitor: As used herein the term "inhibitor" refers to a molecule that decreases, blocks, prevents, delays activation of, inactivates, desensitizes, or down-regulates, e.g., a gene, protein, ligand, receptor, or cell. An inhibitor can also be defined as a molecule that reduces, blocks, or inactivates a constitutive activity of a cell or organism.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

Kabat Numbering: The term "Kabat numbering" as used herein is a term recognized in the art of antibody engineering to refer to a system of numbering amino acid residues which are more variable than other amino acid residues (e.g., hypervariable residues) in the heavy and light chain regions of immunoglobulins (Kabat, et al., (1971) *Ann. NY Acad. Sci.* 190:382-93; Kabat, et al., (1991) *Sequences ofProteins of Immunological Interest*, Fifth Edition, U.S. Department of Health and Human Services, NIH Publication No. 91-3242). For purposes of the present disclosure, the positioning of CDRs in the variable region of an antibody as disclosed herein follows Kabat numbering or simply, "Kabat."

Metastasis: As used herein the term "metastasis" describes the spread of cancer cell from the primary tumor to surrounding tissues and to distant organs.

Ligand: As used herein, the term "ligand" refers to a molecule that specifically binds a receptor and causes a change in the receptor so as to effect a change in the activity of the receptor or a response in cell that expresses that receptor. In one embodiment, the term "ligand" refers to a molecule or complex thereof that can act as an agonist or antagonist of a receptor. As used herein, the term "ligand" encompasses natural and synthetic ligands. "Ligand" also encompasses small molecules, peptide mimetics of cytokines and antibodies. The complex of a ligand and receptor is termed a "ligand-receptor complex." A ligand may comprise one domain of a polyprotein or fusion protein (e.g., either domain of an antibody/ligand fusion protein). The complex of a ligand and receptor is termed a "ligand-receptor complex."

Modified IL2 Mutein: As used herein the term "modified IL2 muteins" is used to refer to IL2 muteins that have comprise one or more extra further modifications (i.e. modifications other than to the core amino acid sequence of the hIL2 mutein) such as PEGylation, glycosylation (N- and O-linked), acylation, or polysialylation or by conjugation (either chemical or as fusion proteins) with other polypeptide carrier molecules including but not limited to albumin fusion polypeptides comprising serum albumin (e.g., human serum albumin (HSA) or bovine serum albumin (BSA) or Fc-fusion proteins or with targeting moieties such as IgG comprising IL2 orthogonal polypeptide fusion proteins, targeted IL2 mutein polypeptides such as ScFv-IL2 mutein polypeptide fusion proteins and VHH-IL2 mutein polypeptide fusion proteins. Modified IL2 muteins may be prepared to order to enhance one or more properties for example, modulating immunogenicity; methods of increasing water solubility, bioavailability, serum half-life, and/or therapeutic half-life; and/or modulating biological activity. Certain modifications can also be useful to, for example, raise antibodies for use in detection assays (e.g., epitope tags) and to provide for ease of protein purification. In some embodiments, the modified IL2 mutein is at least 95, 96, 97, 98, or 99% identical to SEQ ID NO:1 and has one of the combinations of three modifications relative to SEQ ID NO:1 as set forth in Table 4.

Modulate: As used herein, the terms "modulate", "modulation" and the like refer to the ability of a test agent to cause a response, either positive or negative or directly or indirectly, in a system, including a biological system, or biochemical pathway. The term modulator includes both agonists (including partial agonists, full agonists and superagonists) and antagonists.

Mutein: As used herein, the term "mutein" is used to refer to modified versions of wild type polypeptides comprising modifications to the primary structure (i.e. amino acid sequence) of such polypeptide. The term mutein may refer to the polypeptide itself, a composition comprising the polypeptide, or a nucleic acid sequence that encodes it. In some embodiments, the mutein polypeptide comprises from about one to about ten amino acid modifications relative to the parent polypeptide, alternatively from about one to about five amino acid modifications compared to the parent, alternatively from about one to about three amino acid modifications compared to the parent, alternatively from one to two amino acid modifications compared to the parent, alternatively a single amino acid modification compared to the parent. A mutein may be at least about 99% identical to the parent polypeptide, alternatively at least about 98% identical, alternatively at least about 97% identical, alternatively at least about 95% identical, or alternatively at least about 90% identical.

N-Terminus: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

Neoplastic Disease: As used herein and as discussed in more detail below, the term "neoplastic disease" refers to disorders or conditions in a subject arising from cellular hyper-proliferation or unregulated (or dysregulated) cell replication. The term neoplastic disease refers to disorders arising from the presence of neoplasms in the subject. Neoplasms may be classified as: (1) benign (2) pre-malignant (or "pre-cancerous"); and (3) malignant (or "cancerous"). The term "neoplastic disease" includes neoplastic-related diseases, disorders and conditions referring to conditions that are associated, directly or indirectly, with neoplastic disease, and includes, e.g., angiogenesis and precancerous conditions such as dysplasia or smoldering multiple myeloma. Examples of benign disorders arising from dysregulated cell replication include hypertrophic scars such as keloid scars.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

Numbered in accordance with IL2: The term "numbered in accordance with IL2" as used herein refers to the identification of a location of particular amino acid with reference to the position at which that amino acid normally occurs in the mature sequence of the mature wild type hIL2, for example R81 refers to the eighty-first amino acid, arginine, that occurs in SEQ ID NO: 1.

Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Parent Polypeptide: As used herein, the terms "parent polypeptide" or "parent protein" are used interchangeably to designate the source of a second polypeptide (e.g., a derivative or variant) which is modified with respect to a first "parent" polypeptide. In some instances, the parent polypeptide is a wild-type or naturally occurring form of a protein. In some instance, the parent polypeptide may be a modified form a naturally occurring protein that is further modified. The term "parent polypeptide" may refer to the polypeptide itself or compositions that comprise the parent polypeptide (e.g., glycosylated or PEGylated forms and/or fusion proteins comprising the parent polypeptide).

Partial Agonist: As used herein, the term "partial agonist" refers to a molecule that specifically binds to and activates a given receptor but possess only partial activation the receptor relative to a full agonist. Partial agonists may display both agonistic and antagonistic effects. For example when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Clinically, partial agonists can be used to activate receptors to give a desired submaximal response when inadequate amounts of the endogenous ligand are present, or they can reduce the overstimulation of receptors when excess amounts of the endogenous ligand are present. The maximum response (Emax) produced by a partial agonist is called its intrinsic activity and may be expressed on a percentage scale where a full agonist produced a 100% response. An IL2 partial agonist of the present disclosure may have greater than 10%, alternatively greater than 20%, alternatively greater than 30%, alternatively greater than 40%, alternatively greater than 50%, alternatively greater than 60%, or alternatively greater than 70%, alternatively greater than 10% but less than 100%, alternatively greater than 20% but less than 100%, alternatively greater than 30% but less than 100%, alternatively greater than 40% but less than 100%, alternatively greater than 50% but less than 100%, alternatively greater than 60% but less than 100%, alternatively greater than 70% but less than 100%, alternatively greater than 80% but less than 100%, or alternatively greater than 90% but less than 100%, of the activity of the WHO International Standard (NIBSC code: 86/500) wild type mature human IL2 when evaluated at similar concentrations in a comparable assay.

PEG-IL2 Mutein: As used herein the term "PEG-IL2 mutein" refers to an IL2 mutein covalently bound to at least one polyethylene glycol (PEG) molecule, the at least one PEG molecule being covalently attached to at least one amino acid residue of an IL2 mutein. The PEGylated polypeptide may be further referred to as monopegylated, dipegylated, tripegylated (and so forth) to denote PEG-IL2 muteins comprising one, two, three (or more) PEG moieties attached to the IL2 mutein, respectively. In some embodiments, the PEG may be covalently attached directly to the IL2 mutein (e.g., through a lysine side chain, sulfhydryl group of a cysteine or N-terminal amine) or optionally employ a linker between the PEG and the IL2 mutein. In some embodiments the PEG-IL2 mutein comprises more than one PEG molecule each of which is attached to a different amino acid residue. In some embodiments, the PEG-IL2 mutein is derived from SEQ ID NO:1 (naturally occurring hIL2). PEGylated forms of IL2 and the methodology of PEGylation of IL2 polypeptides is well known in the art (see, e.g., Katre, et al., U.S. Pat. No. 4,931,544 issued Jun. 5, 1990; Katre, et al., U.S. Pat. No. 5,206,344 issued Apr. 27, 1993; and Bossard, et al., U.S. Pat. No. 9,861,705 issued Jan. 9, 2018). In some embodiments, the IL2 mutein may be modified by the incorporation of non-natural amino acids with non-naturally occurring amino acid side chains to facilitate site specific PEGylation as described in Ptacin, et al. United States Patent Application Publication US20170369871A1 published Dec. 28, 2017. In other embodiments, cysteine residues may be incorporated at various positions within the IL2 molecule to facilitate site-specific PEGylation via the cysteine side chain as described in Greve, et al. PCT International Patent Application Number PCT/US2015/044462 published as WO2016/025385 on Feb. 18, 2016.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g. antigenic diphtheria or tetanus toxin or toxoid fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed due to genetic, experiential or environmental factors to having a particular disease, disorder or condition. In certain instances, the terms "prevent", "preventing", "prevention" are also used to refer to the slowing of the progression of a disease, disorder or condition from a present its state to a more deleterious state.

Receptor: As used herein, the term "receptor" refers to a polypeptide having a domain that specifically binds a ligand that binding of the ligand results in a change to at least one biological property of the polypeptide. In some embodiments, the receptor is a "soluble" receptor that is not associated with a cell surface. The soluble form of hCD25 is an example of a soluble receptor that specifically binds hIL2. In some embodiments, the receptor is a cell surface receptor that comprises an extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of the ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multi-component complex to facilitate intracellular signaling. For example, the ligand may bind a cell surface molecule having not associated with any intracellular signaling alone but upon ligand binding facilitates the formation of a heteromultimeric including heterodimeric (e.g. the intermediate affinity CD122/CD132 IL2 receptor), heterotrimeric (e.g., the high affinity CD25/CD122/CD132 hIL2 receptor) or homomultimeric (e.g., homodimeric, homotrimeric, homotetrameric) complex that results in the activation of an intracellular signaling cascade (e.g. the Jak/STAT pathway).

Recombinant: As used herein, the term "recombinant" is used as an adjective to refer to the method by which a polypeptide, nucleic acid, or cell was modified using recombinant DNA technology. A "recombinant protein" is a protein produced using recombinant DNA technology and is frequently abbreviated with a lower case "r" preceding the protein name to denote the method by which the protein was produced (e.g., recombinantly produced human growth hormone is commonly abbreviated "rhGH"). Similarly a cell is referred to as a "recombinant cell" if the cell has been modified by the incorporation (e.g. transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of cells present in culture as described in Crouch, et al. (1993) J. Immunol. Methods 160: 81-8 or through the use of commercially available assays such as the CellTiter-Glo® 2.0 Cell Viability Assay or CellTiter-Glo® 3D Cell Viability kits commercially available from Promega Corporation, Madison WI 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art. For example, STAT5 phosphorylation may be measured using flow cytometric techniques as described in Horta, et al. supra., Garcia, et al., supra, or commercially available kits such as the Phospho-STAT5 (Tyr694) kit (commercially available from Perkin-Elmer, Waltham MA as Part Number 64AT5PEG) performed in substantial accordance with the instructions provided by the manufacturer.

Selective: As used herein, the term "selective" is used to refer to a property of an agent to preferentially bind to and/or activate a particular cell type based on a certain property of a population of such cells. In some embodiments, the disclosure provides muteins that are CD25 selective in that such muteins display preferential activation of cells expressing the CD25 and/or CD25/CD122 receptors relative to the cells expressing the CD132 receptor. Selectivity is typically assessed by activity measured in an assay characteristic of the activity induced in response to ligand/receptor binding. In some embodiments, the selective IL2 mutein exhibits significantly reduced binding. In some embodiments, selectivity is measured by activation of cells expressing CD25 (e.g. YTCD25POS or YTCD25+ cells) versus the activation of cells that display significantly lower (preferably undetectable) levels of CD25 (e.g. YTCD25NEG or YTCD25− cells). In some embodiments, the selectivity is measured by activation of T cells expressing CD25 (e.g. Tregs) versus low levels of CD25 (e.g. non stimulated CD8+ or CD4+ T cells). In some embodiments, IL2 muteins of the present disclosure possess at least 3 fold, alternatively least 5 fold, alternatively at least 10 fold, alternatively at least 20 fold, alternatively at least 30 fold, alternatively at least 40 fold, alternatively at least 50 fold, alternatively at least 100 fold, alternatively at least 200 fold difference in EC50 on CD25+ versus CD25−cells as measured in the same assay.

Significantly Reduced Binding: As used herein, the term "exhibits significantly reduced binding" is used with respect to a variant of a first molecule (e.g. a ligand) which exhibits a significant reduction in the affinity for a second molecule (e.g. receptor) relative to the parent form of the first molecule. With respect to antibody variants, an antibody variant "exhibits significantly reduced binding" if the variant binds to the native form of the receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent antibody from which the variant was derived. Similarly, with respect to variant ligands, a variant ligand "exhibits significantly reduced binding" if the variant ligand binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived. Similarly, with respect to variant receptors, a variant ligand "exhibits significantly reduced binding" if the affinity of the variant receptors binds to a with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent receptor from which the variant receptor was derived.

Small Molecule(s): The term "small molecules" refers to chemical compounds (typically pharmaceutically active compounds) having a molecular weight that is less than about 10 kDa, less than about 2 kDa, or less than about lkDa. Small molecules include, but are not limited to, inorganic molecules, organic molecules, organic molecules containing an inorganic component, molecules comprising a radioactive atom, and synthetic molecules. The term "small molecule" is a term well understood to those of ordinary skill in the pharmaceutical arts and is typically used to distinguish organic chemical compounds from biologics.

Soluble hCD25: As used herein the terms "soluble CD25," "soluble human CD25", "soluble hCD25" an "shCD25" are used interchangeably herein to refer to a hCD25 molecule comprising the ECD of hCD25 lacking the transmembrane and intracellular domains. As previously noted, human CD25 ("hCD25") is expressed as a 272 amino acid pre-protein comprising a 21 amino acid signal sequence which is post-translationally removed to render a 251 amino acid mature protein. Amino acids 22-240 (amino acids 1-219 of the mature protein) correspond to the extracellular domain. Amino acids 241-259 (amino acids 220-238 of the mature protein) correspond to transmembrane domain. Amino acids 260-272 (amino acids 239-251 of the mature protein) correspond to intracellular domain. The amino acid sequence of the mature form of hCD25 is provided as SEQ ID NO:2.

Specifically Binds: As used herein the term "specifically binds" refers to the degree of selectivity or affinity for which one molecule binds to another. In the context of binding pairs (e.g. a ligand/receptor, antibody/antigen, antibody/ligand, antibody/receptor binding pairs) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the second molecule of the binding pair (e.g. a protein, antigen, ligand, or receptor) if the equilibrium dissociation constant between antibody and the second molecule of the binding pair is greater than about $10^6$M, alternatively greater than about $10^8$ M, alternatively greater than about $10^{10}$ M, alternatively greater than about $10^{11}$ M, alternatively greater than about $10^{10}$ M, greater than about $10^{12}$ M as determined by, e.g., Scatchard analysis (Munsen, et al. 1980 Analyt. Biochem. 107:220-239). In one embodiment where the ligand is an IL2 mutein and the receptor comprises an orthogonal CD122 ECD, the IL2 mutein specifically binds if the equilibrium dissociation constant of the IL2 mutein/orthogonal CD122 ECD is greater than about $10^5$M, alternatively greater than about $10^6$ M, alternatively greater than about $10^7$M, alternatively greater than about $10^8$M, alternatively greater than about $10^9$ M, alternatively greater than about $10^{10}$ M, or alternatively greater than about $10^{11}$ M. Specific binding may be assessed using techniques known in the art including but not limited to competition ELISA, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET) and surface plasmon resonance assays (see, e.g., Drescher et al., Methods Mol Biol 493:323-343 (2009) with instrumentation commercially available from GE Healthcare Bio-Sciences such as the Biacore 8+, Biacore S200, Biacore T200 (GE Healthcare Bio-Sciences, 100 Results Way, Marlborough MA 01752)); liquid phase ligand binding assays (e.g., real-time polymerase chain reaction (RT-qPCR), and immunoprecipitation); and solid phase ligand binding assays (e.g., multiwell plate assays, on-bead ligand binding assays, on-column ligand binding assays, and filter assays).

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Suffering From: As used herein, the term "suffering from" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95%, of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95%, of the total content of the composition.

T-cell: As used herein the term "T-cell" or "T cell" is used in its conventional sense to refer to a lymphocyte that differentiates in the thymus, possess specific cell-surface antigen receptors, and include some that control the initiation or suppression of cell-mediated and humoral immunity and others that lyse antigen-bearing cells. In some embodiments the T cell includes without limitation naïve $CD8^+$ T cells, cytotoxic $CD8^+$ T cells, naïve $CD4^+$ T cells, helper T cells, e.g. $T_H1$, $T_H2$, $T_H9$, $T_H1$, $T_H22$, $T_{FH}$; regulatory T cells, e.g. $T_R1$, Tregs, inducible Tregs; memory T cells, e.g. central memory T cells, effector memory T cells, NKT cells, tumor infiltrating lymphocytes (TILs) and engineered variants of such T-cells including but not limited to CAR-T cells, recombinantly modified TILs and TCR engineered cells.

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Therapeutically Effective Amount: The phrase "therapeutically effective amount" as used herein in reference to the administration of an agent to a subject, either alone or as part of a pharmaceutical composition or treatment regimen, in a single dose or as part of a series of doses in an amount capable of having any detectable, positive effect on any symptom, aspect, or characteristic of a disease, disorder or condition when administered to the subject. The therapeutically effective amount can be ascertained by measuring relevant physiological effects, and it may be adjusted in connection with a dosing regimen and in response to diagnostic analysis of the subject's condition, and the like. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, biomarkers (such as inflammatory cytokines, IFN-γ, granzyme, and the like), reduction in serum tumor markers, improvement in Response Evaluation Criteria In Solid Tumors (RECIST), improvement in Immune-Related Response Criteria (irRC), increase in duration of survival, extended duration of progression free survival, extension of the time to progression, increased time to treatment failure, extended duration of event free survival, extension of time to next treatment, improvement objective response rate, improvement in the duration of response, reduction of tumor burden, complete response, partial response, stable disease, and the like that that are relied upon by clinicians in the field for the assessment of an improvement in the condition of the subject in response to administration of an agent. As used herein the terms "Complete Response (CR)," "Partial Response (PR)" "Stable Disease (SD)" and "Progressive Disease (PD)" with respect to target lesions and the terms "Complete Response (CR)," "Incomplete Response/Stable Disease (SD)" and Progressive Disease (PD) with respect to non-target lesions are understood to be as defined in the RECIST criteria. As used herein the terms "immune-related Complete Response (irCR)," "immune-related Partial Response (irPR)," "immune-related Progressive Disease (irPD)" and "immune-related Stable Disease (irSD)" as as defined in accordance with the Immune-Related Response Criteria (irRC). As used herein, the term "Immune-Related Response Criteria (irRC)" refers to a system for evaluation of response to immunotherapies as described in Wolchok, et al. (2009) *Guidelines for the Evaluation of Immune Therapy Activity in Solid Tumors: Immune-Related Response Criteria*, Clinical Cancer Research 15(23): 7412-7420. A therapeutically effective amount may be adjusted over a course of treatment of a subject in connection with the dosing regimen and/or evaluation of the subject's condition and variations in the foregoing factors. In one embodiment, a therapeutically effective amount is an amount of an agent when used alone or in combination with another agent does not result in non-reversible serious adverse events in the course of administration to a mammalian subject.

Transmembrane Domain: The term "transmembrane domain" or "TM" refers to the domain of a membrane spanning polypeptide (e.g. a membrane spanning polypeptide such as CD122 or CD132 or a CAR) which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. A transmembrane domain may be homologous (naturally associated with) or heterologous (not naturally associated with) with either or both of the extracellular and/or intracellular domains. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived. Alternatively, the transmembrane domain of the receptor may be an artificial amino acid sequence which spans the plasma membrane. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treat: The terms "treat", "treating", treatment" and the like refer to a course of action (such as administering an IL2 mutein, or a pharmaceutical composition comprising same) initiated with respect to a subject after a disease, disorder or condition, or a symptom thereof, has been diagnosed, observed, or the like in the subject so as to eliminate, reduce, suppress, mitigate, or ameliorate, either temporarily or permanently, at least one of the underlying causes of such disease, disorder, or condition afflicting a subject, or at least one of the symptoms associated with such disease, disorder, or condition. The treatment includes a course of action taken with respect to a subject suffering from a disease where the course of action results in the inhibition (e.g., arrests the development of the disease, disorder or condition or ameliorates one or more symptoms associated therewith) of the disease in the subject.

Treg Cell or Regulatory T Cell. The terms "regulatory T cell" or "Treg cell" as used herein refers to a type of $CD4^+$ T cell that can suppress the responses of other T cells including but not limited to effector T cells (Teff). Treg cells are characterized by expression of CD4, the a-subunit of the IIL2 receptor (CD25), and the transcription factor forkhead box P3 (FOXP3) (Sakaguchi, Annu Rev Immunol 22, 531-62 (2004). By "conventional $CD4^+$ T cells" is meant $CD4^+$ T cells other than regulatory T cells.

Variant: The terms "protein variant" or "variant protein" or "variant polypeptide" are used interchangeably herein to refer to a polypeptide that differs from a parent polypeptide by virtue of at least one amino acid modification. The parent polypeptide may be a naturally occurring or wild type (WT) polypeptide or may be a modified version of a WT polypeptide (i.e. mutein).

Wild Type: By "wild type" or "WT" or "native" herein is meant an amino acid sequence or a nucleotide sequence that is found in nature, including allelic variations. A wild type protein, polypeptide, antibody, immunoglobulin, IgG, etc. has an amino acid sequence or a nucleotide sequence that has not been modified by the hand of man.

Nomenclature Conventions:

In some embodiments, the hIL2 muteins of the present disclosure comprise substitutions, deletions, or insertions relative to the wt hIL2 (SEQ ID NO:1) amino acid sequence. Residues may be designated herein by the one-letter or three-letter amino acid code followed by the wt hIL2 amino acid position, e.g., "Cys125" or "C125" refers to the cysteine residue at position 125 of wt hIL2 (SEQ ID NO:1). The following nomenclature is used herein to refer to substitutions, deletions or insertions. Substitutions are designated herein by the one letter amino acid code for the wt hIL2 residue followed by the IL2 amino acid position followed by the single letter amino acid code for the new substituted amino acid. For example, "K35A" refers to a substitution of the lysine (K) residue at position 35 of Sequence ID No. 1 with an alanine (A) residue. A deletion is referred to as "des" followed by the amino acid residue and its position in wt hIL2 (SEQ ID NO:1). For example the term "des-Ala1" or "desA1" refers to the deletion of the alanine at position 1 of the polypeptide of wt hIL2 (SEQ ID NO:1).

hIL2 Muteins

In some embodiments, the hIL2 muteins useful in the practice of the methods of the present disclosure that are partial agonists have one or more reduced functions as compared to wt hIL2. In some embodiments, the hIL2 mutein consists of 1, 2, 3, 4, 5, 6, 7, 8, 9, 10, 11, 12, 13, 14, or 15 amino acid substitutions, modifications or deletions as compared to wt hIL2 (SEQ ID NO: 1).

The present disclosure provides compositions comprising and methods employing a human IL2 ("hIL2") mutein useful in the treatment and/or prevention of neoplastic disease, wherein the human IL2 mutein exhibits decreased binding affinity for CD132 relative to wild-type hIL2 ("wt hIL2", SEQ ID NO:1) polypeptides, comprising the amino acid sequence according to the following Formula 1(SEQ ID NO:10):

$$\left[\begin{array}{l}(AA1)_a\text{-}(AA2)_b\text{-}(AA3)_c\text{-}(AA4)_d\text{-}(AA5)_e\text{-}(AA6)_f\text{-}(AA7)_g\text{-}(AA8)_h\text{-}\\(AA9)_i\text{-T10-Q11-L12-Q13-L14-E15-H16-L17-(AA18)-L19-D20-L21-}\\\text{(AA22)-M23-I24-L25-N26-G27-I28-N29-N30-Y31-K32-N33-P34-}\\\text{(AA35)-L36-T37-(AA38)-(AA39)-L40-T41-F42-K43-F44-Y45-M46-}\\\text{P47-K48-K49-A50-T51-E52-L53-K54-(AA55)-L56-Q57-C58-L59-}\\\text{E60-E61-E62-L63-K64-P65-L66-E67-E68-(AA69)-L70-N71-L72-}\\\text{A73-(AA74)-S75-K76-N77-F78-H79-(AA80-(AA81)-P82-R83-D84-}\\\text{(AA85)-(AA86)-S87-N88-(AA89)-N90-(AA91)-(AA92)-V93-L94-}\\\text{E95-L96-(AA97)-G98-S99-E100-T101-T102-F103-(AA104)-C105-}\\\text{E106-Y107-A108-(AA109)-E110-T111-A112-(AA113)-I114-V115-}\\\text{E116-F117-L118-N119-R120-W121-I122-T123-F124-(AA125)-}\\\text{(AA126)-S127-I128-I129-(AA130)-T131-L132-T133}\end{array}\right] \quad 1$$

wherein:

each of a, b, c, d, e, f, g, h, and i is individually selected from 0 or 1;

AA1 is A (wild type, a=1) or deleted (a=0);

AA2 is P (wild type, b=1) or deleted (b=0);

AA3 is T (wild type, c=1), C, A, G, Q, E, N, D, R, K, P, or deleted (c=0);

AA4 is S (wild type, d=1) or deleted (d=0);

AA5 is S (wild type, e=1) or deleted (e=0);

AA6 is S (wild type, f=1) or deleted (f=0);

AA7 is T (wild type, g=1) or deleted (g=0);

AA8 is K (wild type, h=1) or deleted (h=0);

AA9 is K (wild type, i=1) or deleted (i=0);

AA18 is L (wild type) or R, L, G, M, F, E, H, W, K, Q, S, V, I, Y, H, D or T;

AA22 is Q (wild type) or F, E, G, A, L, M, F, W, K, S, V, I, Y, H, R, N, D, T, or F;

AA35 is K (wildtype) or E;

AA38 is R (wild type), W or G;

AA39 is M (wildtype), L or V;

AA55 is H (wildtype) or Y;

AA69 is V (wildtype) or A;

AA74 is Q (wild type), P, N, H, S;

AA80 is L (wild type), F or V;

AA81 is R (wild type), I, D or T;

AA85 is L (wild type) or V;

AA86 is I (wild type) or V;

AA89 is I (wild type) or V;

AA91 is V (wild type), R, or K;

AA92 is I (wild type) or F;

AA97 is K (wild type) or Q;

AA104 is M (wild type) or A;

AA109 is D (wildtype), C or a non-natural amino acid with an activated side chain;

AA113 is T (wild type) or N;

AA125 is C (wild type), A or S;

AA126 is Q (wild type) or H, M, K, C, D, E, G, I, R, S, or T; and

AA130 is S (wild type), T, G or R.

The hIL2 muteins of the present disclosure possesses decreased binding affinity to hCD132 (SEQ ID NO:5) or the extracellular domain of hCD132 if the hIL2 mutein binds with <70%, alternatively <65%, alternatively <60%, alternatively <55%, alternatively <50%, alternatively <45%, alternatively <40%, alternatively <35%, alternatively <25%, alternatively <20%, alternatively <15%, alternatively <10%, or alternatively <5% of the affinity of wt hIL2 (SEQ ID NO:1) for hCD132 (or the extracellular domain thereof).

In certain embodiments, the hIL2 mutein disrupts the association of the CD122 with the CD132 such that this CD122/CD132 interaction is reduced by about 2%, about 5%, about 10%, about 15%, about 20%, about 50%, about 75%, about 90%, about 95% or more relative to wild type hIL2.

In some embodiments, the hIL2 mutein exhibits decreased binding affinity for CD132 relative wt hIIL2 and retains significant binding affinity for CD122 and/or CD25.

In some embodiments, the hIL2 mutein exhibits decreased binding affinity for CD132 relative to wt hIL2 and exhibits binding affinity for hCD122 (SEQ ID NO:3), or the ECD thereof (SEQ ID NO:4), comparable to or greater than wt hIL2. An IL2 mutein retains binding affinity for hCD122 (or the ECD thereof) comparable to or greater than wt hIL2 if the hIL2 mutein binds to hCD122 (or the ECD thereof) with greater than about 50%, alternatively >60%, alternatively >65%, alternatively >70%, alternatively >75%, alternatively >80%, alternatively >85%, alternatively >90%, alternatively >90%, alternatively >95%, alternatively >100% the, alternatively >105%, alternatively >110%, alternatively >115%, alternatively >125%, alternatively >150%, alternatively >200%, alternatively >300%, alternatively >400%, alternatively >500% of the binding affinity of wt hIL2 (SEQ ID NO:1) for wild type human CD122 (SEQ ID NO:3) or ECD thereof.

In some embodiments, the hIL2 mutein exhibits decreased binding affinity for CD132 relative to wt hIL2 and retains binding affinity for CD25 comparable to or greater than wt hIL2. An IIL2 mutein retains binding affinity for hCD25 comparable to or greater than wt hIiL2 if the hIL2 mutein binds to hCD25 with greater than about 50%, alternatively >60%, alternatively >65%, alternatively >70%, alternatively >75%, alternatively >80%, alternatively >85%, alternatively >90%, alternatively >90% the affinity of wild type I12, alternatively >95%, alternatively >100% the affinity of wild type IL2, alternatively >105%, alternatively >110%, alternatively >115%, alternatively >125%, alternatively >150%, alternatively >200%, alternatively >300%, alternatively >400%, alternatively >500% of the affinity wt hIL2 (SEQ ID NO:1) for wild type hCD25 (SEQ ID NO:2) and/or shCD25.

In some embodiments, the hIL2 mutein exhibits decreased binding affinity for CD132 relative to wt hIL2 and retains binding affinity for CD122 and CD25 comparable to or greater than wt hIL2.

In some embodiments, the hIL2 mutein exhibits decreased binding affinity for hCD132 relative to wt hIL2 and demonstrates increased binding affinity to the hCD25/hCD122 receptor complex and/or the high affinity hCD25/hCD122/hCD132 receptor complex relative to wt hIL2.

In some embodiments, the hIL2 mutein exhibits decreased binding affinity for hCD132 relative to wt hIL2 and demonstrates binding affinity for the hCD25/hCD122 receptor complex comparable to or greater than to wt hIL2. An hIL2 mutein exhibits decreased binding affinity for hCD132 relative to wt hIL2 and demonstrates binding affinity for the hCD25/hCD122 receptor complex comparable to or greater than to wt hIL2 if the hIL2 mutein binds to hCD25/hCD122 complex with greater than about 50%, alternatively >60%, alternatively >65%, alternatively >70%, alternatively >75%, alternatively >80%, alternatively >85%, alternatively >90%, alternatively >90% the affinity of wild type IL2, alternatively >95%, alternatively >100% the affinity of wild type I12, alternatively >105%, alternatively >110%, alternatively >115%, alternatively >125%, alternatively >150%, alternatively >200%, alternatively >300%, alternatively >400%, alternatively >500% of the affinity wt hIL2 (SEQ ID NO:1) for the hCD25/hCD122 receptor complex.

In some embodiments, the hIL2 mutein exhibits decreased binding affinity for hCD132 relative to wt hIL2 and demonstrates binding affinity for the hCD25/hCD122/CD132 receptor complex comparable to or greater than to wt hIL2. An hIL2 mutein exhibits decreased binding affinity for hCD132 relative to wt hIL2 and demonstrates binding affinity for the hCD25/hCD122/CD132 receptor complex comparable to or greater than to wt hIL2 if the hIL2 mutein binds to hCD25/hCD122/CD132 complex with greater than about 50%, alternatively >60%, alternatively >65%, alternatively >70%, alternatively >75%, alternatively >80%, alternatively >85%, alternatively >90%, alternatively >90% the affinity of wild type IL2, alternatively >95%, alternatively >100% the affinity of wild type IL2, alternatively >105%, alternatively >110%, alternatively >115%, alternatively >125%, alternatively >150%, alternatively >200%, alternatively >300%, alternatively >400%, alternatively >500% of the affinity wt hIL2 (SEQ ID NO:1) for the hCD25/hCD122/hCD132 receptor complex.

In some embodiments, the hIL2 mutein exhibits decreased binding affinity for hCD132 relative to wt hIL2 and demonstrates increased binding affinity to the hCD25/hCD122 receptor complex and the high affinity hCD25/hCD122/hCD132 receptor complex relative to wt hIIL2. In some embodiments, the hIL2 mutein exhibits decreased binding affinity for CD132 relative to wt hIL2 and demonstrates increased binding affinity for CD122 in the presence of CD25, membrane bound CD25 or sCD25, comparable to or greater than wt hIL2. In some embodiments, the hIL2 muteins of the present disclosure comprise one or more amino acid substitutions that decrease CD132 receptor binding. In some embodiments, the one or more amino acid substitutions that decrease CD132 receptor binding affinity are selected from those amino acids that are at the interface between hIL2 and hCD132. The crystal structure of hIL2 and its interface with hCD132 has been published and other studies have been conducted which have identified those positions of the hIL2 molecule which have been identified as interacting with binding of hIL2 to CD132 include residues L18, Q22, Q126, T123, S127, 1129 and S130. In some embodiments, substitutions at L18 include L18R, L18G, L18M, L18F, L18E, L18H, L18W, L18K, L18Q, L18S, L18V, L18I, L18Y, L18H, L18D, L18N and L18T. In some embodiments, substitutions at Q22 include Q22F, Q22E, Q22G, Q22A, Q22L, Q22M, Q22F, Q22W, Q22K, Q22S, Q22V, Q22I, Q22Y, Q22H, Q22R, Q22N, Q22D, Q22T, and F. In some embodiments, substitutions at Q126 include Q126H, Q126M, Q126K, Q126C, Q126D, Q126E, Q126G, Q126I, Q126R, Q126S, or Q126T. In some embodiments, substitutions at S130 include S130R and S130G.

In some embodiments, the hIL2 mutein exhibiting decreased binding affinity for hCD132 relative to wt hIL2 incorporates modifications to the primary structure of the wild type IL2 incorporating modifications at positions 18, 22 and/or 126 numbered in accordance with wild type hIL2. In some embodiments, the hIL2 mutein exhibits decreased binding affinity for hCD132 relative to wt hIL2 when modifications to the primary structure of the wild type IL2 incorporates a single substitution at one of L18, Q22 and/or Q126 numbered in accordance with wild type hIL2 including but not limited to the amino acid substitutions: [Q126H] also referred to herein as "LQH"; [Q22E] also referred to herein as "LEQ"; and [L18R] also referred to herein as "RQQ".

In some embodiments, the hIL2 mutein exhibits decreased binding affinity for hCD132 relative to wt hIL2 incorporate modifications to the primary structure of the wild type IL2 incorporates a single substitution at one of L18, Q22 and/or Q126 numbered in accordance with wild type hIL2 including but not limited to the sets of amino acid substitutions: [Q22E, Q126H] also referred to herein as "LEH"; and [L18R; Q126H] also referred to herein as "RQH".

In certain embodiments, the disclosure provides hIL2 muteins comprising the substitutions at positions 18, 22 and 126 wherein the substitutions at positions 18, 22 and 126 are selected from:

one of L18R, L18G, L18M, L18F, L18E, L18H, L18W, L18K, L18Q, L18S, L18V, L18I, L18Y, L18H, L18D, L18N, and L18T;

one of Q22F, Q22E, Q22G, Q22A, Q22L, Q22M, Q22F, Q22W, Q22K, Q22S, Q22V, Q22I, Q22Y, Q22H, Q22R, Q22N, Q22D, Q22T, and F; and one of Q126H, Q126M, Q126K, Q126C, Q126D, Q126E, Q126G, Q126I, Q126R, Q126S, and Q126T.

Exemplary hIL2 muteins comprising substitutions at positions 18, 22 and 126 numbered in accordance with wild type hIL2 including the sets of amino acid substitutions as provided in Table 4 below.

TABLE 4

18, 22 and 126 Substitution hIL2 Muteins

| | hIL2 Residue Position | | |
|---|---|---|---|
| Abbreviation | 18 | 22 | 126 |
| AEH | A | E | H |
| AEK | A | E | K |
| DEH | D | E | H |
| EEH | E | E | H |
| EEK | E | E | K |
| FEH | F | E | H |
| GEH | G | E | H |
| HEH | H | E | H |
| HEK | H | E | K |
| IEH | I | E | H |
| IEK | I | E | K |
| KEH | K | E | H |
| MEH | M | E | H |
| NEH | N | E | H |
| QEH | Q | E | H |
| RAH | R | A | H |
| RDH | R | D | H |
| REH | R | E | H |
| REE | R | E | E |
| REK | R | E | K |
| REM | R | E | M |
| RET | R | E | T |
| REV | R | E | V |
| REL | R | E | L |
| REF | R | E | F |
| REN | R | E | N |
| RER | R | E | R |
| REY | R | E | Y |
| RFH | R | F | H |
| RGH | R | G | H |
| RHH | R | H | H |
| RIH | R | I | H |
| RKH | R | K | H |
| RLH | R | L | H |
| RMH | R | M | H |
| RNH | R | N | H |
| RRH | R | R | H |
| RSH | R | S | H |
| RTH | R | T | H |
| RTK | R | T | K |
| RVH | R | V | H |
| RWH | R | W | H |
| RYH | R | Y | H |
| SEH | S | E | H |
| TEH | T | E | H |
| VEH | V | E | H |
| VEK | V | E | K |
| WEH | W | E | H |
| YEH | Y | E | H |

Note that the three-letter abbreviation for the particular IL2 mutein reflects an IL2 mutein having the mutations at positions 18, 22 and 126, for example "FEH" is shorthand nomenclature for an IL2 mutein comprising the substitutions L18F, Q22E and Q126H. The names provided above are used throughout this specification to refer to the one or more sets of amino acid substitutions in the hIL2 muteins evaluated herein.

In some embodiments, the hIL2 muteins of the present disclosure comprise one or more amino acid substitutions that increase hCD122 receptor binding (or binding to the ECD of hCD122). In some embodiments, the hIL2 mutein useful in the practice of the methods of the present disclosure having a reduced binding affinity for CD132 receptor further includes 1, 2, 3, 4, 5, 6, 7, 8, 9, or 10 or more mutations that increase CD122 binding affinity. In certain embodiments, the subject IL2 mutein useful in the practice of the methods of the present disclosure includes at least one mutation (e.g., a deletion, addition, or substitution of 1, 2, 3, 4, 5, 6, 7, 8, 9, 10, 11, 12, 13, 14, 15, 16, 17, 18, 19, 20, or more amino acid residues) relative to wt hIL2 such that the hIL2 mutein binds the CD122 with higher affinity than wt hIL2. In certain embodiments, the hIL2 mutein binds CD122 with an affinity that is at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% greater than wild type IL2. The binding affinity of IL2 mutein can also be expressed as 1.2, 1.4, 1.5, 2, 5, 10, 15, 20, 25, 50, 100, 200, 250 or more fold greater affinity for the CD122 than wt hIL2.

In some embodiments, the one or more amino acid substitutions that increase hCD122 receptor binding affinity are selected from those amino acids that are at the interface between hIL2 and hCD122. Based on the crystal structure of hIL2 with its receptor, those positions which have been identified as interacting with binding of hIL2 to hCD122 include but are not limited to Q74, L80, R81, L85, I86, 189V, and 192 numbered in accordance with mature wt hIL2. Examples of amino acid substitutions that enhance CD122 binding affinity include but are not limited to Q74N, Q74H, Q74S, L80F, L80V, R81D, R81T, L85V, I86V, I89V, and/or I92F or combinations thereof. In certain embodiments, the amino acid substitutions that increase CD122 binding affinity comprise: L80F, R81D, L85V, I86V and I92F. In some embodiments, the amino acid substitutions that increase CD122 binding affinity comprise: N74Q, L80F, R81D, L85V, I86V, I89V, and I92F. In some embodiments, the amino acid substitutions that increase CD122 binding affinity comprise: Q74N, L80V, R81T, L85V, I86V, and I92F. In certain embodiments, the amino acid substitutions that increase CD122 binding affinity comprise: Q74H, L80F, R81D, L85V, I86V and I92F. In some embodiments, the amino acid substitutions that increase CD122 binding affinity comprise: Q74S, L80F, R81D, L85V, I86V and I92F. In certain embodiments, the amino acid substitutions that increase CD122 binding affinity comprise: Q74N, L80F, R81D, L85V, I86V and I92F. In certain embodiments, the amino acid substitutions that increase CD122 binding affinity comprise: Q74S, R81T, L85V, and I92F numbered in accordance with mature wt hIL2.

In one aspect, the present disclosure provides hIL2 muteins exhibiting significant or enhanced binding affinity for hCD25 and reduced binding affinity for hCD132 (or the extracellular domain of hCD132) receptor as compared to wild type human IL2 (hIL2). In some embodiments, the hIL2 muteins of the present disclosure comprise one or more amino acid substitutions that increase hCD25 binding. In some embodiments, the one or more amino acid substitutions to increase hCD25 receptor binding affinity are selected from those amino acids that are at the interface between hIL2 and hCD25. In some embodiments, the IL2 muteins comprise one or more mutations in positions of the IL2 sequence that either contact CD25 or alter the orientation of other positions contacting CD25 resulting in an IL2 mutein possessing increased affinity for CD25. Based on the crystal structure of hIL2 with its receptor and other studies, those positions which have been identified as interacting with binding of hIL2 to hCD25 include V69 and Q74, numbered in accordance with mature wt hIL2. In some embodiments, the IL2 muteins of the present disclosure comprise one or more the substitutions V69A and Q74P.

Additional Sequence Modifications:

In addition to the foregoing amino acid substitutions and modifications to the wt hIL2 sequence that modulate the binding activity of the hIL2 mutein with respect to CD25, CD122 and/or CD132, the hIL2 may optionally provide one or more modifications to the primary sequence that provide additional benefits.

Removal of Glycosylation Site: The hL2 muteins of the present disclosure may comprises modifications to eliminate the O-glycosylation site at position Thr3 (T3) to facilitate the production of an a-glycosylated hIL2 mutein when the IL2 mutein is expressed in a eucaryotic expression system, particularly in mammalian host cells such as CHO or HEK cells. In one embodiment, the hIL2 mutein of the present disclosure comprises an amino acid modification, deletion or substitution site at position Thr3 (T3) of human IL2 to prevent the O-glycosylation at T3. In one embodiment, the modification at T3 is an amino acid substitution. Exemplary amino acid substitutions include T3A, T3G, T3Q, T3E, T3N, T3D, T3R, T3K, and T3P which removes the glycosylation site at position 3 without eliminating biological activity (see U.S. Pat. No. 5,116,943; Weiger et al., (1989) Eur. J. Biochem., 180:295-300). In one embodiment, the hIL2 mutein comprises the amino acid substitution T3A.

Minimizing Vascular Leak Syndrome: In some embodiments of the disclosure, the IL2 mutein comprises amino acid substitutions to avoid vascular leak syndrome, a substantial negative and dose limiting side effect of the use of IL2 therapy in human beings without out substantial loss of efficacy. See, Epstein, et al., U.S. Pat. No. 7,514,073B2 issued Apr. 7, 2009. In one embodiment, the hIL2 mutein further comprises one or more an amino acid substitutions selected from R38W, R38G, R39L, R39V, F42K and H55Y.

Oxidation Resistance M104A: In some embodiments of the disclosure, the hIL2 mutein comprises amino acid substitution of methionine 104 with an alanine residue (M104A). Such IL2 muteins may be more resistant to oxidation and loss of activity. (See Koths, et al. U.S. Pat. No. 4,752,585 issued Jun. 21, 1988).

Cys125: The wt hIL2 sequence comprises an unpaired cysteine residue at position 125. Unpaired cysteines present the opportunity for misfolding of the protein by incorrect disulfide bridges between cysteine sulfhydryl groups. This may be a particular issue when the hIL2 mutein expressed recombinantly in bacteria and isolated from inclusion bodies. Consequently, the hIL2 mutein of the present disclosure may optionally comprise an amino acid substitution at position 125. In some embodiments, the substitution is C125A or C125S.

V91: In some embodiments, the CD25 biased IIL2 muteins useful in the practice of the methods of the present disclosure comprise an amino acid substitution at position 91. In some embodiments, the methods of the present disclosure comprise the treatment of a neoplastic disease with an IL2 mutein comprising a substitution at position 91 selected from V91K, V91R, V91K. In some embodiments, the methods of the present disclosure comprise the treatment of a neoplastic disease with an IL2 mutein comprising a substitution at position 91 selected from V91K, V91R, V91K are used in the form of a Fc fusion as more fully described in Gavin, et al. U.S. Pat. No. 9,580,486B2 granted Feb. 28, 2017 the teaching of which is herein incorporated by reference with respect to the construction Fc fusions of IL2 muteins comprising a substitution at position 91.

Incorporation of Non-Natural Amino Acids: In some embodiments, the CD25 biased IL2 muteins useful in the practice of the methods of the present disclosure comprise the incorporation of a PEG structure to interfere with binding to the CD132 and bias the activity of the molecule toward CD25+ T cells. Examples of such molecules which are disclosed as useful in the treatment of inflammatory and autoimmune indications include those described in Ptacin, et al., (PCT International Application No. PCT/US2018/045257 filed Aug. 3, 2018 and published Feb. 7, 2019 as International Publication Number WO 2019/028419A1. One embodiment of such PEG IL2 mutein is the PEGylated IL2 molecule identified as THOR-809 as described in Ptacin, et al. (2019) *THOR-809: An IL2 Engineered from an Expanded Genetic Alphabet for the Potential Treatment of Autoimmune Disorders*, Abstract 89, 2019 PACR/ARP Annual Meeting, Nov. 8-13, 2019 Atlanta; *Arthritis Rheumatol* 2019: 71(*supplement* 10).

Affinity Maturation: In some embodiments, hIL2 muteins may be affinity matured to enhance their affinity for CD25 and/or CD122 resulting in modifications to the amino acid sequence of the hIL2 mutein. An "affinity matured" polypeptide is one having one or more alteration(s) in one or more residues which results in an improvement in the affinity of the polypeptide for its receptor, or vice versa, compared to a parent polypeptide which does not possess those alteration(s). Affinity maturation can be performed to increase the binding affinity of the I12 mutein by at least about 10%, alternatively at least about 50%, alternatively at least about 100% alternatively at least about 150%, or from twofold, threefold, fourfold or fivefold as compared to the parent IL2 mutein polypeptide.

N-terminal Deletions: The hIL2 muteins may further comprise elimination of N-terminal amino acids at one or more of positions 1-9 (compounds of the above Formula 1 where a, b, c, d, e, f, g, h, and i are all zero), alternatively positions 1-8 (compounds of the above Formula 1 where a, b, c, d, e, f, g, and h are all zero), alternatively positions 1-7 (compounds of the above Formula 1 where a, b, c, d, e, f, and g are all zero), alternatively positions 1-6 (compounds of the above Formula 1 where a, b, c, d, e, and f are all zero), alternatively positions 1-5 (compounds of the above Formula 1 where a, b, c, d, and e are all zero), alternatively positions 1-4 (compounds of the above Formula 1 where a, b, c and d are all zero), alternatively positions des1-3 (compounds of the above Formula 1 where a, b, and c are all zero), alternatively positions 1-2 (compounds of the above Formula 1 where a and b are zero), or alternatively positions 1 (compounds of the above Formula 1 where a is zero) while retaining hIL2 activity and reduced binding affinity for CD132.

IL2 muteins may comprise deletion of the first two amino acids (desAla1-desPro2) as well as substitution of the Thr3 glycosylation with a cysteine residue to facilitate for selective N-terminal modification, especially PEGylation of the sulfhydryl group of the cysteine (See, e.g. Katre, et al. U.S. Pat. No. 5,206,344 issued Apr. 27, 1993).

Wt hIL2, when expressed endogenously in mammalian cells, is expressed as a pre-protein comprising a signal peptide which is efficiently cleaved in mammalian cells resulting in the N-terminal amino acid of the mature hIL2 polypeptide being an alanine residue (Ala1). While expression of the hIL2 muteins in mammalian cells is possible, it typically more expensive than bacterial cell production and expression in mammalian cells may also result in non-natural glycosylation of the hIL2 depending on the cell line used. Consequently, production of the hIL2 mutein in bacterial cells may preferred in certain circumstances. However, direct expression (i.e., not as a fusion protein) of a hIL2 peptide in bacterial cells results in the addition of a N-terminal methionine residue. If the Ala1 of the wt IL2 sequence is retained, this results in a proline at the +2 position relative to N-terminal methionine. When a proline is present at the +2 position relative to the N-terminal methionine, the endogenous bacterial methionyl amino peptidase (MAP) does not efficiently cleave the N terminal methionine. Consequently, bacterial direct expression of the Met-IL2 results in a mixture of IL2 species, a fraction having an N-terminal and another species lacking the N-terminal methionine. Such a mixture of IL2 species is difficult to resolve by typical manufacturing procedures which results in increased processing, loss of product and creates difficulties when attempting to conjugate the IL2 mutein to N-terminal moiety such as a targeting moiety or PEG molecule. However, by deleting Ala1 from the IL2 mutein, the residue in the +2 position relative to the N-terminal methionine is a threonine (T3) which results in very efficient cleavage of the N-terminal methionine and facilitates bacterial production of the IL2 mutein. In some embodiments, the present disclosure, provides hIL2 muteins comprising a deletion of the alanine at position 1 (des-Ala1; des-A1 numbered in accordance with hIL2).

Agonist Activity: In some embodiments, an hIL2 mutein of the present disclosure is a partial agonist, full agonist or superagonist with respect to activation and/or proliferation of immune cells such as T cells including engineered T cells or isolated T cells. In some embodiments, an hIL2 mutein of the present disclosure is a partial agonist, full agonist or super-agonist of STAT5 phosphorylation in an immune cell. In some embodiments, the hIL2 mutein of the present disclosure is a partial agonist that induces STAT5 phosphorylation in an hIL2 receptor positive immune cell at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild type IL2 stimulates STATS phosphorylation in the same cell type In some embodiments, the hIL2 mutein of the present disclosure is a full agonist that induces STAT5 phosphorylation in an hIL2 receptor positive immune cell at a level of from 95% to 105% of the level that wild type IL2 stimulates STAT5 phosphorylation in the same cell type. In some embodiments, the hIL2 mutein of the present disclosure is a super agonist that induces STAT5 phosphorylation in an hIL2 receptor positive immune cell at a level of greater than 105%, alternatively greater than 110%, alternatively greater than 120%, alternatively greater than 150%, alternatively greater than 200% (twofold), alternatively greater than 300% (threefold) of the level that wild type IL2 stimulates STATS phosphorylation in the same cell type. In particular embodiments, the immune cell is a T cell. In particular embodiments, the immune cell is a CD8+ T cell. In some embodiments, the CD8+ T cell is a freshly isolated CD8+ T cell. In some embodiments the freshly isolated CD8+ cell is a TIL. In other embodiments, the CD8+ T cell is an activated CD8+ T cell. In particular embodiments, the immune cell is an engineered immune cell including but not limited to a CAR T cell, TCR engineered cell, engineered Treg, or engineered NK cell.

In some embodiments, an hIL2 mutein of the present disclosure is a partial agonist, full agonist or super-agonist of pERK1/ERK2 signaling in an hIL2 receptor positive immune cell. In some embodiments, the hIL2 mutein of the present disclosure is a partial agonist that stimulates pERK1/ERK2 signaling at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild type IL2 stimulates pERK1/ERK2 signaling in the same cell type In some embodiments, the hIL2 mutein of the present disclosure is a full agonist that stimulates pERK1/ERK2 signaling in an hIL2 receptor positive immune cell at a level of from 95% to 105% of the level that wild type IL2 stimulates pERK1/ERK2 signaling in the same cell type. In some embodiments, the hIL2 mutein of the present disclosure is a super agonist that stimulates pERK1/ERK2 signaling in an hIL2 receptor positive immune cell at a level of greater than 105%, alternatively greater than 110%, alternatively greater than 120%, alternatively greater than 150%, alternatively greater than 200% (2 fold), alternatively greater than 300% (3 fold) of the level that wild type IL2 stimulates pERK1/ERK2 signaling in the same cell type. In particular embodiments, the immune cell is a T cell. In particular embodiments, the immune cell is a CD8+ T cell. In some embodiments, the CD8+ T cell is a freshly isolated CD8+ T cell. In some embodiments the freshly isolated CD8+ cell is a TIL. In other embodiments, the CD8+ T cell is an activated CD8+ T cell. In particular embodiments, the immune cell is an engineered immune cell including but not limited to a CAR T cell, TCR engineered cell, engineered Treg, or engineered NK cell.

STAT5 and ERK1/2 signaling can be measured, for example, by phosphorylation of STAT5 and ERK1/2 using any suitable method known in the art. For example, STAT5 and ERK1/2 phosphorylation can be measured using antibodies specific for the phosphorylated version of these molecules.

In certain embodiments, the hIL2 mutein of the present disclosure mutein useful in the practice of the methods of the present disclosure is a partial, full or super agonist as measured by the ability of the hIL2 mutein to induce lymphocyte proliferation as compared to wild type hIL2. In some embodiments, the hIL2 mutein of the present disclosure is a partial agonist that induces lymphocyte proliferation at a level that is 1%, 5%, 10%, 15%, 20%, 25%, 30%, 35%, 40%, 45%, 50%, 55%, 60%, 65%, 70%, 75%, 80%, 85%, 90%, 95% or less of the level that wild type IL2 induces lymphocyte proliferation in the same cell type In some embodiments, the hIL2 mutein of the present disclosure is a full agonist that induces lymphocyte proliferation in an hIL2 receptor positive immune cell at a level of from 95% to 105% of the level that wild type IL2 induces lymphocyte proliferation in the same cell type. In some embodiments, the hIL2 mutein of the present disclosure is a super agonist that induces lymphocyte proliferation signaling in an hIL2 receptor positive immune cell at a level of greater than 105%, alternatively greater than 110%, alternatively greater than 120%, alternatively greater than 150%, alternatively greater than 200% (2 fold), alternatively greater than 300% (3 fold) of the level that wild type IL2 induces lymphocyte proliferation in the same cell type. In particular embodiments, the immune cell is a T cell. In particular embodiments, the immune cell is a CD8+ T cell. In some embodiments, the CD8+ T cell is a freshly isolated CD8+ T cell. In some embodiments the freshly isolated CD8+ cell is a TIL. In other embodiments, the CD8+ T cell is an activated CD8+ T cell. In particular embodiments, the immune cell is an engineered immune cell including but not limited to a CAR T cell, TCR engineered cell, engineered Treg, or engineered NK cell. In some embodiments, the lymphocyte is a T cell. In particular embodiments, the lymphocyte is a primary CD8+ T cell. In other embodiments, the lymphocyte is an activated CD8+ T cell. Immune cell proliferation can be measured using any suitable method known in the art. For example, lymphocyte proliferation can be measured using a carboxyfluorescein diacetate succinimidyl diester (CFSE) dilution assay or by [31-1]-thymidine incorporation, as described herein.

As the hIL2 mutein of Formula 1 retains binding to both the CD122 and CD132 receptor components, the hIL2 mutein may act as a partial agonist of natural killer (NK) cells. IL2 activation of NK cells can be measured by any suitable method known in the art, for example, by measuring IL2 induced CD69 expression and/or cytotoxicity, as described herein.

In Vitro Evaluation of hIL2 Muteins:

To demonstrate the activity of the hTL2 muteins having decreased binding affinity for CD132 relative to wild-type hIL2 of the present disclosure and their preferential activation of CD25 expressing cells, a series of hIL2 muteins were prepared and evaluated for their ability to provide selective activation of YT cells, an NK cell expressing the intermediate affinity dimeric form of the IL2 receptor and a YT cell variant referred as YT CD25 which is a YT cell that has been modified to express CD25 on its surface (iCD25+) resulting in a human immune cell that expresses all three components of the high affinity trimeric IL2 receptor.

Figure 2:
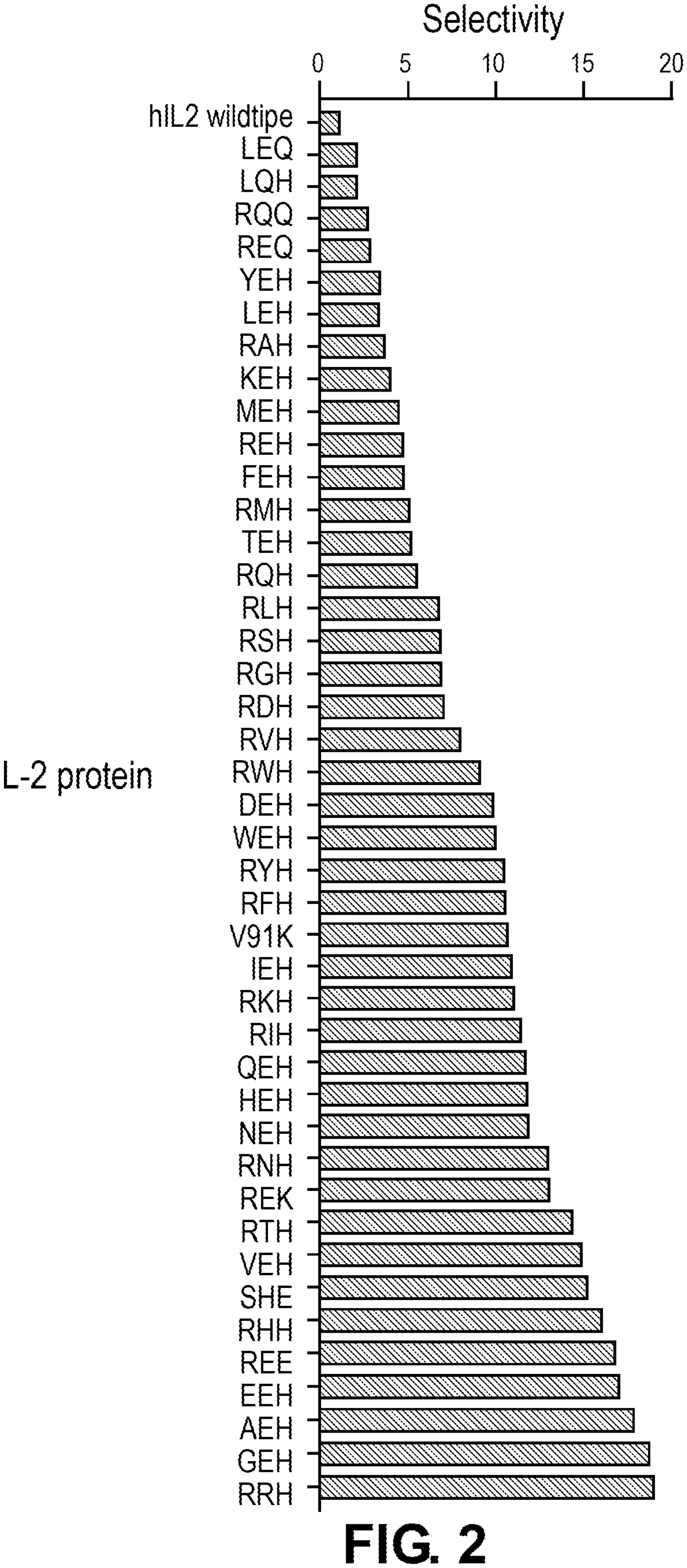
FIG. 2 of the attached drawings provides comparative pSTAT5 activity in CD25 positive and CD25 negative YT cells treated with 293T transfection supernatant containing the indicated IL2 muteins (and controls) as described in the Examples. The vertical axis is a measure of selectivity calculated as the ratio of the level of pSTAT5 activity observed on CD25 positive YT cells divided by the level of pSTAT5 activity measured on CD25 negative YT cells and each bar indicates the level of activity of the particular IL2 peptide evaluated as identified by its 3 letter abbreviation as described in the Examples.

A series of exemplary hIL2 muteins of Formula 1 were prepared and tested comprising amino acid substitutions at positions 18, 22 and/or 126 which interface with CD132. The molecules were prepared and tested in substantial accordance with the teaching of the Examples 1-7 herein. The results of these experiments are provided in FIGS. 1, 2 and 3 of the attached drawings. As illustrated in FIG. 1, the hIL2 muteins comprising amino acid substitutions involved in the binding of hIL2 to hCD132 at positions 18, 22 and/or 126 demonstrated significant increases in pSTAT5 signaling demonstrating in YT CD25 cells that the hIL2 muteins retain significant hIL2 activity relative to wt hIL2. As illustrated in FIG. 2, hIL2 muteins of the present disclosure demonstrated preferential pSTAT5 signaling activity relative to wild type hIL2 on CD25 positive YT CD25 cells relative to the CD25 negative YT cells. The data from the dilution of these molecules is provided in FIG. 3 of the attached drawings.

An additional study was conducted to evaluate additional hIL2 muteins of the present disclosure for activity in CD4 positive human T cells, 3F8 cells. The 3F8 cell line was generated by activation of PBMCs obtained from a healthy human donor with the EBV transformed B cell line JY. The CD4 positive T cell clone 3F8 expresses CD25 and CD122 and proliferates and produces IFNγ in response to IL-2. Additional representative hIL2 muteins of the Formula 1 as detailed in Table 5 below were evaluated for proliferative activity and IFNγ production in 3F8 cells accordance with the teaching of Example 8 herein. The data from this experiment is provided in Table 5 below and FIG. 4 (cell proliferation) and FIG. 5 (IFNγ) production) of the attached drawings. The $IC_{50}$ is corrected for the protein concentration in the transfection supernatant.

TABLE 5

Proliferation and IFN□ Production by Human CD4 Positive T Cell Clone 3F8 In Response to hIL2 Muteins

| Construct | Proliferation $IC_{50}$ (pM) | IFN□ Production $IC_{50}$ (pM) |
|---|---|---|
| IL-2 | 30.7 | 19.7 |
| REK | 14.2 | 17.7 |
| REE | 33.0 | 18.4 |

TABLE 5-continued

Proliferation and IFN□ Production by Human CD4 Positive T Cell Clone 3F8 In Response to hIL2 Muteins

| Construct | Proliferation $IC_{50}$ (pM) | IFN□ Production $IC_{50}$ (pM) |
|---|---|---|
| REM | 32.6 | 12.7 |
| REV | 20.8 | 21.2 |
| REL | 68.4 | 33.8 |
| REF | 37.6 | 38.3 |
| REN | 13.7 | 15.7 |
| RER | 13.1 | 13.1 |
| REY | 19.3 | 22.1 |
| AEK | 13.7 | 19.0 |
| EEK | 36.0 | 58.7 |
| VEK | 15.5 | 4.6 |
| HEK | 20.9 | 30.4 |
| IEK | 10.0 | 8.8 |
| RTK | 62.8 | NA |

Figure 4A:
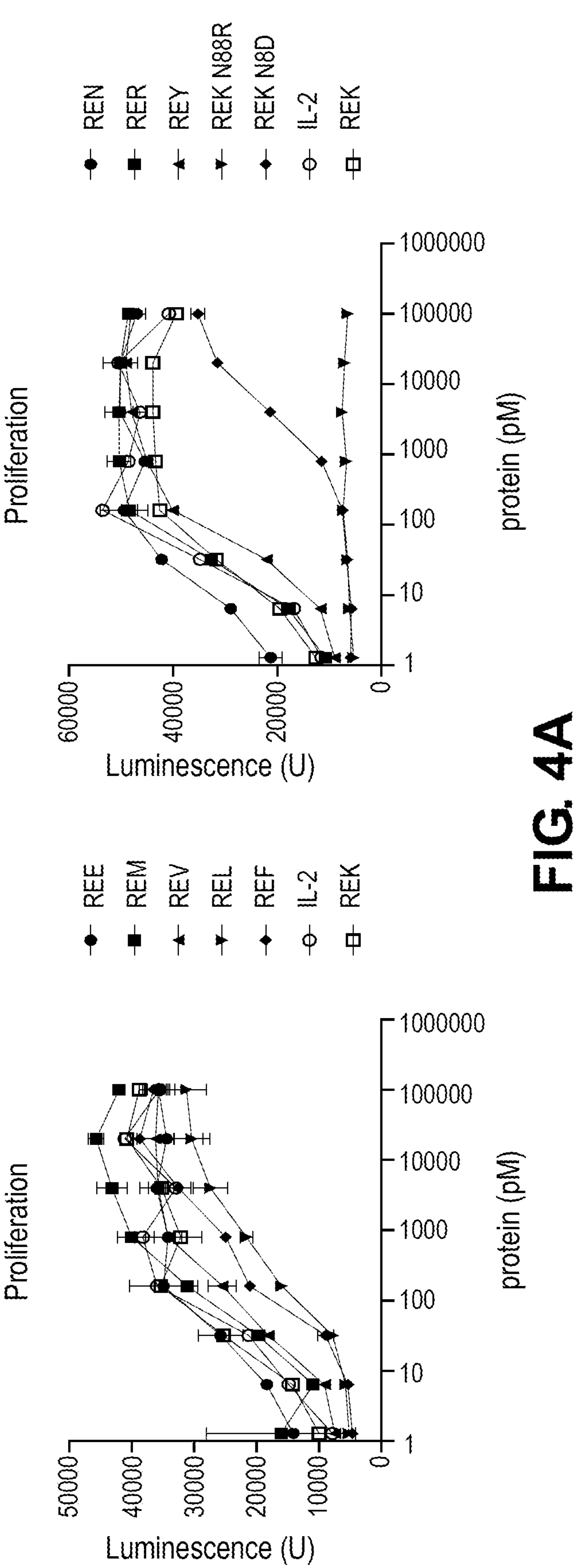
FIG. 4 provides data relating to the cell proliferation of 3F8 cells contacted with hIL2 muteins as more fully described in the specification and in Example 8.
Figure 4B:
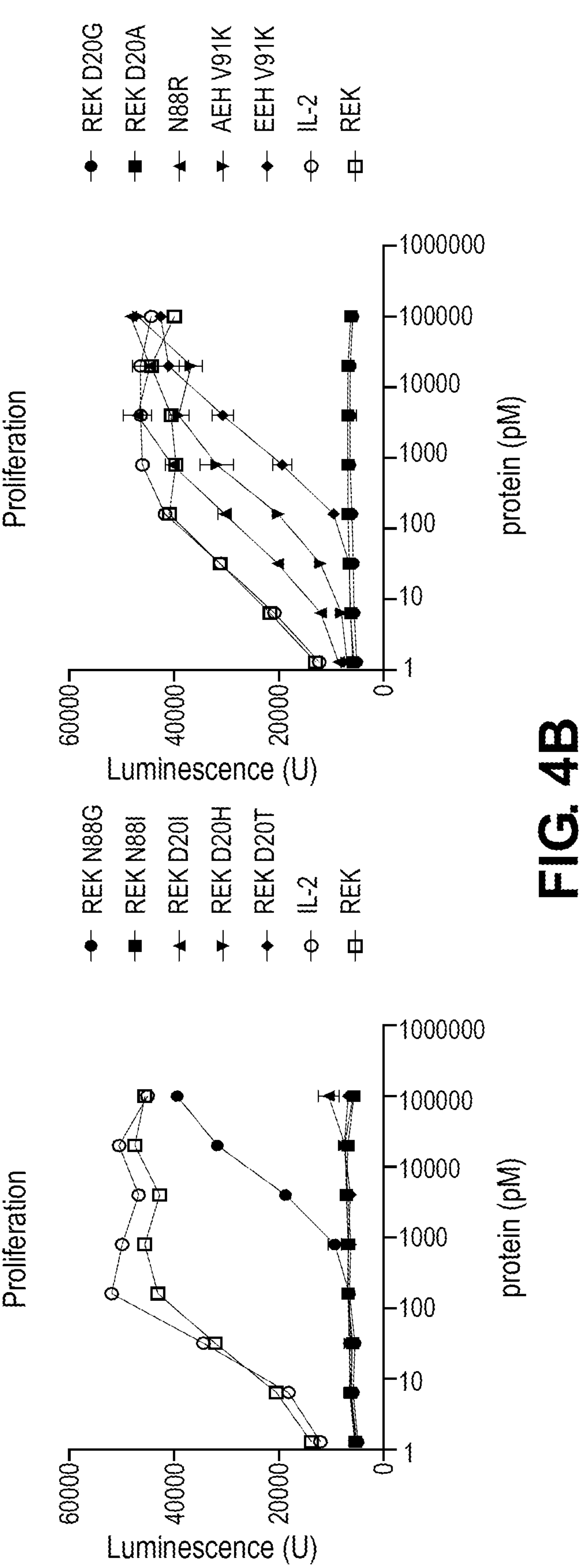
Figure 4C:
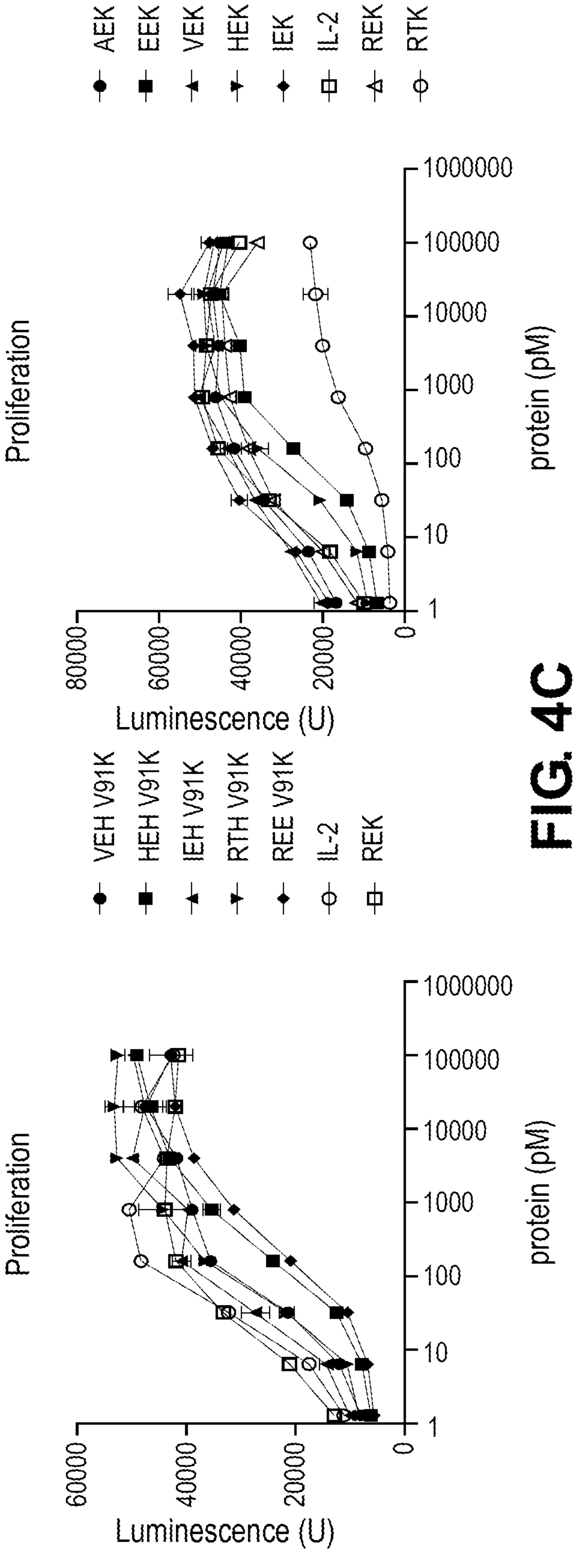
Figure 5B:
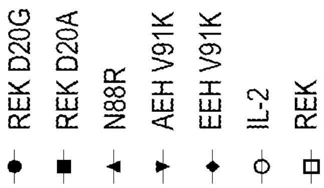
FIG. 5 provides data relating to the interferon gamma production from 3F8 cells contacted with hIL2 muteins as more fully described in the specification and in Example 8.
Figure 5B:
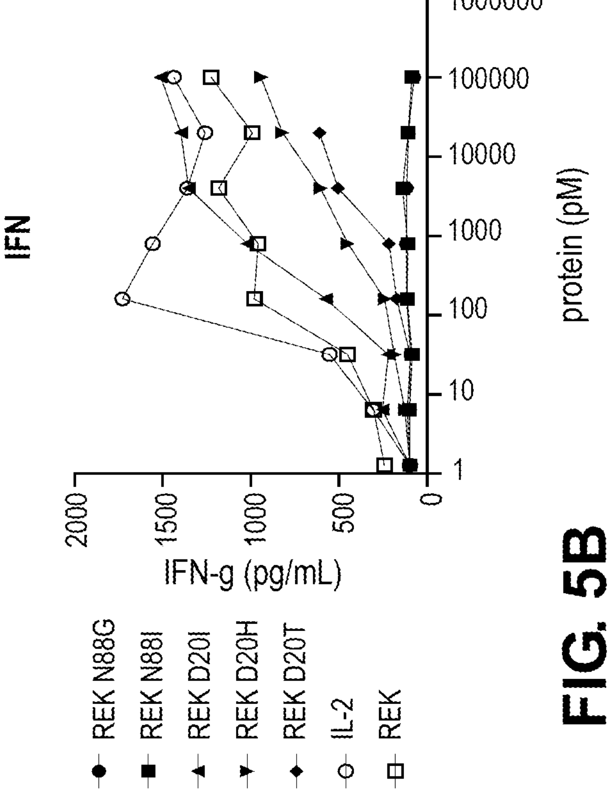
Figure 5B:
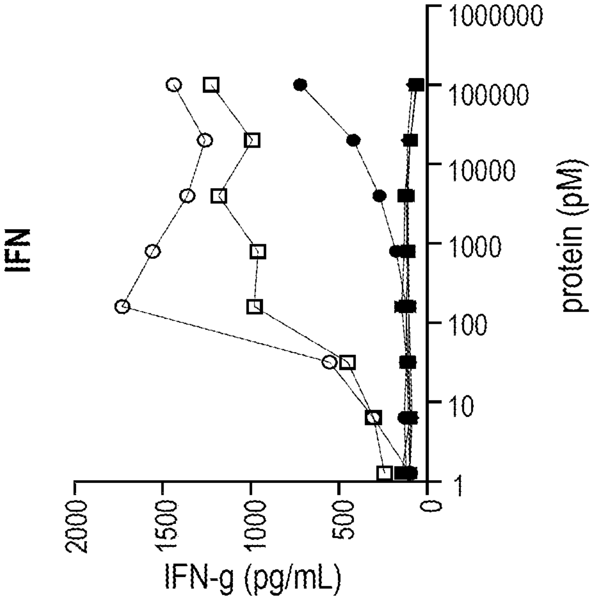

The foregoing data in Table 5 and FIGS. 4 and 5 demonstrate that hIL2 muteins of the present disclosure having decreased binding affinity for CD132 relative to wt hIL2 are effective in stimulating the proliferation of and production of IFNγ from CD25+/CD122+ human immune cells.

Assessment of Anti-Neoplastic Activity

The present disclosure provides compositions and methods employing a hIL2 mutein in the treatment and/or prevention of neoplastic disease, wherein the human IL2 mutein, among other properties, exhibits decreased binding affinity for CD132 relative to wt hIL2. To demonstrate the utility of this approach, additional in vitro characterization studies and in vivo studies to evaluate therapeutic efficacy, toxicity and pharmacokinetics in rodents and non-human primate were performed as described in more detail below. Cumulatively, the results of these studies demonstrate that the hIL2 muteins of the present disclosure at therapeutically effective and well-tolerated doses and exposures provide: (a) selective activation and/or proliferation of human immune cells expressing the high affinity hIL-2 receptor, in particular antigen activated T cells, antigen experienced T cells and regulatory T cells; (b) significantly lower toxicity than wt hIL2 including lower evidence of vascular leak syndrome (VLS); and (c) while exhibiting significantly reduced biological activity on NK cells or naïve, CD25 negative T cells.

hIL2 Mutein Test Agents: To conduct these extensive in vitro characterization studies and in vivo studies demonstrating the utility of the hIL2 muteins of the present disclosure in the effective treatment of neoplastic disease in mammalian subjects, exemplary hIL2 muteins of Formula 1 comprising amino acid substitutions at positions L18, Q22 and Q126 substitutions were evaluated as representative members of the compounds of Formula 1. As previously discussed, modification of hIL2 at positions L18, Q22 and Q126 provides a hIL2 mutein having modulated affinity to hCD132 yet typically exhibits binding to hCD25 and hCD122 comparable to wt hIL2. Two representative L18, Q22 and Q126-modified hIL2 muteins (STK-008 and STK-011) and a surrogate murine IL2 (mIL2) mutein (STK-014), the structures of which are provided below, were used for these studies.

STK-008: An exemplary hIL2 mutein of Formula 1 is the human IL2 mutein comprising the amino acid substitutions L18R, Q22E and Q126H and additionally comprising a deletion of Ala1 referred to herein as des-Ala1 REH, REH and STK-008. The amino acid sequence of STK-008 is provided below (SEQ ID NO:7):

```
                                        (SEQ ID NO: 7)
PTSSSTKKTQLQLEHLRLDLEMILNGINNYKNPKLTRMLTFKFYMPK

KATELKHLQCLEEELKPLEEVLNLAQSKNFHLRPRDLISNINVIVLE

LKGSETTFMCEYADETATIVEFLNRWITFCHSIISTLT
```

STK-011: A second exemplary hIL2 mutein of Formula 1 is the human IL2 mutein comprising the amino acid substitutions L18R, Q22E and Q126K and additionally comprising a deletion of Ala1 referred to herein as des-Ala1 REK, REK and STK-011. The amino acid sequence of STK-011 is provided below (SEQ ID NO:8):

```
                                        (SEQ ID NO: 8)
PTSSSTKKTQLQLEHLRLDLEMILNGINNYKNPKLTRMLTFKFYMPK

KATELKHLQCLEEELKPLEEVLNLAQSKNFHLRPRDLISNINVIVLE

LKGSETTFMCEYADETATIVEFLNRWITFCKSIISTLT
```

Samples of the STK-011 and STK-008 polypeptides were recombinantly produced in *E. coli* using conventional recombinant DNA technology and isolated in substantially pure form by conventional procedures including dialysis, ion exchange chromatography and size exclusion chromatography. By deleting the alanine typically present at position 1 of the hIL2 molecule, the N-terminal methionine is more efficiently removed by the bacterial producer cell by virtue of a proline at the position next to the N terminal methionine rather than an alanine and results in the expression and recovery of a substantially more hIL2 homogenous product which provides both economic and technical advantages such as increased process efficiency, lower cost, and simplified purification and refolding to produce a substantially pure homogenous protein product which results in a more consistent reagent when additional agents such as carrier or targeting molecules are conjugated to the N-terminus of the hIL2 polypeptide. As indicated in earlier reports and confirmed by the present studies, elimination of the alanine at position 1 does not substantially modify the biological activity of the resultant hIL2 polypeptide.

The ability of REH and REK to provide signaling via the IL2 receptor as evaluated by phosphorylation of STAT5 relative to wt hIL2 was evaluated in YT CD25 (CD25 positive) and YT (CD25 negative) cells in substantial accordance with the previous study and as described more fully in Examples 1-7. Briefly, 293T cells were transfected with IL-2 mutein constructs and after 2-3 days, supernatants containing the soluble hIL2 muteins were removed. The supernatants were added to YT and YT CD25 cells following a 20 minute stimulation. YT cells are a NK lymphoma cell line, which does not endogenously express detectable levels of CD25. IL-2 responses of YT cells and a derivative YT cell, exogenously expressing CD25 ("YT CD25) were compared. The expression of the components of the IL-2 receptor on YT CD25 cells was verified by fluorescent flow cytometry and the data presented in FIG. 6 of the attached drawings, Panel A and B demonstrating expression of CD25 (IL2Rα), CD122 (IL2Rβ), and CD132 (IL2Rγ) by YT cells and YT CD25 cells, respectively. Filled histograms indicate stained cells and dashed histograms indicate unstained control cells. Gates indicate the percent positive cells for each stain. The pSTAT5 levels were measured by flow cytometry. IL-2 concentration in supernatants measured by MSD assay. The mean fluorescent intensity data generated from this experiment is provided in Tables 6 and 7 below.

TABLE 6

| pSTAT5 MFI in treated YT CD25+ Cells | | | | | | | | | | |
|---|---|---|---|---|---|---|---|---|---|---|
| Supernatant Dilution | Untransfected | | Empty | | wt hIL2 | | REH | | REK | |
| 1:2 | 991 | 1058 | 1021 | 1015 | 21882 | 20337 | 22248 | 23922 | 21176 | 22404 |
| 1:4 | 1094 | 1084 | 1180 | 1080 | 20568 | 22024 | 20858 | 22407 | 21255 | 21241 |
| 1:8 | 1069 | 1150 | 1019 | 1084 | 21583 | 21557 | 21464 | 21675 | 20648 | 21053 |
| 1:16 | 1133 | 1048 | 1158 | 1067 | 19846 | 22331 | 20627 | 20841 | 20951 | 20588 |
| 1:32 | 1175 | 1081 | 1122 | 1044 | 19023 | 20522 | 21164 | 21890 | 19189 | 19600 |
| 1:64 | 1065 | 1015 | 1057 | 1120 | 20967 | 20823 | 20651 | 21139 | 20930 | 19283 |
| 1:128 | 1068 | 1090 | 1099 | 1044 | 18118 | 21921 | 23158 | 20999 | 18968 | 19482 |

TABLE 7

| P-STAT5 MFI in treated YT (CD25 NEGATIVE) Cells | | | | | | | | | | |
|---|---|---|---|---|---|---|---|---|---|---|
| Supernatant Dilution | Untransfected | | Empty | | wt hIL2 | | REH | | REK | |
| 1:2 | 959 | 988 | 930 | 941 | 25483 | 26572 | 24955 | 26085 | 20485 | 20835 |
| 1:4 | 931 | 1015 | 924 | 856 | 23197 | 23079 | 21713 | 23060 | 12843 | 13798 |
| 1:8 | 868 | 952 | 920 | 843 | 21160 | 22836 | 19475 | 18404 | 8374 | 7907 |
| 1:16 | 961 | 926 | 852 | 1093 | 22670 | 21882 | 17282 | 15044 | 4363 | 4280 |
| 1:32 | 983 | 912 | 886 | 917 | 21323 | 21734 | 12086 | 11940 | 2564 | 2467 |
| 1:64 | 964 | 884 | 920 | 925 | 19220 | 19045 | 7456 | 6895 | 1834 | 1579 |
| 1:128 | 976 | 999 | 902 | 982 | 17318 | 18179 | 4766 | 4711 | 1551 | 1386 |

As the foregoing data in Tables 6 and 7 demonstrates, REH and REK, provide selective activation of CD25 positive T cells relative to CD25 negative T cells as demonstrated by enhanced (comparable to wt hIL2) pSTAT5 production in a human immune cell expressing the high affinity trimeric CD25/CD122/CD132 hIL2 receptor (YT CD25 cells) relative to pSTAT5 in a human immune cell expressing the intermediate affinity dimeric CD122/CD132 hIL2 receptor, YT cells STK-010 and STK-012: To provide favorable pharmacokinetics in vivo (e.g. extended duration of action) the N-terminal prolines of the STK-008 and STK-011 muteins were conjugated to a 40 kd (20 kD×2arm) branched PEG moiety via a linker to provide compounds referred to herein as STK-010 and STK-012, respectively. The branched 40 kD PEG and linker conjugated to the N-terminal prolines of STK-008 and STK-011 to produce STK-010 and STK-012 has the structure:

$$\begin{matrix}\text{PEG(20kD)}-CH_2 \\ \quad\backslash \\ \quad CH-CH_2-O-\overset{\overset{\displaystyle O}{\|}}{C}-NH-CH_2-CH_2-CH_2-NH- \\ \quad/ \\ \text{PEG(20kD)}-CH_2\end{matrix}$$

Figure 6:
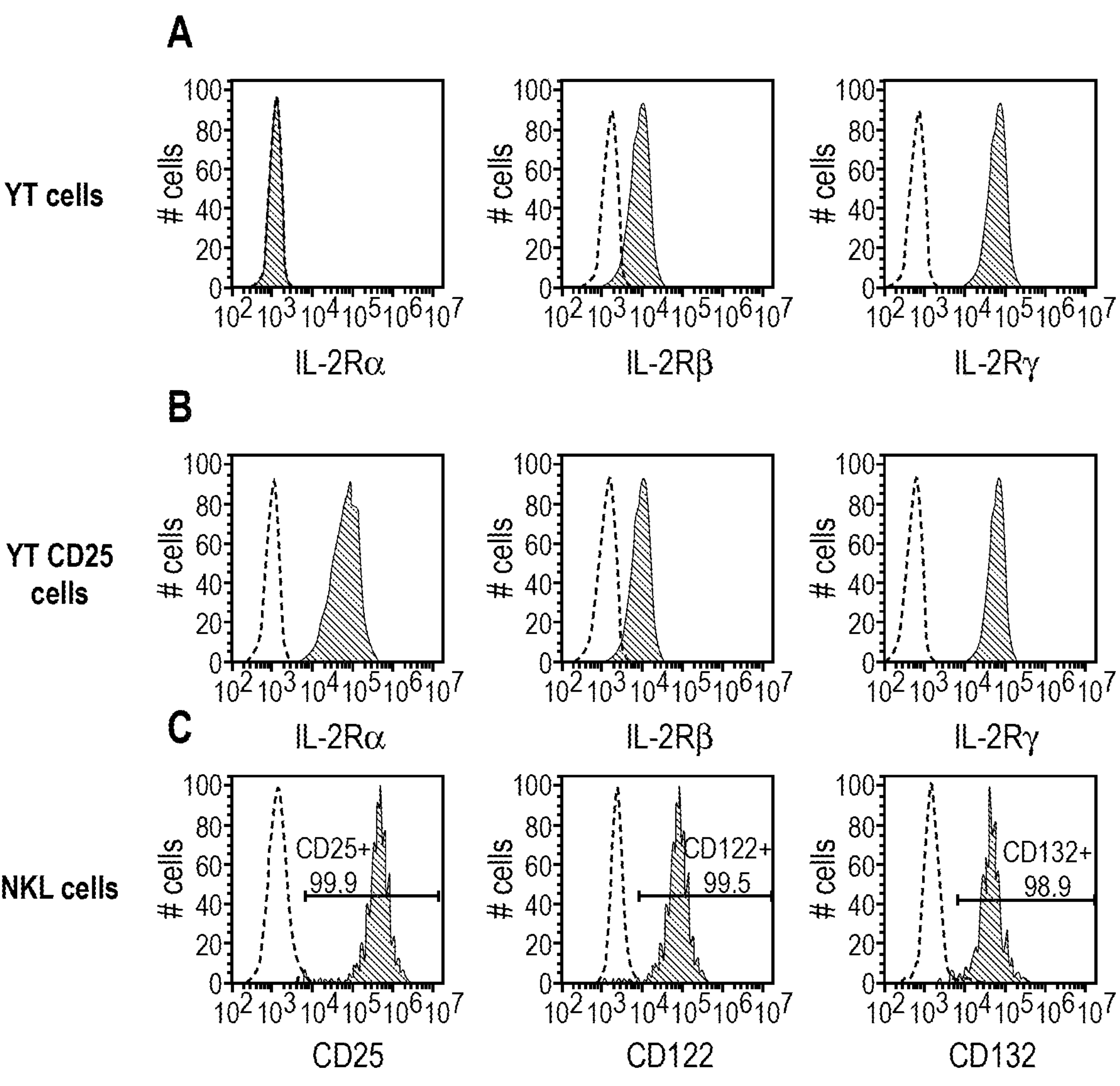
FIG. 6 provides data regarding the expression of the components of the IL-2 receptor on YT CD25 cells was verified by fluorescent flow cytometry Panel A demonstrating expression of CD25 (IL2Rα), panel B demonstrating expression of CD122 (IL2Rb), and panel C demonstrating expression of CD132 (IL2Rg) by YT CD25 NKL cells. Filled histograms indicate stained cells and dashed histograms indicate unstained control cells. Gates indicate the percent positive cells for each stain.

In Vitro Characterization of STK-012: The biological activities of STK-012 were assessed by a proliferation bioassay using NKL cells. NKL is a natural killer cell line that expresses the wildtype human high affinity IL-2 receptor (CD25/CD122/CD132) and is responsive to human IL-2. The expression of the component of the IL-2 receptor was verified by fluorescent flow cytometry (FIG. 6). As indicated by the data presented, expression of the trimeric, high affinity IL-2R renders the NKL cells responsive to STK-012. The biological activity of both wild-type human IL-2 and STK-012 was evaluated in a proliferation assay using the NKL cell line, a human lymphoblastic NK cell line. Specificity of STK-012 for CD25 expressing cells was established in a pSTAT5 activity assay in YT cells and YT CD25. As shown in the data presented in FIG. 7 of the attached drawings, human IL-2 and STK-012 induced proliferation of NKL cells in a similar dose range demonstrating that STK-012 retains the ability to induce pSTAT5 in a human immune cell comparable to wt hIL2.

STK-014: An STK-012 Murine Surrogate For Efficacy Studies in Mice: The interface between IL2 and its receptor components is slightly different between rodent (e.g mouse) IL2 and primate (e.g., human) 112 molecules. Consequently, to demonstrate the activity of the human IL2 muteins in murine models, a representative human I12 mutein of the present disclosure was selected (STK-012) and a murine IL2 mutein surrogate (STK-014) was developed for in vivo studies in mice to correlate activity between the rodent (mouse) and primate (human) environments. The amino acid sequence of the murine IL2 (mIL2) polypeptide component of STK-014 is:

```
                                   (SEQ ID NO: 11)
A P T S S S T S S S T A E A Q Q Q Q Q H L E Q L

R M D L E E L L S R M E N Y R N L K L P R M L T

F K F Y L P K Q A T E L K D L Q C L E D E L G P

L R H V L D L T Q S K S F Q L E D A E N F I S N

I R V T V V K L K G S D N T F E C Q F D D E S A

T V V D F L R R W I A F C H S I I S T S P Q
```

The foregoing IL2 polypeptide is N-terminally PEGylated with a PEG linker of the structure as used in the preparation of STK-010 and STK-012 above to complete the STK-014 molecule.

To demonstrate that STK-014 represents is a valid surrogate for STK-012, a study was conducted to evaluate target specificity on mouse and human cells. A study was performed to evaluate the relative potencies of human wild type IL-2 (huIL-2) and STK-012 by comparing the EC50 of each molecule in inducing phospho-STAT5 (pSTAT5) in primary human CD8+ T cells, activated by anti-CD3/anti-CD28 stimulation, and in primary human NK cells. Both cell types were isolated from fresh donor peripheral blood monocytic cells (PBMCs). As the STK-014 is a murine IL2 mutein, it was tested on equivalent cell populations freshly isolated from mouse spleen. The results of this study are provided in Table 8 below:

TABLE 8

Potency of Human and Murine IL2 muteins in pSTAT5 Assay

| Test Condition | hIL2 | STK-012 | STK-014 |
|---|---|---|---|
| CD25+ CD8+/NK selectivity (p-STAT5) | 5.6 | $>10^3$ | $>10^6$ |
| CD25+ CD8+/CD25− CD8 selectivity (p-STAT5) | 1.75 | $>10^3$ | $>10^6$ |

The data provided in Table 8 demonstrates that STK-014 represents a valid surrogate for STK-012 for use in in vivo efficacy models as STK-014 possesses a similar target specificity on mouse cells as STK-012 exhibits on human cells.

In Vivo Efficacy Studies with STK-014 in Mice

Several in vivo efficacy and in vivo pharmacology studies were performed in mice with STK-014 which serves as a mouse surrogate for human STK-012. These studies were performed to evaluate the ability of STK-014 to expand and activate antigen activated T cells in vivo and to test anti-tumor efficacy and toxicity of STK-014 alone and in combination with anti-PD-1 in mouse tumor models. Additionally, toxicity of the molecules administered was evaluated in the animal involved in the toxicology studies. The activity of STK-014 was compared to pegylated wild-type mouse IL-2 (mPEG-IL-2). STK-014 showed improved anti-tumor activity and increased tumor infiltration by T cells compared to mPEG-IL-2 as well as improved toxicity relative to mPEG-IL-2 including significantly reduced lethality and reduced evidence of capillary leak syndrome (CLS). STK-014 did not show lethality or evidence of significant CLS.

Figure 9:
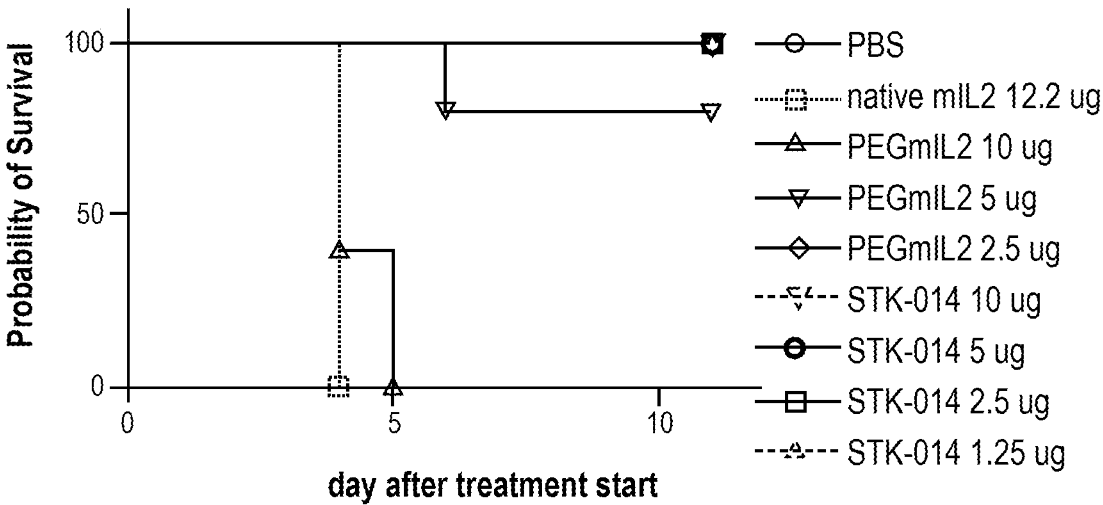
FIG. 9 provides data relating to the survival of mice treated with the various dosages and agents listed and as more fully described in the specification.

Establishing the Maximal Tolerated Dose of STK-014: In clinical oncology practice IL-2 is dosed at or close to the maximally tolerated dose (MTD), in a 3× per day dose schedule to maintain high serum exposure to overcome the short half-life of recombinant IL-2 (Atkins, et al. supra). In order to establish the maximum tolerated dose of PEGmIL2 and/or STK-014 for the in vivo studies, the MTD for recombinant mIL-2, a pegylated mouse wild type IL-2 with a 40 kD PEG moiety covalently linked to the N-terminus (PEGmIL-2) and STK-014 were established. C57BL/6 mice were dosed 3 time per day for five days. Wt IL-2 was dosed 3×/day. All other molecules were dosed every other day with wrong dosing on day 3, so dosing was day 0-2-3-5-7-9 with recombinant mIL-2 and every other day with PEG-mIL2 or STK-014 at the dosages provided in the legend of FIG. 9 and Kaplan-Meier survival plot of the results of the study are presented in FIG. 9 of the attached drawing. As indicated by the data presented in FIG. 9, lethality was observed both with mIL-2 and with PEGmIL-2 (at doses of 5 gg q.o.d. and above) but not with STK-014. The foregoing data demonstrates the hIL2 muteins of the present disclosure possess reduced toxicity relative to wt hIL2 and suggests a significant safety advantage relative to HD-hIL2.

Figure 10:
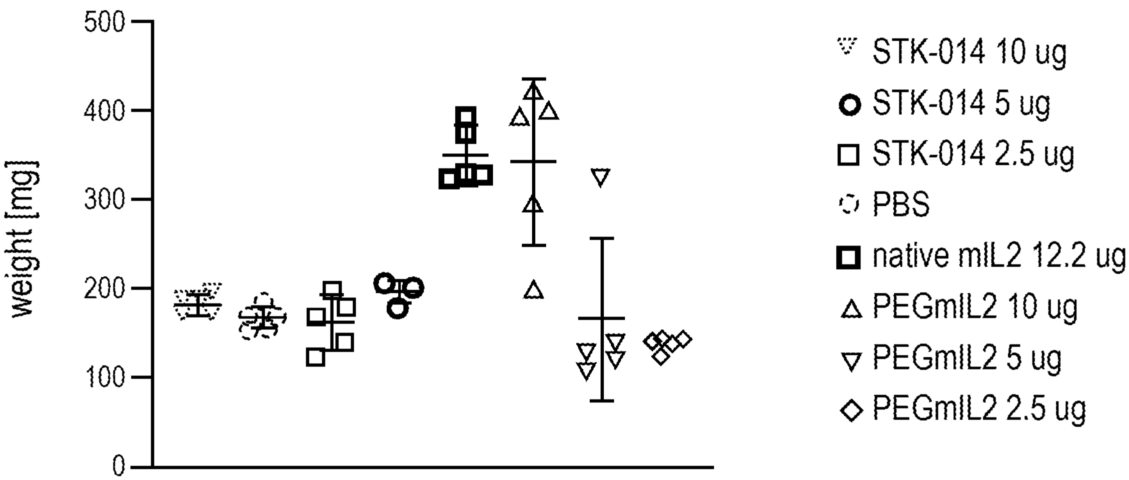
FIG. 10 provides data relating to the water content of the lungs of mice treated with mIL-2 or STK-014, calculated as the differences between the weight of the wet lung minus the lung after desiccation. Lungs were harvested at the end of the study or at the time of premature termination or death (in mIL-2 treated animals).

Evaluation of Capillary Leak in Response to PEGmIL-2 and STK-014: Patients on HD-IL-2 have acute hypotension and CLS after receiving 3 or more days of consecutive HD-IL-2 treatment, or a median of 8 doses given 8 hours apart. In the aforementioned study to establish the MTD lungs were harvested at the end of the study or at the time of premature termination or death (in mIL-2 treated animals). As a measure for CLS, the water content of the lungs from mice treated with mIL-2 or STK-014 was calculated as the differences between the weight of the fresh lung minus the lung weight after desiccation. The results of this study are presented in FIG. 10 of the attached drawings. As the data provided in FIG. 10 illustrates, animals treated with HD-IL-2 or PEGmIL-2 but not mice with STK-014 had an increased wet lung weight, indicative of capillary leak.

Figure 11:
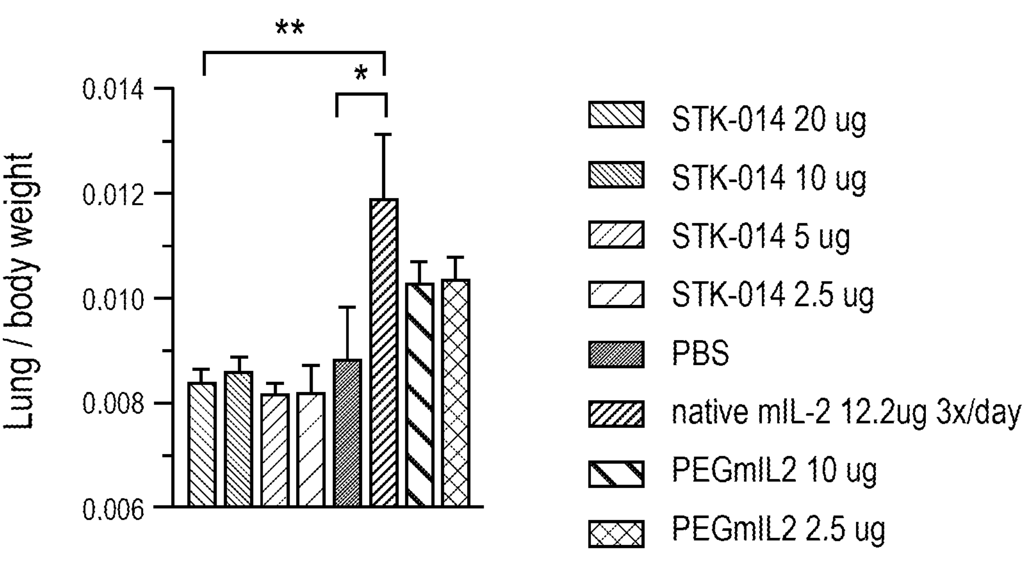
FIG. 11 provides data relating to lung weight as a percentage of bodyweight of mice treated with mIL-2 or STK-014 at the various dosages indicated. Lungs were harvested at the end of the study or at the time of premature termination or death (in mIL-2 treated animals).

To directly compare STK-014 to IL-2 during the early onset of CLS, mice were treated for 3 days with two doses of PEG-mIL2 or STK-014 two days apart at the dose levels indicated in the legend of FIG. 11. Additionally, wt mIL2 (not PEGylated) was administered at a dose of 12.2 ug (HD-mouse IL-2) to simulate the HD-hIL2 therapy. Wet lung weights were determined in relation to the total starting bodyweight. The results of this study are presented in FIG. 11 of the attached drawings. As the data provided in FIG. 11 illustrates, animals treated with HD-IL-2, PEGmIL-2 but not mice with STK-014 had an increased wet lung weight to bodyweight ratio, indicative of capillary leak. The foregoing data demonstrates the hIL2 muteins of the present disclosure possess reduced risk of CLS relative to wt hIL2 and suggests a significant safety advantage relative to HD-hIL2 in the treatment of human subjects.

Evaluation of STK-014 in a Syngeneic CT26 Colon Cancer Model:

The antitumor efficacy of STK-014 was tested in a murine CT-26 colon carcinoma model in Balb/C mice. The study design and treatment groups are summarized in Table 9 below:

TABLE 9

Study Design Evaluating Anti-tumor Efficacy of STK-014

| Group | Cells | Treatment | Dose and Dosing | Mice/ group |
|---|---|---|---|---|
| 1 | CT-26 ($3 \times 10^5$ cells) | PBS | qod. | 9 |
| 2 | CT-26 ($3 \times 10^5$ cells) | mIL-2 native | 10 μg q.d. | 9 |
| 3 | CT-26 ($3 \times 10^5$ cells) | PEG-mIL-2 | 2 μg qod | 9 |
| 4 | CT-26 ($3 \times 10^5$ cells) | STK-014 | 10 μg qod | 9 |

Figure 12:
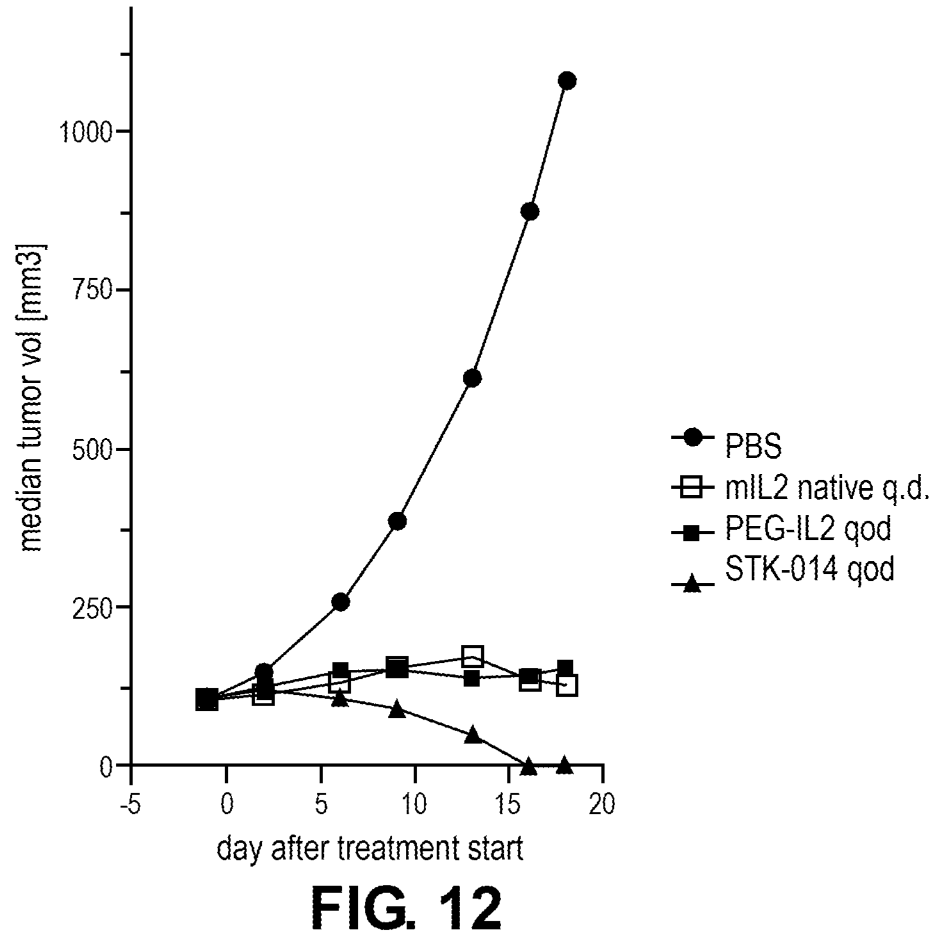
FIG. 12 provides data relating to tumor volume over the course of a CT-26 colon carcinoma model study in mice in response to STK-014 treatment, PEGmIL2 and controls.

Briefly, CT-26 colon carcinoma ($3\times10^5$ cells) were subcutaneously injected, tumors were allowed to grow to a tumor size of >100 $mm^3$ and treatment started after 10 days following tumor cell implant. The mice were dosed in accordance with Table 9. During the treatment phase, tumor size was measured by caliper measurement two times per week. The results of this CT26 study are presented graphically in FIG. 12 of the attached drawings. As shown in FIG. 12, only the STK-014 treatment group (Group 4) resulted in rejection of tumors in more than 50% of mice in the CT-26 Colon carcinoma model. This data suggests that hIL2 muteins of the present disclosure including PEGylated variants thereof possess improved anti-tumor efficacy in human subjects relative to wt hIL2 therapy.

Figure 13:
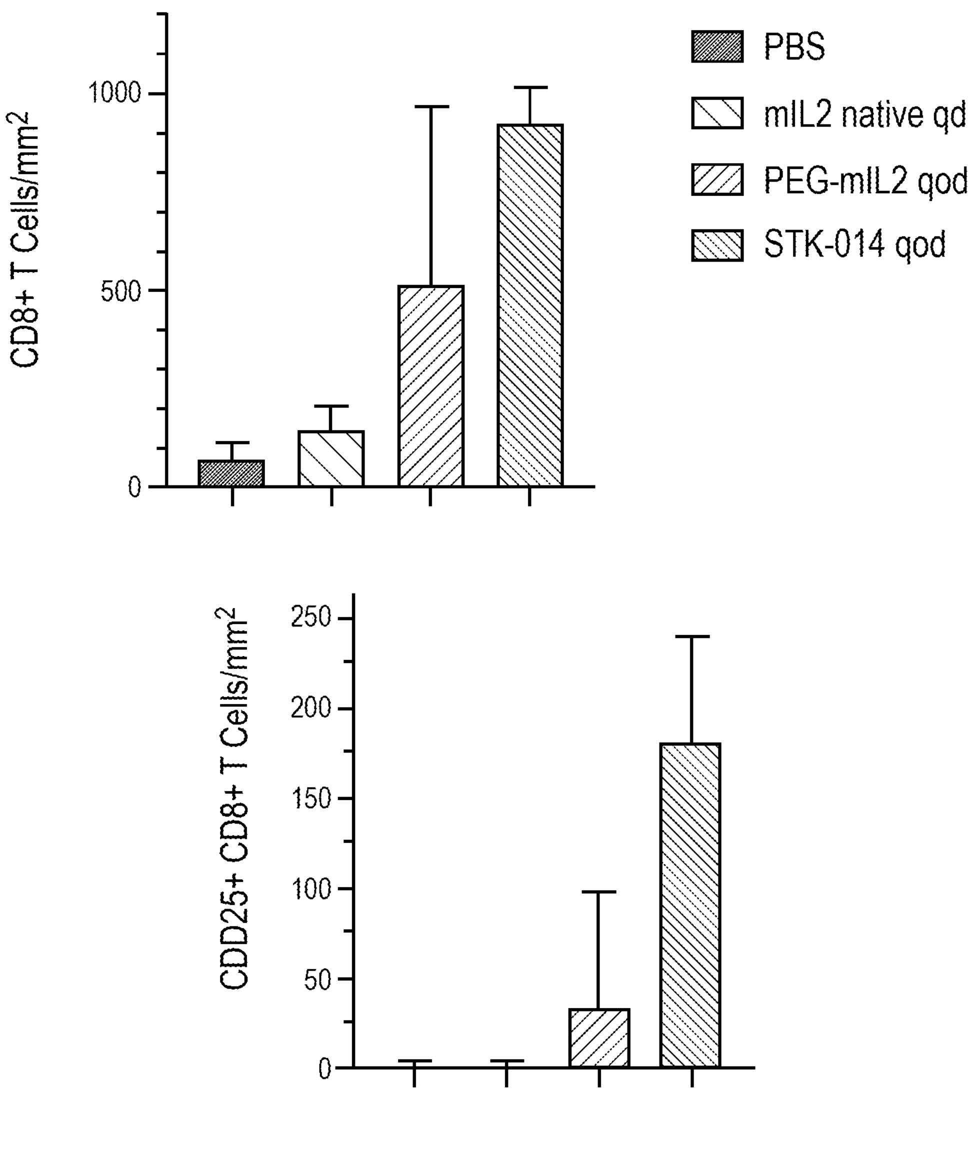
FIG. 13 provides data relating to immunohistochemical evaluation of relating to the intratumoral expansion of CD8+ and CD8+CD25+ T cells in response to STK-014 in a CT-26 colon carcinoma model study.
Figure 14:
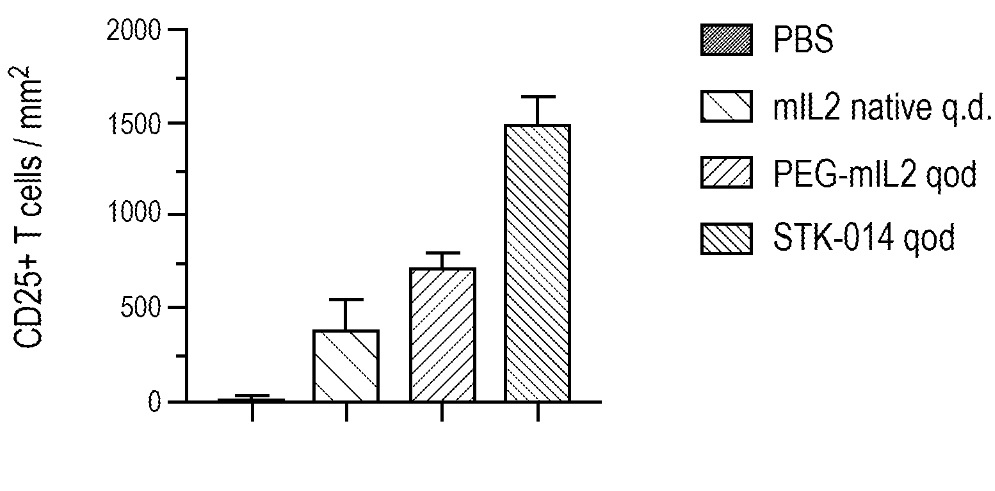
FIG. 14 provides data relating to immunohistochemical evaluation of relating to the expansion of CD25+ T cells in the spleen of mice in response to STK-014 in a CT-26 colon carcinoma model study.

Analysis of Tumor Infiltrating T Cells in the CT-26 Tumor Model: The organs harvested from the animals of the foregoing CT26 tumor model study were evaluated by immunohistochemistry. Immunohistochemical analysis of the tissues demonstrates that the tumors of STK-014 treated mice showed robust expansion of intratumoral CD8+ T cells as compared to PEG-mIL-2 (FIG. 13 Panel A). An even greater expansion of intratumoral CD25+CD8+ T cells was observed in the tumor indicating the CD25 selectivity of STK-014 (FIG. 13 Panel B). CD25+ T cells, including Treg were also strongly expanded by STK-014 treatment and to a lesser degree by PEG-IL-2 in the spleen (FIG. 14). The infiltration of T cells in human tumors are prognostically associated with improved patient survival independently of the tumor staging (Fridman, et al. 2012). Similarly, response to immune checkpoint blockade is correlated with a high infiltration of CD8+ T cells in the tumor (Tumeh, et al. 2014). Consequently, the increased intratumoral infiltration of CD8+T observed with STK-014, the murine surrogate of the hIL2 mutein of the Formula 1, suggests that the hIL2 muteins of the present disclosure similarly exhibit such increases in intratumor T cells which are associated with improved clinical outcomes in human cancer patients.

MC38 Syngeneic Colon Cancer Model:

In addition to the foregoing CT-26 colon carcinoma study, representative compositions and methods of the present disclosure were evaluated in the MC-38 colon cancer model. The study design and treatment groups for the MC38 study are summarized in Table 10 below:

TABLE 10

Study Design Evaluating Anti-tumor Efficacy of MC-38 colon carcinoma

| Group | Cells | Treatment | Dose | Mice/ Group |
|---|---|---|---|---|
| 1 | MC-38 ($1 \times 10^6$ cells) | PBS | q.d. | 8 |
| 2 | MC-38 ($1 \times 10^6$ cells) | PEG-mIL-2 | 2 μg q.o.d. | 8 |
| 3 | MC-38 ($1 \times 10^6$ cells) | STK-014 | 3.3 μg q.o.d. | 8 |
| 4 | MC-38 ($1 \times 10^6$ cells) | STK-014 | 10 μg q.o.d. | 8 |

Figure 15:
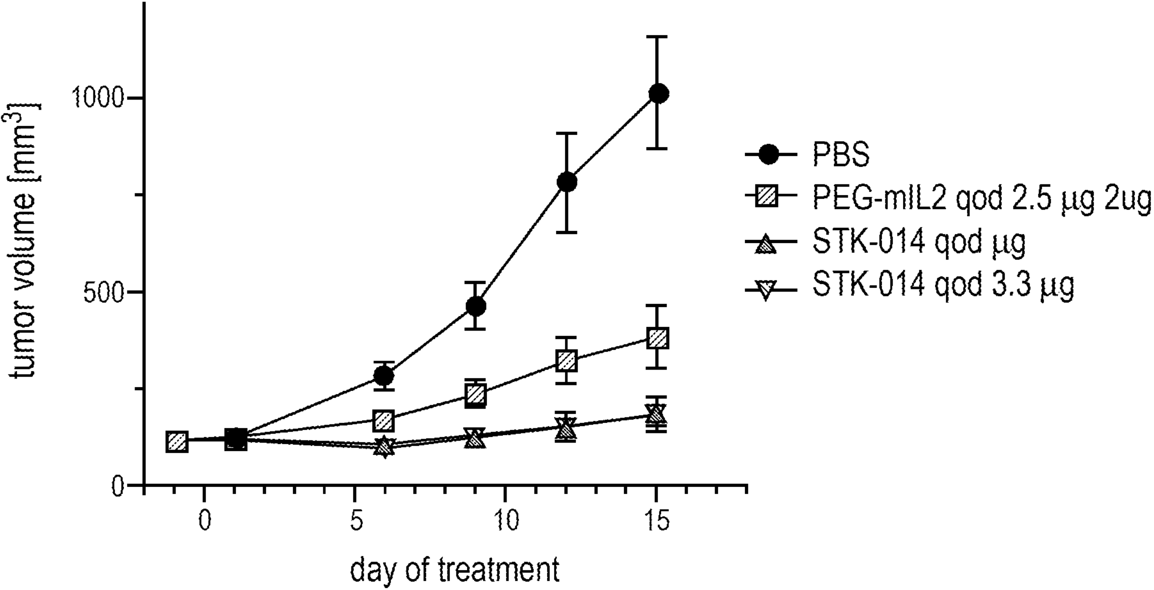
FIG. 15 provides data relating to the tumor volume (y-axis) over the course of the MC38 colon carcinoma model in mice illustrating the change in tumor volume over time in response to STK-014 and PEG-mIL-2.

Briefly, MC-38 colon cancer cells ($1\times10^6$ cells) were injected subcutaneously into mice and allowed to form local tumors for 18 days. Mice were left untreated or were from day 18 treated with STK-014. STK-014 treatment continued throughout the observation period. The results of this study are presented in FIG. 15 of the attached drawings. As illustrated, treatment with STK-014 led to tumor control and regressions, while PEG-mIL-2 monotherapy showed a reduced capability to control the tumor.

Figure 16A:
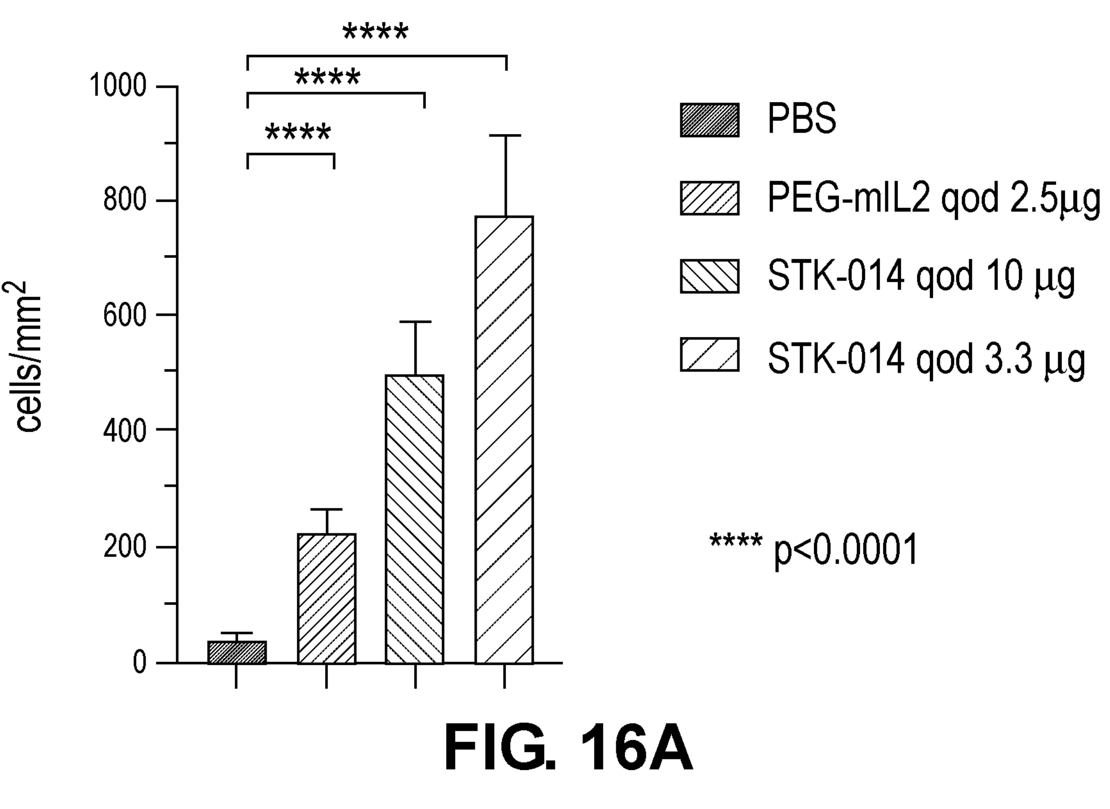
FIG. 16A and FIG. 16B provides data relating to the quantification of CD8+ T cells and CD25+CD8+ T cells by IHC, respectively, within MC38 tumors at the end of the treatment interval with STK-014 and PEG-mIL-2.
Figure 16B:
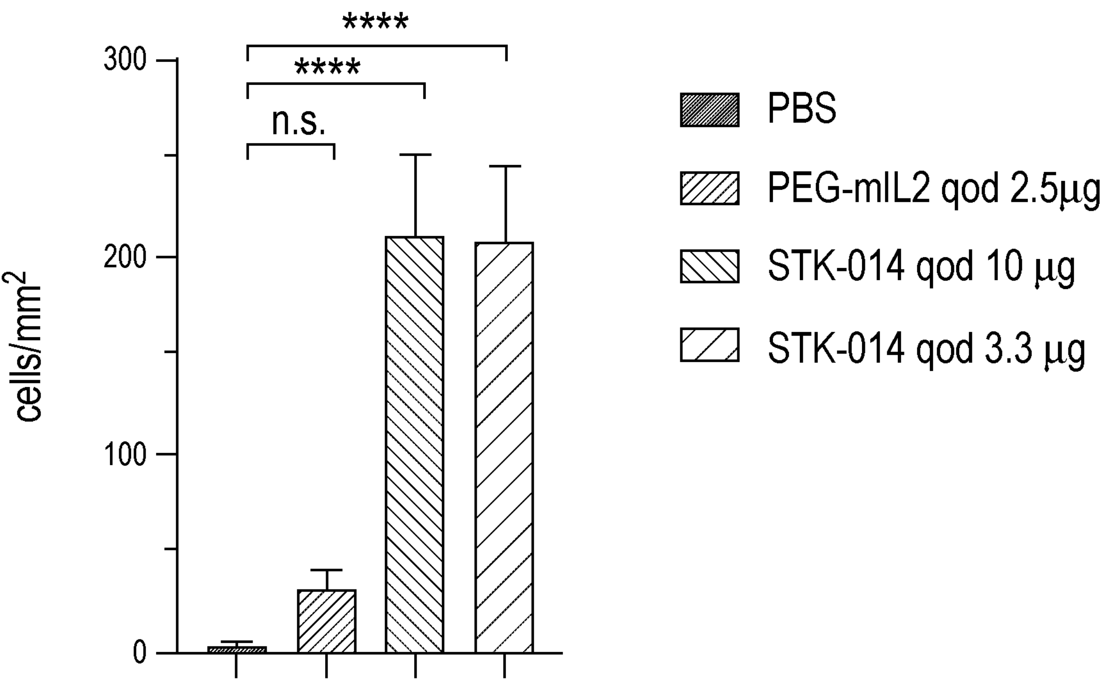

Increased Intratumoral CD8+ T cells: The organs harvested from the animals of the foregoing MC38 tumor model study were evaluated by immunohistochemistry. Immunohistochemical analysis of the tissues demonstrates that the tumors of STK-014 treated mice showed robust expansion of intratumoral CD8+ T cells as compared PEG-mIL-2. As shown in FIG. 16A, treatment with PEG-mIL-2 increased the number of intratumoral CD8+T cells in MC-38 tumors, but treatment with STK-014 further improved T cell infiltration into MC-38 tumors. Similarly, as shown in FIG. 16B, STK-014 also increased the number of CD8+CD25+ T cells in MC-38 tumors.

Vascular Leak Syndrome: As previously discussed, wt hIL2 (particularly HD-hIL2) therapy results in significant toxicity, particularly arising from vascular leak syndrome ("VLS). Exemplary hIL2 muteins of the present disclosure were evaluated in vivo in mouse and non-human primates as discussed in more detail below. In mouse toxicity models STK-014 showed reduced toxicity, without induction of vascular leak syndrome. In efficacy studies with STK-014 in syngeneic mouse tumor models, the hIL2 muteins of the present disclosure provide favorable toxicity relative to wt hIL2.

Figure 19:
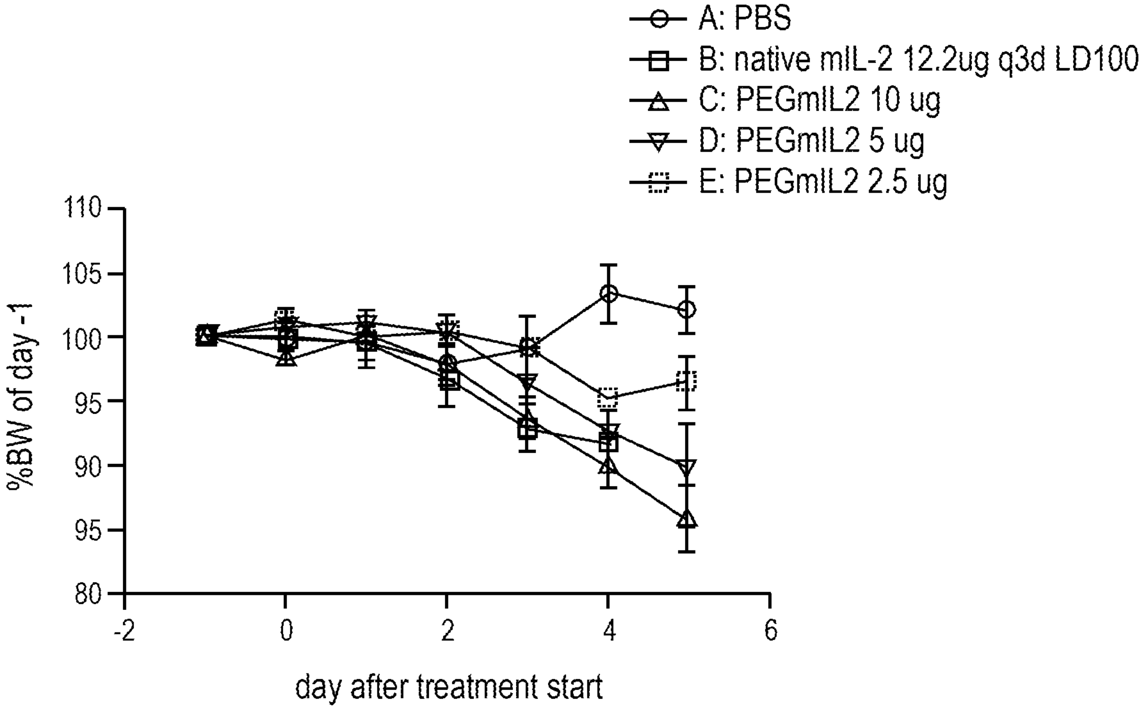
FIG. 19 provides data relating to changes in bodyweight amount in mice in the MC38 tumor model in response to the treatments indicated.
Figure 18:
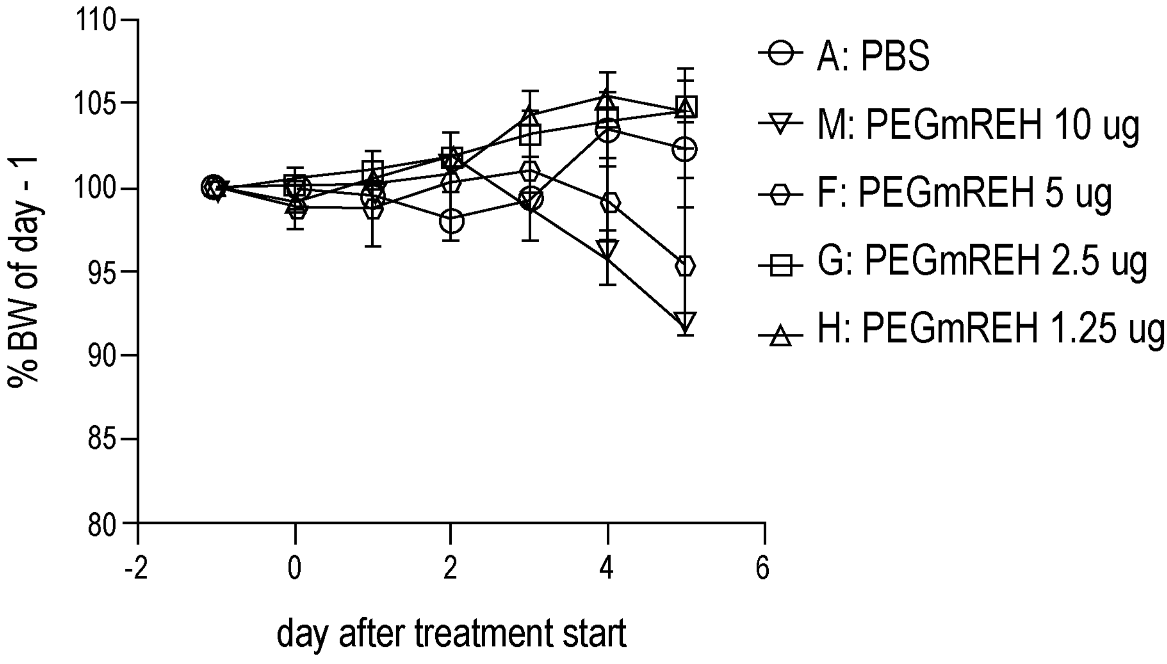
FIG. 18 provides data relating to the quantitation by IHC analysis of CD8+ T cells and Tregs in MC38 tumors at the end of the treatment period.

Assessment of VLS In Mice: As VLS is associated with weight gain and wet organ weight increase, but overall weight loss due to letargy. Briefly, an experiment was conducted where mice were dosed daily with a STK-014 at dosages of 1.25, 2.5 5 and 10 micrograms with a phosphate buffered saline as a control. The results of this experiment as shown in FIG. 18 did not evidence significant weight loss (less than 8% in the test animals indicating the absence of VLS in mice in response to treatment with the compositions of the present disclosure. In addition to weight gain associated with VLS, substantial loss in bodyweight is indicative of systemic toxicity in mice. An experiment was conducted to evaluate the effect of wild type murine IL2 at a dose of 12.2 micrograms given three times daily as well as 40 kD N-terminally PEGylated wt mIL2 molecule at dosages of 2.5, 5 and 10 micrograms. The results of the experiments are provided in graphical format in FIG. 19 of the attached drawings. As shown in FIG. 19, wt mIL2 results in significant weight loss in the mice which is exacerbated by the extended duration PEGylated wt mIL2 molecules. In contrast, the data in FIG. 19 demonstrates that the similarly PEGylated mIL2 REH variant did not induce significant weight loss. Collectively, these data that the molecules of the present disclosure possess reduced toxicity relative to wild-type IL2 in both native and long-acting forms.

Figure 17:
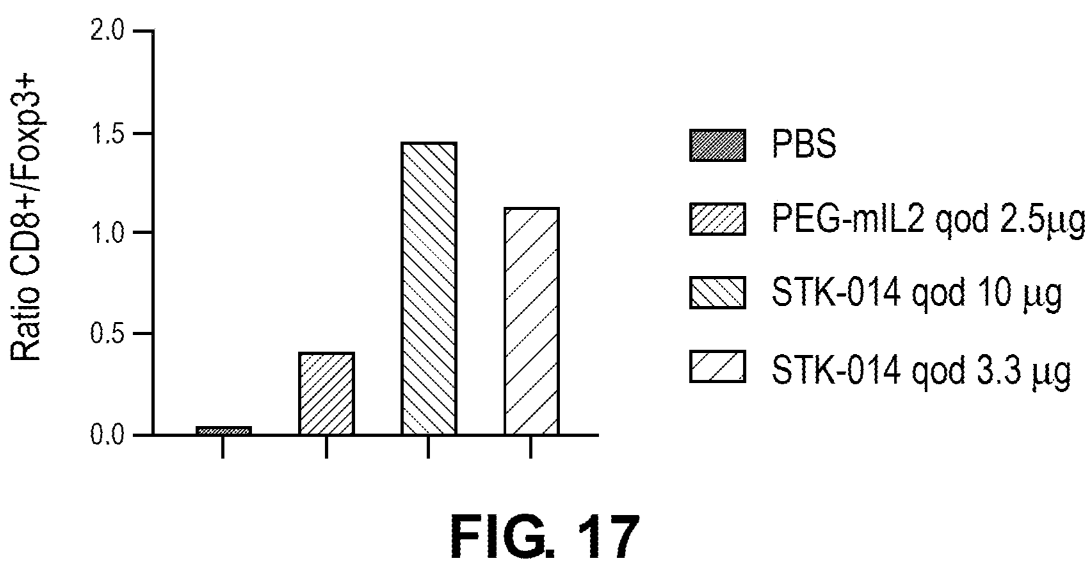
FIG. 17 provides data relating to the intratumoral CD8+ T cell to regulatory T cells in MC38 tumors at the in response to treatment with STK-014 and PEG-mIL-2.

Summary of in vivo Pharmacology Data in Mice: The benefit of immune therapy is often correlated with the relative increase of effector T cells vs. regulatory T cells. STK-014 most significantly increased the CD8/Treg ratio in the tumor (FIG. 17). In efficacy studies with STK-014 in syngeneic mice, STK-014 induces significantly stronger activation and expansion of intratumoral T cells compared to wt-mIL-2. Analysis of T cells in the tumors of treated mice showed robust expansions of intratumoral CD8+ T cells in response to STK-014, compared to PEG-IL-2. An even greater increase was observed with CD25+CD8+ T cells, indicating the CD25 selectivity of STK-014. CD25+ T cells, including Treg were also strongly expanded by STK-014 treatment and to a lesser degree by PEG-IL-2 in the spleen. Additionally STK-014 treatment did not induce HD-IL-2 associated lethality and capillary leak syndrome in mice. STK-014 induced tumor control/complete responses in syngeneic tumor models. STK-014 dosing increases the number of tumor infiltrating CD8+ T cells, CD25+CD8+ T cells and Granzyme (data not shown) expressing cells.

Combination Efficacy of STK-014 with anti-PD-1: Anti-PD-1 immune checkpoint blockade is a hallmark of immune therapy of human tumors. STK-014 combination treatment with anti-PD-1 was evaluated in MC-38 tumors, which are partially responsive to anti-PD-1 therapy. MC-38 tumors were well established prior to the start of the treatment to allow for an immune modulating tumor microenvironment to develop. Mice were treated with anti-PD-i, PEG-mIL-2 or STK-014 alone or in combination (Table 11).

TABLE 11

Study Design for Combination Treatment with STK-014 and PD1 inhibitor in MC38 Tumor Model

| Group | Cells | Treatment | Dose | Mice |
|---|---|---|---|---|
| 1 | MC-38 ($1 \times 10^6$ cells) | PBS | q.d. | 10 |
| 2 | MC-38 ($1 \times 10^6$ cells) | Anti-PD-1 | 10 mg/kg q4d | 10 |

TABLE 11-continued

Study Design for Combination Treatment with STK-014 and PD1 inhibitor in MC38 Tumor Model

| Group | Cells | Treatment | Dose | Mice |
|---|---|---|---|---|
| 3 | MC-38 (1 × $10^6$ cells) | PEG-mIL-2 | 0.125 mg/kg qod | 10 |
| 4 | MC-38 (1 × $10^6$ cells) | STK-014 | 0.5 mg/kg qod | 8 |
| 5 | MC-38 (1 × $10^6$ cells) | Anti-PD-1/ PEG-mIL-2 | 10 mg/kg q4d/ 0.125 mg/kg qod | 10 |
| 6 | MC-38 (1 × $10^6$ cells) | Anti-PD-1/ STK-014 | 10 mg/kg q4d/ 0.5 mg/kg qod | 8 |

Figure 20:
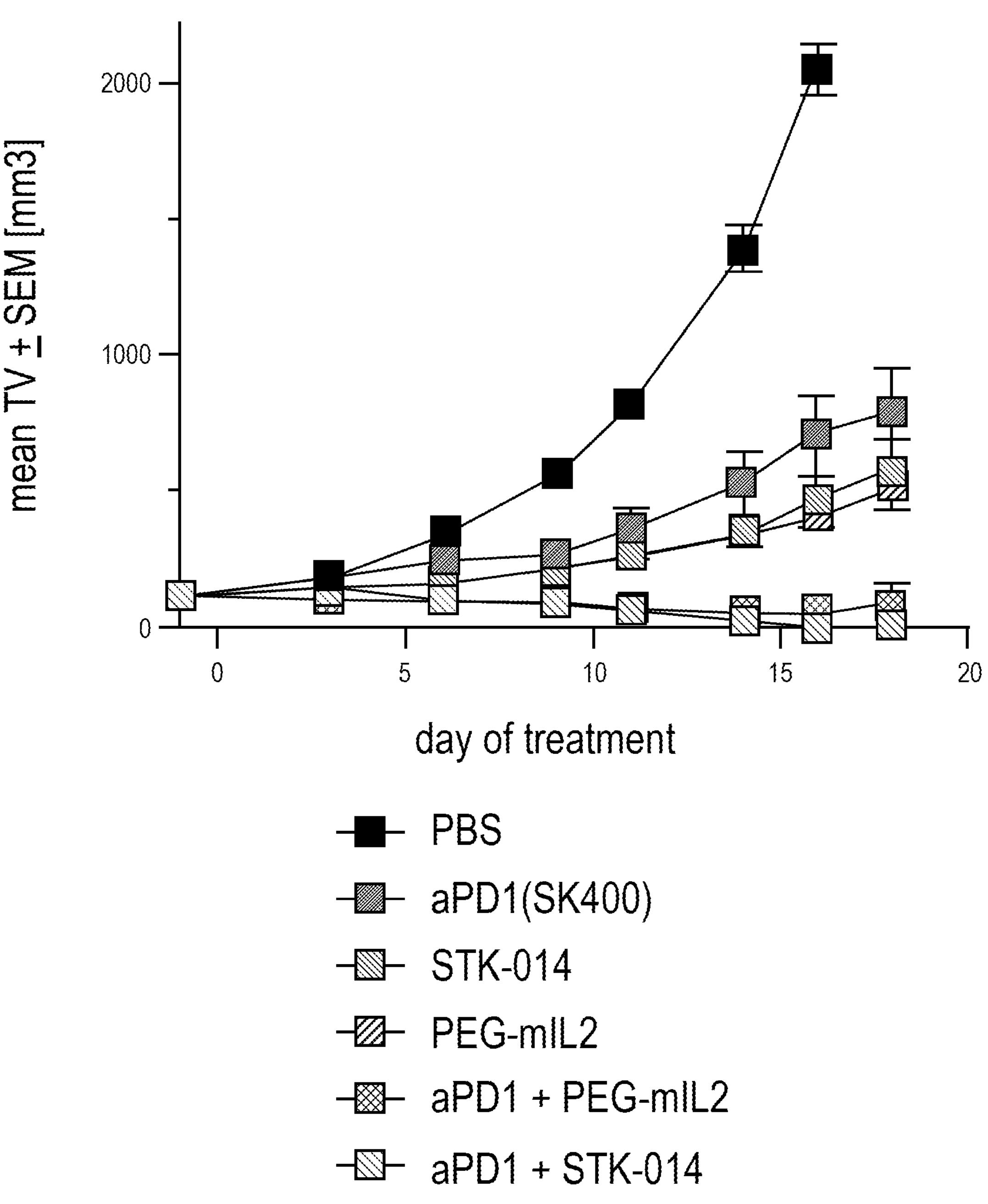
FIG. 20 provides data relating to tumor volume in an MC38 tumor model in mice in response to treatment with STK-014 in combination with anti-PD-1 treatment.
Figure 21:
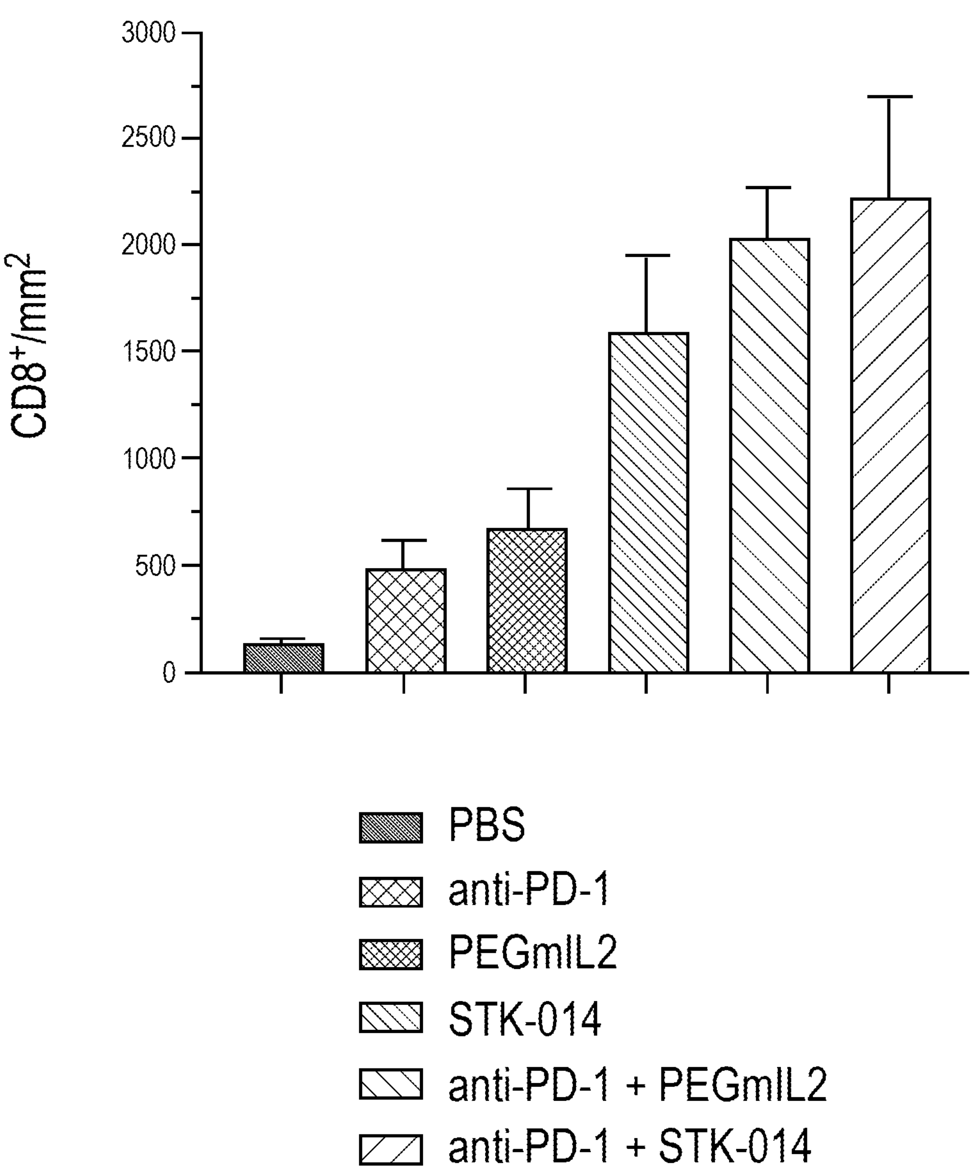
FIG. 21 provides data relating to the levels of intratumoral T cells in MC38 tumor model in mice in response to treatment with STK-014, an anti-PD1 antibody and the combination of STKO14 and anti-PD-1 treatment.

The results of the foregoing study are provided in FIG. 20 of the attached drawings. Both, PEG-IL-2 and STK-014 had single agent efficacy inducing partial response in this tumor model. Combination of either agent with anti-PD-1 increased the anti-tumor efficacy with 100% complete responses in STK-014+anti-PD-1 combination (FIG. 20). Additionally the presence of intratumor T cells was evaluated as above and the results provided in FIG. 21 of the attached drawings. As shown, the combination of STK-014 and anti-PD-1 results in tumor eradication in mouse model and is associated with the increased number of intratumoral CD8+ T cells.

Non-Human Primate Studies:

In addition to the foregoing toxicity studies in mice, the STK-012 was evaluated in a non-human primate (NHP) toxicology study. STK-012 was tolerated in a 2-week pharmacokinetic (PK) and tolerability study at supra-efficacious doses and exposures. In summary, STK-012 and its murine surrogate STK-014 did not show toxicities associated with pegylated murine IL-2 despite significantly higher exposures.

Non-GLP Tolerability and Toxicology Study of STK-012 in Non-Human Primates A non-GLP tolerability and toxicokinetic multiple ascending dose (MAD) study for STK-012 in cynomolgus monkeys has been performed by Sponsor. Nonhuman primates (NHP) were dosed for up to two weeks and up to two doses with STK-012 (Table 12) below:

TABLE 12

Dose Frequency and Dose Level for non-GLP Tolerability and Toxicology Study in Non-Human Primates

| | | | Dose Level (mg/kg) | |
|---|---|---|---|---|
| Group | Test Material | Dose Frequency | Day 1 | Day 8 |
| 1 | Proleukin (control) | single dose | 0.037 | — |
| 2 | STK-012 | q7d | 0.01 | 0.05 |
| 3 | STK-012 | q7d | 0.1 | 0.36 |

Serum PK, cytokine analysis, cell flow cytometry, clinical chemistry and hematology analysis was performed throughout the study. Macroscopic and microscopic analysis of organs was performed at the terminal takedown. Recombinant human IL-2 (Proleukin) was used as a positive control.

Figure 22:
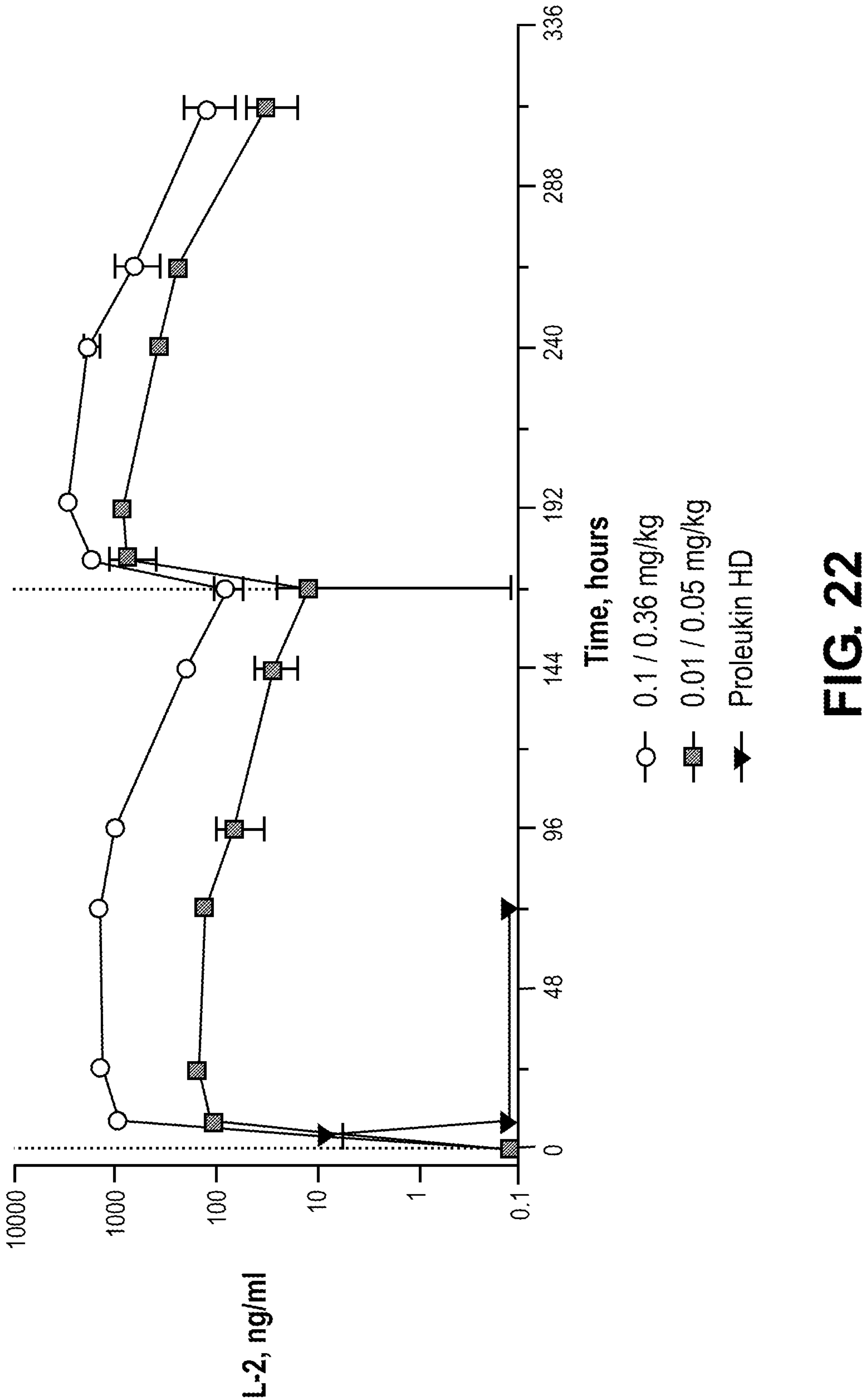
FIG. 22 provides data relating systemic exposure at various doses of STK-012 as evaluated in non-human primates. Concentration of STK-012 (dosed as indicated day 1/day 8) compared to one dose of Proleukin (equivalent to high dose (HD) Proleukin).

Toxicokinetic Analysis of STK-012: Serum concentration of STK-012 increased rapidly after STK-012 SC injection, reaching $C_{max}$ at 24 h post injection (PI). The STK-012 exposure was stable with a slow clearance between doses (7 days) (FIG. 22), compared to similar sized PEG-IL-2 muteins binding the intermediate IL-2 receptor which had a T½ of 11 h (Milla, et al. 2018). The T½ of STK-012 was 23-27 hours after the first dose (Table 13).

TABLE 13

Pharmacokinetic Data of STK-012 in Cynomolgus Monkeys

| | | Dose | Dose (mg/kg) | | | |
|---|---|---|---|---|---|---|
| Group | STK-012/Day | Fre-quency | Dose (mg/kg) | $C_{max}$ (ng/mL) | $T_{1/2}$ (h) | AUC (h*ng/mL) |
| 1 | Proleukin | single dose | 0.037 | 7.66 | n.d. | n.d. |
| 2 | STK-012 Day 1 | q7 d | 0.01 | 154 | 27.53 | 13,800 |
| 2 | STK-012 Day 8 | q7 d | 0.5 | 970 | 19.18 | 60,400 |
| 3 | STK-012 Day 1 | q7 d | 0.1 | 1570 | 23.43 | 155,000 |
| 3 | STK-012 Day 8 | q7 d | 0.36 | 2920 | 13.78 | 210,000 |

Figure 23:
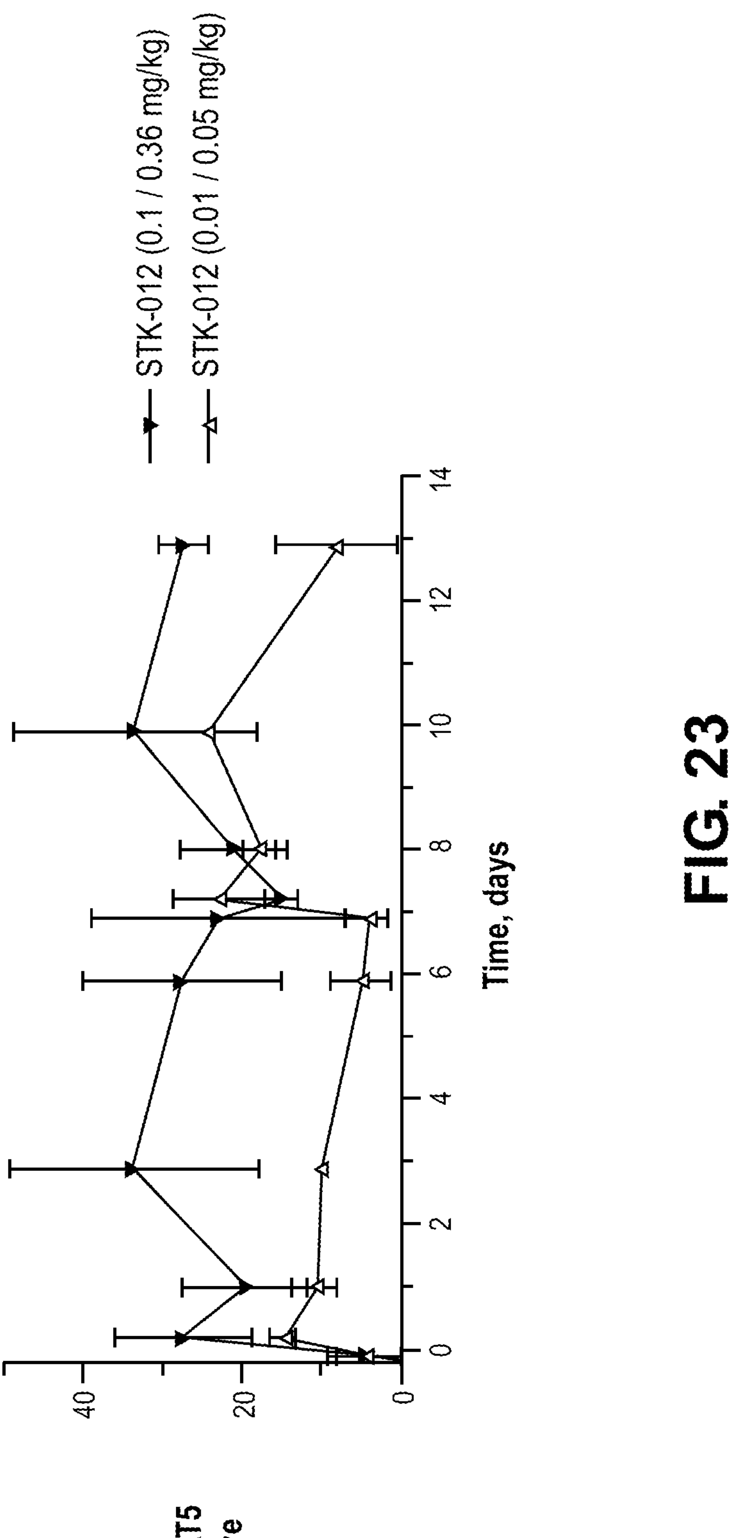
FIG. 23 provides data relating to pSTAT5 in response to STK-012 in a non-human primate FACS analysis for P-STAT5 in CD25+CD4+ T cells isolated from STK-012 treated cynomolgus monkeys demonstrating that a single dose of STK-012 induced sustained p-STAT5 signaling for 7 days.
Figure 24:
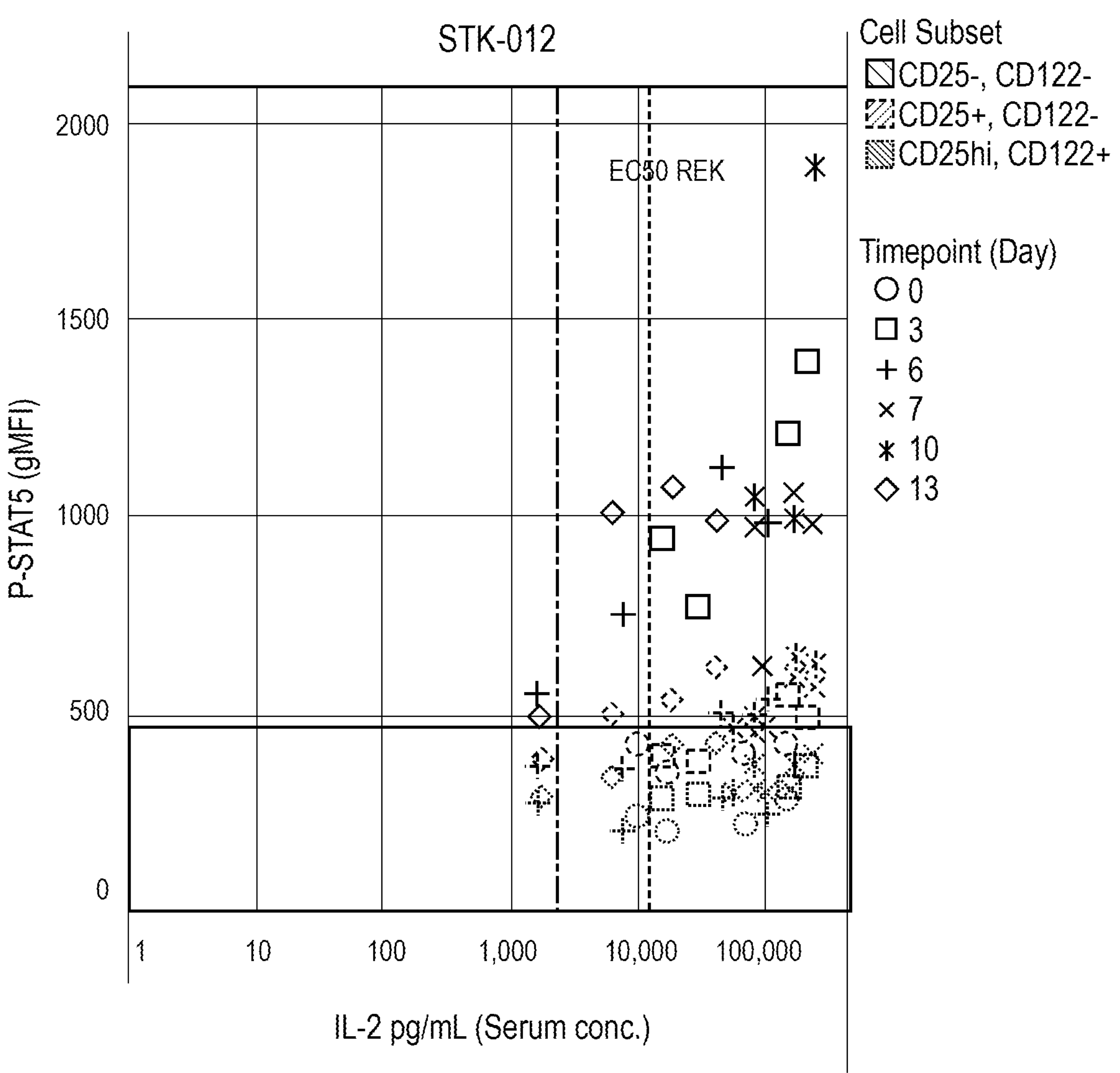
FIG. 24 provides data relating to STAT5 phosphorylation (Y-Axis) in relation to STK-012 serum concentration in three cell types from peripheral blood (CD25−CD122− CD8+ T cells, CD25+CD122−CD8+ T cells and CD25+ CD122+CD8+ T cells in the relation to the serum concentration of STK-012.
Figure 25:
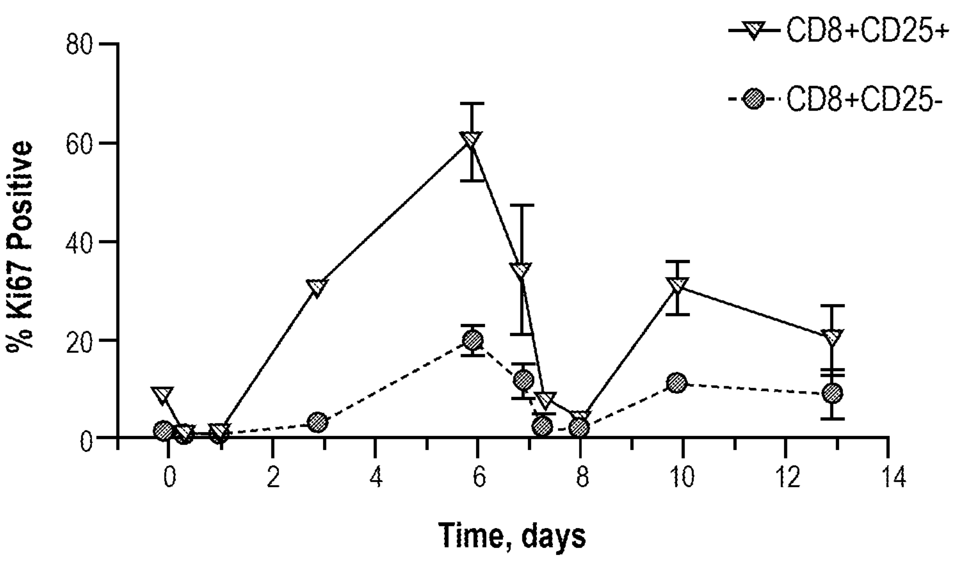
FIG. 25 provides data relating STK-012 (0.1/0.35 mg/kg) induced proliferation (KI67+) in CD8+CD25+ T cells and CD25 negative cells.
Figure 26:
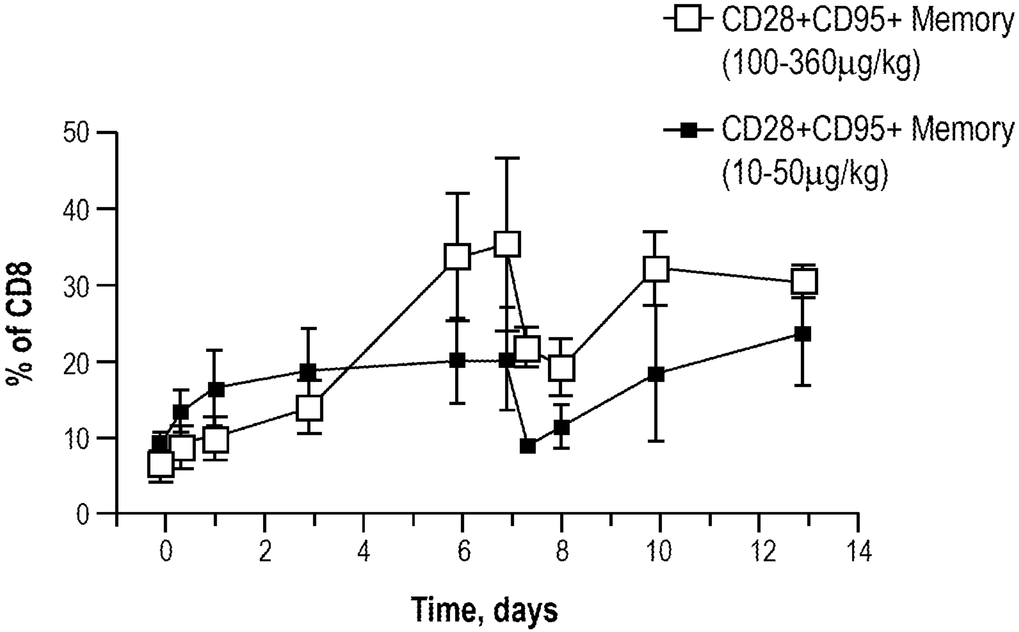
FIG. 26 provides data relating to the concentration of memory T cells of CD8 T tells in NHP in response to STK-012.

Pharmacodynamic Assessment of STK-012: STK-012 showed biological activity, including STAT5 phosphorylation restricted to a CD25+CD122+ subset of T cells (FIG. 24) in the NHP study. STK-012 doses at or above 0.05 mg/kg induced phosphorylated STAT5 (P-STAT5) in a subset of CD25+CD4+ T cells in the blood. STK-012 was sustained at a level sufficient to maintain P-STAT5 positivity in the STK-012 sensitive population throughout the dose interval (FIG. 23). STK-012 aims to target specifically T cells which had a recent TCR mediated upregulation of CD25 and CD122. Dependent on the concentration, STK-012 induced STAT5 phosphorylation specifically in cells expressing high levels of CD25 and CD122 on the surface (FIG. 24). STK-012 specifically binds and activates CD25+ T cells in vitro and in cynomolgus monkeys (FIG. 24). In support of STK-012 specificity, CD25+CD8+ T cells proliferated (detected by KI-67+) earlier and to a higher percentage in response to STK-012 than CD25−CD8+ T cells (FIG. 25). The proliferation of CD25−CD8+ T cells is delayed in respect to STK-012 dosing and proliferation of CDD25+CD8+ T cells and may be the consequence of wtIL-2 secretion by CD25+ T cells. CD28+CD95+CD8+ central memory T cells (Tcm) represent an antigen experienced T cell population. In melanoma patients, treatment with anti-PD-1 antibodies induces the proliferation and expansion of CD28+ Tcm, correlating with tumor response (Huang, et al. 2017). STK-012 treatment induced the expansion of CD28+CD95+CD8+ T cells in the blood of NHP (FIG. 26).

Summary of Clinical Observations in Nonclinical Studies: Administration of STK-012 at 0.36 mg/kg on Day 8 was associated with behavioral changes in clinical observations including hunched posture, lethargy, swollen eyelids, flaky skins, soft and liquid feces. Hunched posture was noted in the male on Days 9, 12, 14 and 15 and in the female on Days 14 and 15. The male animal was also noted with lethargy on Days 9 and 12, decreased activity on Day 12, bilaterally swollen eyelids on Day 15, flaky skins on the left hindlimb on Days 9 and 12, soft feces on Days 11 to 13 and liquid feces on Days 9 and 10. No test article-related clinical observations were noted in animals at the other STK-012 dose levels. The highest not-severely toxic dose (HNSTD) in this study is therefore 100 μg/kg.

Summary Pathology Assessment Test article-related microscopic findings were noted in the liver, kidneys, and spleen in animals dosed with STK-012: minimal to moderate perivascular mixed inflammatory cell infiltration in the liver (STK-012, 0.01/0.05 and 0.1/0.36 mg/kg); minimal increased cellularity of mononuclear cells in the spleen red pulp (STK-012, 0.1/0.36 mg/kg); mild mononuclear cell infiltration of the cortex in the kidneys (STK-012, 0.01/0.05 and 0.1/0.36 mg/kg). The affected area included mainly perivascular area including both portal and central veins, but no apparent degeneration or necrosis of the hepatocytes were seen. Serum transaminases were un-remarkable.

STK-012 is a structurally modified IL-2, which binds and activates only a high affinity human IL-2R (CD25, CD122 and CD132). This target cell selectivity may reduce target mediated clearance. STK-012 showed reduced clearance and had high exposures when compared to Proleukin (this study) or to other similarly pegylated IL-2s, described in the literature (Milla, Ptacin et al. 2018). Despite high serum exposure STK-012 is tolerated at doses up to 100 μg/kg with sustained high serum concentration. STK-012 showed strong and sustained biological activity, indicated by P-STAT5 in CD25+ T cells.

hIL2 Muteins Having Modified Pharmacokinetics:

The present disclosure further provides modified hIL2 muteins having modified pharmacokinetic (PK) properties. In some embodiments, the hIL2 muteins of the present disclosure having modified PK properties are modified to increase their duration of action in a mammalian subject. Examples of such PK modifications include but are not limited to conjugation to one or more carrier proteins, PEGylation, acylation, or amino acid sequence modifications, substitutions or deletions of the hIL2 mutein.

In some embodiments, modified hIL2 muteins having modified pharmacokinetic (PK) properties comprises a plasma half-life in a human subject of greater than 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, 10 days, 14 days, or 30 days.

Amino Acid Modifications: In some embodiments, the hIiL2 mutein may comprise certain amino acid substitutions that modify the PK of the hIL2 mutein so as to result in prolonged in vivo lifetime. For example, Dakshinamurthi, et al. (International Journal of Bioinformatics Research (2009) 1(2):4-13) state that one or more of the substitutions in the hIL2 polypeptide V91R, K97E and Ti13N provides an hIL2 variant possessing enhanced stability and activity. In some embodiments, the hIL2 muteins of the present disclosure comprise one, two or all three of the V91R, K97E and/or Ti13N modifications.

Conjugation to Carrier Molecules: In some embodiments, the hIL2 muteins of the present disclosure having modified PK properties are conjugated to one more carrier molecules. In some embodiments, the IL2 mutein can be covalently linked to the Fc domain of IgG, albumin, or other molecules to extend its half-life, e.g. by PEGylation, glycosylation, fatty acid acylation, and the like as known in the art.

In some embodiments, the hIL2 mutein of the present disclosure having modified PK properties is expressed as a fusion protein with an albumin molecule (e.g. human serum albumin) which is known in the art to facilitate extended exposure in vivo. In one embodiment of the invention, the hIL2 mutein is conjugated to albumin referred to herein as an "hIL2 mutein albumin fusion." The term "albumin" as used in the context hIL2 analog albumin fusions include albumins such as human serum albumin (HSA), cyno serum albumin, and bovine serum albumin (BSA). In some embodiments, the HSA comprises a C34S or K573P amino acid substitution relative to the wild type HSA sequence. According to the present disclosure, albumin can be conjugated to a hIL2 mutein at the carboxyl terminus, the amino terminus, both the carboxyl and amino termini, and internally (see, e.g., U.S. Pat. Nos. 5,876,969 and 7,056,701). In the HSA-hIL2 mutein polypeptide conjugates contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a hIL2 analog polypeptide fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker such as a peptide linker or modified version thereof as more fully discussed below.

Alternatively, the hIL2 mutein albumin fusion comprises IL2 muteins that are fusion proteins which comprise an albumin binding domain (ABD) polypeptide sequence and an IL2 mutein polypeptide. As alluded to above, fusion proteins which comprise an albumin binding domain (ABD) polypeptide sequence and an hIL2 analog polypeptide can, for example, be achieved by genetic manipulation, such that the nucleic acid coding for HSA, or a fragment thereof, is joined to the nucleic acid coding for the one or more IL2 mutein sequences. In some embodiments, the albumin-binding peptide comprises the amino acid sequence ICLPRWGCLW (SEQ ID NO:6).

In some embodiments, the hIL2 mutein of the present disclosure having modified PK properties is achieved by conjugation to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria, dendritic cells, thyroglobulin; tetanus toxoid; Diphtheria toxoid; polyamino acids such as poly(D-lysine:D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen Such conjugated forms, if desired, can be used to produce antibodies against a polypeptide of the present disclosure.

In some embodiments, the hIL2 mutein of the present disclosure having modified PK properties is achieved by conjugation to XTEN which provides extended duration of akin to PEGylation and may be produced as a recombinant fusion protein in *E. coli*. XTEN polymers suitable for use in conjunction with the IL2 muteins of the present disclosure are provided in Podust, et al. (2016) "*Extension of in vivo half-life of biologically active molecules by XTEN protein polymers*", J Controlled Release 240:52-66 and Haeckel et al. (2016) "*XTEN as Biological Alternative to PEGylation Allows Complete Expression of a Protease-Activatable Killin-Based Cytostatic*" PLOS ONE|DOI:10.1371/journal.pone.0157193 Jun. 13, 2016. The XTEN polymer fusion protein may incorporate a protease sensitive cleavage site between the XTEN polypeptide and the IL2 mutein such as an MMP-2 cleavage site.

The IL2 muteins of the present disclosure may be chemically conjugated to such carrier molecules using well known chemical conjugation methods. Bi-functional cross-linking reagents such as homofunctional and heterofunctional cross-linking reagents well known in the art can be used for this purpose. The type of cross-linking reagent to use depends on the nature of the molecule to be coupled to IL2 mutein and can readily be identified by those skilled in the art. Alternatively, or in addition, the IL2 mutein and/or the molecule to which it is intended to be conjugated may be chemically derivatized such that the two can be conjugated in a separate reaction as is also well known in the art.

PEGylation: In some embodiments, the IL2 mutein is conjugated to one or more water-soluble polymers. Examples of water soluble polymers useful in the practice of the present invention include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol, polysaccharides, poly-alpha-hydroxy acid, polyvinyl alcohol (PVA), polyphosphazene, polyoxazolines (POZ), poly (N-acryloylmorpholine), or a combination thereof. In some embodiments the IL2 mutein is conjugated to one or more polyethylene glycol molecules or "PEGylated." Although the method or site of PEG attachment to IL2 mutein may vary, in certain embodiments the PEGylation does not alter, or only minimally alters, the activity of the IL2 mutein. In some embodiments, a cysteine may be substituted for the threonine at position 3 (3TC) to facilitate N-terminal PEGylation using particular chemistries.

In some embodiments, selective PEGylation of the IL2 mutein (for example by the incorporation of non-natural amino acids having side chains to facilitate selective PEG conjugation chemistries as described Ptacin, et al., (PCT International Application No. PCT/US2018/045257 filed Aug. 3, 2018 and published Feb. 7, 2019 as International Publication Number WO 2019/028419A1 may be employed to generate an IL2 mutein with having reduced affinity for one or more subunits (e.g. CD25, CD132) of an IL2 receptor complex. For example, an hIL2 mutein incorporating non-natural amino acids having a PEGylatable specific moiety at those sequences or residues of IL2 identified as interacting with CD25 including amino acids 34-45, 61-72 and 105-109 typically provides an IL2 mutein having diminished binding to CD25. Similarly, an hIL2 mutein incorporating non-natural amino acids having a PEGylatable specific moiety at those sequences or residues of IL2 identified as interacting with hCD132 including amino acids 18, 22, 109, 126, or from 119-133 provides an IL2 mutein having diminished binding to hCD132.

In certain embodiments, the increase in half-life is greater than any decrease in biological activity. PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

A molecular weight of the PEG used in the present disclosure is not restricted to any particular range. The PEG component of the PEG-IL2 mutein can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, alternatively about 30,000 to about 40,000 daltons. In one embodiment of the invention, the PEG is a 40 kD branched PEG comprising two 20 kD arms.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons.

Two widely used first generation activated monomethoxy PEGs (mPEGs) are succinimdyl carbonate PEG (SC-PEG; see, e.g., Zalipsky, et al. (1992) Biotehnol. Appl. Biochem 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

Pegylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein.

The PEG can be bound to an IL2 mutein of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of IL2 muteins is facilitated by the incorporation of non-natural amino acids bearing unique side chains to facilitate site specific PEGylation. The incorporation of non-natural amino acids into polypeptides to provide functional moieties to achieve site specific pegylation of such polypeptides is known in the art. See e.g. Ptacin, et al., (PCT International Application No. PCT/US2018/045257 filed Aug. 3, 2018 and published Feb. 7, 2019 as International Publication Number WO 2019/028419A1. In one embodiment, the IL2 muteins of the present invention incorporate a non-natural amino acid at position D109 of the IL2 mutein. In one embodiment of the invention the IL2 mutein is a PEGylated at position 109 of the IL2 mutein to a PEG molecule having a molecular weight of about 20 kD, alternatively about 30 kD, alternatively about 40 kD.

The PEG conjugated to the polypeptide sequence can be linear or branched. Branched PEG derivatives, "star-PEGs" and multi-armed PEGs are contemplated by the present disclosure. Specific embodiments PEGs useful in the practice of the present invention include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g. Sunbright® ME-200AL, NOF, a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

As previously noted, the PEG may be attached directly to the IL2 mutein or via a linker molecule. Suitable linkers include "flexible linkers" which are generally of sufficient length to permit some movement between the modified polypeptide sequences and the linked components and molecules. The linker molecules are generally about 6-50 atoms long. The linker molecules can also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Examples of flexible linkers include glycine polymers $(G)_n$, glycine-serine polymers, glycine-alanine polymers, alanine-serine polymers, and other flexible linkers. Glycine and glycine-serine polymers are relatively unstructured, and therefore can serve as a neutral tether between components. Further examples of flexible linkers include glycine polymers $(G)_n$, glycine-alanine polymers, alanine-serine polymers, glycine-serine polymers. Glycine and glycine-serine polymers are relatively unstructured, and therefore may serve as a neutral tether between components. A multimer (e.g., 1, 2, 3, 4, 5, 6, 7, 8, 9, 10, 10-20, 20-30, or 30-50) of these linker sequences may be linked together to provide flexible linkers that may be used to conjugate a heterologous amino acid sequence to the polypeptides disclosed herein.

Further, such linkers may be used to link the IL2 mutein to additional heterologous polypeptide components as described herein, the heterologous amino acid sequence may be a signal sequence and/or a fusion partner, such as, albumin, Fc sequence, and the like Acylation: In some embodiments, the IL2 mutein of the present disclosure may be acylated by conjugation to a fatty acid molecule as described in Resh (2016) Progress in Lipid Research 63: 120-131. Examples of fatty acids that may be conjugated include myristate, palmitate and palmitoleic acid. Myristoylate is typically linked to an N-terminal glycine but lysines may also be myristoylated. Palmitoylation is typically achieved by enzymatic modification of free cysteine —SH groups such as DHHC proteins catalyze S-palmitoylation. Palmitoleylation of serine and threonine residues is typically achieved enzymatically using PORCN enzymes.

Acetylation: In some embodiments, the IL2 mutein is acetylated at the N-terminus by enzymatic reaction with N-terminal acetyltransferase and, for example, acetyl CoA. Alternatively, or in addition to N-terminal acetylation, the IL2 mutein is acetylated at one or more lysine residues, e.g. by enzymatic reaction with a lysine acetyltransferase. See, for example Choudhary et al. (2009) Science 325 (5942): 834L2 ortho840.

Fc Fusions: In some embodiments, the IL2 fusion protein may incorporate an Fc region derived from the IgG subclass of antibodies that lacks the IgG heavy chain variable region. The "Fc region" can be a naturally occurring or synthetic polypeptide that is homologous to the IgG C-terminal domain produced by digestion of IgG with papain. IgG Fc has a molecular weight of approximately 50 kDa. The mutant IL2 polypeptides can include the entire Fc region, or a smaller portion that retains the ability to extend the circulating half-life of a chimeric polypeptide of which it is a part. In addition, full-length or fragmented Fc regions can be variants of the wild type molecule. That is, they can contain mutations that may or may not affect the function of the polypeptides; as described further below, native activity is not necessary or desired in all cases. In certain embodiments, the IL2 mutein fusion protein (e.g., an IL2 partial agonist or antagonist as described herein) includes an IgG1, IgG2, IgG3, or IgG4 Fc region. Exemplary Fc regions can include a mutation that inhibits complement fixation and Fc receptor binding, or it may be lytic, i.e., able to bind complement or to lyse cells via another mechanism such as antibody-dependent complement lysis (ADCC).

In some embodiments, the IL2 mutein comprises a functional domain of an Fc-fusion chimeric polypeptide molecule. Fe fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. The "Fe region" useful in the preparation of Fc fusions can be a naturally occurring or synthetic polypeptide that is homologous to an IgG C-terminal domain produced by digestion of IgG with papain. IgG Fc has a molecular weight of approximately 50 kDa. The IL2 muteins may provide the entire Fc region, or a smaller portion that retains the ability to extend the circulating half-life of a chimeric polypeptide of which it is a part. In addition, full-length or fragmented Fc regions can be variants of the wild type molecule. In a typical presentation, each monomer of the dimeric Fc carries a heterologous polypeptide, the heterologous polypeptides being the same or different.

In some embodiments, when the IL2 mutein is to be administered in the format of an Fc fusion, particularly in those situations when the polypeptide chains conjugated to each subunit of the Fc dimer are different, the Fc fusion may be engineered to possess a "knob-into-hole modification." The knob-into-hole modification is more fully described in Ridgway, et al. (1996) Protein Engineering 9(7):617-621 and U.S. Pat. No. 5,731,168, issued Mar. 24, 1998. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g. tyrosine or tryptophan) creating a projection from the surface ("knob") and ii) in the CH3 domain of a second heavy chain, an amino acid residue is replaced with an amino acid residue having a smaller side chain (e.g. alanine or threonine), thereby generating a cavity ("hole") within at interface in the second CH3 domain within which the protruding side chain of the first CH3 domain ("knob") is received by the cavity in the second CH3 domain. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g. an IL2 mutein) on a first Fc monomer with a "knob" modification and a second polypeptide on the second Fc monomer possessing a "hole" modification to facilitate the expression of heterodimeric polypeptide conjugates.

The Fc region can be "lytic" or "non-lytic," but is typically non-lytic. A non-lytic Fe region typically lacks a high affinity Fe receptor binding site and a Clq binding site. The high affinity Fc receptor binding site of murine IgG Fc includes the Leu residue at position 235 of IgG Fc. Thus, the Fc receptor binding site can be inhibited by mutating or deleting Leu 235. For example, substitution of Glu for Leu 235 inhibits the ability of the Fc region to bind the high affinity Fc receptor. The murine Clq binding site can be functionally destroyed by mutating or deleting the Glu 318, Lys 320, and Lys 322 residues of IgG. For example, substitution of Ala residues for Glu 318, Lys 320, and Lys 322 renders IgG1 Fc unable to direct antibody-dependent complement lysis. In contrast, a lytic IgG Fc region has a high affinity Fe receptor binding site and a Clq binding site. The high affinity Fc receptor binding site includes the Leu residue at position 235 of IgG Fc, and the Clq binding site includes the Glu 318, Lys 320, and Lys 322 residues of IgG 1. Lytic IgG Fc has wild type residues or conservative amino acid substitutions at these sites. Lytic IgG Fc can target cells for antibody dependent cellular cytotoxicity or complement directed cytolysis (CDC). Appropriate mutations for human IgG are also known (see, e.g., Morrison et al., The Immunologist 2:119-124, 1994; and Brekke et al., The Immunologist 2: 125, 1994).

In certain embodiments, the amino- or carboxyl-terminus of an IL2 mutein of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product can require less frequent administration. Fe binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

In some embodiments, the Fc domain monomer comprises at least one mutation relative to a wild-type human IgG1, IgG2, or IgG4 Fc region as described in United U.S. Pat. No. 10,259,859B2, the entire teaching of which is herein incorporated by reference. In some embodiments, the polypeptide exhibits a reduction of phagocytosis in a phagocytosis assay compared to a polypeptide with a wild-type human IgG Fc region. In some embodiments, the Fc domain monomer is linked to a second polypeptide comprising a second Fc domain monomer to form an Fc domain dimer.

Chimeric Polypeptides/Fusion Proteins: In some embodiments, embodiment, the IL2 mutein may comprise a functional domain of a chimeric polypeptide. IL2 mutein fusion proteins of the present disclosure may be readily produced by recombinant DNA methodology by techniques known in the art by constructing a recombinant vector comprising a nucleic acid sequence comprising a nucleic acid sequence encoding the IL2 mutein in frame with a nucleic acid sequence encoding the fusion partner either at the N-terminus or C-terminus of the IL2 mutein, the sequence optionally further comprising a nucleic acid sequence in frame encoding a linker or spacer polypeptide.

Antigenic Tags: In other embodiments, the IL2 mutein may optionally be modified to incorporate an additional polypeptide sequence that functions as an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the IL2 mutein polypeptide further comprises a C-terminal c-myc epitope tag.

Additional candidate molecules for conjugation to the hIL2 mutein of the present disclosure include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

His Tags: In some embodiments, the hIL2 muteins (including fusion proteins of such IL2 muteins) of the present invention are expressed as a fusion protein with one or more transition-metal chelating polypeptide sequences. The incorporation of such a transition-metal chelating domain facilitates purification immobilized metal affinity chromatography (IMAC) as described in Smith, et al., U.S. Pat. No. 4,569,794 issued Feb. 11, 1986. Examples of transition-metal chelating polypeptides useful in the practice of the present invention are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present invention are peptides comprising 3-6 contiguous histidine residues such as a six-histidine peptide $(His)_6$ (SEQ ID NO: 12) and are frequently referred to in the art as "His-tags."

Targeted hIL2 Muteins: In some embodiments, the IL2 mutein is provided as a fusion protein with a polypeptide sequence ("targeting domain") to facilitate selective binding to particular cell type or tissue expressing a cell surface molecule that specifically binds to such targeting domain, optionally incorporating a linker molecule of from 1-40 (alternatively 2-20, alternatively 5-20, alternatively 10-20) amino acids between the IL2 mutein sequence and the sequence of the targeting domain of the fusion protein. In other embodiments, a chimeric polypeptide including a hIL2 mutein and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135. Nucleic Acid Molecules Encoding Mutant IL2.

In some embodiments, the targeting domain of the hIL2 mutein fusion protein specifically binds to a cell surface molecule of a tumor cell. In one embodiment wherein the ECD of the CAR of a CAR-T cell specifically binds to CD-19, the IL2 mutein may be provided as a fusion protein with a CD-19 targeting moiety. For example, in one embodiment wherein the ECD of the CAR of an CAR-T cell is an scFv molecule that provides specific binding to CD-19, the IL2 mutein is provided as a fusion protein with a CD-19 targeting moiety such as a single chain antibody (e.g., an scFv or VHH) that specifically binds to CD-19. In some embodiments, the fusion protein comprises an hIL2 mutein and the anti-CD19 scFv FMC63 (Nicholson, et al. (1997) Mol Immunol 34: 1157-1165).

Similarly, in some embodiments wherein the ECD of the CAR of the CAR-T cell specifically binds to BCMA, the hIL2 mutein may be provided as a fusion protein with a BCMA targeting moiety, such as antibody comprising the CDRs of anti-BMCA antibodies as described in in Kalled, et al. (U.S. Pat. No. 9,034,324 issued May 9, 2015) or antibodies comprising the CDRs as described in Brogdon, et al., (U.S. Pat. No. 10,174,095 issued Jan. 8, 2019). In some embodiments the hIL2 mutein may be provided as a fusion protein with a GD2 targeting moiety, such as an antibody comprising the CDRs of described in Cheung, et al., (U.S. Pat. No. 9,315,585 issued Apr. 19, 2016) or the CDRs derived from ME36.1 (Thurin et al., (1987) Cancer Research 47:1229-1233), 14G2a, 3F8 (Cheung, et al., 1985 Cancer Research 45:2642-2649), hu14.18, 8B6, 2E12, or ic9.

In an alternative embodiment, the targeted hIL2 muteins of the present disclosure may be administered in combination with CAR-T cell therapy to provide targeted delivery of the IL2 mutein to the CAR-T cell based on an extracellular receptor of the CAR-T cell such as by employing a targeted hIL2 mutein construct comprising an anti-FMC63 antibody to target the IL2 activity to the CAR-T cells and rejuvenate exhausted CAR-T cells in vivo. Consequently, embodiments of the present disclosure include targeted delivery of IL2 muteins by conjugation of such IL2 muteins to antibodies or ligands that are designed to interact with specific cell surface molecules of CAR-T cells. An example of such a molecule would be an anti-FMC63-hIL2 mutein.

In other embodiments, the chimeric polypeptide includes the mutant IL2 polypeptide and a heterologous polypeptide that functions to enhance expression or direct cellular localization of the mutant IL2 polypeptide, such as the Aga2p agglutinin subunit (see, e.g., Boder and Wittrup, Nature Biotechnol. 15:553-7, 1997).

Protein Transduction Domain Fusion Proteins: In some embodiments, the IL2 mutein may be operably linked to a "Protein Transduction Domain" or "PTD." A PTD is a polypeptide, polynucleotide, carbohydrate, or organic or inorganic molecule that facilitates traversing a lipid bilayer, micelle, cell membrane, organelle membrane, or vesicle membrane. The incorporation of a PTD into an IL2 mutein facilitates the molecule traversing a membrane. In some embodiments, a PTD is covalently linked to the amino or carboxy terminus of an IL2 mutein. In some embodiments, the PTD is incorporated as part of an PTD-IL2 mutein fusion protein, either at the N or C terminus of the molecule. Exemplary protein transduction domains include, but are not limited to, a minimal decapeptide protein transduction domain (corresponding to residues 47-57 of HIV-1 TAT); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila* Antennapedia protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008), Transportan (as described in Wierzbicki, et al., (2014) Folio Histomchemica et Cytobiologica 52(4): 270-280 and Pooga, et a (1998) FASEB J 12(1)67-77 and commercially available from AnaSpec as Catalog No. AS-61256); KALA (as decribed in Wyman et al., (1997) Biochemistry 36(10) 3008-3017 and commercially available from AnaSpec as Catalog No. AS-65459); Antennapedia Peptide (as described in Pietersz et al., (2001) Vaccine 19:1397 and commercially available from AnaSpec as Catalog No. AS-61032); TAT 47-57 (commercially available from AnaSpec as Catalog No. AS-60023).

Conjugation of Supplemental Therapeutic Agents: In some embodiments, the hIL2 mutein may be linked to one or more additional therapeutic agents including but not limited to anti-inflammatory compounds or antineoplastic agents, therapeutic antibodies (e.g. Herceptin), targeting moieties such as anti-tumor antigen antibodies, immune checkpoint modulators, immune checkpoint inhibitors (e.g. anti-PD1 antibodies), or cancer vaccines. Anti-microbial agents include aminoglycosides including gentamicin, antiviral compounds such as rifampicin, 3'-azido-3'-deoxythymidine (AZT) and acylovir, antifungal agents such as azoles including fluconazole, macrolides such as amphotericin B, and candicidin, anti-parasitic compounds, and the like. The IL2 mutein may be conjugated to additional cytokines as CSF, GSF, GMCSF, TNF, erythropoietin, immunomodulators or cytokines such as the interferons or interleukins, a neuropeptide, reproductive hormones such as HGH, FSH, or LH, thyroid hormone, neurotransmitters such as acetylcholine, hormone receptors such as the estrogen receptor. Also included are non-steroidal anti-inflammatories such as indomethacin, salicylic acid acetate, ibuprofen, sulindac, piroxicam, and naproxen, and anesthetics or analgesics. Also included are radioisotopes such as those useful for imaging as well as for therapy.

Synthesis of IL2 Muteins

The IL2 muteins of the present disclosure may be produced by conventional methodology for the construction of polypeptides including recombinant or solid phase syntheses.

Chemical Synthesis: In addition to generating mutant polypeptides via expression of nucleic acid molecules that have been altered by recombinant molecular biological techniques, subject hIL2 muteins can be chemically synthesized. Chemically synthesized polypeptides are routinely generated by those of skill in the art. Chemical synthesis includes direct synthesis of a peptide by chemical means of the protein sequence encoding for an IL2 mutein exhibiting the properties described. This method can incorporate both natural and unnatural amino acids at positions that affect the interactions of IL2 with CD25, CD122 and, CD132.

In some embodiments, the IL2 muteins of the present disclosure may be prepared by chemical synthesis. The chemical synthesis of the IL2 muteins of may proceed via liquid-phase or solid-phase. Solid-phase peptide synthesis (SPPS) allows the incorporation of unnatural amino acids and/or peptide/protein backbone modification. Various forms of SPPS are available for synthesizing IL2 muteins of the present disclosure are known in the art (e.g., Ganesan A. (2006) Mini Rev. Med. Chem. 6:3-10; and Camarero J. A. et al., (2005) Protein Pept Lett. 12:723-8). In the course of chemical synthesis, the alpha functions and any reactive side chains may protected with acid-labile or base-labile groups that are stable under the conditions for linking amide bonds but can readily be cleaved without impairing the peptide chain that has formed.

In the solid phase synthesis, either the N-terminal or C-terminal amino acid of the polypeptide may be coupled to a suitable support material. Suitable support materials are those which are inert towards the reagents and reaction conditions for the stepwise condensation and cleavage reactions of the synthesis process and which do not dissolve in the reaction media being used. Examples of commercially available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. The successive coupling of the protected amino acids can be carried out according to conventional methods in peptide synthesis, typically in an automated peptide synthesizer.

At the end of the solid phase synthesis, the polypeptide is cleaved from the support material while simultaneously cleaving the side chain protecting groups. The polypeptide obtained can be purified by various chromatographic methods including but not limited to hydrophobic adsorption chromatography, ion exchange chromatography, distribution chromatography, high pressure liquid chromatography (HPLC) and reverse-phase HPLC.

Recombinant Production: Alternatively, the IL2 muteins of the present disclosure are produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide. The recombinant protein may be purified and concentrated for further use including incorporation. The process for the recombinant production of IL2 polypeptides is known in the art and described in Fernandes and Taforo, U.S. Pat. No. 4,604,377 issued Aug. 5, 1986 and IL2 muteins in Mark, et al., U.S. Pat. No. 4,512,584 issued May 21, 1985, Gillis, U.S. Pat. No. 4,401,756 issued Aug. 30, 1983 the entire teachings of which are herein incorporated by reference.

Construction of Nucleic Acid Sequences Encoding the IL2 Mutein: In some embodiments, the IL2 mutein is produced by recombinant methods using a nucleic acid sequence encoding the IL2 mutein (or fusion protein comprising the IL2 mutein). The nucleic acid sequence encoding the desired hIL2 mutein can be synthesized by chemical means using an oligonucleotide synthesizer. The nucleic acid molecules are not limited to sequences that encode polypeptides; some or all of the non-coding sequences that lie upstream or downstream from a coding sequence (e.g., the coding sequence of hIL2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the IL2 mutein (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphonamidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the IL2 mutein may be obtained from various commercial sources that provide custom made nucleic acid sequences. Amino acid sequence variants of the IL2 polypeptides to the produce the IL2 muteins of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion is made to arrive at the final construct, provided that the final construct possesses the desired biological activity as defined herein.

Methods for constructing a DNA sequence encoding the hIL2 muteins and expressing those sequences in a suitably transformed host include, but are not limited to, using a PCR-assisted mutagenesis technique. Mutations that consist of deletions or additions of amino acid residues to an hIL2 polypeptide can also be made with standard recombinant techniques. In the event of a deletion or addition, the nucleic acid molecule encoding hIL2 is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

An IL2 mutein of the present disclosure may be produced recombinantly not only directly, but also as a fusion polypeptide with a heterologous polypeptide, e.g. a signal sequence or other polypeptide having a specific cleavage site at the N-terminus or C-terminus of the mature IL2 mutein. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. In some embodiments, the signal sequence is the signal sequence that is natively associated with the IL2 mutein (i.e. the human IIL2 signal sequence). The inclusion of a signal sequence depends on whether it is desired to secrete the hIL2 mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild type hIL2 signal sequence be used. Alternatively, heterologous mammalian signal sequences may be suitable, such as signal sequences from secreted polypeptides of the same or related species, as well as viral secretory leaders, for example, the herpes simplex gD signal. When the recombinant host cell is a yeast cell such as *Saccharomyces cerevisiae*, the alpha mating factor secretion signal sequence may be employed to achieve extracellular secretion of the IL2 mutein into the culture medium as described in Singh, U.S. Pat. No. 7,198,919 B1 issued Apr. 3, 2007.

In the event the IL2 mutein to be expressed is to be expressed as a chimera (e.g., a fusion protein comprising an IL2 mutein and a heterologous polypeptide sequence), the chimeric protein can be encoded by a hybrid nucleic acid molecule comprising a first sequence that encodes all or part of the hIL2 mutein and a second sequence that encodes all or part of the heterologous polypeptide. For example, subject hIL2 muteins described herein may be fused to a hexa-histidine tag (SEQ ID NO: 13) to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the IL2 mutein. For example, the N-terminus may be linked to a targeting domain and the C-terminus linked to a hexa-histidine tag (SEQ ID NO: 13) purification handle.

The complete amino acid sequence of the polypeptide (or fusion/chimera) to be expressed can be used to construct a back-translated gene. A DNA oligomer containing a nucleotide sequence coding for hIL2 mutein can be synthesized. For example, several small oligonucleotides coding for portions of the desired polypeptide can be synthesized and then ligated. The individual oligonucleotides typically contain 5' or 3' overhangs for complementary assembly.

Codon Optimization: In some embodiments, the nucleic acid sequence encoding the IL2 mutein may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g. Hawash, et al., (2017) 9:46-53 and Mauro and Chappell in *Recombinant Protein Expression in Mammalian Cells: Methods and Protocols*, edited by David Hacker (Human Press New York). Additionally, there are a variety of web based on-line software packages that are freely available to assist in the preparation of codon optimized nucleic acid sequences.

Expression Vectors:

Once assembled (by synthesis, site-directed mutagenesis or another method), the nucleic acid sequence encoding an hIL2 mutein will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors.

Selectable Marker: Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Regulatory Control Sequences: To facilitate efficient expression of the recombinant polypeptide, the nucleic acid sequence encoding the polypeptide sequence to be expressed is operably linked to transcriptional and translational regulatory control sequences that are functional in the chosen expression host. Expression vectors for IL2 muteins of the present disclosure contain a regulatory sequence that is recognized by the host organism and is operably linked to nucleic acid sequence encoding the IL2 mutein. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject hIL2 mutein, particularly as regards potential secondary structures.

Promoters: In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Enhancers: Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context.

Proper assembly of the expression vector can be confirmed by nucleotide sequencing, restriction mapping, and expression of a biologically active polypeptide in a suitable host.

Host Cells:

The present disclosure further provides prokaryotic or eukaryotic cells that contain and express a nucleic acid molecule that encodes a hIL2 mutein of the present disclosure. A cell of the present disclosure is a transfected cell, i.e., a cell into which a nucleic acid molecule, for example a nucleic acid molecule encoding a mutant hIL2 polypeptide, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this invention, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant hIL2 muteins or biologically active variants thereof can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast *S. cerenvisiae* include pYepSecl (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The hIL2 mutein can be produced in a prokaryotic host, such as the bacterium *E. coli*, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, hIL2 muteins obtained will be glycosylated or unglycosylated depending on the host organism used to produce the mutein. If bacteria are chosen as the host then the hIL2 mutein produced will be unglycosylated. Eukaryotic cells, on the other hand, will glycosylate the hIL2 muteins, although perhaps not in the same way as native-IL2 is glycosylated.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection:

The expression constructs of the can be introduced into host cells to thereby produce the hIL2 muteins disclosed herein or to produce biologically active muteins thereof. Vector DNA can be introduced into prokaryotic or eukaryotic cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals.

In order to facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture:

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins:

Recombinantly produced IL2 mutein polypeptides can be recovered from the culture medium as a secreted polypeptide if a secretion leader sequence is employed. Alternatively, the IL2 mutein polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Purification:

Various purification steps are known in the art and find use, e.g. affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g. gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

The hIL2 mutein produced by the transformed host can be purified according to any suitable method. Various methods are known for purifying IL2. See, e.g. Current Protocols in Protein Science, Vol 2. Eds: John E. Coligan, Ben M. Dunn, Hidde L. Ploehg, David W. Speicher, Paul T. Wingfield, Unit 6.5 (Copyright 1997, John Wiley and Sons, Inc. hIL2 muteins can be isolated from inclusion bodies generated in *E. coli*, or from conditioned medium from either mammalian or yeast cultures producing a given mutein using cation exchange, gel filtration, and or reverse phase liquid chromatography.

The substantially purified forms of the recombinant polypeptides can be purified from the expression system using routine biochemical procedures, and can be used, e.g., as therapeutic agents, as described herein.

The biological activity of the hIL2 muteins can be assayed by any suitable method known in the art and may be evaluated as substantially purified forms or as part of the cell lysate or cell medium when secretion leader sequences are employed for expression. Such activity assays include CTLL-2 proliferation, induction of phospho-STAT5 (pSTAT5) activity in T cells, PHA-blast proliferation and NK cell proliferation.

Formulations:

In embodiments of the therapeutic methods of the present disclosure involve the administration of a pharmaceutical formulation comprising an IL2 mutein (and/or nucleic acids encoding the IL2 mutein) to a subject in need of treatment. Administration to the subject may be achieved by intravenous injection, as a bolus or by continuous infusion over a period of time. Alternative routes of administration include intramuscular, intraperitoneal, intra-cerobrospinal, subcutaneous, intra-articular, intrasynovial, intrathecal, oral, topical, or inhalation routes. The IL2 muteins also are suitably administered by intratumoral, peritumoral, intralesional, intranodal or perilesional routes or to the lymph, to exert local as well as systemic therapeutic effects.

In some embodiments, subject hIL2 muteins (and/or nucleic acids encoding the IL2 mutein) can be incorporated into compositions, including pharmaceutical compositions. Such compositions typically include the polypeptide or nucleic acid molecule and a pharmaceutically acceptable carrier. A pharmaceutical composition is formulated to be compatible with its intended route of administration and is compatible with the therapeutic use for which the IL2 mutein is to be administered to the subject in need of treatment or prophyaxis.

Parenteral Formulations: In some embodiments, the methods of the present disclosure involve the parental administration of a hIL2 mutein. Examples of parenteral routes of administration include, for example, intravenous, intradermal, subcutaneous, transdermal (topical), transmucosal, and rectal administration. Parenteral formulations comprise solutions or suspensions used for parenteral application can include vehicles the carriers and buffers. Pharmaceutical formulations for parenteral administration include sterile aqueous solutions (where water soluble) or dispersions and sterile powders for the extemporaneous preparation of sterile injectable solutions or dispersion.

Carriers: Carriers include a sterile diluent such as water for injection, saline solution, fixed oils, polyethylene glycols, glycerine, propylene glycol or other synthetic solvents. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. For intravenous administration, suitable carriers include physiological saline, bacteriostatic water, Cremophor ELTM. (BASF, Parsippany, N.J.) or phosphate buffered saline (PBS).

Buffers: The term buffers includes buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5).

Dispersions: Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Preservatives: The pharmaceutical formulations for parenteral administration to a subject should be sterile and should be fluid to facilitate easy syringability. It should be stable under the conditions of manufacture and storage and are preserved against the contamination. Prevention of the action of microorganisms can be achieved by various antibacterial and antifungal agents, for example, agents such as benzyl alcohol or methyl parabens; antioxidants such as ascorbic acid or sodium bisulfite; chelating agents such as ethylenediaminetetraacetic acid, parabens, chlorobutanol, phenol, ascorbic acid, thimerosal, and the like. Sterile solutions can be prepared by incorporating the active compound in the required amount in an appropriate solvent with one or a combination of ingredients enumerated above, as required, followed by filtered sterilization.

Tonicity Agents: In many cases, it will be preferable to include isotonic agents, for example, sugars, polyalcohols such as mannitol, sorbitol, sodium chloride in the composition.

Oral Compositions: Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

Inhalation Formulations: In the event of administration by inhalation, subject hIL2 muteins, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Mucosal and Transdermal: Systemic administration of the subject hIL2 muteins or nucleic acids can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories suppositories (e.g., with conventional suppository bases such as cocoa butter and other glycerides) or retention enemas for rectal delivery. For transdermal administration, the active compounds are formulated into ointments, salves, gels, or creams as generally known in the art and may incorporate permeation enhancers such as ethanol or lanolin.

Extended Release and Depot Formulations: In some embodiments of the method of the present disclosure, the IL2 mutein is administered to a subject in need of treatment in a formulation to provide extended release of the IL2 mutein agent. Examples of extended release formulations of the injectable compositions can be brought about by including in the composition an agent which delays absorption, for example, aluminum monostearate and gelatin. In one embodiment, the subject hIL2 muteins or nucleic acids are prepared with carriers that will protect the mutant hIL2 polypeptides against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Administration of Nucleic Acids Encoding the IL2 Mutein (Gene Therapy): In some embodiments of the method of the present disclosure, nucleic acids encoding the IL2 mutein is administered to the subject by transfection or infection using methods known in the art, including but not limited to the methods described in McCaffrey et al. (Nature 418:6893, 2002), Xia et al. (Nature Biotechnol. 20: 1006-1010, 2002), or Putnam (Am. J. Health Syst. Pharm. 53: 151-160, 1996, erratum at Am. J. Health Syst. Pharm. 53:325, 1996). In some embodiments, the IIL2 mutein is administered to a subject by the administration of a pharmaceutically acceptable formulation of recombinant expression vector. In one embodiment, the recombinant expression vector is a viral vector. In some embodiments, the recombinant vector is a recombinant viral vector. In some embodiments the recombinant viral vector is a recombinant adeno-associated virus (rAAV) or recombinant adenovirus (rAd), in particular a replication deficient adenovirus derived from human adenovirus serotypes 3 and/or 5. In some embodiments, the replication deficient adenovirus has one or more modifications to the E1 region which interfere with the ability of the virus to initiate the cell cycle and/or apoptotic pathways in a human cell. The replication deficient adenoviral vector may optionally comprise deletions in the E3 domain. In some embodiments the adenovirus is a replication competent adenovirus. In some embodiments the adenovirus is a replication competent recombinant virus engineered to selectively replicate in lymphocytes.

In one embodiment, the IL2 mutein formulation is provided in accordance with the teaching of Fernandes and Taforo, U.S. Pat. No. 4,604,377 issued Aug. 5, 1986 the teaching of which is herein incorporated by reference. And Yasui, et al., U.S. Pat. No. 4,645,830.

The parenteral preparation can be enclosed in ampoules, disposable syringes or multiple dose vials made of glass or plastic. In one embodiment, the formulation is provided in a prefilled syringe for parenteral administration.

Methods of Treatment

The present disclosure provides methods of use of IL2 muteins in the treatment of subjects suffering from a neoplastic disease disorder or condition by the administration of a therapeutically effective amount of an IL2 mutein (or nucleic acid encoding an IL2 mutein including recombinant vectors encoding IL2 muteins) as described herein.

The present disclosure provides methods and compositions for the treatment and/or prevention of neoplastic diseases, disorders or conditions by the administration of a therapeutically effective amount of hIL2 muteins that have decreased binding affinity for CD132 yet retain significant binding affinity for CD122 and/or CD25 comparable to the affinity of wild-type human IL2.

In some embodiments, the disclosure methods and compositions for the treatment and/or prevention of neoplastic diseases, disorders or conditions by the administration of a therapeutically effective amount of an human IL2 muteins that have decreased binding affinity for CD132 yet retain significant binding affinity for CD122 and/or CD25 comparable to the activity of wild-type hIL2 in combination with a supplementary agents, including but not limited to one or more of chemotherapeutics, immune checkpoint modulators, radiotherapy and/or physical interventional treatment methods such as surgery.

In some embodiments, the present disclosure provides human interleukin-2 (IL2) muteins providing modified binding properties to one or more IL2 receptors for the treatment of neoplastic disease.

Neoplasms amenable to treatment: The compositions and methods of the present disclosure are useful in the treatment of subject suffering from a neoplastic disease characterized by the presence neoplasms, including benign and malignant neoplasms, and neoplastic disease.

Examples of benign neoplasms amenable to treatment using the compositions and methods of the present disclosure include but are not limited to adenomas, fibromas, hemangiomas, and lipomas. Examples of pre-malignant neoplasms amenable to treatment using the compositions and methods of the present disclosure include but are not limited to hyperplasia, atypia, metaplasia, and dysplasia. Examples of malignant neoplasms amenable to treatment using the compositions and methods of the present disclosure include but are not limited to carcinomas (cancers arising from epithelial tissues such as the skin or tissues that line internal organs), leukemias, lymphomas, and sarcomas typically derived from bone fat, muscle, blood vessels or connective tissues). Also included in the term neoplasms are viral induced neoplasms such as warts and EBV induced disease (i.e., infectious mononucleosis), scar formation, hyperproliferative vascular disease including intimal smooth muscle cell hyperplasia, restenosis, and vascular occlusion and the like.

The term "neoplastic disease" includes cancers characterized by solid tumors and non-solid tumors including but not limited to breast cancers; sarcomas (including but not limited to osteosarcomas and angiosarcomas and fibrosarcomas), leukemias, lymphomas, genitourinary cancers (including but not limited to ovarian, urethral, bladder, and prostate cancers); gastrointestinal cancers (including but not limited to colon esophageal and stomach cancers); lung cancers; myelomas; pancreatic cancers; liver cancers; kidney cancers; endocrine cancers; skin cancers; andbrain or central and peripheral nervous (CNS) system tumors, malignant or benign, including gliomas and neuroblastomas, astrocytomas, myelodysplastic disorders; cervical carcinoma-ii-situ; intestinal polyposes; oral leukoplakias; histiocytoses, hyperprofroliferative scars including keloid scars, hemangiomas; hyperproliferative arterial stenosis, psoriasis, inflammatory arthritis; hyperkeratoses and papulosquamous eruptions including arthritis.

The term neoplastic disease includes carcinomas. The term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The term neoplastic disease includes adenocarcinomas. An "adenocarcinoma" refers to a carcinoma derived from glandular tissue or in which the tumor cells form recognizable glandular structures.

As used herein, the term "hematopoietic neoplastic disorders" refers to neoplastic diseases involving hyperplastic/neoplastic cells of hematopoietic origin, e.g., arising from myeloid, lymphoid or erythroid lineages, or precursor cells thereof.

Myeloid neoplasms include, but are not limited to, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage. Exemplary myeloid disorders amenable to treatment in accordance with the present disclosure include, but are not limited to, acute promyeloid leukemia (APML), acute myelogenous leukemia (AML) and chronic myelogenous leukemia (CML).

Lymphoid neoplasms include, but are not limited to, precursor lymphoid neoplasms, mature B-cell neoplasms, mature T-cell neoplasms, Hodgkin's Lymphoma, and immunodeficiency-associated lymphoproliferative disorders. Exemplary lymphic disorders amenable to treatment in accordance with the present disclosure include, but are not limited to, acute lymphoblastic leukemia (ALL) which includes B-lineage ALL and T-lineage ALL, chronic lymphocyticleukemia (CLL), prolymphocytic leukemia (PLL), hairy cell leukemia (HLL) and Waldenstrom's macroglobulinemia (WM).

In some instances, the hematopoietic neoplastic disorder arises from poorly differentiated acute leukemias (e.g., erythroblastic leukemia and acute megakaryoblastic leukemia). As used herein, the term "hematopoietic neoplastic disorders" refers malignant lymphomas including, but are not limited to, non-Hodgkins lymphoma and variants thereof, peripheral T cell lymphomas, adult T-cell leukemia/ lymphoma (ATL), cutaneous T cell lymphoma (CTCL), large granular lymphocytic leukemia (LGF), Hodgkin's disease and Reed-Stemberg disease.

The determination of whether a subject is "suffering from a neoplastic disease" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment.

Tumor Mutation Burden And Immunotherapy: The adaptive immune system recognizes the display of certain cell surface proteins in response to tumor mutations facilitating the recognition and elimination of neoplastic cells. Tumors that possess a higher tumor mutation burden (TMB) are more likely to exhibit such "tumor antigens." Indeed, clinical experience shows that tumors comprised of neoplastic cells exhibiting a high tumor mutation burden are more likely to respond to immune therapies, including immune checkpoint blockade (Rizvi, et al. (2015) Science 348 (6230): 124-128; Marabelle, et al. (2020) Lancet Oncol 21(10):1353-1365). Tumor mutation burden is useful as a biomarker to identify tumors with an increased sensitivity to immune therapies such as those provided in the present disclosure.

In some embodiments, the compositions and methods of the present disclosure are useful in the treatment of neoplastic disease associated with the formation of solid tumors exhibiting an intermediate or high tumor mutational burden (TMB). In some embodiments, the compositions and compositions and methods of the present disclosure are useful in the treatment of immune sensitive solid tumors exhibiting an intermediate or high tumor mutational burden (TMB). Examples of neoplastic diseases associated with the formation of solid tumors having an intermediate or high tumor mutational burden amenable to treatment with the compositions and methods of the present disclosure include, but are not limited to, non-small cell lung cancer and renal cell cancer. In one embodiment, the compositions and methods are useful in the treatment of non-small cell lung cancer (NSCLC) exhibiting an intermediate or high TMB. NSCLC cells typically harbor a significant number of mutations and are therefore more sensitive to immune therapies. The current standard of care for NSCLC is stratified by the cancer initiating mechanisms and generally follows the recommendations of NCCN or ASCO. A large proportion of NSCLC has increased TMB and is therefore initially more sensitive to immune therapies. However, most tumors eventually relapse on immune checkpoint inhibition. Patients with relapsed tumors typically show reduced T cell infiltration in the tumor, systemic T cell exhaustion and a suppressed immune response compared to the lesions prior to immune checkpoint inhibition. Therefore, improved immune therapies are required, re-activating and expanding the exhausted, rare tumor infiltrating T cells.

Tumor Mutation Burden: As used herein, the term "tumor mutation burden (TMB)" refers to the number of somatic mutations present in a tumor sample expressed as the number of mutations per megabase as determined by nucleic acid sequencing wherein at least 0.2 megabase of the nucleic acid in the tumor sample is sequenced, alternatively wherein at least 0.5 megabases of the nucleic acid in the tumor sample is sequenced, alternatively wherein at least 1 megabase of the nucleic acid in the tumor sample is sequenced, or alternatively wherein at least 5 megabases or alternatively wherein at least ten megabases of the nucleic acid in the tumor sample is sequenced. It is understood that the rate of tumor mutation burden varies among neoplastic diseases so tumor mutation burden should be assessed in the context of a given disease type: For example, certain types of cancers exhibit a wide range of mutation rates from less than 1 mutation per megabase to hundreds of mutations per megabase. As described in Chalmers, et al. (2017) Genome Medicine 9:34, the accuracy in assessing low tumor mutation burden (low TMB) is improved using the Foundation-One® assay (Foundation Medicine, Cambridge MA as described in Frampton, et al. (2013) Nature Biotechnology 31:1023-31; He, et al. (2016) Blood 127:3004-14).

High, Low and Intermediate TMB: Tumors are commonly characterized in clinical practice as exhibiting "high," "low" or "intermediate" tumor mutation burden. As used herein, the term "intermediate tumor mutation burden" means a tumor mutation burden of greater than the upper threshold of the level of tumor mutation burden applied to the term low mutation burden in the particular context. In some embodiments, the term intermediate tumor mutation burden is greater than about 15 mutations per megabase sequenced but less than about 100 mutations per megabase sequenced, alternatively greater than about 10 mutations per megabase sequenced but less than 75 mutations per megabase sequenced, alternatively greater than about 5 mutations per megabase sequenced but less than 50 mutations per megabase sequenced, alternatively greater than about 1 mutations per megabase sequenced but less than 30 mutations per megabase sequenced, alternatively greater than about 1 mutation per megabase sequenced but less than 20 mutations per megabase sequenced. As used herein, the term high tumor mutation is a tumor mutation burden in excess of an intermediate tumor mutation burden greater than or equal to 100 mutations per megabase sequenced, alternatively greater than or equal to 75 mutations per megabase sequenced, alternatively greater than or equal to 50 mutations per megabase sequenced, alternatively greater than or equal to 30 mutations per megabase sequenced, alternatively greater than or equal to 20 mutations per megabase sequenced, or alternatively greater than or equal to 10 mutations per megabase sequenced. As used herein, the term "low tumor mutation burden" means a tumor mutation burden of less than or equal to 15 mutations per megabase sequenced, less than or equal to 10 mutations per megabase sequenced, alternatively less than or equal to 7 mutations per megabase sequenced, alternatively less than or equal to 5 mutations per megabase sequenced, alternatively less than or equal to 2 mutations per megabase sequenced, or alternatively less than or equal to 1 mutation per megabase sequenced. Sequencing to assess TMB may be achieved by any of a variety of art accepted methods including partial genome sequencing, whole exome sequencing (WES) or whole genome sequencing (WGS) using next-generation sequencing (NGS) technologies well established in the art. Although the accuracy of the assessment of TMB increases with the quantity of nucleic acid sequenced, but that the percentage deviation is lower in samples having TMB such that high TMB can be effectively identified by targeted sequencing of only several hundred genes whereas intermediate TMB is improved by the sequence of at least 0.5 Mb sequenced, whereas reliable assessment of low TMB is improved by the sequencing of 5 megabases, alternatively, 10 megabases or more of nucleic acid in the tumor sample.

Assessing Anti-Neoplastic Efficacy: The determination of efficacy of the methods of the present disclosure in the treatment of cancer is generally associated with the achievement of one or more art recognized parameters such as reduction in lesions particularly reduction of metastatic lesion, reduction in metastasis, reduction in tumor volume, improvement in ECOG score, and the like. Determining response to treatment can be assessed through the measurement of biomarker that can provide reproducible information useful in any aspect of IL2 mutein therapy, including the existence and extent of a subject's response to such therapy and the existence and extent of untoward effects caused by such therapy. By way of example, but not limitation, biomarkers include enhancement of IFN7, and upregulation of granzyme A, granzyme B, and perforin; increase in CD8+ T-cell number and function; enhancement of IFNγ, an increase in ICOS expression on CD8+ T-cells, enhancement of IL-10 expressing $TRe_g$ cells. The response to treatment may be characterized by improvements in conventional measures of clinical efficacy may be employed such as Complete Response (CR), Partial Response (PR), Stable Disease (SD) and with respect to target lesions, Complete Response (CR)," Incomplete Response/Stable Disease (SD) as defined by RECIST as well as immune-related Complete Response (irCR), immune-related Partial Response (irPR), and immune-related Stable Disease (irSD) as defined Immune-Related Response Criteria (irRC) are considered by those of skill in the art as evidencing efficacy in the treatment of neoplastic disease in mammalian (e.g. human) subjects.

Maintenance of Serum Concentration: In some embodiments of the invention the present disclosure provides methods and compositions for the treatment and/or prevention of neoplastic diseases, disorders or conditions by the administration of a therapeutically effective amount of an hIL2 muteins that have decreased binding affinity for CD132 yet retain significant binding affinity for CD122 and/or CD25 comparable to wild-type hIL2 wherein the serum concentration of the hIL2 mutein is maintained for a majority (i.e., greater than about 50% of the period of time, alternatively greater than about 60%, alternatively greater than about 70%, alternatively greater than about 80%, alternatively greater than about 90%) of a period of time (e.g. at least 24 hours, alternatively at least 48 hours, alternatively at least 72 hours, alternatively at least 96 hours, alternatively at least 120 hours, alternatively at least 144 hours, alternatively at least 7 days, alternatively at least 10 days, alternatively at least 12 days, alternatively at least 14 days, alternatively at least 28 days, alternatively at least 45 days, alternatively at least 60 days, or longer) at a serum concentration at or above the effective concentration of the IL2 mutein sufficient to promote proliferation of CD3-activated primary human T-cells (e.g., at or above $EC_{10}^{PRO}$, alternatively at or above $EC_{20}^{PRO}$, alternatively at or above $EC_{30}^{PRO}$, alternatively at or above $EC_{40}^{PRO}$, at or above $EC_{50}^{PRO}$, alternatively at or above $EC_{60}^{PRO}$) with respect to such IL2 mutein but at a serum concentration at or below of the effective concentration at a serum concentration of such IL2 mutein sufficient to induce activation of T-cells (e.g., at or below $EC_{100}^{PRO}$, alternatively at or below $EC_{90}^{PRO}$, alternatively at or below $EC_{50}^{PRO}$, alternatively at or below $EC_{70}^{PRO}$, at or below $EC_{60}^{PRO}$, alternatively at or below $EC_{50}^{PRO}$) with respect to such IL2 mutein.

Combination of IL2 Muteins with Supplementary Therapeutic Agents:

The present disclosure provides the for the use of the IL2 muteins of the present disclosure in combination with one or more additional active agents ("supplementary agents"). Such further combinations are referred to interchangeably as "supplementary combinations" or "supplementary combination therapy" and those therapeutic agents that are used in combination with IL2 muteins of the present disclosure are referred to as "supplementary agents." As used herein, the term "supplementary agents" includes agents that can be administered or introduced separately, for example, formulated separately for separate administration (e.g., as may be provided in a kit) and/or therapies that can be administered or introduced in combination with the hIL2 muteins.

In Combination With: As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g. hIL2 mutein) is considered to be administered in combination with a second agent (e.g. a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g. nivolumab or pembrolizumab) are typically administered by IV infusion every two weeks or every three weeks while the hIL2 muteins of the present disclosure are typically administered more frequently, e.g. daily, BID, or weekly. However, the administration of the first agent (e.g. pembrolizumab) provides a therapeutic effect over an extended time and the administration of the second agent (e.g. an hIL2 mutein) provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the hIL2 mutein and the supplementary agent(s) are administered or applied sequentially, e.g., where one agent is administered prior to one or more other agents. In other embodiments, the hIL2 mutein and the supplementary agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Establishing Optimum Combinatorial Therapies: Further embodiments comprise a method or model for determining the optimum amount of an agent(s) in a combination. An optimum amount can be, for example, an amount that achieves an optimal effect in a subject or subject population, or an amount that achieves a therapeutic effect while minimizing or eliminating the adverse effects associated with one or more of the agents. In some embodiments, the methods involving the combination of an hIL2 mutein and a supplementary agent which is known to be, or has been determined to be, effective in treating or preventing a disease, disorder or condition described herein (e.g., a cancerous condition) in a subject (e.g., a human) or a subject population, and an amount of one agent is titrated while the amount of the other agent(s) is held constant. By manipulating the amounts of the agent(s) in this manner, a clinician is able to determine the ratio of agents most effective for, for example, treating a particular disease, disorder or condition, or eliminating the adverse effects or reducing the adverse effects such that are acceptable under the circumstances.

Supplementary Agents:

Chemotherapeutic Agents: In some embodiments, the supplementary agent is a chemotherapeutic agent. In some embodiments the supplementary agent is a "cocktail" of multiple chemotherapeutic agents. IN some embodiments the chemotherapeutic agent or cocktail is administered in combination with one or more physical methods (e.g. radiation therapy). The term "chemotherapeutic agents" includes but is not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins such as bleomycin $A_2$, cactinomycin, calicheamicin, carabicin, caminomycin, carzinophilin, chromomycins, dactinomycin, daunorubicin and derivaties such as demethoxy-daunomycin, 11-deoxydaunorubicin, 13-deoxydaunorubicin, detorubicin, 6-diazo-5-oxo-L-norleucine, doxorubicin, epirubicin, esorubicin, idarubicin, marcellomycin, mitomycins such as mitomycin C, N-methyl mitomycin C; mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate, dideazatetrahydrofolic acid, and folinic acid; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel and doxetaxel; chlorambucil; gemcitabine; 6-thioguanine; mercaptopurine; methotrexate; platinum and platinum coordination complexes such as cisplatin, oxaplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; taxanes such as paclitaxel, docetaxel, cabazitaxel; carminomycin, adriamycins such as 4'-epiadriamycin, 4-adriamycin-14-benzoate, adriamycin-14-octanoate, adriamycin-14-naphthaleneacetate; cholchicine and pharmaceutically acceptable salts, acids or derivatives of any of the above.

The term "chemotherapeutic agents" also includes anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above.

In some embodiments, a supplementary agent isone or more chemical or biological agents identified in the art as useful in the treatment of neoplastic disease, including, but not limited to, a cytokines or cytokine antagonists such as IL-12, INFα, or anti-epidermal growth factor receptor, irinotecan; tetrahydrofolate antimetabolites such as pemetrexed; antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, signal transduction inhibitors (e.g., Gleevec® or Herceptin®) or an immunomodulator to achieve additive or synergistic suppression of tumor growth, non-steroidal anti-inflammatory drugs (NSAIDs), cyclooxygenase-2 (COX-2) inhibitors, steroids, TNF antagonists (e.g., Remicade® and Enbrel®), interferon-β1a (Avonex®), and interferon-β1b (Betaseron®) as well as combinations of one or more of the foreoing as practied in known chemotherapeutic treatment regimens including but not limited to TAC, FOLFOX, TPC, FEC, ADE, FOLFOX-6, EPOCH, CHOP, CMF, CVP, BEP, OFF, FLOX, CVD, TC, FOLFIRI, PCV, FOLFOXIRI, ICE-V, XELOX, and others that are readily appreciated by the skilled clinician in the art.

In some embodiments, the hIL2 mutein is administered in combination with BRAF/MEK inhibitors, kinase inhibitors such as sunitinib, PARP inhibitors such as olaparib, EGFR inhibitors such as osimertinib (Ahn, et al. (2016) J Thorac Oncol 11:S115), IDO inhibitors such as epacadostat, and oncolytic viruses such as talimogene laherparepvec (T-VEC).

Combination with Therapeutic Antibodies

In some embodiments, a "supplementary agent" is a therapeutic antibody (including bi-specific and tri-specific antibodies which bind to one or more tumor associated antigens including but not limited to bispecific T cell engagers (BITEs), dual affinity retargeting (DART) constructs, and trispecific killer engager (TriKE) constructs).

In some embodiments, the therapeutic antibody is an antibody that binds to at least one tumor antigen selected from the group consisting of HER2 (e.g. trastuzumab, pertuzumab, ado-trastuzumab emtansine), nectin-4 (e.g. enfortumab), CD79 (e.g. polatuzumab vedotin), CTLA4 (e.g. ipilumumab), CD22 (e.g. moxetumomab pasudotox), CCR4

(e.g. magamuizuimab), IL23p19 (e.g. tildrakizumab), PDL1 (e.g. durvalumab, avelumab, atezolizumab), IL17a (e.g. ixekizumab), CD38 (e.g. daratumumab), SLAMF7 (e.g. elotuzumab), CD20 (e.g. rituximab, tositumomab, ibritumomab and ofatumumab), CD30 (e.g. brentuximab vedotin), CD33 (e.g. gemtuzumab ozogamicin), CD52 (e.g. alemtuzumab), EpCam, CEA, fpA33, TAG-72, CAIX, PSMA, PSA, folate binding protein, GD2 (e.g. dinuntuximab), GD3, IL6 (e.g. silutxumab) GM2, $Le^y$, VEGF (e.g. bevacizumab), VEGFR, VEGFR2 (e.g. ramucirumab), PDGFRa (e.g. olartumumab), EGFR (e.g. cetuximab, panitumumab and necitumumab), ERBB2 (e.g. trastuzumab), ERBB3, MET, IGF1R, EPHA3, TRAIL R1, TRAIL R2, RANKL RAP, tenascin, integrin aVp3, and integrin a4p31.

Examples of antibody therapeutics which are FDA approved and may be used as supplementary agents for use in the treatment of neoplastic disease include those provided in Table 14 below.

In some embodiments, where the antibody is a bispecific antibody targeting a first and second tumor antigen such as HLER2 andFHER3 (abbreviated HER2×HIER3), FAP×DR-5 bispecific antibodies, CEA×CD3 bispecific antibodies, CD20×CD3 bispecific antibodies, EGFR-EDV-miR16 trispecific antibodies, gp100×CD3 bispecific antibodies, Ny-eso×CD3 bispecific antibodies, EGFR×cMet bispecific antibodies, BCMA×CD3 bispecific antibodies, EGFR-EDV bispecific antibodies, CLEC12A×CD3 bispecific antibodies, HAER2×HER3 bispecific antibodies, Lgr5×EGFR bispecific antibodies, PD1×CThA-4 bispecific antibodies, CD123×CD3 bispecific antibodies, gpA33×CD3 bispecific antibodies, B7-H3×CD3 bispecific antibodies, LAG-3×PD1 bispecific antibodies, DLL4×VEGF bispecific antibodies, Cadherin-P×CD3 bispecific antibodies, BCMA×CD3 bispecific antibodies, DLL4×VEGF bispecific antibodies, CD20×CD3 bispecific antibodies, Ang-2×VEGF-A bispecific antibodies,

TABLE 14

Approved Antineoplastic Disease Antibodies and Indications

| Name | Tradename(s) | Target; format | Indication |
|---|---|---|---|
| [fam]-trastuzumab deruxtecan | Enhertu | HER2; Humanized IgG1 ADC | HER2+ breast cancer |
| Enfortumab vedotin | Padcev | Nectin-4; Human IgG1 ADC | Urothelial cancer |
| Polatuzumab vedotin | Polivy | CD79b; Humanized IgG1 ADC | Diffuse large B-cell lymphoma |
| Cemiplimab | Libtayo | PD-1; Human mAb | Cutaneous squamous cell carcinoma |
| Moxetumomab pasudotox | Lumoxiti | CD22; Murine IgG1 dsFv immunotoxin | Hairy cell leukemia |
| Mogamuizumab | Poteligeo | CCR4; Humanized IgG1 | Cutaneous T cell lymphoma |
| Tildrakizumab | Ilumya | IL23p19; Humanized IgG1 | Plaque psoriasis |
| Ibalizumab | Trogarzo | CD4; Humanized IgG4 | HIV infection |
| Durvalumab | IMFINZI | PD-L1; Human IgG1 | Bladder cancer |
| Inotuzumab ozogamicin | BESPONSA | CD22; Humanized IgG4, ADC | Hematological malignancy |
| Avelumab | Bavencio | PD-L1; Human IgG1 | Merkel cell carcinoma |
| Atezolizumab | Tecentriq | PD-L1; Humanized IgG1 | Bladder cancer |
| Olaratumab | Lartruvo | PDGRFα; Human IgG1 | Soft tissue sarcoma |
| Ixekizumab | Taltz | IL-17a; Humanized IgG4 | Psoriasis |
| Daratumumab | Darzalex | CD38; Human IgG1 | Multiple myeloma |
| Elotuzumab | Empliciti | SLAMF7; Humanized IgG1 | Multiple myeloma |
| Necitumumab | Portrazza | EGFR; Human IgG1 | Non-small cell lung cancer |
| Dinutuximab | Unituxin | GD2; Chimeric IgG1 | Neuroblastoma |
| Nivolumab | Opdivo | PD1; Human IgG4 | Melanoma, non-small cell lung cancer |
| Blinatumomab | Blincyto | CD19, CD3; Murine bispecific tandem scFv | Acute lymphoblastic leukemia |
| Pembrolizumab | Keytruda | PD1; Humanized IgG4 | Melanoma |
| Ramucirumab | Cyramza | VEGFR2; Human IgG1 | Gastric cancer |
| Siltuximab | Sylvant | IL-6; Chimeric IgG1 | Castleman disease |
| Obinutuzumab | Gazyva | CD20; Humanized IgG1; Glycoengineered | Chronic lymphocytic leukemia |
| Ado-trastuzumab emtansine | Kadcyla | HER2; Humanized IgG1, ADC | Breast cancer |
| Pertuzumab | Perjeta | HER2; Humanized IgG1 | Breast Cancer |
| Brentuximab vedotin | Adcetris | CD30; Chimeric IgG1, ADC | Hodgkin lymphoma, systemic anaplastic large cell lymphoma |
| Ipilimumab | Yervoy | CTLA-4; Human IgG1 | Metastatic melanoma |
| Ofatumumab | Arzerra | CD20; Human IgG1 | Chronic lymphocytic leukemia |
| Certolizumab pegol | Cimzia | TNF; Humanized Fab, pegylated | Crohn disease |
| Catumaxomab | Removab | EPCAM/CD3; Rat/mouse bispecific mAb | Malignant ascites |
| Panitumumab | Vectibix | EGFR; Human IgG2 | Colorectal cancer |
| Bevacizumab | Avastin | VEGF; Humanized IgG1 | Colorectal cancer |
| Cetuximab | Erbitux | EGFR; Chimeric IgG1 | Colorectal cancer |
| Tositumomab-I131 | Bexxar | CD20; Murine IgG2a | Non-Hodgkin lymphoma |
| Ibritumomab tiuxetan | Zevalin | CD20; Murine IgG1 | Non-Hodgkin lymphoma |
| Gemtuzumab ozogamicin | Mylotarg | CD33; Humanized IgG4, ADC | Acute myeloid leukemia |
| Trastuzumab | Herceptin | HER2; Humanized IgG1 | Breast cancer |
| Infliximab | Remicade | TNF; Chimeric IgG1 | Crohn disease |
| Rituximab | MabThera, Rituxan | CD20; Chimeric IgG1 | Non-Hodgkin lymphoma |
| Edrecolomab | Panorex | EpCAM; Murine IgG2a | Colorectal cancer |

CD20×CD3 bispecific antibodies, CD123×CD3 bispecific antibodies, SSTR2×CD3 bispecific antibodies, PD1×CTLA-4 bispecific antibodies, HJER2×HiER2 bispecific antibodies, GPC3×CD3 bispecific antibodies, PSMA×CD3 bispecific antibodies, LAG-3×PD-L1 bispecific antibodies, CD38×CD3 bispecific antibodies, HER2×CD3 bispecific antibodies, GD2×CD3 bispecific antibodies, and CD33×CD3 bispecific antibodies. Such therapeutic antibodies may be further conjugated to one or more chemotherapeutic agents (e.g antibody drug conjugates or ADCs) directly or through a linker, especially acid, base or enzymatically labile linkers.

Combination with Physical Methods: In some embodiments, a supplementary agent is one or more non-pharmacological modalities (e.g., localized radiation therapy or total body radiation therapy or surgery). By way of example, the present disclosure contemplates treatment regimens wherein a radiation phase is preceded or followed by treatment with a treatment regimen comprising an IL2 mutein and one or more supplementary agents. In some embodiments, the present disclosure further contemplates the use of an IL2 mutein in combination with surgery (e.g. tumor resection). In some embodiments, the present disclosure further contemplates the use of an IL2 mutein in combination with bone marrow transplantation, peripheral blood stem cell transplantation or other types of transplantation therapy.

Combination with Immune Checkpoint Modulators: In some embodiments, a "supplementary agent" is an immune checkpoint modulator for the treatment and/or prevention neoplastic disease in a subject as well as diseases, disorders or conditions associated with neoplastic disease. The term "immune checkpoint pathway" refers to biological response that is triggered by the binding of a first molecule (e.g. a protein such as PD1) that is expressed on an antigen presenting cell (APC) to a second molecule (e.g. a protein such as PDL1) that is expressed on an immune cell (e.g. a T-cell) which modulates the immune response, either through stimulation (e.g. upregulation of T-cell activity) or inhibition (e.g. downregulation of T-cell activity) of the immune response. The molecules that are involved in the formation of the binding pair that modulate the immune response are commonly referred to as "immune checkpoints." The biological responses modulated by such immune checkpoint pathways are mediated by intracellular signaling pathways that lead to downstream immune effector pathways, such as cell activation, cytokine production, cell migration, cytotoxic factor secretion, and antibody production. Immune checkpoint pathways are commonly triggered by the binding of a first cell surface expressed molecule to a second cell surface molecule associated with the immune checkpoint pathway (e.g. binding of PD1 to PDL1, CTLA4 to CD28, etc.). The activation of immune checkpoint pathways can lead to stimulation or inhibition of the immune response.

An immune checkpoint whose activation results in inhibition or downregulation of the immune response is referred to herein as a "negative immune checkpoint pathway modulator." The inhibition of the immune response resulting from the activation of a negative immune checkpoint modulator diminishes the ability of the host immune system to recognize foreign antigen such as a tumor-associated antigen. The term negative immune checkpoint pathway includes, but is not limited to, biological pathways modulated by the binding of PD1 to PDL1, PD1 to PDL2, and CTLA4 to CDCD80/86. Examples of such negative immune checkpoint antagonists include but are not limited to antagonists (e.g. antagonist antibodies) that bind T-cell inhibitory receptors including but not limited to PD1 (also referred to as CD279), TIM3 (T-cell membrane protein 3; also known as HAVcr2), BTLA (B and T lymphocyte attenuator; also known as CD272), the VISTA (B7-H5) receptor, LAG3 (lymphocyte activation gene 3; also known as CD233) and CTLA4 (cytotoxic T-lymphocyte associated antigen 4; also known as CD152).

In one embodiment, an immune checkpoint pathway the activation of which results in stimulation of the immune response is referred to herein as a "positive immune checkpoint pathway modulator." The term positive immune checkpoint pathway modulator includes, but is not limited to, biological pathways modulated by the binding of ICOSL to ICOS(CD278), B7-H6 to NKp30, CD155 to CD96, OX40L to OX40, CD70 to CD27, CD40 to CD40L, and GITRL to GITR. Molecules which agonize positive immune checkpoints (such natural or synthetic ligands for a component of the binding pair that stimulates the immune response) are useful to upregulate the immune response. Examples of such positive immune checkpoint agonists include but are not limited to agonist antibodies that bind T-cell activating receptors such as ICOS (such as JTX-2011, Jounce Therapeutics), OX40 (such as MEDI6383, Medimmune), CD27 (such as varlilumab, Celldex Therapeutics), CD40 (such as dacetuzmumab CP-870,893, Roche, Chi Lob 7/4), HVEM, CD28, CD137 4-1BB, CD226, and GITR (such as MEDI1873, Medimmune; INCAGN1876, Agenus).

As used herein, the term "immune checkpoint pathway modulator" refers to a molecule that inhibits or stimulates the activity of an immune checkpoint pathway in a biological system including an immunocompetent mammal. An immune checkpoint pathway modulator may exert its effect by binding to an immune checkpoint protein (such as those immune checkpoint proteins expressed on the surface of an antigen presenting cell (APC) such as a cancer cell and/or immune T effector cell) or may exert its effect on upstream and/or downstream reactions in the immune checkpoint pathway. For example, an immune checkpoint pathway modulator may modulate the activity of SHP2, a tyrosine phosphatase that is involved in PD-1 and CTLA-4 signaling. The term "immune checkpoint pathway modulators" encompasses both immune checkpoint pathway modulator(s) capable of down-regulating at least partially the function of an inhibitory immune checkpoint (referred to herein as an "immune checkpoint pathway inhibitor" or "immune checkpoint pathway antagonist") and immune checkpoint pathway modulator(s) capable of up-regulating at least partially the function of a stimulatory immune checkpoint (referred to herein as an "immune checkpoint pathway effector" or "immune checkpoint pathway agonist.").

The immune response mediated by immune checkpoint pathways is not limited to T-cell mediated immune response. For example, the KIR receptors of NK cells modulate the immune response to tumor cells mediated by NK cells. Tumor cells express a molecule called HLA-C, which inhibits the KIR receptors of NK cells leading to a dimunition or the anti-tumor immune response. The administration of an agent that antagonizes the binding of HLA-C to the KIR receptor such an anti-KIR3 mab (e.g. lirilumab, BMS) inhibits the ability of HLA-C to bind the NK cell inhibitory receptor (KIR) thereby restoring the ability of NK cells to detect and attack cancer cells. Thus, the immune response mediated by the binding of HLA-C to the KIR receptor is an example a negative immune checkpoint pathway the inhibition of which results in the activation of a of non-T-cell mediated immune response.

In one embodiment, the immune checkpoint pathway modulator is a negative immune checkpoint pathway inhibitor/antagonist. In another embodiment, immune checkpoint pathway modulator employed in combination with the IL2 mutein is a positive immune checkpoint pathway agonist. In another embodiment, immune checkpoint pathway modulator employed in combination with the IL2 mutein is an immune checkpoint pathway antagonist.

The term "negative immune checkpoint pathway inhibitor" refers to an immune checkpoint pathway modulator that interferes with the activation of a negative immune checkpoint pathway resulting in the upregulation or enhancement of the immune response. Exemplary negative immune checkpoint pathway inhibitors include but are not limited to programmed death-1 (PD1) pathway inhibitors, programed death ligand-1 (PDL1) pathway inhibitors, TIM3 pathway inhibitors and anti-cytotoxic T-lymphocyte antigen 4 (CTLA4) pathway inhibitors.

In one embodiment, the immune checkpoint pathway modulator is an antagonist of a negative immune checkpoint pathway that inhibits the binding of PD1 to PDL1 and/or PDL2 ("PD1 pathway inhibitor"). PD1 pathway inhibitors result in the stimulation of a range of favorable immune response such as reversal of T-cell exhaustion, restoration cytokine production, and expansion of antigen-dependent T-cells. PD1 pathway inhibitors have been recognized as effective variety of cancers receiving approval from the USFDA for the treatment of variety of cancers including melanoma, lung cancer, kidney cancer, Hodgkins lymphoma, head and neck cancer, bladder cancer and urothelial cancer.

The term PD1 pathway inhibitors includes monoclonal antibodies that interfere with the binding of PD1 to PDL1 and/or PDL2. Antibody PD1 pathway inhibitors are well known in the art. Examples of commercially available PD1 pathway inhibitors that monoclonal antibodies that interfere with the binding of PD1 to PDL1 and/or PDL2 include nivolumab (Opdivo®, BMS-936558, MDX1106, commercially available from BristolMyers Squibb, Princeton NJ), pembrolizumab (Keytruda@MK-3475, lambrolizumab, commercially available from Merck and Company, Kenilworth NJ), and atezolizumab (Tecentriq®, Genentech/Roche, South San Francisco CA). Additional PD1 pathway inhibitors antibodies are in clinical development including but not limited to durvalumab (MEDI4736, Medimmune/AstraZeneca), pidilizumab (CT-011, CureTech), PDR001 (Novartis), BMS-936559 (MDX1105, BristolMyers Squibb), and avelumab (MSB0010718C, Merck Serono/Pfizer) and SHR-1210 (Incyte). Additional antibody PD1 pathway inhibitors are described in U.S. Pat. No. 8,217,149 (Genentech, Inc) issued Jul. 10, 2012; U.S. Pat. No. 8,168,757 (Merck Sharp and Dohme Corp.) issued May 1, 2012, U.S. Pat. No. 8,008,449 (Medarex) issued Aug. 30, 2011, U.S. Pat. No. 7,943,743 (Medarex, Inc) issued May 17, 2011.

The term PD1 pathway inhibitors are not limited to antagonist antibodies. Non-antibody biologic PD1 pathway inhibitors are also under clinical development including AMP-224, a PD-L2 IgG2a fusion protein, and AMP-514, a PDL2 fusion protein, are under clinical development by Amplimmune and Glaxo SmithKline. Aptamer compounds are also described in the literature useful as PD1 pathway inhibitors (Wang, et al. (2018) 145:125-130.).

The term PD1 pathway inhibitors includes peptidyl PD1 pathway inhibitors such as those described in Sasikumar, et al., U.S. Pat. No. 9,422,339 issued Aug. 23, 2016, and Sasilkumar, et al., U.S. Pat. No. 8,907,053 issued Dec. 9, 2014. CA-170 (AUPM-170, Aurigene/Curis) is reportedly an orally bioavailable small molecule targeting the immune checkpoints PDL1 and VISTA. Pottayil Sasikumar, et al. *Oral immune checkpoint antagonists targeting PD-L1/VISTA or PD-L1/Tim3 for cancer therapy*. [abstract]. In: Proceedings of the 107th Annual Meeting of the American Association for Cancer Research; 2016 Apr. 16-20; New Orleans, LA. Philadelphia (PA): AACR; Cancer Res 2016; 76(14 Suppl): Abstract No.4861. CA-327 (AUPM-327, Aurigene/Curis) is reportedly an orally available, small molecule that inhibit the immune checkpoints, Programmed Death Ligand-1 (PDL1) and T-cell immunoglobulin and mucin domain containing protein-3 (TIM3).

The term PD1 pathway inhibitors includes small molecule PD1 pathway inhibitors. Examples of small molecule PD1 pathway inhibitors useful in the practice of the present invention are described in the art including Sasikumar, et al., 1,2,4-*oxadiazole and thiadiazole compounds as immunomodulators* (PCT/IB2016/051266 filed Mar. 7, 2016, published as WO2016142833A1 Sep. 15, 2016) and Sasikumar, et al. 3-substituted-1,2,4-oxadiazole and thiadiazole PCT/IB2016/051343 filed Mar. 9, 2016 and published as WO2016142886A2), BMS-1166 and Chupak L S and Zheng X. *Compounds useful as immunomodulators*. Bristol-Myers Squibb Co. (2015) WO 2015/034820 A1, EP3041822 B1 granted Aug. 9, 2017; WO2015034820 A1; and Chupak, et al. *Compounds useful as immunomodulators*. Bristol-Myers Squibb Co. (2015) WO 2015/160641 A2. WO 2015/160641 A2, Chupak, et al. *Compounds useful as immunomodulators*. Bristol-Myers Squibb Co. Sharpe, et al. Modulators of immunoinhibitory receptor PD-1, and methods of use thereof, WO 2011082400 A2 published Jul. 7, 2011; U.S. Pat. No. 7,488,802 (Wyeth) issued Feb. 16, 2009;

In some embodiments, combination of IL2 muteins and one or more PD1 immune checkpoint modulators are useful in the treatment of neoplastic conditions for which PD1 pathway inhibitors have demonstrated clinical effect in human beings either through FDA approval for treatment of the disease or the demonstration of clinical efficacy in clinical trials including but not limited to melanoma, non-small cell lung cancer, small cell lung cancer, head and neck cancer, renal cell cancer, bladder cancer, ovarian cancer, uterine endometrial cancer, uterine cervical cancer, uterine sarcoma, gastric cancer, esophageal cancer, DNA mismatch repair deficient colon cancer, DNA mismatch repair deficient endometrial cancer, hepatocellular carcinoma, breast cancer, Merkel cell carcinoma, thyroid cancer, Hodgkins lymphoma, follicular lymphoma, diffuse large B-cell lymphoma, mycosisfungoides, peripheral T-cell lymphoma. In some embodiments, the combination of IL2 muteins and an PD1 immune checkpoint modulator is useful in the treatment of tumors characterized by high levels of expression of PDL1, where the tumor has a tumor mutational burden, where there are high levels of CD8+ T-cell in the tumor, an immune activation signature associated with IFN7 and the lack of metastatic disease particularly liver metastasis.

In some embodiments, the IL2 mutein is administered in combination with an antagonist of a negative immune checkpoint pathway that inhibits the binding of CTLA4 to CD28 ("CTLA4 pathway inhibitor"). Examples of CTLA4 pathway inhibitors are well known in the art (See, e.g., U.S. Pat. No. 6,682,736 (Abgenix) issued Jan. 27, 2004; U.S. Pat. No. 6,984,720 (Medarex, Inc.) issued May 29, 2007; U.S. Pat. No. 7,605,238 (Medarex, Inc.) issued Oct. 20, 2009)

In some embodiments, the IL2 mutein is administered in combination with an antagonist of a negative immune checkpoint pathway that inhibits the binding of BTLA to HVEM ("BTLA pathway inhibitor"). A number of approaches targeting the BTLA/HVEM pathway using anti-BTLA antibodies and antagonistic HVEM-Ig have been evaluated, and such approaches have suggested promising utility in a number of diseases, disorders and conditions, including transplantation, infection, tumor, and autoimmune disease (See e.g. Wu, et al., (2012) Int. J. Biol. Sci. 8:1420-30).

In some embodiments, the IL2 mutein is administered in combination with an antagonist of a negative immune checkpoint pathway that inhibits the ability TIM3 to binding to TIM3-activating ligands ("TIM3 pathway inhibitor"). Examples of TI43 pathway inhibitors are known in the art and with representative non-limiting examples described in PCT International Patent Publication No. WO 2016/144803 published Sep. 15, 2016; Lifke, et al. United States Patent Publication No. US 20160257749 A1 published Sep. 8, 2016 (F. Hoffman-LaRoche); Karunsky, U.S. Pat. No. 9,631,026 issued Apr. 27, 2017; Karunsky, Sabatos-Peyton, et al. U.S. Pat. No. 8,841,418 issued Sep. 23, 2014; U.S. Pat. No. 9,605,070; Takayanagi, et al., U.S. Pat. No. 8,552,156 issued Oct. 8, 2013.

In some embodiments, the IL2 mutein is administered in combination with an inhibitor of both LAG3 and PD1 as the blockade of LAG3 and PD1 has been suggested to synergistically reverse anergy among tumor-specific CD8+ T-cells and virus-specific CD8+ T-cells in the setting of chronic infection. IMP321 (ImmuFact) is being evaluated in melanoma, breast cancer, and renal cell carcinoma. See generally Woo et al., (2012) Cancer Res 72:917-27; Goldberg et al., (2011) Curr. Top. Microbiol. Immunol. 344:269-78; Pardoll (2012) Nature Rev. Cancer 12:252-64; Grosso et al., (2007) J. Clin. Invest. 117:3383-392.

In some embodiments, the IL2 mutein is administered in combination with an A2aR inhibitor. A2aR inhibits T-cell responses by stimulating CD4+ T-cells towards developing into TReg cells. A2aR is particularly important in tumor immunity because the rate of cell death in tumors from cell turnover is high, and dying cells release adenosine, which is the ligand for A2aR. In addition, deletion of A2aR has been associated with enhanced and sometimes pathological inflammatory responses to infection. Inhibition of A2aR can be effected by the administration of molecules such as antibodies that block adenosine binding or by adenosine analogs. Such agents may be used in combination with the I12 muteins for use in the treatment disorders such as cancer and Parkinson's disease.

In some embodiments, the IL2 mutein is administered in combination with an inhibitor of IDO (Indoleamine 2,3-dioxygenase). IDO down-regulates the immune response mediated through oxidation of tryptophan resulting in in inhibition of T-cell activation and induction of T-cell apoptosis, creating an environment in which tumor-specific cytotoxic T lymphocytes are rendered functionally inactive or are no longer able to attack a subject's cancer cells. Indoximod (NewLink Genetics) is an IDO inhibitor being evaluated in metastatic breast cancer.

As previously described, the present invention provides for a method of treatment of neoplastic disease (e.g. cancer) in a mammalian subject by the administration of a IL2 mutein in combination with an agent(s) that modulate at least one immune checkpoint pathway including immune checkpoint pathway modulators that modulate two, three or more immune checkpoint pathways.

In some embodiments the IL2 mutein is administered in combination with an immune checkpoint modulator that is capable of modulating multiple immune checkpoint pathways. Multiple immune checkpoint pathways may be modulated by the administration of multi-functional molecules which are capable of acting as modulators of multiple immune checkpoint pathways. Examples of such multiple immune checkpoint pathway modulators include but are not limited to bi-specific or poly-specific antibodies. Examples of poly-specific antibodies capable of acting as modulators or multiple immune checkpoint pathways are known in the art. For example, United States Patent Publication No. 2013/0156774 describes bispecific and multispecific agents (e.g., antibodies), and methods of their use, for targeting cells that co-express PD1 and TIM3. Moreover, dual blockade of BTLA and PD1 has been shown to enhance antitumor immunity (Pardoll, (April 2012) Nature Rev. Cancer 12:252-64). The present disclosure contemplates the use of hIL2 muteins in combination with immune checkpoint pathway modulators that target multiple immune checkpoint pathways, including but limited to bi-specific antibodies which bind to both PD1 and LAG3. Thus, antitumor immunity can be enhanced at multiple levels, and combinatorial strategies can be generated in view of various mechanistic considerations.

In some embodiments, the IL2 mutein may be administered in combination with two, three, four or more checkpoint pathway modulators. Such combinations may be advantageous in that immune checkpoint pathways may have distinct mechanisms of action, which provides the opportunity to attack the underlying disease, disorder or conditions from multiple distinct therapeutic angles.

It should be noted that therapeutic responses to immune checkpoint pathway inhibitors often manifest themselves much later than responses to traditional chemotherapies such as tyrosine kinase inhibitors. In some instance, it can take six months or more after treatment initiation with immune checkpoint pathway inhibitors before objective indicia of a therapeutic response are observed. Therefore, a determination as to whether treatment with an immune checkpoint pathway inhibitors(s) in combination with a IL2 mutein of the present disclosure must be made over a time-to-progression that is frequently longer than with conventional chemotherapies. The desired response can be any result deemed favorable under the circumstances. In some embodiments, the desired response is prevention of the progression of the disease, disorder or condition, while in other embodiments the desired response is a regression or stabilization of one or more characteristics of the disease, disorder or conditions (e.g., reduction in tumor size). In still other embodiments, the desired response is reduction or elimination of one or more adverse effects associated with one or more agents of the combination.

Cell Therapy Agents and Methods as Supplementary Agents:

In some embodiments, the methods of the disclosure may include the combination of the administration of an IL2 muteins with supplementary agents in the form of cell therapies for the treatment of neoplastic, autoimmune or inflammatory diseases. Examples of cell therapies that are amenable to use in combination with the methods of the present disclosure include but are not limited to engineered T cell products comprising one or more activated CAR-T cells, engineered TCR cells, tumor infiltrating lymphocytes (TILs), engineered Treg cells. As engineered T-cell products are commonly activated ex vivo prior to their administration to the subject and therefore provide upregulated levels of CD25, cell products comprising such activated engineered T cells types are amenable to further support via the administration of an CD25 biased IL2 mutein as described herein.

CAR-T Cells

In some embodiments of the methods of the present disclosure, the supplementary agent is a "chimeric antigen receptor T-cell" and "CAR-T cell" are used interchangeably to refer to a T-cell that has been recombinantly modified to express a chimeric antigen receptor. As used herein, the terms As used herein, the terms "chimeric antigen receptor" and "CAR" are used interchangeably to refer to a chimeric polypeptide comprising multiple functional domains arranged from amino to carboxy terminus in the sequence: (a) an antigen binding domain (ABD), (b) a transmembrane domain (TD); and (c) one or more cytoplasmic signaling domains (CSDs) wherein the foregoing domains may optionally be linked by one or more spacer domains. The CAR may also further comprise a signal peptide sequence which is conventionally removed during post-translational processing and presentation of the CAR on the cell surface of a cell transformed with an expression vector comprising a nucleic acid sequence encoding the CAR. CARs useful in the practice of the present invention are prepared in accordance with principles well known in the art. See e.g., Eshhaar et al. U.S. Pat. No. 7,741,465 B1 issued Jun. 22, 2010; Sadelain, et al (2013) Cancer Discovery 3(4):388-398; Jensen and Riddell (2015) Current Opinions in Immunology 33:9-15; Gross, et al. (1989) PNAS(USA) 86(24):10024-10028; Curran, et al. (2012) J Gene Med 14(6):405-15. Examples of commercially available CAR-T cell products that may be modified to incorporate an orthogonal receptor of the present invention include axicabtagene ciloleucel (marketed as Yescarta® commercially available from Gilead Pharmaceuticals) and tisagenlecleucel (marketed as Kymriah® commercially available from Novartis).

As used herein, the term antigen binding domain (ABD) refers to a polypeptide that specifically binds to an antigen expressed on the surface of a target cell. The ABD may be any polypeptide that specifically binds to one or more cell surface molecules (e.g. tumor antigens) expressed on the surface of a target cell. In some embodiments, the ABD is a polypeptide that specifically binds to a cell surface molecule associated with a tumor cell is selected from the group consisting of GD2, BCMA, CD19, CD33, CD38, CD70, GD2, IL3Rα2, CD19, mesothelin, Her2, EpCam, Muc1, ROR1, CD133, CEA, EGRFRVIII, PSCA, GPC3, Pan-ErbB and FAP. In some embodiments, the ABD is an antibody (as defined hereinabove to include molecules such as one or more VHHs, scFvs, etc.) that specifically binds to at least one cell surface molecule associated with a tumor cell (i.e. at least one tumor antigen) wherein the cell surface molecule associated with a tumor cell is selected from the group consisting of GD2, BCMA, CD19, CD33, CD38, CD70, GD2, IL3Rα2, CD19, mesothelin, Her2, EpCam, Muc1, ROR1, CD133, CEA, EGRFRVIII, PSCA, GPC3, Pan-ErbB and FAP. Examples of CAR-T cells useful as supplementary agents in the practice of the methods of the present disclosure include but are not limited to CAR-T cells expressing CARs comprising an ABD further comprising at least one of: anti-GD2 antibodies, anti-BCMA antibodies, anti-CD19 antibodies, anti-CD33 antibodies, anti-CD38 antibodies, anti-CD70 antibodies, anti-GD2 antibodies and IL3Rα2 antibodies, anti-CD19 antibodies, anti-mesothelin antibodies, anti-Her2 antibodies, anti-EpCam antibodies, anti-Muc1 antibodies, anti-RORI antibodies, anti-CD133 antibodies, anti-CEA antibodies, anti-PSMA antibodies, anti-EGRFRVIII antibodies, anti-PSCA antibodies, anti-GPC3 antibodies, anti-Pan-ErbB antibodies, anti-FAP antibodies, CARs of CAR-T cells useful in the practice of the methods of the present disclosure further comprise a transmembrane domain joining the ABD (or linker, if employed, see discussion of linkers below) to the intracellular cytoplasmic domain of the CAR. The transmembrane domain is comprised of any polypeptide sequence which is thermodynamically stable in a eukaryotic cell membrane. The transmembrane spanning domain may be derived from the transmembrane domain of a naturally occurring membrane spanning protein or may be synthetic. In designing synthetic transmembrane domains, amino acids favoring alpha-helical structures are preferred. Transmembrane domains useful in construction of CARs are comprised of approximately 10, 11, 12, 13, 14, 15, 16, 17, 18, 19, 20, 21, 22, 22, 23, or 24 amino acids favoring the formation having an alpha-helical secondary structure. Amino acids having a to favor alpha-helical conformations are well known in the art. See, e.g., Pace, et al. (1998) Biophysical Journal 75: 422-427. Amino acids that are particularly favored in alpha helical conformations include methionine, alanine, leucine, glutamate, and lysine. In some embodiments, the CAR transmembrane domain may be derived from the transmembrane domain from type I membrane spanning proteins, such as CD3ζ, CD4, CD8, CD28, etc.

The cytoplasmic domain of the CAR polypeptide comprises one or more intracellular signal domains. In one embodiment, the intracellular signal domains comprise the cytoplasmic sequences of the T-cell receptor (TCR) and co-receptors that initiate signal transduction following antigen receptor engagement and functional derivatives and sub-fragments thereof. A cytoplasmic signaling domain, such as those derived from the T cell receptor zeta-chain, is employed as part of the CAR in order to produce stimulatory signals for T lymphocyte proliferation and effector function following engagement of the chimeric receptor with the target antigen. Examples of cytoplasmic signaling domains include but are not limited to the cytoplasmic domain of CD27, the cytoplasmic domain S of CD28, the cytoplasmic domain of CD137 (also referred to as 4-1BB and TNFRSF9), the cytoplasmic domain of CD278 (also referred to as ICOS), p110α, β, or δ catalytic subunit of PI3 kinase, the human CD3 ζ-chain, cytoplasmic domain of CD134 (also referred to as OX40 and TNFRSF4), FcER1γ and β chains, MB1 (Igα) chain, B29 (Igβ) chain, etc.), CD3 polypeptides (δ, Δ and ε), syk family tyrosine kinases (Syk, ZAP 70, etc.), src family tyrosine kinases (Lck, Fyn, Lyn, etc.) and other molecules involved in T-cell transduction, such as CD2, CD5 and CD28.

In some embodiments, the CAR may also provide a co-stimulatory domain. The term "co-stimulatory domain", refers to a stimulatory domain, typically an endodomain, of a CAR that provides a secondary non-specific activation mechanism through which a primary specific stimulation is propagated. The co-stimulatory domain refers to the portion of the CAR which enhances the proliferation, survival or development of memory cells. Examples of co-stimulation include antigen nonspecific T cell co-stimulation following antigen specific signaling through the T cell receptor and antigen nonspecific B cell co-stimulation following signaling through the B cell receptor. Co-stimulation, e.g., T cell co-stimulation, and the factors involved have been described in Chen & Flies (2013) Nat Rev Immunol 13(4):227-42. In some embodiments of the present disclosure, the CSD comprises one or more of members of the TNFR superfamily, CD28, CD137 (4-1BB), CD134 (OX40), Dap10, CD27, CD2, CD5, ICAM-1, LFA-1 (CD11a/CD18), Lek, TNFR-I, TNFR-II, Fas, CD30, CD40 or combinations thereof.

CARs useful in the practice of the methods of the present disclosure may optionally include one or more polypeptide spacers linking the domains of the CAR, in particular the linkage between the ABD to the transmembrane spanning domain of the CAR. Although not an essential element of the CAR structure, the inclusion of a spacer domain is generally considered desirable to facilitate antigen recognition by the ARD. As used in conjunction with the CAR-T cell technology described herein, the terms "linker", "linker domain" and "linker region" refer to a polypeptide from about 1 to 100 amino acids in length. Linkers are typically be composed of amino acid residues which permit flexibility of the polypeptide (e.g. glycine and serine) so that the adjacent domains of the CAR are provided greater freedom of movement relative to one another. Although there is no particularly defined length or sequence of amino acids that is necessary for the spacer to achieve its function, but the typical properties of the spacer are flexibility to enable freedom of movement of the ABD to facilitate targeting antigen recognition. Similarly, it has been found that there is there is substantial leniency in spacer length while retaining CAR function. Jensen and Riddell (2014) Immunol. Review 257(1) 127-144. Sequences useful as spacers in the construction of CARs useful in the practice of the present invention include but are not limited to the hinge region of IgG1, the immunoglobulinlCH2-CH3 region, IgG4 hinge-CH2-CH3, IgG4 hinge-CH3, and the IgG4 hinge. The hinge and transmembrane domains may be derived from the same molecule such as the hinge and transmembrane domains of CD8-alpha. Imai, et al. (2004) Leukemia 18(4):676-684.

CARs are often referred to as first, second, third or fourth generation. The term first-generation CAR refers to a CAR wherein the cytoplasmic domain transmits the signal from antigen binding through only a single signaling domain, for example a signaling domain derived from the high-affinity receptor for IgE FcεR1γ or the CD3ζ chain. The domain contains one or three immunoreceptor tyrosine-based activating motif(s) [ITAM(s)] for antigen-dependent T-cell activation. The ITAM-based activating signal endows T-cells with the ability to lyse the target tumor cells and secret cytokines in response to antigen binding. Second-generation CARs include a co-stimulatory signal in addition to the CD3 ζ signal. Coincidental delivery of the co-stimulatory signal enhances cytokine secretion and antitumor activity induced by CAR-transduced T-cells. The co-stimulatory domain is usually be membrane proximal relative to the CD3C domain. Third-generation CARs include a tripartite signaling domain, comprising for example a CD28, CD3ζ, OX40 or 4-1BB signaling region. In fourth generation, or "armored car" CAR T-cells are further modified to express or block molecules and/or receptors to enhance immune activity such as the expression of IL-12, IL-18, IL-7, and/or IL-10; 4-1BB ligand, CD-40 ligand. Examples of intracellular signaling domains comprising may be incorporated into the CAR of the present invention include (amino to carboxy): CD3ζ; CD28 –41BB–CD3ζ; CD28-OX40–CD3ζ; CD28 –41BB–CD3ζ; 41BB-CD-28–CD3ζ and 41BB–CD3ζ.

The term CAR includes CAR variants including but not limited split CARs, ON-switch CARS, bispecific or tandem CARs, inhibitory CARs (iCARs) and induced pluripotent stem (iPS) CAR-T cells. The term "Split CARs" refers to CARs wherein the extracellular portion, the ABD and the cytoplasmic signaling domain of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR molecules and derivatives thereof (i.e., CAR variants) are described, e.g., in PCT Application Nos. US2014/016527, US1996/017060, US2013/063083; Fedorov et al. *Sci Transl Med* (2013); 5(215):215ra172; Glienke et al. *Front Pharmacol* (2015) 6:21; Kakarla & Gottschalk 52 *Cancer J* (2014) 20(2):151-5; Riddell et al. *Cancer J* (2014) 20(2):141-4; Pegram et al. *Cancer J* (2014) 20(2): 127-33; Cheadle et al. *Immunol Rev* (2014) 257(1):91-106; Barrett et al. *Annu Rev Med* (2014) 65:333-47; Sadelain et al. *Cancer Discov* (2013) 3(4):388-98; Cartellieri et al., *J Biomed Biotechnol* (2010) 956304; the disclosures of which are incorporated herein by reference in their entirety. The term "bispecific or tandem CARs" refers to CARs which include a secondary CAR binding domain that can either amplify or inhibit the activity of a primary CAR. The term "inhibitory chimeric antigen receptors" or "iCARs" are used interchangeably herein to refer to a CAR where binding iCARs use the dual antigen targeting to shut down the activation of an active CAR through the engagement of a second suppressive receptor equipped with inhibitory signaling domains of a secondary CAR binding domain results in inhibition of primary CAR activation. Inhibitory CARs (iCARs) are designed to regulate CAR-T cells activity through inhibitory receptors signaling modules activation. This approach combines the activity of two CARs, one of which generates dominant negative signals limiting the responses of CAR-T cells activated by the activating receptor. iCARs can switch off the response of the counteracting activator CAR when bound to a specific antigen expressed only by normal tissues. In this way, iCARs-T cells can distinguish cancer cells from healthy ones, and reversibly block functionalities of transduced T cells in an antigen-selective fashion. CTLA-4 or PD-1 intracellular domains in iCARs trigger inhibitory signals on T lymphocytes, leading to less cytokine production, less efficient target cell lysis, and altered lymphocyte motility. The term "tandem CAR" or "TanCAR" refers to CARs which mediate bispecific activation of T cells through the engagement of two chimeric receptors designed to deliver stimulatory or costimulatory signals in response to an independent engagement of two different tumor associated antigens.

Typically, the chimeric antigen receptor T-cells (CAR-T cells) are T-cells which have been recombinantly modified by transduction with an expression vector encoding a CAR in substantial accordance with the teaching above.

In some embodiments, the engineered T cell is allogeneic with respect to the individual that is treated. Graham et al. (2018) Cell 7(10) E155. In some embodiments an allogeneic engineered T cell is fully HLA matched. However not all patients have a fully matched donor and a cellular product suitable for all patients independent of HLA type provides an alternative.

Because the cell product may consist of a subject's own T-cells, the population of the cells to be administered is to the subject is necessarily variable. Consequently identifying the optimal concentration of the Additionally, since the CAR-T cell agent is variable, the response to such agents can vary and thus involves the ongoing monitoring and management of therapy related toxicities which are managed with a course of pharmacologic immunosuppression or B cell depletion prior to the administration of the CAR-T cell treatment. Usually, at least $1\times10^6$ cells/kg will be administered, at least $1\times10^7$ cells/kg, at least $1\times10^8$ cells/kg, at least $1\times10^9$ cells/kg, at least $1\times10^{10}$ cells/kg, or more, usually being limited by the number of T cells that are obtained during collection. The engineered cells may be infused to the subject in any physiologically acceptable medium by any convenient route of administration, normally intravascularly, although they may also be introduced by other routes, where the cells may find an appropriate site for growth If the T cells used in the practice of the present invention are allogeneic T cells, such cells may be modified to reduce graft versus host disease. For example, the engineered cells of the present invention may be TCRap receptor knock-outs achieved by gene editing techniques. TCRaP is a heterodimer and both alpha and beta chains need to be present for it to be expressed. A single gene codes for the alpha chain (TRAC), whereas there are 2 genes coding for the beta chain, therefore TRAC loci KO has been deleted for this purpose. A number of different approaches have been used to accomplish this deletion, e.g. CRISPR/Cas9; meganuclease; engineered I-CreI homing endonuclease, etc. See, for example, Eyquem et al. (2017) Nature 543:113-117, in which the TRAC coding sequence is replaced by a CAR coding sequence; and Georgiadis et al. (2018) Mol. Ther. 26:1215-1227, which linked CAR expression with TRAC disruption by clustered regularly interspaced short palindromic repeats (CRISPR)/Cas9 without directly incorporating the CAR into the TRAC loci. An alternative strategy to prevent GVHD modifies T cells to express an inhibitor of TCRαβ signaling, for example using a truncated form of CD3ζ as a TCR inhibitory molecule.

Chemokine and Cytokine Agents as Supplementary Agents:

In some embodiments the IL2 mutein is administered in combination with additional cytokines including but not limited to IL-7, IL-12, 11-15 and 11-18 including analogs and variants of each thereof.

Activation-Induced Cell Death Inhibitors

In some embodiments the IL2 mutein is administered in combination with one or more supplementary agents that inhibit Activation-Induced Cell Death (AICD). AICD is a form of programmed cell death resulting from the interaction of Fas receptors (e.g., Fas, CD95) with Fas ligands (e.g., FasL, CD95 ligand), helps to maintain peripheral immune tolerance. The AICD effector cell expresses FasL, and apoptosis is induced in the cell expressing the Fas receptor. Activation-induced cell death is a negative regulator of activated T lymphocytes resulting from repeated stimulation of their T-cell receptors. Examples of agents that inhibit AICD that may be used in combination with the IL2 muteins described herein include but are not limited to cyclosporin A (Shih, et al., (1989) Nature 339:625-626, IL-16 and analogs (including rhIL-16, Idziorek, et al., (1998) Clinical and Experimental Immunology 112:84-91), TGFb1 (Genesteir, et al., (1999) J Exp Med 189(2): 231-239), and vitamin E (Li-Weber, et al., (2002) J Clin Investigation 110(5):681-690).

Physical Methods In some embodiments, the supplementary agent is a anti-neoplastic physical methods including but not limited to radiotherapy, cryotherapy, hyperthermic therapy, surgery, laser ablation, and proton therapy.

Dosage: Dosage, toxicity and therapeutic efficacy of such subject IL2 muteins or nucleic acids compounds can be determined by standard pharmaceutical procedures in cell cultures or experimental animals. The data obtained from the cell culture assays and animal studies can be used in formulating a range of dosage for use in humans. The dosage of such compounds lies preferably within a range of circulating concentrations that include the ED50 with minimal acceptable toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 as determined in cell culture. Such information can be used to more accurately determine useful doses in humans. Levels in plasma may be measured, for example, by high performance liquid chromatography.

As defined herein, a therapeutically effective amount of a subject IL2 mutein (i.e., an effective dosage) depends on the polypeptide selected. For instance, single dose amounts in the range of approximately 0.001 to 0.1 mg/kg of patient body weight can be administered; in some embodiments, about 0.005, 0.01, 0.05 mg/kg may be administered. In some embodiments, 600,000 IU/kg is administered (IU can be determined by a lymphocyte proliferation bioassay and is expressed in International Units (IU) as established by the World Health Organization 1st International Standard for Interleukin-2 (human)).

In some embodiments, the pharmaceutically acceptable forms of the IL2 muteins of the present disclosure are administered to a subject in accordance with a "low-dose" treatment protocol as described in Klatzman, et al. U.S. Pat. Nos. 9,669,071 and 10,293,028B2 the entire teachings of which are herein incorporated by reference. Additional low dose protocols are described in Smith, K. A. (1993) Blood 81(6):1414-1423, He, et al., (2016) Nature Medicine 22(9): 991-993

In some embodiments of the invention the present disclosure provides methods and compositions for the treatment and/or prevention of neoplastic diseases, disorders or conditions in a subject by the administration to the subject a therapeutically effective amount of an hIL2 mutein of the present disclosure wherein the serum concentration of is maintained for a majority (i.e., greater than about 50% of the period of time, alternatively greater than about 60%, alternatively greater than about 70%, alternatively greater than about 80%, alternatively greater than about 90%) of a period of time (e.g. at least 24 hours, alternatively at least 48 hours, alternatively at least 72 hours, alternatively at least 96 hours, alternatively at least 120 hours, alternatively at least 144 hours, alternatively at least 7 days, alternatively at least 10 days, alternatively at least 12 days, alternatively at least 14 days, alternatively at least 28 days, alternatively at least 45 days, alternatively at least 60 days, or longer) at a serum concentration at or above the effective concentration of the IL2 mutein sufficient to promote proliferation of CD3-activated primary human T-cells (e.g., at or above $EC_{10}^{PRO}$, alternatively at or above $EC_{20}^{PRO}$, alternatively at or above $EC_{30}^{PRO}$, alternatively at or above $EC_{40}^{PRO}$, at or above $EC_{50}^{PRO}$, alternatively at or above $EC_{60}^{PRO}$) with respect to such IL2 mutein but at a serum concentration at or below of the effective concentration at a serum concentration of such IL2 mutein sufficient to induce activation of T-cells (e.g., at or below $EC_{100}^{PRO}$, alternatively at or below $EC_{90}^{PRO}$, alternatively at or below $EC_{50}^{PRO}$, alternatively at or below $EC_{70}^{PRO}$, at or below $EC_{60}^{PRO}$, alternatively at or below $EC_{50}^{PRO}$) with respect to such IL2 mutein.

In some embodiments of the invention the present disclosure provides methods and compositions for the treatment and/or prevention of neoplastic diseases, disorders or conditions in a subject by the administration to the subject wherein a therapeutically effective amount of an hIL2 mutein sufficient to maintain a serum concentration of human said IL2 mutein at or above the effective concentration of the IL2 mutein sufficient to promote proliferation of CD3-activated primary human T-cells ($>EC_{10}^{PRO}$) and at or below a serum concentration of such IL2 mutein sufficient to induce activation of T-cells with respect to such IL2 mutein (i.e. below $EC_{90}^{PRO}$) for more than about 50%, alternatively greater than about 60%, alternatively greater than about 70%, alternatively greater than about 80%, alternatively greater than about 90%) of a period of time of at least 24 hours, alternatively at least 96 hours, alternatively at least 120 hours, alternatively at least 144 hours, alternatively at least 7 days, alternatively at least 10 days, alternatively at least 12 days, alternatively at least 14 days, alternatively at least 28 days, alternatively at least 45 days, alternatively at least 60 days, or longer.

In some embodiments of the invention the present disclosure provides methods and compositions for the treatment and/or prevention of neoplastic diseases, disorders or conditions in a subject by the administration to the subject wherein a therapeutically effective amount of an hIL2 mutein sufficient to maintain a serum concentration of human said IL2 mutein at or above the effective concentration of the IL2 mutein sufficient to promote proliferation of CD3-activated primary human T-cells (>$EC_{10}^{PRO}$) and at or below a serum concentration of such IL2 mutein sufficient to induce activation of T-cells with respect to such IL2 mutein (i.e. below $EC_{90}^{PRO}$) for more than about 50%, alternatively greater than about 60%, alternatively greater than about 70%, alternatively greater than about 80%, alternatively greater than about 90%) of a period of time of at least 24 hours, alternatively at least 96 hours, alternatively at least 120 hours, alternatively at least 144 hours, alternatively at least 7 days, alternatively at least 10 days, alternatively at least 12 days, alternatively at least 14 days, alternatively at least 28 days, alternatively at least 45 days, alternatively at least 60 days, or longer wherein the IL2 a hIL2 polypeptide comprises a set of mutations selected from the group consisting of the following sets of mutations: L18R, Q22E, and Q126H; L18R, Q22E, and Q126K; L18R, Q22E and Q126M; L18R, Q22E Q126T; L18R; Q22E; V91K; V91R; Q126H; L18R, and Q126H; Q22E, and Q126H; L18G, Q22E and Q126H; L18A, Q22E and Q126H; L18M, Q22E and Q126H; L18F, Q22E and Q126H; L18W, Q22E and Q126H; L18K, Q22E and Q126H; L18Q, Q22E and Q126H; L18E, Q22E and Q126H; L18S, Q22E and Q126H; L18V, Q22E and Q126H; L18I, Q22E and Q126H; L18Y, Q22E and Q126H; L18H, Q22E and Q126H; L18N, Q22E and Q126H; L18D, Q22E and Q126H; L18T, Q22E and Q126H; L18R, Q22G and Q126H; L18R, Q22A and Q126H; L18R, Q22L and Q126H; L18R, Q22M and Q126H; L18R, Q22F and Q126H; L18R, Q22W and Q126H; L18R, Q22K and Q126H; L18R, Q22S and Q126H; L18R, Q22V and Q126H; L18R, Q22I and Q126H; L18R Q22Y and Q126H; L18R Q22H and Q126H; L18R Q22R and Q126H; L18R Q22N and Q126H; L18R Q22D and Q126H; and L18R Q22T and Q126H.

In accordance with another aspect of the present invention, there is provided a method for stimulating the immune system of an animal by administering the IL2 muteins of the present disclosure. The method is useful to treat disease states where the host immune response is deficient. In treating a subject, a therapeutically effective dose of compound (i.e., active ingredient) is administered. A therapeutically effective dose refers to that amount of the active ingredient that produces amelioration of symptoms or a prolongation of survival of a subject. An effective dose will vary with the characteristics of the IL2 mutein to be administered, the physical characteristics of the subject to be treated, the nature of the disease or condition, and the like. A single administration can range from about 50,000 IU/kg to about 1,000,000 IU/kg or more, more typically about 600,000 IU/kg. This may be repeated several times a day (e.g., 2-3 times per day) for several days (e.g., about 3-5 consecutive days) and then may be repeated one or more times following a period of rest (e.g., about 7-14 days). Thus, an effective dose may comprise only a single administration or many administrations over a period of time (e.g., about 20-30 individual administrations of about 600,000 RIU/kg each given over about a 10-20 day period).

The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the subject IL2 muteins can include a single treatment or, can include a series of treatments. In one embodiment, the compositions are administered every 8 hours for five days, followed by a rest period of 2 to 14 days, e.g., 9 days, followed by an additional five days of administration every 8 hours. In another embodiment, the the compositions are administered every other day for a period of at least 6 days, optionally at least 10 days, optionally at least 14 days, optionally at least 30 days, optionally at least 60 days. The skilled artisan will recognize that the treatment may be extended for the treatment of chronic conditions and the prevent the reoccurrence of symptoms of chronic diseases such as autoimmune diseases (e.g. psoriasis, IBD, etc.)

The pharmaceutical compositions can be included in a container, pack, or dispenser together with instructions for administration.

While compounds that exhibit toxic side effects may be used, care should be taken to design a delivery system that targets such compounds to the site of affected tissue in order to minimize potential damage to uninfected cells and, thereby, reduce side effects. Toxicity and therapeutic efficacy of an IL2 mutein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LC_{50}/EC_{50}$. IL2 muteins that exhibit large therapeutic indices are preferred. The data obtained from these cell culture assays and animal studies can be used in formulating a range of dosages suitable for use in humans. The dosage of such mutants lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like.

A therapeutically effective dose can be estimated initially from cell culture assays by determining an $EC_{50}$. A dose can then be formulated in animal models to achieve a circulating plasma concentration range that includes the $EC_{50}$ as determined in cell culture. Such information can be used to more accurately determine useful doses in humans. Levels in plasma may be measured, for example, by HPLC. The exact formulation, route of administration and dosage can be chosen by the individual physician in view of the patient's condition.

The attending physician for patients treated with IL2 mutants would know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Kits: The present disclosure also contemplates kits comprising pharmaceutical compositions IL2 muteins and a pharmaceutical composition thereof. The kits are generally in the form of a physical structure housing various components, as described below, and can be utilized, for example, in practicing the methods described above. A kit may comprise an IL2 mutein in the form of a pharmaceutical composition suitable for administration to a subject that is ready for use or in a form or requiring preparation for example, thawing, reconstitution or dilution prior to administration. When the IL2 mutein is in a form that needs to be reconstituted by a user, the kit may also comprise a sterile container providing a reconstitution medium comprising buffers, pharmaceutically acceptable excipients, and the like. A kit of the present disclosure can be designed for conditions necessary to properly maintain the components housed therein (e.g., refrigeration or freezing). A kit may further contain a label or packaging insert including identifying information for the components therein and instructions for their use. Each component of the kit can be enclosed within an individual container, and all of the various containers can be within a single package. Labels or inserts can include manufacturer information such as lot numbers and expiration dates. The label or packaging insert can be, e.g., integrated into the physical structure housing the components, contained separately within the physical structure, or affixed to a component of the kit (e.g., an ampule, syringe or vial). Labels or inserts may be provided in a physical form or a computer readable medium. In some embodiments, the actual instructions are not present in the kit, but rather the kit provides a means for obtaining the instructions from a remote source, e.g., via an internet site, including by secure access by providing a password (or scannable code such as a barcode or QR code on the container of the IL2 mutein or kit comprising) in compliance with governmental regulations (e.g., HIPAA) are provided.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure and are to be included within the spirit and purview of this application.

EXAMPLES

The following examples are provided to describe certain embodiments of the invention provided herein and are not to be construed to as limiting.

Example 1: Generation of the Human IL2 Expression Vector pcDNA3.1/Hygro(+)-huIL2

The human IL2 DNA open reading frame ("ORF") (Genbank NM_000586.3) was synthesized (Life Technologies GeneArt Service, Carlsbad, CA), and amplified via PCR using Platinum SuperFi II DNA polymerase kit (commercially available as catalog #12361050, ThermoFisher) in substantial accordance with the manufacturer's protocol, and using primers 5' TATAGTCAGCGCCACcCATGTACAGGATGCAACTCCTGTC 3' (SEQ ID NO: 14), which incorporates an NheI restriction site, and 5' TATAGGGCCCTATCAAGTCAGTGTTGAGATG 3' (SEQ ID NO: 15), which incorporates an ApaI restriction site. The PCR fragment was visualized on a 1% agarose gel (item #54803, Lonza, Rockland, ME), excised from the gel and purified using a QIAquick PCR Purification kit (commercially available as catalog #28106, Qiagen, Germany) according to the manufacturer's protocol.

The purified PCR fragment and mammalian expression vector pcDNA 3.1/Hygro(+) (commercially available as catalog #V87020, ThermoFisher, Carlsbad CA) were digested with NheI and ApaI (commercially available as catalog #RO111S and #RO114L, New England Biolabs, Ipswich, MA) restriction enzymes. The expression vector was further treated with a Quick Dephosphorylation kit (commercially available as catalog #M0508L, New England Biolabs) in substantial accordance with the manufacturer's protocol. The PCR fragment was ligated into pcDNA 3.1/Hygro(+) using the Rapid DNA Ligation Kit (commercially available as catalog #11635379001, Sigma Aldrich, St. Louis, MO) in substantial accordance with the manufacturer's protocol, transformed into One Shot TOP10 Chemically Competent *E. coli* (commercially available as catalog #C404006, Life Technologies, Carlsbad, CA), plated onto LB Agar plates containing 100 ug/ml carbenicillin (commercially available as catalog #L1010, Teknova, Hollister, CA), and grown overnight at 37C.

The following day individual bacterial colonies were picked and used to start a 3 ml bacterial culture in LB Broth (#10855-001, Life Technologies) with 100 ug/ml ampicillin (commercially available as catalog #A9626, Teknova). The cultures were grown overnight at 37 C. The following day the *E. coli* were pelleted (6,000 rpm, 10 minutes, tabletop centrifuge #5424, commercially available as catalog Eppendorf, Hauppauge, NY), and the DNA expression vector isolated using QIAprep Spin Miniprep Kit (#27106, Qiagen). The plasmid DNA was sequence verified (MCLab, South San Francisco, CA).

Example 2. Generation of the Human IL2 REH Expression Vector pcDNA3.1/Hygro(+)-huIL2-REH An expression vector which introduced three mutations into the human IL2 ORF (L38R, Q42E and Q146H; all numbering based on the full length human IL2 ORF NM_000586.3 numbering, i.e. the hIL2 as expressed including the signal peptide not the 20 amino acid sequence of the mature hIL2 molecule) was assembled in substantial accordance with the teaching of Example 1 with the following exceptions: The initial template DNA used for PCR was synthesized with the L38R (L18R of the mature protein), Q42E (Q22E of the mature protein) and Q146H (Q126H of the mature protein) mutations.

Example 3. Generation of the Human IL2 REM Expression Vector pcDNA3.1/Hygro(+)-huIL2 REM An expression vector which introduced three mutations into the human IL2 ORF (L38R, Q42E and Q146M; all numbering based on the full length human IL2 ORF NM_000586.3 numbering) was assembled exactly as described for the human IL2 expression vector in pcDNA3.1/Hygro(+), with the following exceptions: The initial template DNA used for PCR was synthesized with the L38R, Q42E and Q146M mutations.

Example 4. Introduction of Mutations or Back-Mutations into pcDNA3.1/Hy Ro(+)-huIL2 and pcDNA3.1/Hyro(+)-huIL2 REH Expression Vectors All mutations or back-mutations (reverting a mutation in pcDNA3.1/hygro(+)-huIL2-REHb ack to match the wild type human I12 ORF) were introduced into the pcDNA3.1/Hygro(+)-huIL2 or pcDNA3.1/Hygro(+)-huIL2-REH expression vectors using a Quik Change II Site Directed Mutagenesis Kit (#200524, Agilent Technologies, Santa Clara, CA) in substantial accordance with the manufacturer's protocol. Tables 15 and 16 lists the mutations generated, the template into which the mutation was introduced, and the primer sets used to introduce the mutation. The transformation of the Quik Change PCR reactions into *E. coli*, as well as the isolation and sequence analysis of the plasmid DNA, was performed using the same protocol as in the generation of the pcDNA3.1/Hygro-huIL2 expression vector.

TABLE 15

Quik Change Mutagenesis

| hIL2 Wild Type human IL2 Residue | Full ORF # 38 / Mature Peptide # 18 L | Full ORF # 42 / Mature Peptide # 22 Q | Full ORF # 146 / Mature Peptide # 126 Q | Primer Set (5'→3') | SEQ ID NO: | Template* |
|---|---|---|---|---|---|---|
| REE | R | E | E | GATGGATTACCTTTTGTGAGAGCATCAT CTCAACA | 16 | IL2 REK |
| | | | | TGTTGAGATGATGCTCTCACAAAAGGTA ATCCATC | 17 | |
| REM | R | E | M | GGATTACCTTTTGTATGAGCATCATCTC AAC | 18 | IL2 REK |
| | | | | GTTGAGATGATGCTCATACAAAAGGTAA TCC | 19 | |
| REV | R | E | V | GGATTACCTTTTGTGTGAGCATCATCTC AACAC | 20 | IL2 REK |
| | | | | GTGTTGAGATGATGCTCACACAAAAGGT AATCC | 21 | |
| REL | R | E | L | GGATTACCTTTTGTCTGAGCATCATCTC AACAC | 22 | IL2 REK |
| | | | | GTGTTGAGATGATGCTCAGACAAAAGGT AATCC | 23 | |
| REF | R | E | F | GGATTACCTTTTGTTTCAGCATCATCTC AACAC | 24 | IL2 REK |
| | | | | GTGTTGAGATGATGCTGAAACAAAAGGT AATCC | 25 | |
| REN | R | E | N | GGATTACCTTTTGTAACAGCATCATCTC AACAC | 26 | IL2 REK |
| | | | | GTGTTGAGATGATGCTGTTACAAAAGGT AATCC | 27 | |
| RER | R | E | R | GGATTACCTTTTGTAGGAGCATCATCTC AACAC | 28 | IL2 REK |
| | | | | GTGTTGAGATGATGCTCCTACAAAAGGT AATCC | 29 | |
| REY | R | E | Y | GGATTACCTTTTGTTACAGCATCATCTC AACAC | 30 | IL2 REK |
| | | | | GTGTTGAGATGATGCTGTAACAAAAGGT AATCC | 31 | |

TABLE 15-continued

Quik Change Mutagenesis

| hIL2 Wild Type human IL2 Residue | Full ORF # 38 / Mature Peptide # 18 L | Full ORF # 42 / Mature Peptide # 22 Q | Full ORF # 146 / Mature Peptide # 126 Q | Primer Set (5'→3') | SEQ ID NO: | Template* |
|---|---|---|---|---|---|---|
| AEK | A | E | K | GGATTACCTTTTGTAAGAGCATCATCTC | 32 | IL2 AEH |
| | | | | GAGATGATGCTCTTACAAAAGGTAATCC | 33 | |
| EEK | E | E | K | GGATTACCTTTTGTAAGAGCATCATCTC | 32 | IL2 EEH |
| | | | | GAGATGATGCTCTTACAAAAGGTAATCC | 33 | |
| VEK | V | E | K | GGATTACCTTTTGTAAGAGCATCATCTC | 32 | IL2 VEH |
| | | | | GAGATGATGCTCTTACAAAAGGTAATCC | 33 | |
| HEK | H | E | K | GGATTACCTTTTGTAAGAGCATCATCTC | 32 | IL2 HEH |
| | | | | GAGATGATGCTCTTACAAAAGGTAATCC | 33 | |
| IEK | I | E | K | GGATTACCTTTTGTAAGAGCATCATCTC | 32 | IL2 IEH |
| | | | | GAGATGATGCTCTTACAAAAGGTAATCC | 33 | |
| RTK | R | T | K | GGATTACCTTTTGTAAGAGCATCATCTC | 32 | IL2 RTH |
| | | | | GAGATGATGCTCTTACAAAAGGTAATCC | | |

*Templates
IL2: pcDNA3.1/hygro(+)-huIL2
IL2 REH: pcDNA3.1/Hygro(+)-huIL2 REH
IL2 REK: pcDNA3.1/Hygro(+)-huIL2 REK
IL2 AEH: pcDNA3.1/Hygro(+)-huIL2 AEH
IL2 EEH: pcDNA3.1/Hygro(+)-huIL2 EEH
IL2 VEH: pcDNA3.1/Hygro(+)-huIL2 VEH
IL2 HEH: pcDNA3.1/Hygro(+)-huIL2 HEH
IL2 IEH: pcDNA3.1/Hygro(+)-huIL2 IEH
IL2 RTH: pcDNA3.1/Hygro(+)-huIL2 RTH

TABLE 16 hIL2 Ortholog Constructs

| Name | Primer Set (5'→3') + | SEQ ID NO: | Template |
|---|---|---|---|
| REE | GATGGATTACCTTTTGTGAGAGCATCATCTCAACA | 16 | pExSyn2.0- |
| | TGTTGAGATGATGCTCTCACAAAAGGTAATCCATC | 17 | hIL2 REK |
| REM | GGATTACCTTTTGTATGAGCATCATCTCAAC | 18 | pExSyn2.0- |
| | GTTGAGATGATGCTCATACAAAAGGTAATCC | 19 | hIL2 REK |
| REV | GGATTACCTTTTGTGTGAGCATCATCTCAACAC | 20 | pExSyn2.0- |
| | GTGTTGAGATGATGCTCACACAAAAGGTAATCC | 21 | hIL2 REK |
| REL | GGATTACCTTTTGTCTGAGCATCATCTCAACAC | 22 | pExSyn2.0- |
| | GTGTTGAGATGATGCTCAGACAAAAGGTAATCC | 23 | hIL2 REK |
| REF | GGATTACCTTTTGTTTCAGCATCATCTCAACAC | 24 | pExSyn2.0- |
| | GTGTTGAGATGATGCTGAAACAAAAGGTAATCC | 25 | hIL2 REK |
| REN | GGATTACCTTTTGTAACAGCATCATCTCAACAC | 26 | pExSyn2.0- |
| | GTGTTGAGATGATGCTGTTACAAAAGGTAATCC | 27 | hIL2 REK |
| RER | GGATTACCTTTTGTAGGAGCATCATCTCAACAC | 28 | pExSyn2.0- |
| | GTGTTGAGATGATGCTCCTACAAAAGGTAATCC | 29 | hIL2 REK |
| REY | GGATTACCTTTTGTTACAGCATCATCTCAACAC | 30 | pExSyn2.0- |
| | GTGTTGAGATGATGCTGTAACAAAAGGTAATCC | 31 | hIL2 REK |
| REK + | GACTTAATCAGCCGTATCAACGTAATA | 34 | pExSyn2.0- |
| N88R | TATTACGTTGATACGGCTGATTAAGTC | 35 | hIL2 REK |
| REK + | GGACTTAATCAGCGATATCAACGTAAT | 36 | pExSyn2.0- |
| N88D | ATTACGTTGATATCGCTGATTAAGTCC | 37 | hIL2 REK |

TABLE 16-continued hIL2 Ortholog Constructs

| Name | Primer Set (5'→3') + | SEQ ID NO: | Template |
|---|---|---|---|
| REK + N88G | GGGACTTAATCAGCGGTATCAACGTAAT<br>ATTACGTTGATACCGCTGATTAAGTCCC | 38<br>39 | pExSyn2.0-hIL2 REK |
| REK + N88I | GGACTTAATCAGCATTATCAACGTAAT<br>ATTACGTTGATAATGCTGATTAAGTCC | 40<br>41 | pExSyn2.0-hIL2 REK |
| REK + D20I | GCATTTAAGGCTGATTTTAGAGATGATTTTG<br>CAAAATCATCTCTAAAATCAGCCTTAAATGC | 42<br>43 | pExSyn2.0-hIL2 REK |
| REK + D20H | GAGCATTTAAGGCTGCATTTAGAGATG<br>CATCTCTAAATGCAGCCTTAAATGCTC | 44<br>45 | pExSyn2.0-hIL2 REK |
| REK + D20T | GCATTTAAGGCTGACTTTAGAGATGATTTTG<br>CAAAATCATCTCTAAAGTCAGCCTTAAATGC | 46<br>47 | pExSyn2.0-hIL2 REK |
| REK + D20G | GCATTTAAGGCTGGGTTTAGAGATGA<br>TCATCTCTAAACCCAGCCTTAAATGC | 48<br>49 | pExSyn2.0-hIL2 REK |
| REK + D20A | GCATTTAAGGCTGGCTTTAGAGATGATTTTG<br>CAAAATCATCTCTAAAGCCAGCCTTAAATGC | 50<br>51 | pExSyn2.0-hIL2 REK |
| AEH + V91K | CAGCAATATCAACAAGATAGTTCTGGAAC<br>GTTCCAGAACTATCTTGTTGATATTGCTG | 52<br>53 | pExSyn2.0-hIL2 AEH |
| EEH + V91K | CAGCAATATCAACAAGATAGTTCTGGAAC<br>GTTCCAGAACTATCTTGTTGATATTGCTG | 52<br>53 | pExSyn2.0-hIL2 EEH |
| VEH + V91K | CAGCAATATCAACAAGATAGTTCTGGAAC<br>GTTCCAGAACTATCTTGTTGATATTGCTG | 52<br>53 | pExSyn2.0-hIL2 VEH |
| HEH + V91K | CAGCAATATCAACAAGATAGTTCTGGAAC<br>GTTCCAGAACTATCTTGTTGATATTGCTG | 52<br>53 | pExSyn2.0-hIL2 HEH |
| IEH + V91K | CAGCAATATCAACAAGATAGTTCTGGAAC<br>GTTCCAGAACTATCTTGTTGATATTGCTG | 52<br>53 | pExSyn2.0-hIL2 IEH |
| RTH + V91K | CAGCAATATCAACAAGATAGTTCTGGAAC<br>GTTCCAGAACTATCTTGTTGATATTGCTG | 52<br>53 | pExSyn2.0-hIL2 RTH |
| REE + V91K | CAGCAATATCAACAAGATAGTTCTGGAAC<br>GTTCCAGAACTATCTTGTTGATATTGCTG | 52<br>53 | pExSyn2.0-hIL2 REE |
| AEK | GGATTACCTTTTGTAAGAGCATCATCTC<br>GAGATGATGCTCTTACAAAAGGTAATCC | 32<br>33 | pExSyn2.0-hIL2 AEH |
| EEK | GGATTACCTTTTGTAAGAGCATCATCTC<br>GAGATGATGCTCTTACAAAAGGTAATCC | 32<br>33 | pExSyn2.0-hIL2 EEH |
| VEK | GGATTACCTTTTGTAAGAGCATCATCTC<br>GAGATGATGCTCTTACAAAAGGTAATCC | 32<br>33 | pExSyn2.0-hIL2 VEH |
| HEK | GGATTACCTTTTGTAAGAGCATCATCTC<br>GAGATGATGCTCTTACAAAAGGTAATCC | 32<br>33 | pExSyn2.0-hIL2 HEH |
| IEK | GGATTACCTTTTGTAAGAGCATCATCTC<br>GAGATGATGCTCTTACAAAAGGTAATCC | 32<br>33 | pExSyn2.0-hIL2 IEH |
| RTK | GGATTACCTTTTGTAAGAGCATCATCTC<br>GAGATGATGCTCTTACAAAAGGTAATCC | 32<br>33 | pExSyn2.0-hIL2 RTH |
| N88R | GACTTAATCAGCCGTATCAACGTAATA<br>TATTACGTTGATACGGCTGATTAAGTC | 34 | pExSyn2.0-hIL2 |

Example 5. Transient Transfections in HEK293 Cells

All expression vectors were transiently transfected into HEK293 cells (#CRL-1573, ATCC, Manassas, VA). ~1E6 HEK293 cells were plated into each well of a 6 well tissue culture plate in 2 ml of DMEM (#10569044, Life Technologies) supplemented with 10% Fetal Bovine serum (#SH30071.03, Fisher Scientific, Chicago, IL), and grown overnight at 37C and 5% $CO_2$. The next day the cells were transfected using Lipofectamine 3000 Reagent (#L3000150; Life Technologies) following the manufacturer's protocol, using 2.5 ug DNA, 5 ul P3000 reagent, and 7.5 ul Lipofectamine 3000 per transfection. The transfected cells were grown at 37C, 5% CO2 for 48-72 hours and then the conditioned media was harvested.

Example 6. Analysis of Protein Expression

Protein expression was measured by ELISA using the Human IL2 V-PLEX ELISA kit (#K151QQD-4, Mesoscale Diagnostics, Baltimore, MD) following the manufacturer's protocol (transfected media was diluted 1:4 initially, then 1:2 serially). The plate was read on a Meso Quickplex SQ120 (Mesoscale Diagnostics) using the manufacture's preprogrammed setting for this ELISA kit. The human IL2 standard in the kit was used to compute an approximate expression level in the conditioned media samples.

Example 7 Determination of IL2 Activity (STAT5) on CD25− and CD25+ Cells

Following a 2-3 day incubation, samples of the supernatants from the 293T cells containing the soluble IL2 protein were prepared in accordance with Example 5 above and added to YT cells (CD25NEG) and YT cells which have been engineered to constitutively express CD25 (YTCD25POS) for a period of approximately 20 minutes. The level of phospho-STAT5 (pSTAT5) induction was measured by flow cytometry. The results of the fold induction of pSTAT5 level is show in FIG. 2 of the accompanying drawings. Selectivity of the IL2 proteins for CD25 status was calculated as the level of phospho-STAT5 elevation on CD25+YT cells ($pSTAT5^{YTCD2}$) divided by the level of phospho-STAT5 in CD25 negative YT cells ($pSTAT5^{YT}$). The results of these experiments are provided in FIG. 2 of the attached drawings.

As can be seen from the data presented, the IL2 muteins of the present disclosure provide for selective induction of pSTAT5 on CD25 positive cells and retain significant IL2 activity.

Example 8. Evaluation of Activity of Orthologs in Human T Cell Clone 3F8

A panel of representative hIL-2 muteins was evaluated for activity in CD4 positive human T cell clone 3F8 cells. The CD4 positive T cell clone 3F8 was generated by activation of PBMC of a healthy donor with the EBV transformed B cell line JY in two successive rounds of Mixed Leukocyte Reactions followed by single cell cloning by limited dilution as described (Yssel and Spits (2002) Current Protocols in Immunology 7.19.1-7.19.12). The CD4 positive T cell clone 3F8 expresses CD25 and CD122 and proliferates and produces IFNγ in response to IL-2.

3F8 cells were contacted with supernatants from 293T cells transfected with hIL-2 muteins as follows: Cells were grown in growth medium consisting of Yssel's medium (Iscove's modified Dulbecco's Medium (ThermoFisher), 0.25% w/v percent human albumin (Sigma), 1 percent penicillin/streptomycin (ThermoFisher), 1 percent ITS-X Insulin, Transferrin, Selenium (Gibco), 30 mg/L Transferrin (Roche), 2 mg/L Palmitic Acid (Sigma), 1 percent LA-OA-Albumin Linoleic Acid, Oleic Acid (Sigma), 1 percent human serum (Gemini) (Yssel et al (1984) J Immunol Methods 72: 219-227) at 0.2 million cells per ml with 50 Gy irradiated JY cells at 0.1 million cells per well and 40 Gy irradiated allogeneic PBMC at 1 million cells per mL. After six days of culture and expansion with human IL-2 at 100 pM, cells were washed and seeded into black, clear bottom 96 well plates (Costar) at 50 thousand cells per well in 75 μl growth medium. Five-fold serial dilutions of transfected 293T cell supernatants were made in growth medium and 75 μl of each dilution was added to plates of 3F8 cells in duplicate at final titrations ranging from 1:2 to 1:78125. Plates were transferred to a humidified incubator (ThermoFisher) and incubated at 37 degrees centigrade, 5 percent carbon dioxide for three days.

Plates were removed from the incubator and 40 μl of culture supernatant was harvested in to a 96 well flat bottom plate (Costar). Supernatants from duplicate wells were pooled. Cells were lysed by adding 100 μl per well of Celltiterglo (Promega) according to manufacturer's instructions. Cell lysates were mixed on an orbital shaker (VWR Scientific) for two minutes at 300 rpm then held at room temperature for 10 minutes. Luminescence for 3F8 cell lysates were read as counts per second on an Envision 2103 Multilabel Plate Reader (Perkin Elmer).

Production of IFNγ in the culture supernatants was measured using the MSD IFNγ V-Plex kit (MSD K151QOD) according to manufacturer's instructions. Briefly, mAb precoated MSD IFNγ assay plates were washed 3 times with 150 μL Tris Wash Buffer and IFNγ standards were diluted in Diluent 2. Culture supernatants were diluted 1:1 with Diluent 2 and 50 μL of samples and standards were added to the IFNγ assay plates and incubated for 120 min on an orbital shaker (VWR Scientific) at 300 rpm at room temperature. Plates were washed 3 times with Tris Wash Buffer and 25 μL 1×detection antibody in Diluent 3 was added to each well. Plates were incubated for 60 min on an orbital shaker (VWR Scientific) at 300 rpm at room temperature. Plates were washed 3 times with Tris Wash Buffer and 150 μL 2× Read Buffer T was added to each well and Luminescence signal was read on a Mesoscale Quickplex SQ120 instrument. Concentration of IFNγ in the supernatants were calculated based on the standard curve with MSD software.

To compare the effect of each hIL-2 mutein upon 3F8 cell proliferation and IFNγ production, CelltiterGlo values and IFNγ concentrations for cells treated with the supernatants were compared to those obtained for control cells treated with growth medium alone, wild-type IL-2 transfection, or supernatant from human REK IL-2 transfection. The data from these experiments is presented in Table 5 and FIG. 4. These data demonstrate correlation between activity of the hIL-2 muteins to induce proliferation and IFNγ production.

Informal Sequence Listing

| Seq ID NO | Name or Description | AA Sequence |
|---|---|---|
| 1 | Wild Type Human IL2 | APTSSSTKKTQLQLEHLLLDLQMILNGI NNYKNPKLTRMLTFKFYMPKKATELKHL QCLEEELKPLEEVLNLAQSKNFHLRPRD LISNINVIVLELKGSETTFMCEYADETA TIVEFLNRWITFCQSIISTLT |
| 2 | Mature hCD25 | ELCDDDPPEIPHATFKAMAYKEGTMLNC ECKRGFRRIKSGSLYMLCTGNSSHSSWD NQCQCTSSATRNTTKQVTPQPEEQKERK TTEMQSPMQPVDQASLPGHCREPPPWEN EATERIYHFVVGQMVYYQCVQGYRALHR GPAESVCKMTHGKTRWTQPQLICTGEME TSQFPGEEKPQASPEGRPESETSCLVTT TDFQIQTEMAATMETSIFTTEYQVAVAG CVFLLISVLLLSGLTWQRRQRKSRRTI |
| 3 | mature hCD122 | AVNGTSQFTCFYNSRANISCVWSQDGAL QDTSCQVHAWPDRRRWNQTCELLPVSQA SWACNLILGAPDSQKLTTVDIVTLRVLC REGVRWRVMAIQDFKPFENLRLMAPISL QVVHVETHRCNISWEISQASHYFERHLE FEARTLSPGHTWEEAPLLTLKQKQEWIC |

-continued

Informal Sequence Listing

| Seq ID NO | Name or Description | AA Sequence |
|---|---|---|
| | | LETLTPDTQYEFQVRVKPLQGEFTTWSP WSQPLAFRTKPAALGKDTIPWLGHLLVG LSGAFGFIILVYLLINCRNTGPWLKKVL KCNTPDPSKFFSQLSSEHGGDVQKWLSS PFPSSSFSPGGLAPEISPLEVLERDKVT QLLLQQDKVPEPASLSSNHSLTSCFTNQ GYFFFHLPDALEIEACQVYFTYDPYSEE DPDEGVAGAPTGSSPQPLQPLSGEDDAY CTFPSRDDLLLFSPSLLGGPSPPSTAPG GSGAGEERMPPSLQERVPRDWDPQPLGP PTPGVPDLVDFQPPPELVLREAGEEVPD AGPREGVSFPWSRPPGQGEFRALNARLP LNTDAYLSLQELQGQDPTHLV |
| 4 | ECD of hCD122 | AVNGTSQFTCFYNSRANISCVWSQDGAL QDTSCQVHAWPDRRRWNQTCELLPVSQA SWACNLILGAPDSQKLTTVDIVTLRVLC REGVRWRVMAIQDFKPFENLRLMAPISL QVVHVETHRCNISWEISQASHYFERHLE FEARTLSPGHTWEEAPLLTLKQKQEWIC LETLTPDTQYEFQVRVKPLQGEFTTWSP WSQPLAFRTKPAALGKDT |
| 5 | the mature hCD132 protein | LNTTILTPNGNEDTTADFFLTTMPTDSL SVSTLPLPEVQCFVFNVEYMNCTWNSSS EPQPTNLTLHYWYKNSDNDKVQKCSHYL FSEEITSGCQLQKKEIHLYQTFVVQLQD PREPRRQATQMLKLQNLVIPWAPENLTL HKLSESQLELNWNNRFLNHCLEHLVQYR TDWDHSWTEQSVDYRHKFSLPSVDGQKR YTFRVRSRFNPLCGSAQHWSEWSHPIHW |

-continued

Informal Sequence Listing

| Seq ID NO | Name or Description | AA Sequence |
|---|---|---|
| | | GSNTSKENPFLFALEAVVISVGSMGLII SLLCVYFWLERTMPRIPTLKNLEDLVTE YHGNFSAWSGVSKGLAESLQPDYSERLC LVSEIPPKGGALGEGPGASPCNQHSPYW APPCYTLKPET |
| 6 | Albumin binding peptide | ICLPRWGCLW |
| 7 | Des Ala1 REH (STK-008) | PTSSSTKKTQLQLEHLRLDLEMILNGIN NYKNPKLTRMLTFKFYMPKKATELKHLQ CLEEELKPLEEVLNLAQSKNFHLRPRDL ISNINVIVLELKGSETTFMCEYADETAT IVEFLNRWITFCHSIISTLT |
| 8 | Des Ala1 REK (STK-011) | PTSSSTKKTQLQLEHLRLDLEMILNGIN NYKNPKLTRMLTFKFYMPKKATELKHLQ CLEEELKPLEEVLNLAQSKNFHLRPRDL ISNINVIVLELKGSETTFMCEYADETAT IVEFLNRWITFCKSIISTLT (SEQ ID NO: 8) |
| 9 | STK-014 | PTSSSTSSSTAEAQQQQQQQQQQQQHLE QLRMDLEELLSRMENYRNLKLPRMLTFK FYLPKQATELKDLQCLEDELGPLRHVLD LTQSKSFQLEDAENFISNIRVTVVKLKG SDNTFECQFDDESATVVDFLRRWIAFCH SIISTSPQ |

We claim:

1. A method of treating a human subject suffering from cancer, the method comprising, administering to said subject a pharmaceutical formulation comprising a polypeptide comprising SEQ ID NO:8, wherein the administering ameliorates one or more symptoms associated with the cancer.

2. The method of claim 1, wherein the polypeptide is PEGylated.

3. The method of claim 2, wherein the polypeptide is PEGylated with a poly ethylene glycol (PEG) having a molecular weight of 10,000 to 50,000 Daltons.

4. The method of claim 1, wherein the pharmaceutical formulation is administered subcutaneously.

5. The method of claim 2, wherein the pharmaceutical formulation is administered subcutaneously.

6. The method of claim 1, further comprising administering a supplementary agent to said subject.

7. The method of claim 6, wherein said supplementary agent is selected from the group consisting of a chemotherapeutic agent, an antibody, an immune checkpoint modulator, tumor infiltrating lymphocytes (TILs), a chimeric antigen receptor (CAR)-T cell, and a physical method.

8. The method of claim 7, wherein the supplementary agent is an immune checkpoint inhibitor.

9. The method of claim 8, wherein the immune checkpoint inhibitor is an anti-PD-1 antibody or an anti-PD-L1 antibody.

10. The method of claim 9, wherein the immune checkpoint inhibitor is nivolumab.

11. The method of claim 9, wherein the immune checkpoint inhibitor is pembrolizumab.

12. The method of claim 2, wherein said method further comprises administering a supplementary agent to said subject.

13. The method of claim 12, wherein said supplementary agent is selected from the group consisting of a chemotherapeutic agent, an antibody, an immune checkpoint modulator, tumor infiltrating lymphocytes (TILs), a CAR-T cell, and a physical method.

14. The method of claim 12, wherein the supplementary agent is an immune checkpoint inhibitor.

15. The method of claim 14, wherein the immune checkpoint inhibitor is an anti-PD-1 antibody or an anti-PD-L1 antibody.

16. The method of claim 14, wherein the immune checkpoint inhibitor is nivolumab.

17. The method of claim 14, wherein the immune checkpoint inhibitor is pembrolizumab.

18. The method of claim 1, wherein the cancer is a solid tumor.

19. The method of claim 1, wherein the cancer is an ovarian cancer, prostate cancer or lung cancer.

20. The method of claim 1, wherein the cancer is colon cancer.

21. The method of claim 2, wherein the cancer is a solid tumor.

22. The method of claim 2, wherein the cancer is an ovarian cancer, prostate cancer or lung cancer.

23. The method of claim 2, wherein the cancer is colon cancer.

24. The method of claim 17, wherein the cancer is a solid tumor.

25. The method of claim 17, wherein the cancer is an ovarian cancer, prostate cancer or lung cancer.

26. The method of claim 17, wherein the cancer is colon cancer.

27. The method of claim 1, wherein the polypeptide is administered at a dosage of 0.001 to 0.1 mg/kg of subject body weight.

28. The method of claim 2, wherein the polypeptide is administered at a dosage of 0.001 to 0.1 mg/kg of subject body weight.

29. The method of claim 1, wherein the pharmaceutical formulation is administered weekly.

30. The method of claim 29, further comprising administering pembrolizumab or nivolumab by IV infusion every two weeks or every three weeks.

31. The method of claim 2, wherein the pharmaceutical formulation is administered weekly.

32. The method of claim 31, further comprising administering pembrolizumab or nivolumab by IV infusion every two weeks or every three weeks.

33. The method of claim 6, wherein the supplementary agent is Blinatumomab.

34. The method of claim 6, wherein the supplementary agent is a bispecific antibody.

35. The method of claim 12, wherein the supplementary agent is Blinatumomab.

36. The method of claim 12, wherein the supplementary agent is a bispecific antibody.

37. The method of claim 9, wherein the immune checkpoint inhibitor is a bispecific antibody.

38. The method of claim 15, wherein the immune checkpoint inhibitor is a bispecific antibody.

* * * * *

SEQUENCE LISTING

<160> NUMBER OF SEQ ID NOS: 53

<210> SEQ ID NO 1
<211> LENGTH: 133
<212> TYPE: PRT
<213> ORGANISM: Homo sapiens

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 2
<211> LENGTH: 251
<212> TYPE: PRT
<213> ORGANISM: Homo sapiens

<400> SEQUENCE: 2

```
Glu Leu Cys Asp Asp Asp Pro Pro Glu Ile Pro His Ala Thr Phe Lys
1               5                   10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
        35                  40                  45

Asn Ser Ser His Ser Ser Trp Asp Asn Gln Cys Gln Cys Thr Ser Ser
    50                  55                  60

Ala Thr Arg Asn Thr Thr Lys Gln Val Thr Pro Gln Pro Glu Glu Gln
65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
        115                 120                 125

Tyr Gln Cys Val Gln Gly Tyr Arg Ala Leu His Arg Gly Pro Ala Glu
    130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
        195                 200                 205

Met Glu Thr Ser Ile Phe Thr Thr Glu Tyr Gln Val Ala Val Ala Gly
    210                 215                 220

Cys Val Phe Leu Leu Ile Ser Val Leu Leu Leu Ser Gly Leu Thr Trp
225                 230                 235                 240

Gln Arg Arg Gln Arg Lys Ser Arg Arg Thr Ile
                245                 250
```

<210> SEQ ID NO 3
<211> LENGTH: 525
<212> TYPE: PRT
<213> ORGANISM: Homo sapiens

<400> SEQUENCE: 3

```
Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80
```

-continued

```
Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr Ile Pro Trp Leu Gly His Leu Leu Val Gly
    210                 215                 220

Leu Ser Gly Ala Phe Gly Phe Ile Ile Leu Val Tyr Leu Leu Ile Asn
225                 230                 235                 240

Cys Arg Asn Thr Gly Pro Trp Leu Lys Lys Val Leu Lys Cys Asn Thr
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
        275                 280                 285

Pro Gly Gly Leu Ala Pro Glu Ile Ser Pro Leu Glu Val Leu Glu Arg
    290                 295                 300

Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
        355                 360                 365

Gly Val Ala Gly Ala Pro Thr Gly Ser Ser Pro Gln Pro Leu Gln Pro
    370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
                405                 410                 415

Thr Ala Pro Gly Gly Ser Gly Ala Gly Glu Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Pro Glu
    450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
                485                 490                 495

Arg Ala Leu Asn Ala Arg Leu Pro Leu Asn Thr Asp Ala Tyr Leu Ser
```

```
            500                 505                 510

Leu Gln Glu Leu Gln Gly Gln Asp Pro Thr His Leu Val
        515                 520                 525


<210> SEQ ID NO 4
<211> LENGTH: 214
<212> TYPE: PRT
<213> ORGANISM: Homo sapiens

<400> SEQUENCE: 4

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210


<210> SEQ ID NO 5
<211> LENGTH: 347
<212> TYPE: PRT
<213> ORGANISM: Homo sapiens

<400> SEQUENCE: 5

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
```

```
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

Val Val Ile Ser Val Gly Ser Met Gly Leu Ile Ile Ser Leu Leu Cys
                245                 250                 255

Val Tyr Phe Trp Leu Glu Arg Thr Met Pro Arg Ile Pro Thr Leu Lys
            260                 265                 270

Asn Leu Glu Asp Leu Val Thr Glu Tyr His Gly Asn Phe Ser Ala Trp
        275                 280                 285

Ser Gly Val Ser Lys Gly Leu Ala Glu Ser Leu Gln Pro Asp Tyr Ser
    290                 295                 300

Glu Arg Leu Cys Leu Val Ser Glu Ile Pro Pro Lys Gly Gly Ala Leu
305                 310                 315                 320

Gly Glu Gly Pro Gly Ala Ser Pro Cys Asn Gln His Ser Pro Tyr Trp
                325                 330                 335

Ala Pro Pro Cys Tyr Thr Leu Lys Pro Glu Thr
            340                 345


<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Cys Leu Pro Arg Trp Gly Cys Leu Trp
1               5                   10


<210> SEQ ID NO 7
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
```

```
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys His Ser Ile Ile
        115                 120                 125

Ser Thr Leu Thr
    130


<210> SEQ ID NO 8
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Pro Thr Ser Ser Ser Thr Lys Lys Thr Gln Leu Gln Leu Glu His Leu
1               5                   10                  15

Arg Leu Asp Leu Glu Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Cys Lys Ser Ile Ile
        115                 120                 125

Ser Thr Leu Thr
    130


<210> SEQ ID NO 9
<211> LENGTH: 148
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Pro Thr Ser Ser Ser Thr Ser Ser Ser Thr Ala Glu Ala Gln Gln Gln
1               5                   10                  15

Gln Gln Gln Gln Gln Gln Gln Gln Gln His Leu Glu Gln Leu Arg Met
            20                  25                  30

Asp Leu Glu Glu Leu Leu Ser Arg Met Glu Asn Tyr Arg Asn Leu Lys
```

```
        35                  40                  45

Leu Pro Arg Met Leu Thr Phe Lys Phe Tyr Leu Pro Lys Gln Ala Thr
    50                  55                  60

Glu Leu Lys Asp Leu Gln Cys Leu Glu Asp Glu Leu Gly Pro Leu Arg
65                  70                  75                  80

His Val Leu Asp Leu Thr Gln Ser Lys Ser Phe Gln Leu Glu Asp Ala
                85                  90                  95

Glu Asn Phe Ile Ser Asn Ile Arg Val Thr Val Val Lys Leu Lys Gly
            100                 105                 110

Ser Asp Asn Thr Phe Glu Cys Gln Phe Asp Asp Glu Ser Ala Thr Val
        115                 120                 125

Val Asp Phe Leu Arg Arg Trp Ile Ala Phe Cys His Ser Ile Ile Ser
    130                 135                 140

Thr Ser Pro Gln
145
```

<210> SEQ ID NO 10
<211> LENGTH: 133
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: A or absent
<220> FEATURE:
<221> NAME/KEY: MOD_RES
<222> LOCATION: (2)..(2)
<223> OTHER INFORMATION: P or absent
<220> FEATURE:
<221> NAME/KEY: MOD_RES
<222> LOCATION: (3)..(3)
<223> OTHER INFORMATION: T, C, A, G, Q, E, N, D, R, K, P, or absent
<220> FEATURE:
<221> NAME/KEY: MOD_RES
<222> LOCATION: (4)..(4)
<223> OTHER INFORMATION: S or absent
<220> FEATURE:
<221> NAME/KEY: MOD_RES
<222> LOCATION: (5)..(5)
<223> OTHER INFORMATION: S or absent
<220> FEATURE:
<221> NAME/KEY: MOD_RES
<222> LOCATION: (6)..(6)
<223> OTHER INFORMATION: S or absent
<220> FEATURE:
<221> NAME/KEY: MOD_RES
<222> LOCATION: (7)..(7)
<223> OTHER INFORMATION: T or absent
<220> FEATURE:
<221> NAME/KEY: MOD_RES
<222> LOCATION: (8)..(8)
<223> OTHER INFORMATION: K or absent
<220> FEATURE:
<221> NAME/KEY: MOD_RES
<222> LOCATION: (9)..(9)
<223> OTHER INFORMATION: K or absent
<220> FEATURE:
<221> NAME/KEY: MOD_RES
<222> LOCATION: (18)..(18)
<223> OTHER INFORMATION: L, R, G, M, F, E, H, W, K, Q, S, V, I, Y, H, D, or T
<220> FEATURE:
<221> NAME/KEY: MOD_RES
<222> LOCATION: (22)..(22)
<223> OTHER INFORMATION: Q, F, E, G, A, L, M, F, W, K, S, V, I, Y, H, R, N, D, T, or F
<220> FEATURE:
<221> NAME/KEY: MOD_RES
<222> LOCATION: (35)..(35)
<223> OTHER INFORMATION: K or E
<220> FEATURE:
<221> NAME/KEY: MOD_RES
<222> LOCATION: (38)..(38)
<223> OTHER INFORMATION: R, W, or G
<220> FEATURE:
<221> NAME/KEY: MOD_RES
<222> LOCATION: (39)..(39)
<223> OTHER INFORMATION: M, L, or V
<220> FEATURE:
<221> NAME/KEY: MOD_RES
<222> LOCATION: (55)..(55)
<223> OTHER INFORMATION: H or Y
<220> FEATURE:
<221> NAME/KEY: MOD_RES
<222> LOCATION: (69)..(69)
<223> OTHER INFORMATION: V or A
<220> FEATURE:
<221> NAME/KEY: MOD_RES
<222> LOCATION: (74)..(74)
<223> OTHER INFORMATION: Q, P, N, H, or S
<220> FEATURE:
<221> NAME/KEY: MOD_RES
<222> LOCATION: (80)..(80)
<223> OTHER INFORMATION: L, F, or V
<220> FEATURE:
<221> NAME/KEY: MOD_RES
<222> LOCATION: (81)..(81)
<223> OTHER INFORMATION: R, I, D, or T
<220> FEATURE:
<221> NAME/KEY: MOD_RES
<222> LOCATION: (85)..(85)
<223> OTHER INFORMATION: L or V
<220> FEATURE:
<221> NAME/KEY: MOD_RES
<222> LOCATION: (86)..(86)
<223> OTHER INFORMATION: I or V
<220> FEATURE:
<221> NAME/KEY: MOD_RES
<222> LOCATION: (89)..(89)
<223> OTHER INFORMATION: I or V
<220> FEATURE:
<221> NAME/KEY: MOD_RES
<222> LOCATION: (91)..(91)
<223> OTHER INFORMATION: V, R, or K
<220> FEATURE:
<221> NAME/KEY: MOD_RES
<222> LOCATION: (92)..(92)
<223> OTHER INFORMATION: I or F
<220> FEATURE:
<221> NAME/KEY: MOD_RES
<222> LOCATION: (97)..(97)
<223> OTHER INFORMATION: K or Q
<220> FEATURE:
<221> NAME/KEY: MOD_RES
<222> LOCATION: (104)..(104)
<223> OTHER INFORMATION: M or A
<220> FEATURE:
<221> NAME/KEY: MOD_RES
<222> LOCATION: (109)..(109)
<223> OTHER INFORMATION: D, C, or a non-natural amino acid with an
activated side chain
<220> FEATURE:
<221> NAME/KEY: MOD_RES
<222> LOCATION: (113)..(113)
<223> OTHER INFORMATION: T or N
<220> FEATURE:
<221> NAME/KEY: MOD_RES
<222> LOCATION: (125)..(125)
<223> OTHER INFORMATION: C, A, or S
<220> FEATURE:
<221> NAME/KEY: MOD_RES
<222> LOCATION: (126)..(126)
<223> OTHER INFORMATION: Q, H, M, K, C, D, E, G, I, R, S, or T
<220> FEATURE:
<221> NAME/KEY: MOD_RES
<222> LOCATION: (130)..(130)
<223> OTHER INFORMATION: S, T, G, or R

<400> SEQUENCE: 10

```
Xaa Xaa Xaa Xaa Xaa Xaa Xaa Xaa Xaa Thr Gln Leu Gln Leu Glu His
1               5                   10                  15

Leu Xaa Leu Asp Leu Xaa Met Ile Leu Asn Gly Ile Asn Asn Tyr Lys
            20                  25                  30

Asn Pro Xaa Leu Thr Xaa Xaa Leu Thr Phe Lys Phe Tyr Met Pro Lys
        35                  40                  45

Lys Ala Thr Glu Leu Lys Xaa Leu Gln Cys Leu Glu Glu Glu Leu Lys
    50                  55                  60

Pro Leu Glu Glu Xaa Leu Asn Leu Ala Xaa Ser Lys Asn Phe His Xaa
65                  70                  75                  80

Xaa Pro Arg Asp Xaa Xaa Ser Asn Xaa Asn Xaa Xaa Val Leu Glu Leu
                85                  90                  95

Xaa Gly Ser Glu Thr Thr Phe Xaa Cys Glu Tyr Ala Xaa Glu Thr Ala
            100                 105                 110

Xaa Ile Val Glu Phe Leu Asn Arg Trp Ile Thr Phe Xaa Xaa Ser Ile
        115                 120                 125

Ile Xaa Thr Leu Thr
    130
```

<210> SEQ ID NO 11
<211> LENGTH: 142
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Ala Pro Thr Ser Ser Ser Thr Ser Ser Ser Thr Ala Glu Ala Gln Gln
1               5                   10                  15

Gln Gln Gln His Leu Glu Gln Leu Arg Met Asp Leu Glu Glu Leu Leu
            20                  25                  30

Ser Arg Met Glu Asn Tyr Arg Asn Leu Lys Leu Pro Arg Met Leu Thr
        35                  40                  45

Phe Lys Phe Tyr Leu Pro Lys Gln Ala Thr Glu Leu Lys Asp Leu Gln
    50                  55                  60

Cys Leu Glu Asp Glu Leu Gly Pro Leu Arg His Val Leu Asp Leu Thr
65                  70                  75                  80

Gln Ser Lys Ser Phe Gln Leu Glu Asp Ala Glu Asn Phe Ile Ser Asn
                85                  90                  95

Ile Arg Val Thr Val Val Lys Leu Lys Gly Ser Asp Asn Thr Phe Glu
            100                 105                 110

Cys Gln Phe Asp Asp Glu Ser Ala Thr Val Val Asp Phe Leu Arg Arg
        115                 120                 125

Trp Ile Ala Phe Cys His Ser Ile Ile Ser Thr Ser Pro Gln
    130                 135                 140
```

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
<220> FEATURE:
<221> NAME/KEY: SITE
<222> LOCATION: (1)..(6)

<223> OTHER INFORMATION: This sequence may encompass 3-6 residues

<400> SEQUENCE: 12

His His His His His His
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 13

His His His His His His
1               5

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
tatagtcagc gccacccatg tacaggatgc aactcctgtc 40

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
tatagggccc tatcaagtca gtgttgagat g 31

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gatggattac cttttgtgag agcatcatct caaca 35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tgttgagatg atgctctcac aaaaggtaat ccatc 35

<210> SEQ ID NO 18
<211> LENGTH: 31
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 18
ggattacctt ttgtatgagc atcatctcaa c 31

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gttgagatga tgctcataca aaaggtaatc c 31

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggattacctt ttgtgtgagc atcatctcaa cac 33

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gtgttgagat gatgctcaca caaaaggtaa tcc 33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggattacctt ttgtctgagc atcatctcaa cac 33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtgttgagat gatgctcaga caaaaggtaa tcc 33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
ggattacctt ttgtttcagc atcatctcaa cac 33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gtgttgagat gatgctgaaa caaaaggtaa tcc 33

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ggattacctt ttgtaacagc atcatctcaa cac 33

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
gtgttgagat gatgctgtta caaaaggtaa tcc 33

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ggattacctt ttgtaggagc atcatctcaa cac 33

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
gtgttgagat gatgctccta caaaaggtaa tcc 33

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
ggattacctt ttgttacagc atcatctcaa cac 33

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
gtgttgagat gatgctgtaa caaaaggtaa tcc 33

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
ggattacctt ttgtaagagc atcatctc 28

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gagatgatgc tcttacaaaa ggtaatcc 28

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
gacttaatca gccgtatcaa cgtaata 27

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
tattacgttg atacggctga ttaagtc 27

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ggacttaatc agcgatatca acgtaat 27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 37
attacgttga tatcgctgat taagtcc 27

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 38
gggacttaat cagcggtatc aacgtaat 28

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
attacgttga taccgctgat taagtccc 28

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ggacttaatc agcattatca acgtaat 27

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
attacgttga taatgctgat taagtcc 27

<210> SEQ ID NO 42
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gcatttaagg ctgattttag agatgatttt g 31

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
caaaatcatc tctaaaatca gccttaaatg c 31

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
gagcatttaa ggctgcattt agagatg 27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
catctctaaa tgcagcctta aatgctc 27

<210> SEQ ID NO 46
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gcatttaagg ctgactttag agatgatttt g 31

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
caaaatcatc tctaaagtca gccttaaatg c 31

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 48

-continued

```
gcatttaagg ctgggtttag agatga                                          26


<210> SEQ ID NO 49
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

tcatctctaa acccagcctt aaatgc                                          26


<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

gcatttaagg ctggctttag agatgatttt g                                    31


<210> SEQ ID NO 51
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

caaaatcatc tctaaagcca gccttaaatg c                                    31


<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52

cagcaatatc aacaagatag ttctggaac                                       29


<210> SEQ ID NO 53
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53

gttccagaac tatcttgttg atattgctg                                       29
```